(12) United States Patent
Thorarensen et al.

(10) Patent No.: US 11,111,242 B2
(45) Date of Patent: Sep. 7, 2021

(54) PYRROLO[2,3-D]PYRIMIDINYL, PYRROLO[2,3-B]PYRAZINYL AND PYRROLO[2,3-D]PYRIDINYL ACRYLAMIDES

(71) Applicant: Pfizer Inc., New York, NY (US)

(72) Inventors: Atli Thorarensen, Stow, MA (US); Matthew Frank Brown, Stonington, CT (US); Agustin Casimiro-Garcia, Concord, MA (US); Ye Che, Groton, CT (US); Jotham Wadsworth Coe, Niantic, CT (US); Mark Edward Flanagan, Gales Ferry, CT (US); Adam Matthew Gilbert, Guilford, CT (US); Matthew Merrill Hayward, Old Lyme, CT (US); Jonathan David Langille, Quaker Hill, CT (US); Justin Ian Montgomery, Ledyard, CT (US); Jean-Baptiste Telliez, Lexington, MA (US); Rayomand Jal Unwalla, Bedford, MA (US); John I. Trujillo, Ledyard, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/446,500

(22) Filed: Mar. 1, 2017

(65) Prior Publication Data
US 2017/0247372 A1    Aug. 31, 2017

Related U.S. Application Data

(62) Division of application No. 14/559,294, filed on Dec. 3, 2014, now Pat. No. 9,617,258.

(60) Provisional application No. 61/912,074, filed on Dec. 5, 2013.

(51) Int. Cl.
| | |
|---|---|
| *A61K 31/4523* | (2006.01) |
| *C07D 471/04* | (2006.01) |
| *C07D 471/08* | (2006.01) |
| *C07D 487/04* | (2006.01) |
| *C07D 487/10* | (2006.01) |
| *C07D 498/04* | (2006.01) |

(52) U.S. Cl.
CPC ........ *C07D 471/04* (2013.01); *A61K 31/4523* (2013.01); *C07D 471/08* (2013.01); *C07D 487/04* (2013.01); *C07D 487/10* (2013.01); *C07D 498/04* (2013.01)

(58) Field of Classification Search
CPC .................................................. C07D 471/04
See application file for complete search history.

(56) References Cited

U.S. PATENT DOCUMENTS

| | | | |
|---|---|---|---|
| 7,960,396 B2 | 6/2011 | Honigberg et al. | |
| 8,232,280 B2 | 7/2012 | Honigberg et al. | |
| 10,144,737 B2 * | 12/2018 | Zhang .................. | C07D 473/34 |
| 2010/0185419 A1 | 7/2010 | Singh et al. | |
| 2014/0336207 A1 | 11/2014 | Zhang et al. | |

FOREIGN PATENT DOCUMENTS

| | | |
|---|---|---|
| WO | 99/65908 A1 | 12/1999 |
| WO | 99/65909 A1 | 12/1999 |
| WO | 01/42246 A2 | 6/2001 |
| WO | 02/00661 A1 | 1/2002 |
| WO | 02/096909 A1 | 12/2002 |
| WO | 2004/046112 A2 | 6/2004 |
| WO | 2006/069080 A2 | 6/2006 |
| WO | 2007/012953 A2 | 2/2007 |
| WO | 2007/062459 A1 | 6/2007 |
| WO | 2007/070514 A1 | 6/2007 |
| WO | 2007/077949 A1 | 7/2007 |
| WO | 2010/016005 A1 | 2/2010 |

(Continued)

OTHER PUBLICATIONS

Wu et al. FDA-approved small-molecule kinase inhibitors. Trends in Pharmacological Sciences, 2015, 36, 422-439.*
Cochi et al, "Access to Optically Active 3-Azido- and 3-Aminopiperidine Derivatives by Enantioselective Ring Expansion of Prolinols", Organic Letters 13(16):4442-4445 (2011).
Cochi et al, "Access to Optically Active 3-Aminopiperidines by Ring Expansion of Prolinols: Thermodynamic versus Kinetic Control", European Journal of Organic Chemistry 10:2023-2040 (2012).

(Continued)

*Primary Examiner* — Brian E McDowell
(74) *Attorney, Agent, or Firm* — A. David Joran

(57) ABSTRACT

The present invention provides pharmaceutically active pyrrolo[2,3-d]pyrimidinyl and pyrrolo[2,3-d]pyridinyl acrylamides and analogues thereof, having the structure:

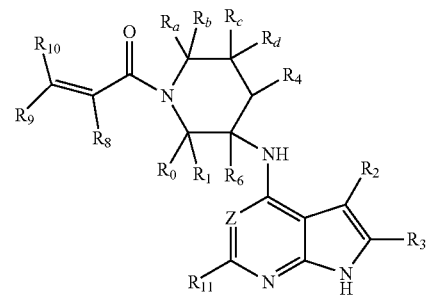

or a pharmaceutically acceptable salt thereof, as set forth in the Description. Such compounds are useful for inhibiting Janus Kinase (JAK). This invention also is directed to compositions comprising methods for making such compounds, and methods for treating and preventing conditions mediated by JAK.

12 Claims, No Drawings

(56) References Cited

FOREIGN PATENT DOCUMENTS

| | | | |
|---|---|---|---|
| WO | 2010/063634 | A1 | 6/2010 |
| WO | 2010/129053 | A2 | 11/2010 |
| WO | 2011/003418 | A1 | 1/2011 |
| WO | 2011/029046 | A1 | 3/2011 |
| WO | 2011/072174 | A1 | 6/2011 |
| WO | 2011/101161 | A1 | 8/2011 |
| WO | 2011/144585 | A1 | 11/2011 |
| WO | 2012/003829 | A1 | 1/2012 |
| WO | 2012/054364 | A2 | 4/2012 |
| WO | 2013/085802 | A1 | 6/2013 |
| WO | 2014/039714 | A2 | 3/2014 |
| WO | 2014/075392 | A1 | 5/2014 |
| WO | 2014/081732 | A1 | 5/2014 |
| WO | 2014/101295 | A2 | 7/2014 |

OTHER PUBLICATIONS

Hill, R.J., et al., "Discovery of a highly potent, selective, reversible covalent inhibitor of JAK3", Arthritis and Rheumatism. Conference: Annual Scientific Meeting of the American College of Rheumatology and Association of Rheumatology Health Professionals 2012, Washington, DC, United States, Conference Publication: (var. pagings). 64 (pp. S982), 2012. Date of Publication: Oct. 2012. Abstract.

Kisseleva et al, "Signaling through the JAK/STAT pathway, recent advances and future challenges", Gene 285:1-24 (2002).

Murray, "The JAK-STAT Signaling Pathway: Input and Output Integration", The Journal of Immunology 178:2623-2629 (2007).

Neubauer et al, "Jak2 Deficiency Defines an Essential Developmental Checkpoint in Definitive Hematopoiesis", Cell 93:397-409 (1998).

Norman, P., "Highly selective Janus kinase 3 inhibitors based on a pyrrolo [2,3-d]pyrimidine scaffold: evaluation of WO2013085802", Expert Opin, Ther. Patents, 24(1):121-125 (2014).

O'Shea et al, "Cytokine Signaling in 2002: New Surprises in the Jak/Stat Pathway", Cell 109:S121-S131 (2002).

Padilla et al, "Pyrrolopyrazines as Selective Spleen Tyrosine Kinase Inhibitors", Journal of Medicinal Chemistry 56(4):1677-1692 (2013).

Jarganas et al, "Jak2 Is Essential for Signaling through a Variety of Cytokine Receptors", Cell 93:385-395 (1998).

Joss, J., et al., "Characterization of ABT-494, A Second Generation Jak 1 Selective Inhibitor", 78th ACR/ARHP Annual Scientific Meeting, Nov. 14-19, 2014, Boston, Massachusetts, Abbvie Bioresearch Center, Oct. 20, 2014, Abstract.

Wrobleski, S.T., et al., "Advances in the Discovery of Small Molecule JAK3 Inhibitors", Annual Reports in Medicinal Chemistry, 44:247-264 (2009).

Yamaoka et al, "The Janus kinases (Jaks)", Genome Biology 5(12):Article 253 (2004).

* cited by examiner

PYRROLO[2,3-D]PYRIMIDINYL, PYRROLO[2,3-B]PYRAZINYL AND PYRROLO[2,3-D]PYRIDINYL ACRYLAMIDES

This application is a divisional of Ser. No. 14/559,294, filed Dec. 3, 2014, which claimed the benefit under 35 U.S.C. § 119(e) of Ser. No. 61/912,074, filed Dec. 5, 2013.

FIELD OF THE INVENTION

The present invention provides pharmaceutically active heterocyclic acrylamides, inter alia, pyrrolo[2,3-d]pyrimidinyl, pyrrolo[2,3-b]pyrazinyl and pyrrolo[2,3-d]pyridinyl acrylam ides and analogues thereof. Such compounds are useful for inhibiting Janus Kinase (JAK). This invention also is directed to compositions comprising methods for making such compounds, and methods for treating and preventing conditions mediated by JAK.

BACKGROUND OF THE INVENTION

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation or de-regulation, as well as over- or underproduction of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility implicated in the aforementioned and related diseases.

Thus, protein kinases have emerged as an important class of enzymes as targets for therapeutic intervention. In particular, the JAK family of cellular protein tyrosine kinases (JAK1, JAK2, JAK3, and Tyk2) play a central role in cytokine signaling (Kisseleva, et al., Gene, 2002, 285, 1; Yamaoka, et al. Genome Biology, 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression. Numerous cytokines are known to activate the JAK family. These cytokines include, the IFN family (IFN-alpha, IFN-beta, IFN-omega, Limitin, IFN-gamma, IL-10, IL-19, IL-20, IL-22), the gp130 family (IL-6, IL-11, OSM, LIF, CNTF, NNT-1/BSF-3, G-CSF, CT-1, Leptin, IL-12, IL-23, IL-27 and IL-35), gamma-common chain family (IL-2, IL-4, IL-7, IL-9, IL-15, IL-21), and IL-13, TLSP, IL-3 family (IL-3, IL-5, GM-CSF), single chain family (EPO, GH, PRL, TPO), receptor tyrosine kinases (EGF, PDGF, CSF-1, HGF), and G-protein coupled receptors (AT1).

There remains a need for new compounds that effectively and selectively inhibit specific JAK enzymes, and JAK3 in particular. JAK3 is a member of the Janus family of protein kinases composed of JAK1, JAK2, JAK3 and TYK2, and is expressed to various levels in all tissues. Many cytokine receptors signal through pairs of JAK kinases in the following combinations: JAK1/JAK2, JAK1/JAK3, JAK1/TYK2, JAK2/TYK2 or JAK2/JAK2. Animal studies have shown that JAK3 is implicated in the development, function and homeostasis of the immune system. Modulation of immune activity through inhibition of JAK3 kinase activity can prove useful in the treatment of various immune disorders (Murray, P. J. *J. Immunol.*, 178, 2623-2629 (2007); Kisseleva, T., et al., *Gene*, 285, 1-24 (2002); O'Shea; J. J., et al., *Cell* 109, (suppl.) S121-S131 (2002)) while avoiding JAK2 dependent erythropoietin (EPO) and thrombopoietin (TPO) signaling (Neubauer, H., et al., *Cell*, 93(3), 397-409 (1998); Parganas, E., et al., *Cell*, 93(3), 385-95 (1998)).

SUMMARY OF THE INVENTION

The present invention provides a c a compound having the structure:

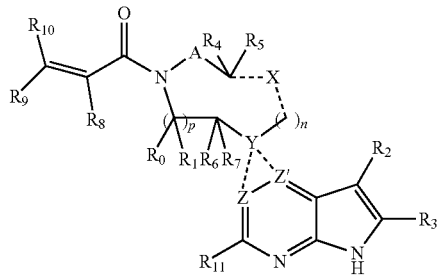

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonyl, ($C_1$-$C_6$ linear or branched chain alkyl) aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —($CR_aR_b)_q$—($CR_cR_d)_r$—, wherein $R_a$, $R_b$, $R_c$, and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_5$, $R_6$, $R_7$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$ or $R_7$, respectively together with either of $R_4$, $R_5$, $R_a$, $R_b$, $R_c$ or $R_d$, may independently form a bond or a $C_1$-$C_6$ linear alkyl chain; and/or, alternatively, $R_4$ or $R_5$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms;

$R_{11}$ is hydrogen or deuterium;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

Y is O or N, where when Y is O, n is 0;

one and only one of the dotted bonds to Z and Z' constitutes a single bond, the other being absent, and either Z is C when the dotted bond to Z is a single bond, and Z' is N or $CR_{16}$; or, Z is $CR_{16}$ or N when the dotted bond to Z' is a single bond, and Z' is C; where $R_{16}$ is $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain alkyl)heterocyclic, where said alkyl is further optionally substituted with one or more substituents selected from the group consisting of halo, hydroxy, methoxy, amino, $CF_3$, and $C_3$-$C_6$ cycloalkyl;

X and the dotted bonds thereto may be present or absent, whereby, (a) if X is present, Y is N, and X is O or —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, whereby when n is 0, and X is O, said O is bonded to H, and said dotted bond between X and —$(CH_2)_n$— is absent, and when X is —$(CR_eR_f)_s$—, and X is bonded directly to Y; and (b) if X is absent, said dotted bonds are absent and n is 0, whereby when Y is N, either (i) said N atom is substituted by H, (ii) Z is C, Z' is C or N, the dotted bond to Z is a single bond, the dotted bond to Z' being absent, or (iii) Z is C or N, Z' is C, the dotted bond to Z' is a single bond, the dotted bond to Z being absent, where said Y being an N atom may together with $R_2$ and the atoms intervening therebetween form a 6-membered ring optionally substituted by $C_1$-$C_6$ linear or branched chain alkyl or $C_3$-$C_6$ cycloalkyl; and, n, p, q, r and s are independently 0, 1 or 2.

In other aspects, the present invention also provides:

pharmaceutical compositions which comprise a pharmaceutically acceptable carrier and a compound of the invention;

methods for treating or preventing a disorder or condition selected from rheumatoid arthritis, myositis, vasculitis, pemphigus, bullous pemphigoid, inflammatory bowel disease including Crohn's disease and ulcerative colitis, celiac diseases, proctitis, eosinophilic gastroenteritis, or mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis nodosa, dry eye syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation, including Cogan's syndrome, ankylosing spondylitis, Wegener's granulomatosis, autoimmune alopecia, Type I or juvenile onset diabetes, and complications from diabetes, or thyroiditis, chronic pulmonary obstructive disorder, acute respiratory disease, cachexia, cancer, including alimentary/gastrointestinal tract cancer, colon cancer, liver cancer, skin cancer including mast cell tumor and squamous cell carcinoma, breast and mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma including oral and metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, or angiogenic-associated disorders including solid tumors, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotropic Lateral Sclerosis, Huntington's disease, cerebral ischemia, fronto-temporal lobe dementia, and with neuropsychiatric disorders including schizophrenia, bipolar disorder, treatment resistant depression, Post Traumatic Stress Disorder, anxiety, and auto-antibodies mediated encephalopathies, Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi- Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization, comprising the step of administering to a subject an effective amount of a composition comprising a compound or a pharmaceutically acceptable salt thereof set forth herein;

methods for treating conditions or disorders including atopic dermatitis, eczema, psoriasis, scleroderma, lupus, pruritus, other pruritic conditions, allergic reactions including allergic dermatitis in mammal, horse allergic diseases including bite hypersensitivity, summer eczema, sweet itch in horses, heaves, inflammatory airway disease, recurrent airway obstruction, airway hyper-responsiveness, and chronic obstruction pulmonary disease by administering to a mammal in need a therapeutically effective amount of a compound of the invention, or a pharmaceutically acceptable salt thereof; and, methods for the preparation of compounds of the present invention. The present invention will be further understood from the following description given by way of example only. The present invention is directed to a class of pyrrolo [2,3-d]pyrimidinyl and pyrrolo[2,3-d]pyridinyl acrylam ides and analogues thereof. In particular, the present invention is directed to compounds including pyrrolo[2,3-d]pyrimidinyl and pyrrolo[2,3-d]pyridinyl acrylam ides which are useful as inhibitors of JAK, and particularly JAK3. While the present invention is not so limited, an appreciation of various aspects of the invention will be gained through the following discussion and the examples.

The term "alkyl", alone or in combination, means an acyclic, saturated hydrocarbon group of the formula $C_n-H_{2n+1}$ which may be linear or branched. Examples of such groups include methyl, ethyl, n-propyl, isopropyl, n-butyl, isobutyl, sec-butyl, tert-butyl, pentyl, iso-amyl and hexyl. Unless otherwise specified, an alkyl group comprises from 1 to 6 carbon atoms. The carbon atom content of alkyl and various other hydrocarbon-containing moieties is indicated by a prefix designating a lower and upper number of carbon atoms in the moiety, that is, the prefix $C_i$-$C_j$ indicates a moiety of the integer "i" to the integer "j" carbon atoms, inclusive. Thus, for example, $C_1$-$C_6$ alkyl refers to alkyl of one to six carbon atoms, inclusive.

The term "hydroxy," as used herein, means an OH radical. The term "heterocyclic" refers to a saturated or partially saturated (i.e. non aromatic) heterocycle which may be attached via a ring nitrogen atom (when the heterocycle is attached to a carbon atom) or a ring carbon atom (in all cases). Equally, when substituted, the substituent may be located on a ring nitrogen atom (if the substituent is joined through a carbon atom) or a ring carbon atom (in all cases). Specific examples include oxiranyl, aziridinyl, oxetanyl, azetidinyl, tetrahydrofuranyl, pyrrolidinyl, tetrahydropyranyl, piperidinyl, 1,4-dioxanyl, morpholinyl, piperazinyl, azepanyl, oxepanyl, oxazepanyl and diazepinyl.

The term "aryl" refers to an aromatic monocyclic or bicyclic hydrocarbon which may be attached via a ring carbon atom. Equally, when substituted, the substituent may be located on a ring carbon atom. Specific examples include phenyl, toluyl, xylyl, trimethylphenyl, and naphthyl. Examples of aryl substituents include alkyl, hydroxyl, halo, nitrile, alkoxy, trifluoromethyl, carboxamido, $SO_2Me$, benzyl, and substituted benzyl.

The term "heteroaryl" refers to an aromatic heterocycle which may be attached via a ring carbon atom (in all cases) or a ring nitrogen atom with an appropriate valency (when the heterocycle is attached to a carbon atom). Equally, when substituted, the substituent may be located on a ring carbon atom (in all cases) or a ring nitrogen atom with an appropriate valency (if the substituent is joined through a carbon atom). Specific examples include thienyl, furanyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl and pyrazinyl. The term "cycloalkyl" means a monocyclic, saturated hydrocarbon group of the formula $C_n-H_{2n-1}$. Examples include cyclopropyl, cyclobutyl, cyclopentyl, cyclohexyl, and cycloheptyl. Unless otherwise specified, a cycloalkyl group comprises from 3 to 8 carbon atoms.

The terms "halo" and "halogen" refer to fluoride (F), chloride (Cl), bromide (Br) or iodide (I).

The term "mammal" refers to human, livestock or companion animals.

The term "companion animal" or "companion animals" refers to animals kept as pets or household animal. Examples of companion animals include dogs, cats, and rodents including hamsters, guinea pigs, gerbils and the like, rabbits, ferrets and birds.

The term "livestock" refers to animals reared or raised in an agricultural setting to make products such as food or fiber, or for its labor. In some embodiments, livestock are suitable for consumption by mammals, for example humans. Examples of livestock animals include cattle, goats, horses, pigs, sheep, including lambs, and rabbits, as well as birds, such as chickens, ducks and turkeys.

The term "treating" or "treatment" means an alleviation of symptoms associated with a disease, disorder or condition, or halt of further progression or worsening of those symptoms. Depending on the disease and condition of the patient, the term "treatment" as used herein may include one or more of curative, palliative and prophylactic treatment. Treatment can also include administering a pharmaceutical formulation of the present invention in combination with other therapies.

The term "therapeutically-effective" indicates the capability of an agent to prevent, or improve the severity of, the disorder, while avoiding adverse side effects typically associated with alternative therapies. The phrase "therapeutically-effective" is to be understood to be equivalent to the phrase "effective for the treatment, prevention, or amelioration", and both are intended to qualify the amount of each agent for use in the combination therapy which will achieve the goal of improvement in the severity of cancer, cardiovascular disease, or pain and inflammation and the frequency of incidence over treatment of each agent by itself, while avoiding adverse side effects typically associated with alternative therapies.

"Pharmaceutically acceptable" means suitable for use in mammals, companion animals or livestock animals.

If substituents are described as being "independently selected" from a group, each substituent is selected independent of the other. Each substituent therefore may be identical to or different from the other substituent(s).

DETAILED DESCRIPTION OF THE INVENTION

The present invention is related to novel compounds which are selective JAK3 modulators useful for the treatment of diseases and conditions associated with dysregulation of the JAK3. The present invention further provides pharmaceutical compositions comprising such JAK3 modulators as well as methods of treating and preventing such diseases and conditions. Accordingly, the present invention provides a compound having the structure:

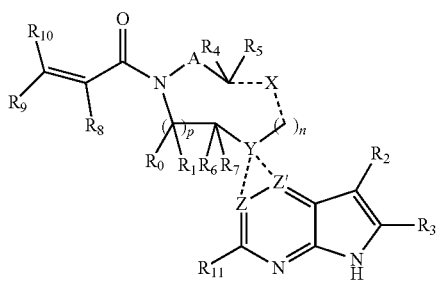

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$, and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_5$, $R_6$, $R_7$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$ or $R_7$, respectively together with either of $R_4$, $R_5$, $R_a$, $R_b$, $R_c$ or $R_d$, may independently form a bond or a $C_1$-$C_6$ linear alkyl chain; and/or, alternatively, $R_4$ or $R_5$, respectively together with either of $R_a$, $R_b$, $R_c$ or $R_d$, may independently form a bond or a $C_1$-$C_6$ linear alkyl chain; and/or, alternatively, $R_8$ and $R_9$ may together form a 3-6-membered ring optionally containing one or two O or N atoms;

$R_{11}$ is hydrogen or deuterium;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

Y is O or N, where when Y is O, n is 0;

one and only one of the dotted bonds to Z and Z' constitutes a single bond, the other being absent, and either Z is C when the dotted bond to Z is a single bond, and Z' is N or $CR_{16}$; or, Z is $CR_{16}$ or N when the dotted bond to Z' is a single bond, and Z' is C; where $R_{16}$ is $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain alkyl)heterocyclic, where said alkyl is further optionally substituted with one or more substituents selected from the group consisting of halo, hydroxy, methoxy, amino, $CF_3$, and $C_3$-$C_6$ cycloalkyl;

X and the dotted bonds thereto may be present or absent, whereby, (a) if X is present, Y is N, and X is O or —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, whereby when n is 0, and X is O, said O is bonded to H, and said dotted bond between X and —$(CH_2)_n$— is absent, and when X is —$(CR_eR_f)_s$—, and X is bonded directly to Y; and (b) if X is absent, said dotted bonds are absent and n is 0, whereby when Y is N, either (i) said N atom is substituted by H, (ii) Z is C, Z' is C or N, the dotted bond to Z is a single bond, the dotted bond to Z' being absent, or (iii) Z is C or N, Z' is C, the dotted bond to Z' is a single bond, the dotted bond to Z being absent, where said Y being an N atom may together with $R_2$ and the atoms intervening therebetween form a 6-membered ring optionally substituted by $C_1$-$C_6$ linear or branched chain alkyl or $C_3$-$C_6$ cycloalkyl; and, n, p, q, r and s are independently 0, 1 or 2.

In one embodiment, the invention provides a compound having the structure:

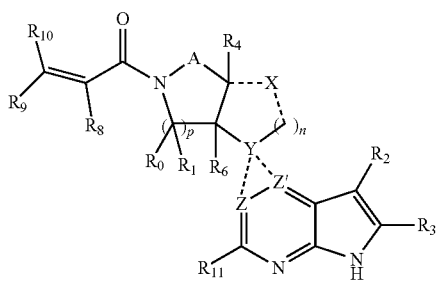

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$, and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms;

$R_{11}$ is hydrogen or deuterium;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

Y is O or N, where when Y is O, n is 0;

one and only one of the dotted bonds to Z and Z' constitutes a single bond, the other being absent, and either Z is C when the dotted bond to Z is a single bond, and Z' is N or $CR_{16}$; or, Z is $CR_{16}$ or N when the dotted bond to Z' is a single bond, and Z' is C; where $R_{16}$ is $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain alkyl)heterocyclic, where said alkyl is further optionally substituted with one or more substituents selected from the group consisting of halo, hydroxy, methoxy, amino, $CF_3$, and $C_3$-$C_6$ cycloalkyl;

X and the dotted bonds thereto may be present or absent, whereby, (a) if X is present, Y is N, and X is O or —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, whereby when n is 0, and X is O, said O is bonded to H, and said dotted bond between X and —$(CH_2)_n$— is absent, and when X is —$(CR_eR_f)_s$—, and X is bonded directly to Y; and (b) if X is absent, said dotted bonds are absent and n is 0, whereby when Y is N, either (i) said N atom is substituted by H, (ii) Z is C, Z' is C or N, the dotted bond to Z is a single bond, the dotted bond to Z' being absent, or (iii) Z is C or N, Z' is C, the dotted bond to Z' is a single bond, the dotted bond to Z being absent, where said Y being an N atom may together with $R_2$ and the atoms intervening therebetween form a 6-membered ring optionally substituted by $C_1$-$C_6$ linear or branched chain alkyl or $C_3$-$C_6$ cycloalkyl; and, n, p, q, r and s are independently 0, 1 or 2.

In another embodiment, the invention provides a compound having the structure:

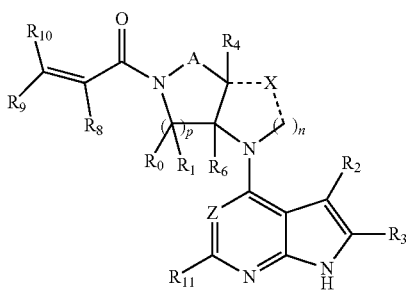

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$, and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms;

$R_{11}$ is hydrogen or deuterium;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

Z is $CR_{16}$ or N, where $R_{16}$ is $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain alkyl)heterocyclic, where said alkyl is further optionally substituted with one or more substituents selected from the group consisting of halo, hydroxy, methoxy, amino, $CF_3$, and $C_3$-$C_6$ cycloalkyl;

X and the dotted bonds thereto may be present or absent, whereby, (a) if X is present, X is O or —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, whereby when n is 0, and X is O, said O is bonded to H, and said dotted bond between X and —$(CH_2)_n$— is absent; and (b) if X is absent, said dotted bonds are absent and n is 0, whereby either (i) the adjacent N atom is substituted by H, or (ii) said N atom may together with $R_2$ and the atoms intervening therebetween form a 6-membered ring optionally substituted by $C_1$-$C_6$ linear or branched chain alkyl or $C_3$-$C_6$ cycloalkyl; and, n, p, q, r and s are independently 0, 1 or 2.

In another embodiment, the invention provides the compound having the structure:

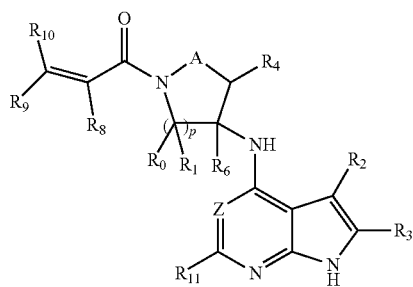

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, $-SOR_{12}$, $-SO_2R_{12}$, $-NR_{13}SO_2R_{12}$, $-SO_2NR_{13}R_{14}$, and $-NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is $-(CR_aR_b)_q-(CR_cR_d)_r-$, wherein $R_a$, $R_b$, $R_c$, and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms;

Z is $CR_{16}$ or N, where $R_{16}$ is $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain alkyl)heterocyclic, where said alkyl is further optionally substituted with one or more substituents selected from the group consisting of halo, hydroxy, methoxy, amino, $CF_3$, and $C_3$-$C_6$ cycloalkyl;

$R_{11}$ is hydrogen or deuterium;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl; and, p, q, and r are independently 0, 1 or 2.

In another embodiment, the invention provides the compound having the structure:

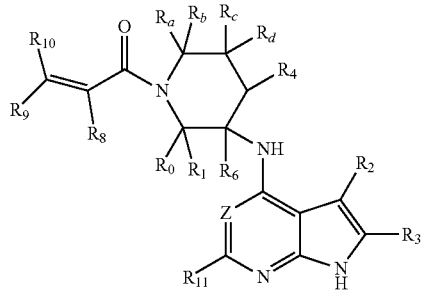

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, $-SOR_{12}$, $-SO_2R_{12}$, $-NR_{13}SO_2R_{12}$, $-SO_2NR_{13}R_{14}$, and $-NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

$R_a$, $R_b$, $R_c$, and $R_d$ are independently selected from hydrogen, $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms;

Z is $CR_{16}$ or N, where $R_{16}$ is $C_1$-$C_4$ alkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, or ($C_1$-$C_6$ linear or branched chain alkyl)heterocyclic, where said alkyl is further optionally substituted with one or more substituents selected from the group consisting of halo, hydroxy, methoxy, amino, $CF_3$, and $C_3$-$C_6$ cycloalkyl;

$R_{11}$ is hydrogen or deuterium; and, $R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl.

In another embodiment, the invention provides the compound having the structure:

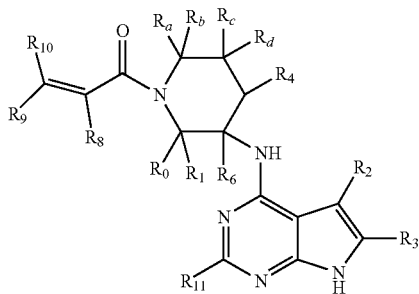

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, $-SOR_{12}$, $-SO_2R_{12}$, $-NR_{13}SO_2R_{12}$, $-SO_2NR_{13}R_{14}$, and $-NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

$R_a$, $R_b$, $R_c$, and $R_d$ are independently selected from hydrogen, $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms;

$R_{11}$ is hydrogen or deuterium; and, $R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl.

In another embodiment, the invention provides the compound having the structure:

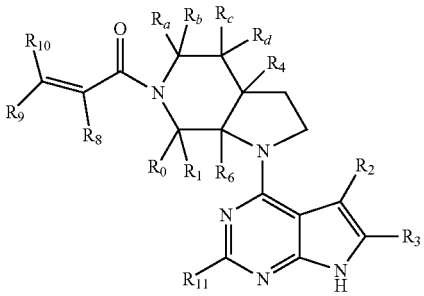

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

$R_a$, $R_b$, $R_c$, and $R_d$ are independently selected from hydrogen, $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms;

$R_{11}$ is hydrogen or deuterium; and, $R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl.

In another embodiment, the invention provides the compound having the structure:

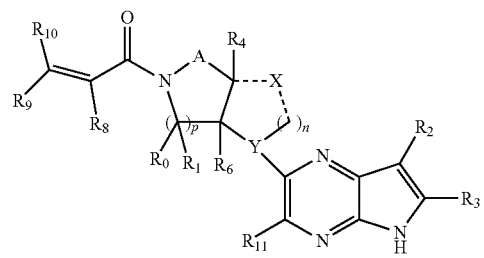

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl) aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —($CR_aR_b$)$_q$—($CR_cR_d$)$_r$—, wherein $R_a$, $R_b$, $R_c$, and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_a$, $R_b$, $R_c$, and $R_d$ are independently selected from hydrogen, $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, wherein said alkyl is further optionally substituted with one or more substituents selected from the group consisting of halo, hydroxy, methoxy, amino, alkylamino, dialkylamino, $CF_3$, and $C_3$-$C_6$ cycloalkyl, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms; and, $R_{11}$ is hydrogen or deuterium;

Y is O or N, where when Y is O, n is 0;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

X and the dotted bonds thereto may be present or absent, whereby, (a) if X is present, Y is N, and X is O or —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, whereby when n is 0, and X is O, said O is bonded to H, and said dotted bond between X and —$(CH_2)_n$— is absent, and when X is —$(CR_eR_f)_s$—, and X is bonded directly to Y; and (b) if X is absent, said dotted bonds are absent and n is 0, whereby when Y is N, either (i) said N atom is substituted by H, or (ii) said N atom may together with $R_2$ and the atoms intervening therebetween form a 6-membered ring optionally substituted by $C_1$-$C_6$ linear or branched chain alkyl or $C_3$-$C_6$ cycloalkyl; and, n, p, q, r and s are independently 0, 1 or 2.

In another embodiment, the invention provides the compound having the structure:

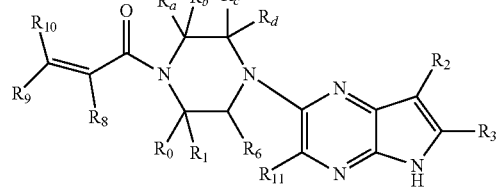

or a pharmaceutically acceptable salt thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{16}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

$R_0$, $R_1$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms;

$R_{11}$ is hydrogen or deuterium; and, $R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl.

In another embodiment, the invention provides the compound having the structure:

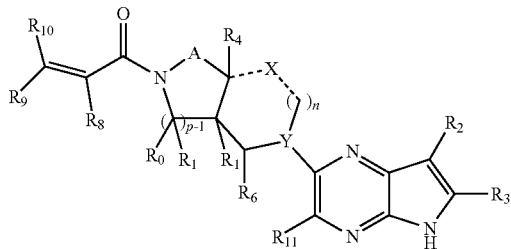

or a pharmaceutically acceptable salt or solvate thereof, or an enantiomer or diastereomer thereof, and wherein $R_2$ is selected from the group consisting of hydrogen, deuterium, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, ($C_1$-$C_6$ linear or branched chain alkyl)heterocyclic, $C_1$-$C_6$ linear or branched chain perfluoroalkyl, $C_1$-$C_6$ linear or branched chain alkoxy, $C_1$-$C_6$ linear or branched chain perfluoroalkoxy, halogen, cyano, hydroxyl, amino, carboxy, aminocarbonyl, ($C_1$-$C_6$ linear or branched chain alkyl)aminocarbonylamino, ($C_1$-$C_6$ linear or branched chain alkyl)aminocarbonyl, —$SOR_{12}$, —$SO_2R_{12}$, —$NR_{13}SO_2R_{12}$, —$SO_2NR_{13}R_{14}$, and —$NR_{13}SO_2NR_{14}R_{15}$; where said alkyl, aryl and heteroaryl is independently optionally substituted with one or more substituents selected from the group consisting of halo, hydroxy, methoxy, amino, cyano, alkylamino, dialkylamino, $CF_3$, aminocarbonyl, ($C_1$-$C_6$ linear or branched chain alkyl)aminocarbonyl, and $C_3$-$C_6$ cycloalkyl;

$R_3$ is selected from the group consisting of hydrogen, deuterium, $C_1$-$C_6$ linear or branched chain alkyl, $C_1$-$C_6$ linear or branched chain perfluoroalkyl, halogen, and cyano;

A is —$(CR_aR_b)_q$—$(CR_cR_d)_r$—, wherein $R_a$, $R_b$, $R_c$, and $R_d$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, alkylaryl, (aryl)$C_1$-$C_6$ linear or branched chain alkyl, (heteroaryl)$C_1$-$C_6$ linear or branched chain alkyl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_a$, $R_b$, $R_c$, and $R_d$ are independently selected from hydrogen, $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl) aryl, ($C_1$-$C_6$ linear or branched chain alkyl)heteroaryl, and ($C_1$-$C_6$ linear or branched chain alkyl)heterocyclic, wherein said alkyl is further optionally substituted with one or more substituents selected from the group consisting of halo, hydroxy, methoxy, amino, alkylamino, dialkylamino, $CF_3$, and $C_3$-$C_6$ cycloalkyl, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, $R_6$, $R_8$, $R_9$ and $R_{10}$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl) heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$, or $R_d$, may independently form a bond or a $C_1$-$C_6$ linear alkyl chain; and/or, alternatively, $R_4$, respectively together with either of $R_a$, $R_b$, $R_c$, or $R_d$, may independently form a bond or a $C_1$-$C_6$ linear alkyl chain; and/or, alternatively, $R_8$ and $R_9$ may together form a 3-6-membered ring optionally containing one or two O or N atoms; and, $R_{11}$ is hydrogen or deuterium;

Y is O or N, where when Y is O, n is 0;

$R_{12}$, $R_{13}$, $R_{14}$ and $R_{15}$ are independently selected from hydrogen, $C_1$-$C_6$ linear or branched chain alkyl, $C_1$-$C_6$ linear or branched chain perfluoroalkyl, $C_6$-$C_{10}$ aryl, alkylaryl, and (aryl)$C_1$-$C_6$ linear or branched chain alkyl;

X and the dotted bonds thereto may be present or absent, whereby, (a) if X is present, Y is N, and X is O or —$(CR_eR_f)_s$—, where $R_e$ and $R_f$ are independently hydrogen, deuterium, halo, hydroxy, $C_1$-$C_4$ alkoxy, amino, $CF_3$, $C_1$-$C_6$ linear or branched chain alkyl, $C_3$-$C_6$ cycloalkyl, $C_6$-$C_{10}$ aryl, monocyclic or bicyclic heteroaryl, comprising 5- and/or 6-membered rings, (aryl)$C_1$-$C_6$ linear or branched chain alkyl, ($C_1$-$C_6$ linear or branched chain alkyl)heteroaryl, (heteroaryl)$C_1$-$C_6$ linear or branched chain alkyl, or (heterocyclic)$C_1$-$C_6$ linear or branched chain alkyl, and said dotted bonds are present and are single bonds, whereby when n is 0, and X is O, said O is bonded to H, and said dotted bond between X and —$(CH_2)_n$— is absent, and when X is —$(CR_eR_f)_s$—, and X is bonded directly to Y; and (b) if X is absent, said dotted bonds are absent and n is 0, whereby when Y is N, either (i) said N atom is substituted by H, or (ii) said N atom may together with $R_2$ and the atoms intervening therebetween form a 6-membered ring optionally substituted by $C_1$-$C_6$ linear or branched chain alkyl or $C_3$-$C_6$ cycloalkyl; and, n, p, q, r and s are independently 0, 1 or 2.

Specifically, the invention provides compounds selected from the group consisting of:

2-(1-acryloylpiperidin-4-ylamino)-N-isopropyl-5H-pyrrolo [2,3-b]pyrazine-7-carboxamide;
N-isopropyl-2-(3-(N-methylacrylamido)azetidin-1-yl)-5H-pyrrolo[2,3-b]pyrazine-7-carboxamide;
2-((3R,4R)-1-acryloyl-3-hydroxypiperidin-4-ylamino)-N-isopropyl-5H-pyrrolo[2,3-b]pyrazine-7-carboxamide;
(S)-2-(1-acryloylpyrrolidin-3-ylamino)-N-isopropyl-5H-pyrrolo[2,3-b]pyrazine-7-carboxamide;
(S)-2-((1-acryloylpyrrolidin-2-yl)methylamino)-N-isopropyl-5H-pyrrolo[2,3-b]pyrazine-7-carboxamide;
2-((1R,3R)-3-acrylamidocyclobutylamino)-N-isopropyl-5H-pyrrolo[2,3-b]pyrazine-7-carboxamide; and,
(S)-2-((1-acryloylpyrrolidin-3-yl)methylamino)-N-isopropyl-5H-pyrrolo[2,3-b]pyrazine-7-carboxamide; or, a pharmaceutically acceptable salt thereof.

The invention further provides additional compounds selected from the group consisting of:
(R)-4-(1-acryloylpiperidin-3-ylamino)-1H-pyrrolo[2,3-b] pyridine-3-carbonitrile;
(R)-4-(1-acryloylpiperidin-3-ylamino)-1H-pyrrolo[2,3-b] pyridine-3-carbonitrile;
(R)-1-(3-(5-chloro-7H-pyrrolo[2,3-d]pyrimidin-4-ylamino) piperidin-1-yl)prop-2-en-1-one;
1-((2S,5R)-5-(7H-pyrrolo[2,3-d]pyrimidin-4-ylamino)-2-methylpiperidin-1-yl)prop-2-en-1-one;
1-((3R,5S)-3-(7H-pyrrolo[2,3-d]pyrimidin-4-ylamino)-5-hydroxypiperidin-1-yl)prop-2-en-1-one;
(R)-1-(3-(5-(2-methoxyethyl)-7H-pyrrolo[2,3-d]pyrimidin-4-ylamino)piperidin-1-yl)prop-2-en-1-one;
1-(5-(7H-pyrrolo[2,3-d]pyrimidin-4-ylamino)-2-(hydroxymethyl)piperidin-1-yl)prop-2-en-1-one;
1-((3R,5S)-3-(7H-pyrrolo[2,3-d]pyrimidin-4-ylamino)-5-fluoropiperidin-1-yl)prop-2-en-1-one;
1-((3R,4S)-3-(7H-pyrrolo[2,3-d]pyrimidin-4-ylamino)-4-methylpiperidin-1-yl)prop-2-en-1-one;
1-((3S,4R)-3-(7H-pyrrolo[2,3-d]pyrimidin-4-ylamino)-4-fluoropiperidin-1-yl)prop-2-en-1-one;
1-((2S,5R)-5-(7H-pyrrolo[2,3-d]pyrimidin-4-ylamino)-2-ethylpiperidin-1-yl)prop-2-en-1-one;
(R)-1-(3-(7H-pyrrolo[2,3-d]pyrimidin-4-ylamino)piperidin-1-yl)prop-2-en-1-one;
1-((3aS,7aS)-1-(7H-pyrrolo[2,3-d]pyrimidin-4-yl)tetrahydro-1H-pyrrolo[2,3-c]pyridin-6(2H,7H,7aH)-yl)prop-2-en-1-one;
(R)-1-(3-(3-chloro-1H-pyrrolo[2,3-b]pyridin-4-ylamino)piperidin-1-yl)prop-2-en-1-one;
1-((1R,2R,5R)-2-(7H-pyrrolo[2,3-d]pyrimidin-4-ylamino)-8-azabicyclo[3.2.1]octan-8-yl)prop-2-en-1-one;
1-((2R,5R)-5-(7H-pyrrolo[2,3-d]pyrimidin-4-ylamino)-2-(hydroxymethyl)piperidin-1-yl)prop-2-en-1-one;
1-((3R,5R)-3-(7H-pyrrolo[2,3-d]pyrimidin-4-ylamino)-5-fluoropiperidin-1-yl)prop-2-en-1-one;
(R)-1-(3-(5-methyl-7H-pyrrolo[2,3-d]pyrimidin-4-ylamino) piperidin-1-yl)prop-2-en-1-one;
1-((3R,5S)-3-(7H-pyrrolo[2,3-d]pyrimidin-4-ylamino)-5-methylpiperidin-1-yl)prop-2-en-1-one;
1-((2S,5R)-5-(5-(2-methoxyethyl)-7H-pyrrolo[2,3-d]pyrimidin-4-ylamino)-2-methylpiperidin-1-yl)prop-2-en-1-one;
1-((3R,5S)-3-(7H-pyrrolo[2,3-d]pyrimidin-4-ylamino)-5-methylpiperidin-1-yl)prop-2-en-1-one;
1-((3R,4S)-3-(7H-pyrrolo[2,3-d]pyrimidin-4-ylamino)-4-methylpiperidin-1-yl)prop-2-en-1-one;
(R)-1-(3-(5-ethyl-7H-pyrrolo[2,3-d]pyrimidin-4-ylamino) piperidin-1-yl)prop-2-en-1-one;
1-((2S,5R)-5-(7H-pyrrolo[2,3-d]pyrimidin-4-ylamino)-2-methylpiperidin-1-yl)prop-2-en-1-one;
(R)-1-(3-(5-fluoro-7H-pyrrolo[2,3-d]pyrimidin-4-ylamino) piperidin-1-yl)prop-2-en-1-one;
(R)-4-(1-acryloylpiperidin-3-ylamino)-7H-pyrrolo[2,3-d] pyrimidine-5-carbonitrile; and,
(3R,5R)-5-(7H-pyrrolo[2,3-d]pyrimidin-4-ylamino)-1-acryloylpiperidine-3-carbonitrile;
or, a pharmaceutically acceptable salt thereof.

In particular, the invention provides 2-(1-acryloylpiperidin-4-ylamino)-N-isopropyl-5H-pyrrolo[2,3-b]pyrazine-7-carboxamide; or, a pharmaceutically acceptable salt thereof; N-isopropyl-2-(3-(N-methylacrylamido)azetidin-1-yl)-5H-pyrrolo[2,3-b]pyrazine-7-carboxamide; or, a pharmaceutically acceptable salt thereof; 2-((3R,4R)-1-acryloyl-3-hydroxypiperidin-4-ylamino)-N-isopropyl-5H-pyrrolo[2,3-b] pyrazine-7-carboxamide; or, a pharmaceutically acceptable salt thereof; (S)-2-(1-acryloylpyrrolidin-3-ylamino)-N-isopropyl-5H-pyrrolo[2,3-b]pyrazine-7-carboxamide; or, a pharmaceutically acceptable salt thereof; (S)-2-((1-acryloylpyrrolidin-2-yl)methylamino)-N-isopropyl-5H-pyrrolo [2,3-b]pyrazine-7-carboxamide; or a pharmaceutically acceptable salt thereof; 1-((3aS,7aS)-1-(7H-pyrrolo[2,3-d] pyrimidin-4-yl)tetrahydro-1H-pyrrolo[2,3-c]pyridin-6(2H, 7H,7aH)-yl)prop-2-en-1-one; or a pharmaceutically acceptable salt thereof; 1-((1R,2R,5R)-2-((7H-pyrrolo[2,3-d] pyrimidin-4-yl)amino)-8-azabicyclo[3.2.1]octan-8-yl)prop-2-en-1-one, or a pharmaceutically acceptable salt thereof; 1-((3R,4S)-3-((7H-pyrrolo[2,3-d]pyrimidin-4-yl)amino)-4-methylpiperidin-1-yl)prop-2-en-1-one, or a pharmaceutically acceptable salt thereof; 1-((2S,5R)-5-(7H-pyrrolo[2,3-d]pyrimidin-4-ylamino)-2-methylpiperidin-1-yl)prop-2-en-1-one; or, a pharmaceutically acceptable salt thereof; (R)-4-(1-acryloylpiperidin-3-ylamino)-1H-pyrrolo[2,3-b] pyridine-3-carbonitrile; or, a pharmaceutically acceptable salt thereof.

The present invention also provides a pharmaceutical or a veterinary composition comprising a compound described above, or a pharmaceutically acceptable salt thereof, and a pharmaceutically acceptable carrier.

The present invention also provides a method for treating or preventing a disorder or condition selected from rheumatoid arthritis, myositis, vasculitis, pemphigus, bullous pemphigoid, inflammatory bowel disease including Crohn's disease and ulcerative colitis, celiac diseases, proctitis, eosinophilic gastroenteritis, or mastocytosis, Alzheimer's disease, lupus, nephritis, systemic lupus erythematosus, psoriasis, eczema dermatitis, pruritus or other pruritic conditions, vitiligo, alopecia, autoimmune thyroid disorders, multiple sclerosis, major depression disorder, allergy, asthma, Sjogren's disease, Reiter's syndrome, polymyositis-dermatomyositis, systemic sclerosis, polyarteritis nodosa, dry eye syndrome, Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, membranous glomerulopathy, organ transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, or xeno transplantation, including Cogan's syndrome, ankylosing spondylitis, Wegener's granulomatosis, autoimmune alopecia, Type I or juvenile onset diabetes, and complications from diabetes, or thyroiditis, chronic pulmonary obstructive disorder, acute respiratory disease, cachexia, cancer, including alimentary/gastrointestinal tract cancer, colon cancer, liver cancer, skin cancer including mast cell tumor and squamous cell carcinoma, breast and mammary cancer, ovarian cancer, prostate cancer, leukemia, adult T cell leukemia activated B-cell like, diffuse large B cell lymphoma, kidney cancer, lung cancer, muscle cancer, bone cancer, bladder cancer, brain cancer, melanoma including oral and metastatic melanoma, Kaposi's sarcoma septic shock, cardiopulmonary dysfunction, acute myeloid leukemia, T cell acute lymphoblastic leukemia, multiple myeloma, myeloproliferative disorders, proliferative diabetic retinopathy, or angiogenic-associated disorders including solid tumors, pancreatic cancer, brain tumors, gliomas including astrocytoma, oligodendroglioma, and glioblastoma, acute CNS trauma including traumatic brain injury, encephalitis, stroke, and spinal cord injury, epilepsy, seizures, chronic neuroinflammation associated with neurodegeneration including Alzheimer's disease, Parkinson's disease, Amyotropic Lateral Sclerosis, Huntington's disease, cerebral ischemia, fronto-temporal lobe dementia, and with neuropsychiatric disorders including schizophrenia, bipolar disorder, treatment resistant depression, Post Traumatic Stress Disorder, anxiety, and auto-antibodies mediated encephalopathies, Eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization, comprising the step of administering to a subject an effective amount of a composition comprising a compound set forth hereinabove.

In specific embodiments, the invention provides the method of treatment or prevention noted above, wherein the compound is selected from the group consisting of:
2-(1-acryloylpiperidin-4-ylamino)-N-isopropyl-5H-pyrrolo[2,3-b]pyrazine-7-carboxamide;
N-isopropyl-2-(3-(N-methylacrylamido)azetidin-1-yl)-5H-pyrrolo[2,3-b]pyrazine-7-carboxamide;
2-((3R,4R)-1-acryloyl-3-hydroxypiperidin-4-ylamino)-N-isopropyl-5H-pyrrolo[2,3-b]pyrazine-7-carboxamide;
(S)-2-(1-acryloylpyrrolidin-3-ylamino)-N-isopropyl-5H-pyrrolo[2,3-b]pyrazine-7-carboxamide;
(S)-2-((1-acryloylpyrrolidin-2-yl)methylamino)-N-isopropyl-5H-pyrrolo[2,3-b]pyrazine-7-carboxamide;
2-((1R,3R)-3-acrylamidocyclobutylamino)-N-isopropyl-5H-pyrrolo[2,3-b]pyrazine-7-carboxamide;
(S)-2-((1-acryloylpyrrolidin-3-yl)methylamino)-N-isopropyl-5H-pyrrolo[2,3-b]pyrazine-7-carboxamide;
(R)-4-(1-acryloylpiperidin-3-ylamino)-1H-pyrrolo[2,3-b]pyridine-3-carbonitrile;
(R)-4-(1-acryloylpiperidin-3-ylamino)-1H-pyrrolo[2,3-b]pyridine-3-carbonitrile;
(R)-1-(3-(5-chloro-7H-pyrrolo[2,3-d]pyrimidin-4-ylamino)piperidin-1-yl)prop-2-en-1-one;
1-((2S,5R)-5-(7H-pyrrolo[2,3-d]pyrimidin-4-ylamino)-2-methylpiperidin-1-yl)prop-2-en-1-one;
1-((3R,5S)-3-(7H-pyrrolo[2,3-d]pyrimidin-4-ylamino)-5-hydroxypiperidin-1-yl)prop-2-en-1-one;
(R)-1-(3-(5-(2-methoxyethyl)-7H-pyrrolo[2,3-d]pyrimidin-4-ylamino)piperidin-1-yl)prop-2-en-1-one;
1-(5-(7H-pyrrolo[2,3-d]pyrimidin-4-ylamino)-2-(hydroxymethyl)piperidin-1-yl)prop-2-en-1-one;
1-((3R,5S)-3-(7H-pyrrolo[2,3-d]pyrimidin-4-ylamino)-5-fluoropiperidin-1-yl)prop-2-en-1-one;
1-((3R,4S)-3-(7H-pyrrolo[2,3-d]pyrimidin-4-ylamino)-4-methylpiperidin-1-yl)prop-2-en-1-one;
1-((3S,4R)-3-(7H-pyrrolo[2,3-d]pyrimidin-4-ylamino)-4-fluoropiperidin-1-yl)prop-2-en-1-one;
1-((2S,5R)-5-(7H-pyrrolo[2,3-d]pyrimidin-4-ylamino)-2-ethylpiperidin-1-yl)prop-2-en-1-one;
(R)-1-(3-(7H-pyrrolo[2,3-d]pyrimidin-4-ylamino)piperidin-1-yl)prop-2-en-1-one;
1-((3aS,7aS)-1-(7H-pyrrolo[2,3-d]pyrimidin-4-yl)tetrahydro-1H-pyrrolo[2,3-c]pyridin-6(2H,7H,7aH)-yl)prop-2-en-1-one;
(R)-1-(3-(3-chloro-1H-pyrrolo[2,3-b]pyridin-4-ylamino)piperidin-1-yl)prop-2-en-1-one;
1-((1R,2R,5R)-2-(7H-pyrrolo[2,3-d]pyrimidin-4-ylamino)-8-azabicyclo[3.2.1]octan-8-yl)prop-2-en-1-one;
1-((2R,5R)-5-(7H-pyrrolo[2,3-d]pyrimidin-4-ylamino)-2-(hydroxymethyl)piperidin-1-yl)prop-2-en-1-one;
1-((3R,5R)-3-(7H-pyrrolo[2,3-d]pyrimidin-4-ylamino)-5-fluoropiperidin-1-yl)prop-2-en-1-one;
(R)-1-(3-(5-methyl-7H-pyrrolo[2,3-d]pyrimidin-4-ylamino)piperidin-1-yl)prop-2-en-1-one;
1-((3R,5S)-3-(7H-pyrrolo[2,3-d]pyrimidin-4-ylamino)-5-methylpiperidin-1-yl)prop-2-en-1-one;
1-((2S,5R)-5-(5-(2-methoxyethyl)-7H-pyrrolo[2,3-d]pyrimidin-4-ylamino)-2-methylpiperidin-1-yl)prop-2-en-1-one;
1-((3R,5S)-3-(7H-pyrrolo[2,3-d]pyrimidin-4-ylamino)-5-methylpiperidin-1-yl)prop-2-en-1-one;
1-((3R,4S)-3-(7H-pyrrolo[2,3-d]pyrimidin-4-ylamino)-4-methylpiperidin-1-yl)prop-2-en-1-one;
(R)-1-(3-(5-ethyl-7H-pyrrolo[2,3-d]pyrimidin-4-ylamino)piperidin-1-yl)prop-2-en-1-one;
1-((2S,5R)-5-(7H-pyrrolo[2,3-d]pyrimidin-4-ylamino)-2-methylpiperidin-1-yl)prop-2-en-1-one;
(R)-1-(3-(5-fluoro-7H-pyrrolo[2,3-d]pyrimidin-4-ylamino)piperidin-1-yl)prop-2-en-1-one;
(R)-4-(1-acryloylpiperidin-3-ylamino)-7H-pyrrolo[2,3-d]pyrimidine-5-carbonitrile; and,
(3R,5R)-5-(7H-pyrrolo[2,3-d]pyrimidin-4-ylamino)-1-acryloylpiperidine-3-carbonitrile; or, a pharmaceutically acceptable salt thereof.

The present invention also provides a method for treating or preventing inflammatory bowel disease by administering to a mammal in need a therapeutically effective amount of a compound described above, or a pharmaceutically acceptable salt thereof.

In specific embodiments, the invention provides the method for treating or preventing inflammatory bowel disease, wherein the compound is selected from the group consisting of:
2-(1-acryloylpiperidin-4-ylamino)-N-isopropyl-5H-pyrrolo[2,3-b]pyrazine-7-carboxamide;
N-isopropyl-2-(3-(N-methylacrylamido)azetidin-1-yl)-5H-pyrrolo[2,3-b]pyrazine-7-carboxamide;
2-((3R,4R)-1-acryloyl-3-hydroxypiperidin-4-ylamino)-N-isopropyl-5H-pyrrolo[2,3-b]pyrazine-7-carboxamide;
(S)-2-(1-acryloylpyrrolidin-3-ylamino)-N-isopropyl-5H-pyrrolo[2,3-b]pyrazine-7-carboxamide;
(S)-2-((1-acryloylpyrrolidin-2-yl)methylamino)-N-isopropyl-5H-pyrrolo[2,3-b]pyrazine-7-carboxamide;
2-((1R,3R)-3-acrylamidocyclobutylamino)-N-isopropyl-5H-pyrrolo[2,3-b]pyrazine-7-carboxamide;
(S)-2-((1-acryloylpyrrolidin-3-yl)methylamino)-N-isopropyl-5H-pyrrolo[2,3-b]pyrazine-7-carboxamide;
(R)-4-(1-acryloylpiperidin-3-ylamino)-1H-pyrrolo[2,3-b]pyridine-3-carbonitrile;

(R)-4-(1-acryloylpiperidin-3-ylamino)-1H-pyrrolo[2,3-b]pyridine-3-carbonitrile;
(R)-1-(3-(5-chloro-7H-pyrrolo[2,3-d]pyrimidin-4-ylamino)piperidin-1-yl)prop-2-en-1-one;
1-((2S,5R)-5-(7H-pyrrolo[2,3-d]pyrimidin-4-ylamino)-2-methylpiperidin-1-yl)prop-2-en-1-one;
1-((3R,5S)-3-(7H-pyrrolo[2,3-d]pyrimidin-4-ylamino)-5-hydroxypiperidin-1-yl)prop-2-en-1-one;
(R)-1-(3-(5-(2-methoxyethyl)-7H-pyrrolo[2,3-d]pyrimidin-4-ylamino)piperidin-1-yl)prop-2-en-1-one;
1-(5-(7H-pyrrolo[2,3-d]pyrimidin-4-ylamino)-2-(hydroxymethyl)piperidin-1-yl)prop-2-en-1-one;
1-((3R,5S)-3-(7H-pyrrolo[2,3-d]pyrimidin-4-ylamino)-5-fluoropiperidin-1-yl)prop-2-en-1-one;
1-((3R,4S)-3-(7H-pyrrolo[2,3-d]pyrimidin-4-ylamino)-4-methylpiperidin-1-yl)prop-2-en-1-one;
1-((3S,4R)-3-(7H-pyrrolo[2,3-d]pyrimidin-4-ylamino)-4-fluoropiperidin-1-yl)prop-2-en-1-one;
1-((2S,5R)-5-(7H-pyrrolo[2,3-d]pyrimidin-4-ylamino)-2-ethylpiperidin-1-yl)prop-2-en-1-one;
(R)-1-(3-(7H-pyrrolo[2,3-d]pyrimidin-4-ylamino)piperidin-1-yl)prop-2-en-1-one;
1-((3aS,7aS)-1-(7H-pyrrolo[2,3-d]pyrimidin-4-yl)tetrahydro-1H-pyrrolo[2,3-c]pyridin-6(2H,7H,7aH)-yl)prop-2-en-1-one;
(R)-1-(3-(3-chloro-1H-pyrrolo[2,3-b]pyridin-4-ylamino)piperidin-1-yl)prop-2-en-1-one;
1-((1R,2R,5R)-2-(7H-pyrrolo[2,3-d]pyrimidin-4-ylamino)-8-azabicyclo[3.2.1]octan-8-yl)prop-2-en-1-one;
1-((2R,5R)-5-(7H-pyrrolo[2,3-d]pyrimidin-4-ylamino)-2-(hydroxymethyl)piperidin-1-yl)prop-2-en-1-one;
1-((3R,5R)-3-(7H-pyrrolo[2,3-d]pyrimidin-4-ylamino)-5-fluoropiperidin-1-yl)prop-2-en-1-one;
(R)-1-(3-(5-methyl-7H-pyrrolo[2,3-d]pyrimidin-4-ylamino)piperidin-1-yl)prop-2-en-1-one;
1-((3R,5S)-3-(7H-pyrrolo[2,3-d]pyrimidin-4-ylamino)-5-methylpiperidin-1-yl)prop-2-en-1-one;
1-((2S,5R)-5-(5-(2-methoxyethyl)-7H-pyrrolo[2,3-d]pyrimidin-4-ylamino)-2-methylpiperidin-1-yl)prop-2-en-1-one;
1-((3R,5S)-3-(7H-pyrrolo[2,3-d]pyrimidin-4-ylamino)-5-methylpiperidin-1-yl)prop-2-en-1-one;
1-((3R,4S)-3-(7H-pyrrolo[2,3-d]pyrimidin-4-ylamino)-4-methylpiperidin-1-yl)prop-2-en-1-one;
(R)-1-(3-(5-ethyl-7H-pyrrolo[2,3-d]pyrimidin-4-ylamino)piperidin-1-yl)prop-2-en-1-one;
1-((2S,5R)-5-(7H-pyrrolo[2,3-d]pyrimidin-4-ylamino)-2-methylpiperidin-1-yl)prop-2-en-1-one;
(R)-1-(3-(5-fluoro-7H-pyrrolo[2,3-d]pyrimidin-4-ylamino)piperidin-1-yl)prop-2-en-1-one;
(R)-4-(1-acryloylpiperidin-3-ylamino)-7H-pyrrolo[2,3-d]pyrimidine-5-carbonitrile; and,
(3R,5R)-5-(7H-pyrrolo[2,3-d]pyrimidin-4-ylamino)-1-acryloylpiperidine-3-carbonitrile; or, a pharmaceutically acceptable salt thereof.

More generally, the present invention provides a method of treating a disorder or condition related to dysregulation of JAK, and particularly of JAK3, in a subject, comprising administering to the subject a therapeutically effective amount of the compound described above, or a pharmaceutically acceptable salt thereof.

In certain embodiments, the therapeutically effective amount used in accord with the method is from 0.01 mg/kg of body weight/day to 100 mg/kg of body weight/day. In certain other embodiments, the therapeutically effective amount used in accord with the method is the therapeutically effective amount is from 0.1 mg/kg of body weight/day to 10 mg/kg of body weight/day. In the practice of the method, the compound is preferably selected from those specified above.

In certain embodiments, the therapeutically effective amount used in accord with the method is from 0.01 mg/kg of body weight/day to 100 mg/kg of body weight/day. In certain other embodiments, the therapeutically effective amount used in accord with the method is wherein the therapeutically effective amount is from 0.1 mg/kg of body weight/day to 10 mg/kg of body weight/day. In accord with the method, the mammal treated with the compound of the invention is selected from companion animals, dogs, and livestock. In certain embodiments, the compound of the invention, or a pharmaceutically acceptable salt thereof, may be administered in accord with the method orally, parenterally, or topically.

Compounds that have the same molecular formula but differ in the nature or sequence of bonding of their atoms or the arrangement of their atoms in space are termed "isomers". Isomers that differ in the arrangement of their atoms in space are termed "stereoisomers". It will be appreciated by those skilled in the art that the compound of the invention can exist as cis- and trans-achiral diastereomers.

Included within the scope of the described compounds are all isomers (e.g. cis-, trans-, or diastereomers) of the compounds described herein alone as well as any mixtures. All of these forms, including enantiomers, diastereomers, cis, trans, syn, anti, solvates (including hydrates), tautomers, and mixtures thereof, are included in the described compounds. Stereoisomeric mixtures, e.g. mixtures of diastereomers, can be separated into their corresponding isomers in a known manner by means of suitable separation methods. Diastereomeric mixtures for example may be separated into their individual diastereomers by means of fractionated crystallization, chromatography, solvent distribution, and similar procedures. This separation may take place either at the level of one of the starting compounds or in a compound of the invention itself. Enantiomers may be separated through the formation of diastereomeric salts, for example by salt formation with an enantiomer-pure chiral acid, or by means of chromatography, for example by HPLC, using chromatographic substrates with chiral ligands.

In therapeutic use for treating disorders in a mammal, a compound of the present invention or its pharmaceutical compositions can be administered orally, parenterally, topically, rectally, transmucosally, or intestinally. Parenteral administrations include indirect injections to generate a systemic effect or direct injections to the afflicted area. Topical administrations include the treatment of skin or organs readily accessible by local application, for example, eyes or ears. It also includes transdermal delivery to generate a systemic effect. The rectal administration includes the form of suppositories. The preferred routes of administration are oral and parenteral.

Pharmaceutically acceptable salts of the compounds of the invention include the acid addition and base salts thereof. Suitable acid addition salts are formed from acids which form non-toxic salts. Examples include the acetate, adipate, aspartate, benzoate, besylate, bicarbonate/carbonate, bisulfate/sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts. For a review on suitable salts, see *Handbook of Pharmaceutical Salts: Properties, Selection, and Use* by Stahl and Wermuth (Wiley-VCH, 2002).

Pharmaceutically acceptable salts of compounds of the invention, may be prepared, respectively, by one or more of three methods: (i) by reacting the compound with the desired acid or base; (ii) by removing an acid- or base-labile protecting group from a suitable precursor of the compound of the invention, or by ring-opening a suitable cyclic precursor, for example, a lactone or lactam, using the desired acid or base; or (iii) by converting one salt of the compound of the invention, to another by reaction with an appropriate acid or base or by means of a suitable ion exchange column. All three reactions are typically carried out in solution. The resulting salt may precipitate out and be collected by filtration or may be recovered by evaporation of the solvent. The degree of ionization in the resulting salt may vary from completely ionized to almost non-ionized.

Pharmaceutical compositions of the present invention may be manufactured by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more pharmaceutically acceptable carriers comprising excipients and auxiliaries, which facilitate processing of the active compound into preparations, which can be used pharmaceutically. Proper formulation is dependent upon the route of administration chosen. Pharmaceutically acceptable excipients and carriers are generally known to those skilled in the art and are thus included in the instant invention. Such excipients and carriers are described, for example, in "Remington's Pharmaceutical Sciences" Mack Pub. Co., New Jersey (1991). The formulations of the invention can be designed to be short-acting, fast-releasing, long-acting, and sustained-releasing. Thus, the pharmaceutical formulations can also be formulated for controlled release or for slow release.

Pharmaceutical compositions suitable for use in the present invention include compositions wherein the active ingredients are contained in an amount sufficient to achieve the intended purpose, i.e., control or the treatment of disorders or diseases. More specifically, a therapeutically effective amount means an amount of compound effective to prevent, alleviate or ameliorate symptoms/signs of disease or prolong the survival of the subject being treated.

The quantity of active component, which is the compound of this invention, in the pharmaceutical composition and unit dosage form thereof, may be varied or adjusted widely depending upon the manner of administration, the potency of the particular compound and the desired concentration. Determination of a therapeutically effective amount is well within the capability of those skilled in the art. Generally, the quantity of active component will range between 0.01% to 99% by weight of the composition.

Generally, a therapeutically effective amount of dosage of active component will be in the range of about 0.01 to about 100 mg/kg of body weight/day, preferably about 0.1 to about 10 mg/kg of body weight/day, more preferably about 0.3 to 3 mg/kg of body weight/day, even more preferably about 0.3 to 1.5 mg/kg of body weight/day It is to be understood that the dosages may vary depending upon the requirements of each subject and the severity of the disorders or diseases being treated.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation. If desired, the daily dose may also be divided into multiple doses for administration, e.g., two to four times per day.

There are substantial needs for safe and efficacious agents to control disorders related to JAK, such as atopic dermatitis, both in human and animals. The market for treating atopic dermatitis in animals is currently dominated by corticosteroids, which cause distressing and undesirable side effects in animals, specifically in companion animals such as dogs. APOQUEL™ is a pan-JAK inhibitor recently approved for atopic dermatitis in canines. Antihistamines are also used, but are poorly effective. A canine formulation of cyclosporine (ATOPICA™) is currently being marketed for atopic dermatitis, but is expensive and has a slow onset of efficacy. In addition, there are GI toleration issues with ATOPICA™. Compounds of the present invention are JAK inhibitors with selective efficacy against JAK3. These compounds are expected to provide an alternative to steroid usage and provide resolution of chronic pruritus and inflammation that would either persist in atopic dermatitis or slowly regress following removal of allergen or causative agent, such as fleas in flea-allergic dermatitis.

Compounds of the present invention may be administered in a pharmaceutically acceptable form either alone or in combination with one or more additional agents which modulate a mammalian immune system or with anti-inflammatory agents. These agents may include but are not limited to cyclosporin A (e.g., Sandimmune™ or Neoral™, rapamycin, FK-506 (tacrolimus), leflunomide, deoxyspergualin, mycophenolate (e.g., Cellcept™, azathioprine (e.g., Imuran™), daclizumab (e.g., Zenapax™), OKT3 (e.g., Orthoclolone™), AtGam™, aspirin, acetaminophen, ibuprofen, naproxen, piroxicam, and anti-inflammatory steroids (e.g., prednisolone or dexamethasone), IFN-beta, teriflunomide, Laquinimod, glatiramer acetate, dimethyl fumerate, rituximab, fingolimod, natalizumab, alemtuzumab, mitoxantrone. Sulfasalazine (Azulfidine), Mesalamine (Apriso, Asacol, Lialda, others), balsalazide (Colazal) and olsalazine (Dipentum), and mercaptopurine (Purinethol), antibiotics (antimycobacterial drugs, e.g., Metronidazole, ciprofloxacin), Ustekinumab and vedolizumab These agents may be administered as part of the same or separate dosage forms, via the same or different routes of administration, and on the same or different administration schedules according to standard pharmaceutical practice known to one skilled in the art.

Accordingly, the invention provides methods of treating or preventing a disease, condition or disorder associated with JAK in a subject, such as a human or non-human mammal, comprising administering an effective amount of one or more compounds described herein to the subject. Suitable subjects that can be treated include domestic or wild animals, companion animals, such as dogs, cats, horses and the like; livestock including, cows and other ruminants, pigs, poultry, rabbits and the like; primates, for example monkeys, such as rhesus monkeys and cynomolgus (also known as crab-eating or long-tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier.

Another embodiment provides a method of selectively inhibiting a JAK3 enzyme, which includes contacting the JAK enzyme with either a non-therapeutic amount or a therapeutically effective amount of one or more of the presently taught compounds. Such methods can occur in vivo or in vitro. In vitro contact can involve a screening assay to determine the efficacy of the one or more compounds against a selected enzyme at various amounts or concentrations. In vivo contact with a therapeutically effective amount of the one or more compounds can involve treatment of a described disease, disorder or condition or prophylaxis of organ transplant rejection in the animal in which the contact occurs. The effect of the one or more compounds on the JAK enzyme and/or host animal can also be determined or measured. Methods for determining JAK activity include those described in the Examples as well as those disclosed in WO99/65908, WO 99/65909, WO01/42246, WO02/00661, WO02/096909, WO2004/046112 and WO2007/012953.

Chemical Synthesis

The following schemes and written descriptions provide general details regarding the preparation of the compounds of the invention. It will be apparent to those skilled in the art that sensitive functional groups (PG) may need to be protected and deprotected during the synthesis of a compound of the invention. Protection and deprotection may be achieved by conventional methods, as described, for example, in *Protective Groups in Organic Synthesis* by T. W. Greene and P. G. M. Wuts, John Wiley & Sons Inc. (1999), and references therein.

Several methods exist for the preparation of such compounds, which are well known to those skilled in the art and have been described in texts such as *Advanced Organic Chemistry* by J. March, John Wiley & Sons (1985). It is noted that certain compounds of the invention can be obtained by functional group transformations at a late stage of the synthesis. Such functional group transformations may include one step or multiple steps, for example, reduction of an ester to an alcohol, reoxidation to an aldehyde, addition of an organomagesium reagent to form a secondary alcohol, reoxidation to a ketone and, finally, addition of an organomagesium reagent to yield a tertiary alcohol. The intermediates and compounds were named using ChemDraw11 (CambridgeSoft™) structure to name converter or ACD Labs Name Software v12. The inclusion of rac-(or racemic) modifier indicates material is racemic. When rac-(or racemic) is included with R,S indications this is intended to convey relative stereochemistry, however in the absence of the rac-(or racemic) notation the compounds absolute stereochemistry is known. In some instances the rac-(or racemic) notation conveys the stereochemistry of a fragment of the compound, while the R,S designation conveys absolute stereochemistry of another portion. For cases where racemates are separated into their constituent enantiomers the absolute stereochemistry is arbitrarily assigned, unless otherwise noted.

In executing the synthesis of the compounds of the invention, one skilled in the art will recognize the need to sample and assay reaction mixtures prior to work up in order to monitor the progress of reactions and decide whether the reaction should be continued or whether it is ready to be worked up to obtain the desired product. Common methods for assaying reaction mixtures include thin-layer chromatography (TLC), liquid chromatography/mass spectroscopy (LCMS), and nuclear magnetic resonance (NMR).

One skilled in the art will also recognize that the compounds of the invention may be prepared as mixtures of diastereomers or geometric isomers (e.g., cis and trans substitution on a cycloalkane ring). These isomers can be separated by standard chromatographic techniques, such as normal phase chromatography on silica gel, reverse phase preparative high pressure liquid chromatography or supercritical fluid chromatography. One skilled in the art will also recognize that some compounds of the invention are chiral and thus may be prepared as racemic or scalemic mixtures of enantiomers. Several methods are available and are well known to those skilled in the art for the separation of enantiomers. A preferred method for the routine separation enantiomers is supercritical fluid chromatography employing a chiral stationary phase.

EXPERIMENTAL SECTION

Except where otherwise noted, reactions were run under an atmosphere of nitrogen. Chromatography on silica gel was carried out using 250-400 mesh silica gel using pressurized nitrogen (~10-15 psi) to drive solvent through the column ("flash chromatography"). Where indicated, solutions and reaction mixtures were concentrated by rotary evaporation under vacuum.

Example 1: (R)-1-(3-((3-chloro-1H-pyrrolo[2,3-b]pyridin-4-yl)amino)piperidin-1-yl)prop-2-en-1-one Example 2: (R)-4-((1-acryloylpiperidin-3-yl)amino)-1H-pyrrolo[2,3-b]pyridine-3-carbonitrile Example 3: (R)-1-(3-((5-chloro-7H-pyrrolo[2,3-d]pyrimidin-4-yl)amino)piperidin-1-yl)prop-2-en-1-one

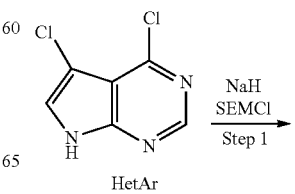

HetAr

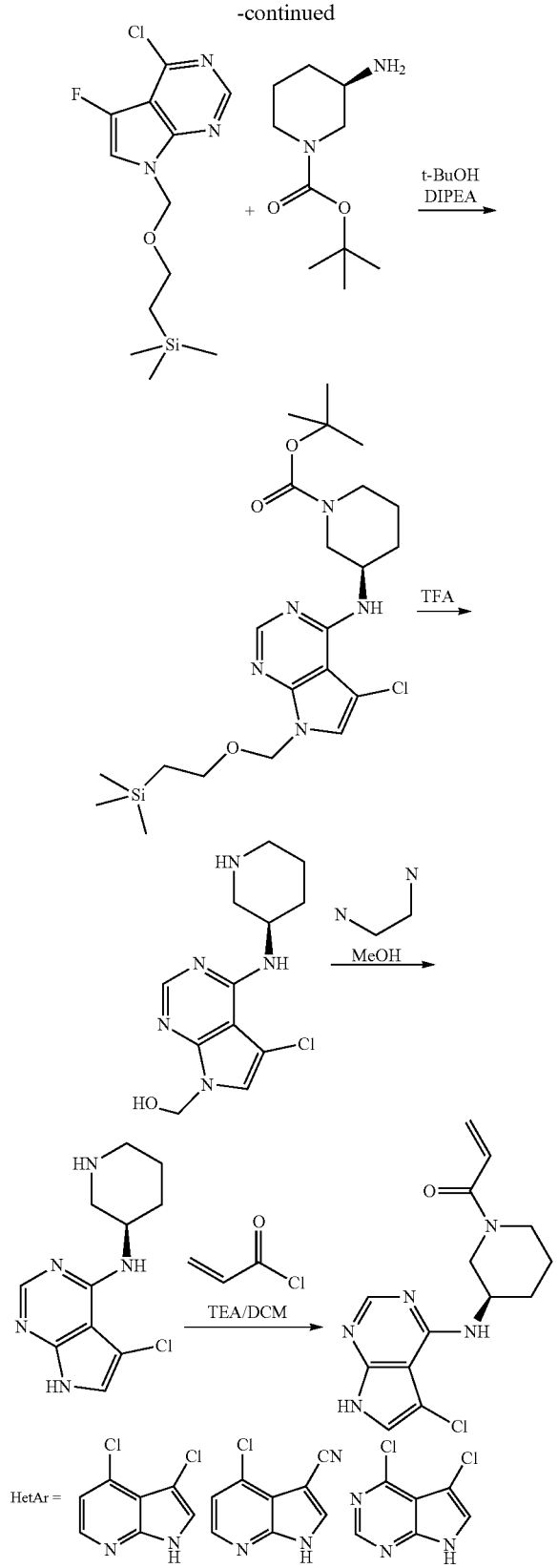

Step 1. Halide monomers (300 μmol) were dissolved anhydrous DMF (10 ml/mmol, 3 ml) under argon atmosphere. NaH (60% suspension in mineral oil, 2 equiv, 600 μmol, ~30 mg) was added at 0° C. to each reaction vial. Each reaction vial was stirred at 0° C. for 30 min. SEM chloride (2 equiv, 600 μmol, 106 μL) was added dropwise to the reaction mixture and stirring was continued at 25° C. for 16 hrs. Completion of reaction was monitored by LCMS/TLC and solvents were stripped off using thermo explorer (1 hr, 5 torr, and 45° C.). The residue was purified by column chromatography using 5-10% ethyl acetate-hexane as eluent. For each monomer yield was around 75-80%.

Step 2. The amine template (0.2 M solution) in anhydrous toluene was prepared (solution A). 0.3 M solution of SEM protected halide monomers in anhydrous toluene was prepared (solution B). One ml of solution A (1 equiv, 200 μmol) was added followed by 1 ml of solution B (1.5 equiv, 300 μmol) to each reaction vial under argon purging condition. Anhydrous t-BuONa (3 equiv, 600 μmol, ~60 mg) was added to each reaction vial. $Pd_2(dba)_3$ (0.03 equiv, 6 μmol, ~6 mg) was dispensed under argon flow followed by BINAP (0.06 equiv, 12 μmol, ~7.5 mg). Each reaction vial was stirred at 90° C. for 16 hrs. The reaction was checked by LCMS. The reaction mixture was filtered and the solvent was evaporated in thermo explorer (1 hr, 5 torr, and 45° C.)

Step 2. (Set 2 monomers) The amine template (0.2 M solution) in t-BuOH was prepared (solution A). 0.3 M solution of SEM protected halide monomers in t-BuOH was prepared (solution B). One ml of solution A (1 equiv, 200 μmol) was added followed by 1 ml of solution B (1.5 equiv, 300 μmol) to each reaction vial. 103 μL (3 equiv, 600 μmol) of DIPEA was dispensed to each vial. Reaction vials were stirred for 16 h at 80° C. The reaction was checked by LC-MS. Solvent was evaporated in thermo explorer (1 hr, 5 torr, and 45° C.)

Step 3 and 4 (Boc Deprotection and Sem Deprotection)

Each step 2 residue was treated with 2 ml of TFA at 25° C. for 4 hrs. LCMS monitoring was done to check complete conversion to intermediate hydroxyl methyl derivative. After completion of reaction, solvents were evaporated using thermo explorer (1 hr, 5 torr, and 45° C.) and azeotroped with toluene to remove traces of TFA (1 hr, 5 torr, and 45° C.). Each residue was dissolved in 2 ml of MeOH and ~70 μL of ethylenediamine was added to each reaction vial and again stirred for 16 hrs at 25° C. Reactions were checked by LC-MS. After completion of reaction, the solvent was evaporated and residue was dissolved in 5 ml ethyl acetate. The organic layer was washed with water (2 ml) and brine (2 ml). The organic extract was dried over anhydrous sodium sulfate and concentrated under reduced pressure.

Step 5 (Rxn with Acryloyl Chloride)

All the calculations were done in 100 μmol scale at the final step. Each step 4 residue was dissolved in anhydrous THF (1 ml) under argon atmosphere. 200 μmol (2 equiv, 28 μL) of TEA was added to each reaction mixture. Reaction mixtures were cooled to 0° C. and a solution of 0.5 equiv of acryloyl chloride in THF (4 μL in 500 μL THF) was added slowly maintaining ice cold condition during the addition. After stirring for 10 min at 0° C., the solvent was evaporated and the residue was dissolved in 1 ml DMSO. 10 μL of the DMSO solution was diluted to 200 μL with DMSO for QC analysis and remaining amount was submitted for prep-HPLC purification. Purification on Xterra® RP18 (19×250 mm, 10μ, $H_2O$ (10 mM $NH_4OAc$): $CH_3CN$).

| Example | LC/MS |
| --- | --- |
| 1 | 305.7 |
| 2 | 296.3 |
| 3 | 306.7 |

Example 4: 1-((3S,4S)-3-((7H-pyrrolo[2,3-d]pyrimidin-4-yl)amino)-4-fluoropiperidin-1-yl)prop-2-en-1-one Step 1. (3S,4S)-Benzyl 4-fluoro-3-((7-trityl-7H-pyrrolo[2,3-d]pyrimidin-4-yl)amino)piperidine-1-carboxylate To a solution of 4-chloro-7-trityl-7H-pyrrolo[2,3-d]pyrimidine (140 mg, 0.354 mmol) and cesium fluoride (430 mg, 2.83 mmol) in DMSO (2.0 mL) was added (3S,4S)-benzyl 3-amino-4-fluoropiperidine-1-carboxylate (prepared as described in WO2010016005) (100 mg, 0.346 mmol). The reaction mixture was heated to 120° C. for 9 hours. LCMS showed that 4-chloro-7-trityl-7H-pyrrolo[2,3-d]pyrimidine was consumed completely. The reaction mixture was diluted with a 1:1 mixture of DCM/water (200 mL). The organic layer was extracted and the aqueous layer was back extracted with DCM (2×50 mL). The organic extracts were combined, washed with brine (2×100 mL), dried over sodium sulfate, filtered, and concentrated in vacuo to yield crude product which was dry loaded with Celite® onto a Silicycle 25 g HP column and purified via normal phase column chromatography (0-75% EtOAc/heptanes over 15 column volumes) to afford (3S,4S)-benzyl 4-fluoro-3-((7-trityl-7H-pyrrolo[2,3-d]pyrimidin-4-yl)amino)piperidine-1-carboxylate (149.6 mg, 69%) as a colorless solid. $^1$H NMR (400 MHz, DMSO-$d_6$) 7.74 (s, 1H), 7.58 (d, J=8.0 Hz, 1H), 7.39-7.18 (m, 15H), 7.09-7.05 (m, 5H), 6.84 (d, J=3.8 Hz, 1H), 6.68 (d, J=3.8 Hz, 1H), 5.05 (s, 2H), 4.84-4.64 (m, 2H), 4.35-4.24 (m, 1H), 4.15-4.05 (m, 1H), 3.95-3.85 (m, 1H), 2.25-2.13 (m, 1H), 1.70-1.58 (m, 1H).

Step 2. N-((3S,4S)-4-Fluoropiperidin-3-yl)-7-trityl-7H-pyrrolo[2,3-d]pyrimidin-4-amine To a dry hydrogenation bottle, 10% Pd/C (65 mg) was added under nitrogen atmosphere. Then a solution of (3S,4S)-benzyl 4-fluoro-3-((7-trityl-7H-pyrrolo[2,3-d]pyrimidin-4-yl)amino)piperidine-1-carboxylate (150 mg, 0.245 mmol) in anhydrous ethanol (5.0 mL) was added and the resulting mixture was hydrogenated under 50 psi of $H_2$ at ambient temperature for 3 hours. LCMS showed the starting material was consumed completely. The reaction mixture was filtered through a thin pad of Celite® and the filter cake was washed with ethanol. The combined filtrate was evaporated, azeotroped with toluene (5×) at 75° C. to afford compound N-((3S,4S)-4-fluoropiperidin-3-yl)-7-trityl-7H-pyrrolo[2,3-d]pyrimidin-4-amine (104 mg, 89%) as a colorless solid, which was used directly in the next step without further purification.

Step 3. 1-((3S,4S)-4-Fluoro-3-((7-trityl-7H-pyrrolo[2,3-d]pyrimidin-4-yl)amino)piperidin-1-yl)prop-2-en-1-one To a solution of N-((3S,4S)-4-fluoropiperidin-3-yl)-7-trityl-7H-pyrrolo[2,3-d]pyrimidin-4-amine (102 mg, 0.214 mmol) in anhydrous d-CHCl$_3$ (5.0 mL) is added Hunig's base (0.2 mL, 1.0 mmol). The reaction mixture was cooled to 2° C. then treated, dropwise, with a solution of acrylic chloride (0.017 mL, 0.214 mmol) in anhydrous d-CHCl$_3$ (1.0 mL). The reaction mixture was allowed to warm to ambient temperature and after 30 minutes, LCMS showed compound N-((3S,4S)-4-fluoropiperidin-3-yl)-7-trityl-7H-pyrrolo[2,3-d]pyrimidin-4-amine was consumed completely. The reaction mixture was cooled to 2° C. and quenched with 10% aqueous sodium bicarbonate (5 mL). The organic layer was extracted and the aqueous layer was back extracted with chloroform (2×2 mL). The organic extracts were combined, dried over magnesium sulfate, filtered, and concentrated in vacuo to yield crude product which was dry loaded with Celite® onto a Silicycle 12 g HP column and purified via normal phase column chromatography (50-80% EtOAc/heptanes over 10 column volumes) to afford 1-((3S,4S)-4-fluoro-3-((7-trityl-7H-pyrrolo[2,3-d]pyrimidin-4-yl)amino)piperidin-1-yl)prop-2-en-1-one (79.0 mg, 69%) as a colorless solid. LCMS (M+H) 532.64.

Step 4. Preparation of 1-((3S,4S)-3-((7H-pyrrolo[2,3-d]pyrimidin-4-yl)amino)-4-fluoropiperidin-1-yl)prop-2-en-1-one A solution of 1-((3S,4S)-4-fluoro-3-((7-trityl-7H-pyrrolo[2,3-d]pyrimidin-4-yl)amino)piperidin-1-yl)prop-2-en-1-one (79.0 mg, 0.150 mmol) in trifluoroacetic acid (1.15 mL) was allowed to stir at ambient temperature for 16 hours. The reaction mixture was concentrated in vacuo and dry loaded with Celite® onto a Silicycle® 12 g HP column and purified via normal phase column chromatography (0-20% MeOH/DCM over 10 column volumes) to afford 1-((3S,4S)-3-((7H-pyrrolo[2,3-d]pyrimidin-4-yl)amino)-4-fluoropiperidin-1-yl)prop-2-en-1-one (37.6 mg, 87%) as a colorless solid. LCMS (M+H) 290.48. HPLC 1.330 min. $^1$H NMR (400 MHz, MeOH-$d_4$) δ 8.20 (s, 1H), 7.23-7.10 (m, 1H), 6.90-6.62 (m, 2H), 6.21 (t, J=20 Hz, 1H), 5.82-5.66 (m, 1H), 4.93-4.71 (m, 1H), 4.62-4.03 (m, 3H), 3.44-3.04 (m, 2H), 2.36-2.24 (m, 1H), 1.89-1.74 (m, 1H).

Example 5: 1-((2S,5R)-5-((7H-pyrrolo[2,3-d]pyrimidin-4-yl)amino)-2-methylpiperidin-1-yl)prop-2-en-1-one Step 1. tert-Butyl(6-methylpyridin-3-yl)carbamate To a solution of 6-methylpyridin-3-amine (25 g, 231. mmol)) in EtOH (100 mL) at 0° C. was added (Boc)$_2$O (55.5 g, 298 mmol) dropwise slowly. After the addition, the solution was stirred at room temperature overnight. TLC (petroleum ether/EtOAc, 2:1) showed 6-methylpyridin-3-amine was consumed completely. The reaction mixture was filtered and the filter cake was washed with EtOH (30 mL×3). The combined filtrate was concentrated in vacuo to afford a yellow residual, which was purified by chromatography (petroleum ether/EtOAc, 4:1 to 1:1) to give tert-butyl (6-methylpyridin-3-yl)carbamate (32.5 g, 67.4%) as a white solid. $^1$H NMR (400 MHz, CDCl$_3$) 8.30 (d, J=2.0 Hz, 1H), 7.86 (br s, 1H), 7.10 (d, J=8.5 Hz, 1H), 6.57 (br s, 1H), 2.49 (s, 3H), 1.51 (s, 9H)

Step 2. rac-cis/trans-tert-Butyl(6-methylpiperidin-3-yl)carbamate

To a dry hydrogenation bottle, PtO$_2$ (2.5 g) was added under Ar atmosphere. Then a solution of tert-butyl(6-methylpyridin-3-yl)carbamate (33 g, 158.5 mmol) in HOAc (300 mL) was added and the resulting mixture was hydrogenated under 55 psi of $H_2$ at 50° C. for 30 hours. TLC (petroleum ether/EtOAc, 2:1) showed the starting material was consumed completely. The reaction mixture was filtered and the filter cake was washed with MeOH (50 mL×2). The combined filtrate was evaporated to give tert-butyl(6-methylpiperidin-3-yl)carbamate (34 g, 100%) as a yellow oil (~2:1 cis/trans), which was used directly to next step without further purification. LC/MS (M+H) 215.2.

Step 3. rac-cis/trans-Benzyl 5-((tert-butoxycarbonyl)amino)-2-methylpiperidine-1-carboxylate To a stirred solution of tert-butyl(6-methylpiperidin-3-yl) carbamate (27.0 g, 126 mmol) and $NaHCO_3$ (74.2 g, 883 mmol) in THF (350 mL)/$H_2O$ (350 mL) was added CbzCl (32.17 g, 189 mmol) dropwise at room temperature. After the addition, the resulting mixture was stirred at room temperature for 2 hours. TLC ($CH_2Cl_2$/MeOH, 10:1) showed the starting material was consumed completely. The reaction mixture was extracted with EtOAc (300 mL×2). The combined organic layer was washed with brine, dried over $Na_2SO_4$, filtered and concentrated to give crude product. The crude product was further purified by chromatography (PE/EA, 30:1-10:1) to give rac-cis/trans benzyl 5-((tert-butoxycarbonyl)amino)-2-methylpiperidine-1-carboxylate (44.0 g, 100%) as a colorless oil. ($^1$H NMR showed ~1 mol of BnOH) $^1$H NMR (400 MHz, $CDCl_3$) δ 7.35-7.19 (m, 9H), 5.14-4.99 (m, 2H), 4.82 (d, J=6.0 Hz, 1H), 4.67-4.59 (m, 2H), 4.48-4.28 (m, 2H), 4.17 (d, J=9.8 Hz, 1H), 3.97 (d, J=13.8 Hz, 1H), 3.73 (br s, 1H), 3.39 (br s, 1H), 3.02 (d, J=14.1 Hz, 1H), 2.49 (t, J=12.0 Hz, 1H), 1.89-1.59 (m, 3H), 1.48 (dd, J=1.5, 13.8 Hz, 1H), 1.39-1.32 (m, 8H), 1.11-1.01 (m, 3H).

Step 4. rac-(2S,5R)-Benzyl 5-((tert-butoxycarbonyl) amino)-2-methylpiperidine-1-carboxylate and rac-(2S,5S)-benzyl 5-((tert-butoxycarbonyl)amino)-2-methylpiperidine-1-carboxylate The rac-cis/trans benzyl 5-((tert-butoxycarbonyl)amino)-2-methylpiperidine-1-carboxylate (44 g) was separated by chiral SFC to give rac-cis-(2S,5R)-benzyl 5-((tert-butoxycarbonyl)amino)-2-methylpiperidine-1-carboxylate (Peak 2, 24.5 g, 55.68%) and rac-trans-(2S,5S)-benzyl 5-((tert-butoxycarbonyl)amino)-2-methylpiperidine-1-carboxylate_ (Peak 1, 12.3 g, 27.95%). Peak 2, cis material was carried on to Boc removal. Prep SFC Column: ChiralCel OD 300 mm×50 mm, 10 μm; Mobile phase: A: Supercritical CO2, B: IPA (0.1% $NH_3H_2O$), A:B=85:15 at 180 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm Peak 1 (trans): $^1$H NMR (400 MHz, $CDCl_3$) δ 7.44-7.28 (m, 5H), 5.23-5.06 (m, 2H), 4.55-4.35 (m, 2H), 4.25 (d, J=10.0 Hz, 1H), 3.58-3.25 (m, 1H), 2.58 (t, J=12.0 Hz, 1H), 1.87 (d, J=11.0 Hz, 1H), 1.82-1.69 (m, 2H), 1.56 (d, J=13.8 Hz, 1H), 1.50-1.36 (m, 9H), 1.21 (d, J=6.3 Hz, 3H).

Peak 2 (cis): $^1$H NMR (400 MHz, $CDCl_3$) δ 7.42-7.29 (m, 5H), 5.20-5.08 (m, 2H), 4.89 (br s, 1H), 4.47 (br s, 1H), 4.05 (d, J=14.1 Hz, 1H), 3.81 (br s, 1H), 3.11 (d, J=13.8 Hz, 1H), 1.93-1.68 (m, 4H), 1.43 (s, 9H), 1.20-1.13 (m, 3H).

Step 5. Racemic (2S,5R)-benzyl 5-amino-2-methylpiperidine-1-carboxylate

To a solution of rac-cis-(2S,5R)-benzyl 5-((tert-butoxycarbonyl)amino)-2-methylpiperidine-1-carboxylate (pk 2, 40.0 g, 115.6 mmol) in $CH_2Cl_2$ (60 mL) at 0° C. was added (4M HCl (g)/dioxane (200 mL) dropwise. After the addition, the solution was stirred at room temperature for 4 hrs. TLC (petroleum ether/EtOAc, 2:1) showed the starting material was consumed completely. The reaction mixture was concentrated to give racemic (2S,5R)-benzyl 5-amino-2-methylpiperidine-1-carboxylate (31.0 g, 94.8%) as a white solid (HCl salt). $^1$H NMR (400 MHz, DMSO-$d_6$) δ 8.37 (br s, 3H), 7.24-7.49 (m, 5H), 5.09 (s, 2H), 4.32 (m, 1H), 4.16 (d, J=8.28 Hz, 1H), 3.00 (br s, 2H), 1.83 (m, 2H), 1.59 (m, 2H), 1.11 (d, J=7.03 Hz, 3H).

Step 6. Racemic (2S,5R)-benzyl 5-((2-chloro-7H-pyrrolo[2,3-d]pyrimidin-4-yl)amino)-2-methylpiperidine-1-carboxylate A mixture of 2,4-dichloro-7H-pyrrolo[2,3-d]pyrimidine (21.8 g, 0.116 mol), DIPEA (67.7 g, 0.525 mol) and racemic (2S,5R)-benzyl 5-amino-2-methylpiperidine-1-carboxylate (30 g, 0.105 mol) in n-BuOH (300 mL) was heated to 140° C. overnight. LC-MS indicated the reaction was completed. The reaction mixture was cooled to room temperature and evaporated to dryness; the residue was partitioned with EtOAc (500 mL) and water (500 mL). The organic layer was washed with brine, dried over $Na_2SO_4$ and concentrated to give crude product, which was triturated with MTBE to give racemic (2S,5R)-benzyl 5-((2-chloro-7H-pyrrolo[2,3-d]pyrimidin-4-yl)amino)-2-methylpiperidine-1-carboxylate (36 g, 86%) as a yellow solid. $^1$H NMR (400 MHz, DMSO-$d_6$) δ 11.70 (br s, 1H), 7.71 (d, J=7.8 Hz, 1H), 7.46-7.25 (m, 5H), 7.10 (br s, 1H), 6.56 (br s, 1H), 5.18-5.00 (m, 2H), 4.38 (d, J=6.8 Hz, 1H), 4.16 (br s, 1H), 4.03 (q, J=7.3 Hz, 2H), 2.76 (t, J=11.8 Hz, 1H), 1.87-1.68 (m, 2H), 1.63 (d, J=7.3 Hz, 1H), 1.19-1.12 (m, 3H).

Step 7. rac-N-((3R,6S)-6-Methylpiperidin-3-yl)-7H-pyrrolo[2,3-d]pyrimidin-4-amine To a dry hydrogenation bottle, 10% dry Pd/C (7 g) was added under Ar atmosphere. Subsequently, a solution of racemic (2S,5R)-benzyl 5-((2-chloro-7H-pyrrolo[2,3-d]pyrimidin-4-yl)amino)-2-methylpiperidine-1-carboxylate (36 g, 0.09 mol) in MeOH (1500 mL) and THF (250 mL) was added and the resulting mixture was shaken on a Parr apparatus (45 psi of $H_2$ at 25° C. for 48 hours). LC-MS indicated the Cbz was removed completely, but ~30% of chloride remained. The reaction mixture was filtered and the filtrate was subjected to the reaction conditions again with 5 g of 10% dry Pd/C under 50 psi of $H_2$ at 45° C. for 12 h. LC-MS showed the reaction was completed. The reaction mixture was filtered through a pad of Celite® and the cake was washed with MeOH three times. The combined filtrates were concentrated to give rac-N-((3R,6S)-6-methylpiperidin-3-yl)-7H-pyrrolo[2,3-d]pyrimidin-4-amine (23 g, 94.6%) as a white solid. $^1$H NMR (400 MHz, DMSO-$d_6$) δ 11.53 (br s, 1H), 8.11 (d, J=12.5 Hz, 1H), 7.30 (dd, J=6.5, 18.6 Hz, 1H), 7.10 (br s, 1H), 6.90-6.73 (m, 1H), 6.59-6.52 (m, 1H), 6.10 (dd, J=1.5, 17.1 Hz, 1H), 5.68 (d, J=10.5 Hz, 1H), 4.86-4.51 (m, 1H), 4.41-3.97 (m, 2H), 3.02-2.55 (m, 1H), 1.89-1.59 (m, 3H), 1.28-1.10 (m, 3H).

Step 8. rac-1-((2S,5R)-5-((7H-Pyrrolo[2,3-d]pyrimidin-4-yl)amino)-2-methylpiperidin-1-yl)prop-2-en-1-one To a stirred solution of rac-N-((3R,6S)-6-methylpiperidin-3-yl)-7H-pyrrolo[2,3-d]pyrimidin-4-amine HCl salt (5.00 g, 18.5 mmol) in THF (250 mL) and saturated aq. NaHCO$_3$ solution (250 mL) was added acryloyl chloride (2.02 g, 22.2 mmol) dropwise at 0° C. carefully. After addition, the resulting mixture was stirred at 0° C. for 4 hours. TLC (DCM/MeOH/NH$_4$OH, 10:1:1) showed rac-N-((3R,6S)-6-methylpiperidin-3-yl)-7H-pyrrolo[2,3-d]pyrimidin-4-amine was consumed completely. The reaction mixture was diluted with H$_2$O (125 mL) and extracted with EtOAc (125 mL×3); the combined organic layer was washed with brine, and dried over Na$_2$SO$_4$. The most volatile components were removed in vacuum. The crude product was purified by column chromatography on silica gel (DCM/MeOH, 10:1) to give pure product. The product was triturated with EtOAc (150 mL) and filtered to give rac-1-((2S,5R)-5-((7H-pyrrolo[2,3-d]pyrimidin-4-yl)amino)-2-methylpiperidin-1-yl)prop-2-en-1-one (2.0 g, 38% yield) as a white solid. $^1$H NMR (400 MHz, DMSO-d$_6$) δ 11.53 (br s, 1H), 8.12 (d, J=12.8 Hz, 1H), 7.30 (dd, J=6.8, 18.8 Hz, 1H), 7.10 (br s, 1H), 6.89-6.71 (m, 1H), 6.56 (d, J=1.8 Hz, 1H), 6.10 (dd, J=2.1, 16.7 Hz, 1H), 5.72-5.61 (m, 1H), 4.81 (br s, 0.5H), 4.56 (d, J=10.3 Hz, 0.5H), 4.37 (br s, 0.5H), 4.20-3.95 (m, 1.5H), 2.96 (t, J=11.9 Hz, 0.5H), 2.60 (t, J=12.0 Hz, 0.5H), 1.92-1.59 (m, 4H), 1.30-1.07 (m, 3H).

Step 9. Preparation of (+)-1-((2R,5S)-5-((7H-pyrrolo[2,3-d]pyrimidin-4-yl)amino)-2-methylpiperidin-1-yl)prop-2-en-1-one (pk 1) and (−) 1-((2S,5R)-5-((7H-pyrrolo[2,3-d]pyrimidin-4-yl)amino)-2-methylpiperidin-1-yl)prop-2-en-1-one (pk 2)

The racemic compound: rac-1-((2S,5R)-5-((7H-pyrrolo[2,3-d]pyrimidin-4-yl)amino)-2-methylpiperidin-1-yl)prop-2-en-1-one (from Step 8) was purified by chiral SFC to give pure enantiomers. Peak 1 (4.63 g, +) and peak 2 (4.42 g, −) SFC conditions: Column: ChiralPak IC (300 mm*50 mm, 10 μm); Mobile phase: 40% ethanol (0.05% NH$_3$ in H$_2$O) in CO$_2$; Flow rate: 200 mL/min; wavelength: 220 nm.

The absolute stereochemistry was assigned based on X-ray crystallographic analysis.

Peak 1: (+) 1-((2R,5S)-5-((7H-pyrrolo[2,3-d]pyrimidin-4-yl)amino)-2-methylpiperidin-1-yl)prop-2-en-1-one $^1$H NMR (400 MHz, DMSO-d$_6$) δ 11.53 (br s, 1H), 8.12 (d, J=12.8 Hz, 1H), 7.30 (dd, J=6.8, 18.8 Hz, 1H), 7.10 (br s, 1H), 6.89-6.71 (m, 1H), 6.56 (d, J=1.8 Hz, 1H), 6.10 (dd, J=2.1, 16.7 Hz, 1H), 5.72-5.61 (m, 1H), 4.81 (br s, 0.5H), 4.56 (d, J=10.3 Hz, 0.5H), 4.37 (br s, 0.5H), 4.20-3.95 (m, 1.5H), 2.96 (t, J=11.9, Hz, 0.5H), 2.60 (t, J=12.0 Hz, 0.5H), 1.92-1.59 (m, 4H), 1.30-1.07 (m, 3H). LC/MS (M+H) 286.2. OR=[a]$_D^{20}$=+0.34 (c=0.6, MeOH).

Peak 2: (−) 1-((2S,5R)-5-((7H-pyrrolo[2,3-d]pyrimidin-4-yl)amino)-2-methylpiperidin-1-yl)prop-2-en-1-one $^1$H NMR (400 MHz, DMSO-d$_6$) δ 11.53 (br s, 1H), 8.12 (d, J=12.8 Hz, 1H), 7.30 (dd, J=6.8, 18.8 Hz, 1H), 7.10 (br s, 1H), 6.89-6.71 (m, 1H), 6.56 (d, J=1.8 Hz, 1H), 6.10 (dd, J=2.1, 16.7 Hz, 1H), 5.72-5.61 (m, 1H), 4.81 (br s, 0.5H), 4.56 (d, J=10.3 Hz, 0.5H), 4.37 (br s, 0.5H), 4.20-3.95 (m, 1.5H), 2.96 (t, J=11.9, Hz, 0.5H), 2.60 (t, J=12.0 Hz, 0.5H), 1.92-1.59 (m, 4H), 1.30-1.07 (m, 3H). LC/MS (M+H) 286.2. OR [a]$_D^{20}$=−0.36 (c=0.6, MeOH).

Example 6: (3R,5R)-5-((7H-pyrrolo[2,3-d]pyrimidin-4-yl)amino)-1-acryloylpiperidine-3-carbonitrile Step 1. Preparation of N-((3R,5R)-1-benzyl-5-((tert-butyldimethylsilyl)oxy)piperidin-3-yl)-7-trityl-7H-pyrrolo[2,3-d]pyrimidin-4-amine To a mixture of 4-chloro-7-trityl-7H-pyrrolo[2,3-d]pyrimidine (16.3 g, 41.18 mmol) and compound (3R,5R)-1-benzyl-5-((tert-butyldimethylsilyl)oxy)piperidin-3-amine (prepared as described in Eur. J. Org. Chem. 2012, 10, 2023. (12 g, 37.44 mmol) in n-BuOH (250 mL) at rt was added DIPEA (14.5 g, 112.32 mmol). The reaction mixture was heated to 110° C. for 3 days. TLC (DCM/MeOH, 10:1) showed most of amine was consumed. The reaction mixture was cooled to room temperature and evaporated to dryness via oil pump at 45° C.; the residue was partitioned with EtOAc (800 mL) and water (500 mL). The organic layer was washed with brine, dried over Na$_2$SO$_4$ and concentrated to give crude product, which was purified by chromatography (EtOAc/PE from 0% to 30%) to give N-((3R,5R)-1-benzyl-5-((tert-butyldimethylsilyl)oxy)piperidin-3-yl)-7-trityl-7H-pyrrolo[2,3-d]pyrimidin-4-amine (15 g, 65%) as a yellow solid. LC/MS (M+H) 679.4. $^1$H NMR (400 MHz, CDCl$_3$) δ −0.03 (d, J=2.01 Hz, 6H) 0.82 (s, 9H) 1.50 (d, J=12.55 Hz, 1H) 2.31 (d, J=11.54 Hz, 2H) 2.74 (d, J=12.55 Hz, 1H) 2.96 (br s, 1H) 3.40-3.73 (m, 2H) 3.99 (br s, 1H) 4.50 (br s, 1H) 5.58 (br s, 1H) 6.32 (d, J=4.02 Hz, 1H) 6.90 (d, J=3.51 Hz, 1H) 7.13-7.38 (m, 20H) 8.00 (s, 1H).

Step 2. (3R,5R)-tert-Butyl 3-((tert-butyldimethylsilyl)oxy)-5-((7-trityl-7H-pyrrolo[2,3-d]pyrimidin-4-yl)amino)piperidine-1-carboxylate To a dry hydrogenation bottle, 10% dry Pd/C (1.5 g) was added. Then a solution of N-((3R,5R)-1-benzyl-5-((tert-butyldimethylsilyl)oxy)piperidin-3-yl)-7-trityl-7H-pyrrolo[2,3-d]pyrimidin-4-amine (14.8 g, 21.76 mmol) and (Boc)$_2$O (5.22 g, 23.94 mmol) in MeOH (300 mL) was added and the resulting mixture was hydrogenated under 50 psi of H$_2$ at 40° C. for 12 hours. TLC (PE/EtOAc 4:1) showed the reaction was complete. The reaction solution was filtered through a pad of Celite® and the cake was washed with MeOH three times. The combined filtrate was concentrated to give (3R,5R)-tert-butyl 3-((tert-butyldimethylsilyl)oxy)-5-((7-trityl-7H-pyrrolo[2,3-d]pyrimidin-4-yl)amino) piperidine-1-carboxylate (14.8 g, ~100%) as a yellow solid, which was used directly to next step without further purification. $^1$H NMR (400 MHz, CDCl$_3$) δ 0.06 (br s, 6H) 0.72-0.94 (m, 9H) 1.16-1.43 (m, 4H) 1.49 (br s, 9H) 1.57-2.40 (m, 3H) 2.93-3.13 (m, 1H) 3.37-4.01 (m, 3H) 4.45 (br s, 1H) 4.72-5.38 (m, 1H) 6.30 (br s, 1H) 6.90 (br s, 1H) 7.08-7.36 (m, 16H) 8.01 (s, 1H).

Step 3. (3R,5R)-tert-Butyl 3-hydroxy-5-((7-trityl-7H-pyrrolo[2,3-d]pyrimidin-4-yl)amino)piperidine-1-carboxylate To a solution of (3R,5R)-tert-butyl 3-((tertbutyldimethylsilyl)oxy)-5-((7-trityl-7H-pyrrolo[2,3-d]pyrimidin-4-yl)amino)piperidine-1-carboxylate (15 g, 21.74 mmol) in anhydrous THF (300 mL) was added n-Bu$_4$NF (11.38 g, 43.47 mmol). The reaction mixture was then heated to 40° C. overnight. TLC (PE/EtOAc 4:1) indicated the reaction was complete. The reaction solution was diluted with water (300 mL) and then extracted with EtOAc (2×200 mL). The combined organic layers were washed with water, brine and dried over Na$_2$SO$_4$, which after concentration gave (3R,5R)-tert-butyl 3-hydroxy-5-((7-trityl-7H-pyrrolo[2,3-d]pyrimidin-4-yl)amino)piperidine-1-carboxylate (14.6 g, ~100%), which was used directly in the next step without further purification. 1H NMR (400 MHz, CDCl$_3$) δ 8.01 (s, 1H), 7.37-7.08 (m, 17H), 6.91 (d, J=3.5 Hz, 1H), 6.30 (br s, 1H), 4.48 (d, J=3.5 Hz, 1H), 4.05 (br s, 1H), 3.83-3.51 (m, 4H), 3.23 (br s, 1H), 1.58-1.29 (m, 10H).

Step 4. (R)-tert-Butyl 3-oxo-5-((7-trityl-7H-pyrrolo[2,3-d]pyrimidin-4-yl)amino)piperidine-1-carboxylate To a solution of compound (3R,5R)-tert-butyl 3-hydroxy-5-((7-trityl-7H-pyrrolo[2,3-d]pyrimidin-4-yl)amino)piperidine-1-carboxylate (5.0 g, 8.68 mmol) in DCM (100 mL) was added Dess-Martin periodinane (4.0 g, 9.55 mmol). The mixture was stirred at room temperature for 18 hours. TLC (DCM/MeOH, 10:1) showed starting material was consumed completely. The reaction mixture was concentrated to give crude product (7.8 g) as yellow solid, which was purified by prep-HPLC to give (R)-tert-butyl 3-oxo-5-((7-trityl-7H-pyrrolo[2,3-d]pyrimidin-4-yl)amino)piperidine-1-carboxylate (3.7 g, 74%) as a white solid. LC/MS (M+H)=574.3. $^1$H NMR (400 MHz, DMSO-$d_6$) δ ppm 1.24 (s, 9H) 2.20-2.45 (m, 2H) 3.04-3.36 (m, 2H) 3.92-4.27 (m, 3H) 6.88-7.46 (m, 16H) 8.29-8.57 (m, 2H) 10.46-10.71 (m, 1H).

Step 5. (5R)-tert-Butyl 3-cyano-5-((7-trityl-7H-pyrrolo[2,3-d]pyrimidin-4-yl)amino)piperidine-1-carboxylate (mixture of isomers)

To a mixture of (R)-tert-butyl 3-oxo-5-((7-trityl-7H-pyrrolo[2,3-d]pyrimidin-4-yl)amino)piperidine-1-carboxylate_ (1.0 g, 1.74 mmol) and TOSMIC (693.7 mg, 3.83 mmol) in DME (30 ml) at 0° C. was added t-BuOK (624.4 mg, 5.58 mmol) and EtOH (176.3 mg, 3.83 mmol) in portions. The resulting mixture was stirred at 0° C. for 0.5 hour. The mixture was allowed to warm to room temperature and stirred for 2 hours. TLC (DCM/MeOH, 10:1) showed the reaction was complete. The reaction solution was filtered, and the filtrate was concentrated to dryness and purified by preparative TLC (petroleum ether/EtOAc, 2:1) to afford (5R)-5-((7-trityl-7H-pyrrolo[2,3-d]pyrimidin-4-yl)amino)piperidine-3-carbonitrile (mixture of isomers, 200 mg, 20%) as a yellow solid. LC/MS (M+H) 585.3.

Step 6. Preparation of (5R)-5-((7-trityl-7H-pyrrolo[2,3-d]pyrimidin-4-yl)amino)piperidine-3-carbonitrile (mixture of isomers)

To a solution of (5R)-tert-butyl 3-cyano-5-((7-trityl-7H-pyrrolo[2,3-d]pyrimidin-4-yl)amino)piperidine-1-carboxylate (235 mg, 0.41 mmol) in DCM (1.5 ml) at 0° C. was added TFA (229.0 mg, 2.0 mmol). The reaction mixture was then stirred at room temperature for 12 hours. TLC (petroleum ether/EtOAc, 1:1) showed the reaction was complete. The reaction mixture was concentrated in vacuo to give (5R)-5-((7-trityl-7H-pyrrolo[2,3-d]pyrimidin-4-yl)amino)piperidine-3-carbonitrile (mixture of isomers) (235 mg, 100%) as a yellow solid. LC/MS (M+H) 485.0.

Step 7. Preparation of (5R)-1-acryloyl-5-((7-trityl-7H-pyrrolo[2,3-d]pyrimidin-4-yl)amino)piperidine-3-carbonitrile (mixture of isomers)

To a stirred solution of (5R)-5-((7-trityl-7H-pyrrolo[2,3-d]pyrimidin-4-yl)amino)piperidine-3-carbonitrile (100 mg, 0.206 mmol) in THF (3 mL):aq. NaHCO$_3$ solution (2.5 mL) at 0° C. was added acryloyl chloride (22.4 mg, 0.247 mmol) dropwise. After addition, the resulting mixture was stirred at 0° C. for 2 hours. TLC (DCM/MeOH, 20:1) showed the reaction was completely. The reaction mixture was diluted with H$_2$O (20 mL) and extracted with EtOAc (30 mL×2), the combined organic layer were washed with brine, dried over Na$_2$SO$_4$ and concentrated to give crude product, which was further purified by preparative TLC (petroleum ether/EtOAC, 1:1) to give (5R)-1-acryloyl-5-((7-trityl-7H-pyrrolo[2,3-d]pyrimidin-4-yl)amino)piperidine-3-carbonitrile and trans isomer (80 mg, 72%) as yellow solid. LC/MS (M+H) 539.1.

Step 8. Preparation of (3S,5R)-5-((7H-pyrrolo[2,3-d]pyrimidin-4-yl)amino)-1-acryloylpiperidine-3-carbonitrile and (3R,5R)-5-((7H-pyrrolo[2,3-d]pyrimidin-4-yl)amino)-1-acryloylpiperidine-3-carbonitrile To a round bottom flask containing (5R)-1-acryloyl-5-((7-trityl-7H-pyrrolo[2,3-d]pyrimidin-4-yl)amino) piperidine-3-carbonitrile and compound 5-1 (80 mg, 0.272 mmol) was added TFA (1 mL). The mixture was stirred at room temperature for 12 hours. TLC (petroleum ether/EtOAC, 1:1) showed 20% starting material remained. The reaction was heated to 30° C. for another 5 h. LCMS indicated completion. The reaction mixture was concentrated to give crude product, which was further purified by prep. TLC (Petroleum ether/EtOAC, 1:1) to give a mixture of (3S,5R)-5-((7H-pyrrolo[2,3-d]pyrimidin-4-yl)amino)-1-acryloylpiperidine-3-carbonitrile and (3R,5R)-5-((7H-pyrrolo[2,3-d]pyrimidin-4-yl)amino)-1-acryloylpiperidine-3-carbonitrile (12 mg, 10% for 3 steps) as a white solid. Chiral HPLC showed it was a mixture of trans/cis, which was purified further by chiral SFC. After chiral SFC, 1.4 mg of peak 1 and 3.3 mg of peak 2 was obtained. Peak 1: (3S,5R)-5-((7H-pyrrolo[2,3-d]pyrimidin-4-yl)amino)-1-acryloyl piperidine-3-carbonitrile and Peak 2: (3R,5R)-5-((7H-pyrrolo[2,3-d]pyrimidin-4-yl)amino)-1-acryloylpiperidine-3-carbonitrile. SFC separation conditions: Column: ChiralPak AD (250 mm×30 mm, 20 μm); Mobile phase: 50% EtOH+NH$_3$/H$_2$O 80 mL/min; Column: Chiralpak AD-H 250×4.6 mm I.D., 5 μm; Mobile phase: ethanol (0.05% DEA) in CO$_2$ from 5% to 40%; Flow rate: 2.35 mL/min; Wavelength: 220 nm; Peak 1: $^1$H NMR (400 MHz, CD$_3$OD) δ 8.16 (br s, 1H), 7.10 (d, J=3.5 Hz, 1H), 6.85 (dd, J=10.4, 16.7 Hz, 1H), 6.57 (d, J=3.5 Hz, 1H), 6.27 (dd, J=1.8, 16.8 Hz, 1H), 5.80 (d, J=9.5 Hz, 1H), 4.85-4.77 (m, 1H), 4.63 (s, 1H), 4.43 (d, J=11.8 Hz, 1H), 4.28-4.19 (m, 1H), 3.14-2.97 (m, 2H), 2.55 (d, J=12.5 Hz, 1H), 2.00 (d, J=14.6 Hz, 1H). Peak 2: $^1$H NMR (400 MHz, CD$_3$OD) δ 8.20 (br s, 1H), 7.09 (d, J=3.5 Hz, 1H), 6.90-6.54 (m, 2H), 6.32-6.07 (m, 1H), 5.90-5.57 (m, 1H), 4.71-4.41 (m, 2H), 4.40-4.01 (m, 2H), 3.71-3.40 (m, 2H), 2.39 (br s, 1H), 2.17 (d, J=9.0 Hz, 1H).

Example 7: 1-((2R,5R)-5-((7H-Pyrrolo[2,3-d]pyrimidin-4-yl)amino)-2-(hydroxymethyl)piperidin-1-yl)prop-2-en-1-one

Step 1. Methyl 5-aminopicolinate

To a stirred solution of 5-aminopicolinic acid (170 g, 1.23 mol) in MeOH (1700 ml) was added SOCl$_2$ (178.6 ml, 2.47 mol) at 0° C. The reaction mixture was then refluxed for 72 h. The mixture was then cooled to 0° C. and additional SOCl$_2$ was added (40 ml, 0.55 mol). The mixture was then refluxed for 24 h. The excess SOCl$_2$ was removed under reduced pressure and the crude material was neutralized with aq. NaHCO$_3$. The mixture was filtered and the filter cake dried at 40-50° C. overnight. The solid was collected to give methyl 5-aminopicolinate (350 g). The filtrate was further extracted with DCM (3×2 L). The organic extract was washed with brine, dried (Na$_2$SO$_4$) and concentrated to dryness to afford crude compound (200 g). All of solids were collected to give methyl 5-aminopicolinate (550 g from 680 g of compound 1, 73%) as a white solid. $^1$H NMR (400 MHz, CDCl$_3$) δ 8.12 (d, J=2.5 Hz, 1H), 7.93 (d, J=8.5 Hz, 1H), 6.97 (dd, J=2.8, 8.5 Hz, 1H), 4.24 (br s, 2H), 3.93 (s, 3H).

Step 2. Methyl 5-((tert-butoxycarbonyl)amino)picolinate

Methyl 5-aminopicolinate (110 g, 0.723 mol) was dissolved in DCM (2000 ml) at 20° C. under N$_2$. To the reaction mixture, Boc-anhydride (173.6 g, 0.80 mol) and DMAP (8.8 g, 0.0723 mol) were added. The reaction mixture was stirred at 20° C. for 20 h. TLC (PE/EA, 2:1) showed that the starting material was consumed completely. The reaction mixture was filtered and washed with DCM (4×3000 ml). H$_2$O (2000 ml) was added and layers were separated. The organic layer was washed with brine, dried over anhydrous Na$_2$SO$_4$ and evaporated under reduced pressure to give crude product. The crude compound was washed with petroleum ether (4000 mL) and stirred for 1.0 hour. Filtration and evaporation in vacuo afforded methyl 5-((tert-butoxycarbonyl)amino) picolinate (750 g from 550 g of methyl 5-aminopicolinate, 82.3%) as a white solid for next step without further purification. LC/MS (M+H)=253.1.

Step 3. tert-Butyl(6-(hydroxymethyl)pyridin-3-yl)carbamate

LAH powder (36 g, 0.96 mol) was suspended in dry THF (1000 ml) under N$_2$ atmosphere and cooled to 0° C. To the mixture was added compound 3 (150 g, 0.60 mol) in dry THF (1000 ml) slowly at 0° C. The reaction mixture was gradually warmed to room temperature and stirred for 12 h. TLC (PE/EA, 1:1) showed that the reaction was complete, and the reaction was quenched with dropwise addition of THF-Water (9:1, 400 mL) followed by 90 ml 15% NaOH aqueous and 50 ml of water at 0° C., stirred for 0.5 h at room temperature, and filtered through a pad of Celite®, and then washed with THF (4×1000 ml). The filtrate was concentrated under reduced pressure to give the crude which was purified by column chromatography over silica gel eluting with PE/EA (2:1~1:2). The desired fraction was concentrated to afford tert-butyl(6-(hydroxymethyl)pyridin-3-yl) carbamate (450 g, 67%) as a white solid. $^1$H NMR (400 MHz, DMSO-d$_6$) δ 9.58-9.40 (m, 1H), 8.59-8.45 (m, 1H), 7.95-7.78 (m, 1H), 7.42-7.22 (m, 1H), 5.42-5.21 (m, 1H), 4.58-4.40 (m, 2H), 1.48 (s, 9H).

Step 4. tert-Butyl(6-(hydroxymethyl)piperidin-3-yl) carbamate

To a solution of tert-butyl(6-(hydroxymethyl)pyridin-3-yl)carbamate (30 g, 0.134 mol) in EtOH (300 ml) and HOAc (20 ml) was added PtO$_2$ (3.0 g, 0.0223 mol) under N$_2$. The mixture was hydrogenated at 65° C./55 psi of H$_2$ for 72 hours. The mixture was filtered through a pad of Celite® and the filter cake was washed with EtOH (3×2000 ml). The filtrate was concentrated under reduced pressure to remove EtOH and HOAc. Saturated aqueous NaHCO$_3$ was added to adjust pH to 6-7 and the aqueous layer was extracted with EtOAc (3×2000 ml). The combined organic layer were washed with brine, dried over Na$_2$SO$_4$ and concentrated to dryness to give the crude product, which was triturated with PE/EA (1:1) for 2 hours and filtered to give recovered tert-butyl(6-(hydroxymethyl)pyridin-3-yl)carbamate (90 g, 50%) as a white solid. The aqueous layer was evaporated to remove most of the water to give a mixture of tert-butyl(6-(hydroxymethyl)piperidin-3-yl)carbamate (90 g, 50%) in aq.NaHCO$_3$, which was directly used for next step without further purification. LC/MS (M+H)=231.2.

Step 5. Benzyl 5-((tert-butoxycarbonyl)amino)-2-(hydroxymethyl)piperidine-1-carboxylate To a stirred solution of tert-Butyl(6-(hydroxymethyl)piperidin-3-yl)carbamate (45 g, 0.20 mol) in THF (600 ml) and H$_2$O (300 ml) was added NaHCO$_3$ (33.6 g, 0.40 mol). To this mixture was added Cbz-Cl (41 g, 0.24 mol) dropwise at 0° C. and the resultant mixture was allowed to come to room temperature and stirred for 12 h. TLC (5% MeOH in DCM) was checked to show starting material was consumed completely. Volatiles were removed under reduced pressure, water (500 ml) was added, and the aqueous mixture was extracted with EtOAc (2×600 ml). The combined organic layers were washed with brine, dried over Na$_2$SO$_4$ and concentrated to dryness to afford the crude product, which was purified by column chromatography (silica gel eluted with DCM/EA (4:1-2:1) to give benzyl 5-((tert-butoxycarbonyl)amino)-2-(hydroxymethyl)piperidine-1-carboxylate (90 g, 63%) as a gum.
$^1$H NMR (400 MHz, DMSO-d$_6$) δ 7.37 (s, 5H), 7.05-6.76 (m, 1H), 5.20-4.99 (m, 2H), 4.89-4.67 (m, 1H), 4.24-3.92 (m, 2H), 3.62-3.40 (m, 2H), 3.34-2.88 (m, 1H), 2.18-1.62 (m, 2H), 1.55-1.13 (m, 12H).

Step 6. (2R,5R)-Benzyl 5-((2-chloro-7-tosyl-7H-pyrrolo[2,3-d]pyrimidin-4-yl)amino)-2-(hydroxymethyl) piperidine-1-carboxylate To a round bottom flask was added 2,4-dichloro-7-tosyl-7H-pyrrolo[2,3-d]pyrimidine (6.03 g, 17.6 mmol), DIPEA (6.8 mL, 2.2 eq), benzyl 5-((tert-butoxycarbonyl)amino)-2-(hydroxymethyl)piperidine-1-carboxylate (5.6 g, 1.0 eq) and n-butanol (50 mL). The reaction mixture was heated to 50° C. overnight. The reaction mixture was poured into ethyl acetate/water and the layers separated. The aqueous layer was extracted (2×EtOAc). The organic extracts were collected, washed with brine, dried (Na$_2$SO$_4$) and the solvent removed to give an oil, which after chromatography (silica, ethyl acetate/heptanes) gave two major peaks with equivalent mass. Pk 1=2.5 g (trans material); Pk 2=3.3 g (cis material): Peak 1 (trans): (2S,5R)-benzyl 2-(hydroxymethyl)-5-((7-tosyl-7H-pyrrolo[2,3-d]pyrimidin-4-yl)amino) piperidine-1-carboxylate. LC/MS (M+H) 570.1 $^1$H NMR (400 MHz, MeOH-d$_4$) δ ppm 1.63-1.81 (m, 2H) 1.99-2.18 (m, 2H) 2.43 (s, 3H) 3.19 (d, J=12.49 Hz, 1H) 3.65-3.82 (m, 2H) 4.16-4.48 (m, 4H) 6.85 (d, J=3.90 Hz, 1H) 6.90-7.20 (m, 5H) 7.29-7.44 (m, 2H) 7.50 (d, J=3.90 Hz, 1H) 8.06 (d, J=8.20 Hz, 2H)
Peak 2 (cis): (2R,5R)-benzyl 5-((2-chloro-7-tosyl-7H-pyrrolo[2,3-d]pyrimidin-4-yl)amino)-2-(hydroxymethyl)piperidine-1-carboxylate. LC/MS (M+H) 570.1. $^1$H NMR (400 MHz, MeOH-d$_4$) δ 1.63-2.02 (m, 4H) 2.42 (s, 3H) 2.71-2.84 (m, 1H) 3.61-3.81 (m, 3H) 4.30-4.41 (m, 2H) 5.08-5.23 (m, 2H) 6.74 (d, J=3.90 Hz, 1H) 7.26-7.44 (m, 7H) 7.49 (br s, 1H) 8.03 (d, J=8.20 Hz, 2H)

Step 7. (2R,5R)-Benzyl 5-((2-chloro-7-tosyl-7H-pyrrolo[2,3-d]pyrimidin-4-yl)amino)-2-(hydroxymethyl) piperidine-1-carboxylate and (2S,5S)-benzyl 5-((2-chloro-7-tosyl-7H-pyrrolo[2,3-d]pyrimidin-4-yl)amino)-2-(hydroxymethyl)piperidine-1-carboxylate Racemic-cis-(2R,5R)-benzyl 5-((2-chloro-7-tosyl-7H-pyrrolo[2,3-d]pyrimidin-4-yl)amino)-2-(hydroxymethyl)piperidine-1-carboxylate (3.31 g) was separated by chiral SFC-Chiral (Lux Cellulose-3 250 mm×21.2 mm, 5 μm, $CO_2$/MeOH, 80 mL/min) to give two peaks, absolute stereochemistry arbitrarily assigned: pk1 (1.5 g) (2R,5R)-benzyl 5-((2-chloro-7-tosyl-7H-pyrrolo[2,3-d]pyrimidin-4-yl)amino)-2-(hydroxymethyl)piperidine-1-carboxylate. OR $a_{[D]}^{20}$=−0.10 (c=0.5, MeOH). Pk2 (1.5 g) (2S,5S)-benzyl 5-((2-chloro-7-tosyl-7H-pyrrolo[2,3-d]pyrimidin-4-yl)amino)-2-(hydroxymethyl)piperidine-1-carboxylate. OR $a_{[D]}^{20}$=+0.12 (c=0.5, MeOH).

Step 8. ((2R,5R)-5-((2-Chloro-7-tosyl-7H-pyrrolo[2,3-d]pyrimidin-4-yl)amino)piperidin-2-yl)methanol To a Parr hydrogenation bottle was added (2R,5R)-benzyl 5-((2-chloro-7-tosyl-7H-pyrrolo[2,3-d]pyrimidin-4-yl)amino)-2-(hydroxymethyl)piperidine-1-carboxylate (in 100 mL of EtOH) and Pd(OH)$_2$ (1.2 g). The reaction was shaken on a Parr shaker apparatus at 20 psi $H_2$ for 4 hr at room temperature. The reaction mixture was then filtered through a pad of Celite® and the solvent removed in vacuo to give ((2R,5R)-5-((2-chloro-7-tosyl-7H-pyrrolo[2,3-d]pyrimidin-4-yl)amino)piperidin-2-yl)methanol (1.73 g, 91%). LC/MS (M+H)=436.1. $^1$H NMR (400 MHz, MeOH-d$_4$) δ 1.33-1.65 (m, 2H) 1.84 (dd, J=13.07, 2.93 Hz, 1H) 2.13 (d, J=12.10 Hz, 1H) 2.46 (m, 3H) 2.52 (t, J=11.32 Hz, 1H) 2.66-2.80 (m, 1H) 3.39-3.64 (m, 3H) 4.21-4.26 (m, 1H) 6.76 (d, J=3.90 Hz, 1H) 7.33-7.44 (m, 2H) 7.49 (d, J=3.90 Hz, 1H) 8.02 (d, J=8.20 Hz, 2H).

Step 9. ((2R,5R)-5-((2-Chloro-7H-pyrrolo[2,3-d]pyrimidin-4-yl)amino)piperidin-2-yl)methanol To a round bottom flask containing (2R,5R)-5-((2-chloro-7-tosyl-7H-pyrrolo[2,3-d]pyrimidin-4-yl)amino)piperidin-2-yl)methanol (1.1 g, 2.52 mmol) was added MeOH (10 mL) and K$_2$CO$_3$ (767 mg, 2.2 eq). The reaction was stirred at room temperature overnight and then poured into water. The aqueous mixture was extracted with n-BuOH. The organic extracts were dried (Na$_2$SO$_4$) and the solvent removed to give the crude product, which was purified by chromatography (silica, DCM/MeOH (10:1, MeOH:NH$_4$OH) to give the desired product (610 mg, 86%). LC/MS (M+H) 282.1. $^1$H NMR (400 MHz, MeOH-d$_4$) δ 1.19-1.67 (m, 2H) 1.84 (dd, J=13.07, 2.93 Hz, 1H) 2.18 (d, J=12.88 Hz, 1H) 2.67 (dd, J=7.22, 4.10 Hz, 1H) 3.40-3.61 (m, 3H) 3.94-4.09 (m, 1H) 4.26 (t, J=11.32 Hz, 1H) 6.58 (d, J=3.51 Hz, 1H) 6.95-7.06 (m, 1H).

Step 10. ((2R,5R)-5-((7H-Pyrrolo[2,3-d]pyrimidin-4-yl)amino)piperidin-2-yl)methanol To a round bottom flask containing (2R,5R)-5-((2-chloro-7H-pyrrolo[2,3-d]pyrimidin-4-yl)amino)piperidin-2-yl)methanol (202 mg, 0.72 mmol) in ethanol (20 mL) was added 10% Pd/C (100 mg) and ammonium formate (233 mg, 5 eq). The reaction mixture was heated to reflux overnight and then filtered through a pad of Celite®. The solvent was removed in vacuo to provide ((2R,5R)-5-((7H-pyrrolo[2,3-d]pyrimidin-4-yl)amino)piperidin-2-yl)methanol (110 mg, 62%). LC/MS (M+H) 248.1. $^1$H NMR (400 MHz, MeOH-d$_4$) δ 1.80-2.24 (m, 4H) 3.35-3.39 (m, 2H) 3.66-3.89 (m, 3H) 4.49 (t, J=4.10 Hz, 1H) 6.70 (d, J=3.51 Hz, 1H) 7.15 (d, J=3.51 Hz, 1H) 8.11-8.28 (m, 1H).

Step 11. 1-((2R,5R)-5-((7H-Pyrrolo[2,3-d]pyrimidin-4-yl)amino)-2-(hydroxymethyl)piperidin-1-yl)prop-2-en-1-one To a solution of ((2R,5R)-5-((7H-pyrrolo[2,3-d]pyrimidin-4-yl)amino)piperidin-2-yl)methanol (172 mg, 0.69 mmol) in DCM/CHCl$_3$/CF$_3$CH$_2$OH (3:1:0.5 mL) was added TEA (0.19 mL, 2.0 eq). The reaction mixture was cooled to 0° C. After 30 min, acryloyl chloride (in DCM, 1 mL) was added dropwise. After 2 hrs, the reaction mixture was poured into water/DCM and the layers separated. The organic layer was collected, dried (Na$_2$SO$_4$) and the solvent removed to give the crude product (224 mg). A portion of the crude product (50 mg) was purified by RP-HPLC to give 1-((2R,5R)-5-((7H-pyrrolo[2,3-d]pyrimidin-4-yl)amino)-2-(hydroxymethyl)piperidin-1-yl)prop-2-en-1-one (4.4 mg). LC/MS (M+H) 302.2. $^1$H NMR (400 MHz, MeOH-d$_4$) δ ppm 1.72-2.22 (m, 4H) 2.81-2.99 (m, 1H) 3.65-3.85 (m, 2H) 3.88-4.17 (m, 2H) 4.25-4.45 (m, 1H) 5.80 (d, J=12.10 Hz, 1H) 6.26 (d, J=16.78 Hz, 1H) 6.80-6.99 (m, 2H) 7.39 (br s, 1H) 8.21-8.40 (m, 1H).

Example 8: 1-((3aS,7aS)-1-(7H-pyrrolo[2,3-d]pyrimidin-4-yl)hexahydro-1H-pyrrolo[2,3-c]pyridin-6(2H)-yl)prop-2-en-1-one

Step 1. tert-Butyl 1H-pyrrolo[2,3-c]pyridine-1-carboxylate

To a solution of 1H-pyrrolo[2,3-c]pyridine (250 g, 2.12 mol) in CH$_3$CN (2 L) was added K$_2$CO$_3$ (584 g, 4.23 mol) and DMAP (12.9 g, 0.11 mol). After 10 min, (Boc)$_2$O (508.7 g, 2.33 mol) was added over a period of 40 min. After the addition, the resulting mixture was stirred at room temperature for 3 hour. TLC (petroleum ether: ethyl acetate, 1:1) indicated starting material was consumed completely. The mixture was filtered, and the filtrate was evaporated to dryness, and then partitioned between EtOAc (4 L) and water (2 L). The organic layer was washed with brine (1 L), dried over Na$_2$SO$_4$ and concentrated to give tert-butyl 1H-pyrrolo[2,3-c]pyridine-1-carboxylate (830 g, 90%) as a white solid. $^1$H NMR (400 MHz, CDCl3) δ 9.3 (bs, 1H) 8.32 (d, 1H), 7.65 (bs, 1H), 7.41-7.39 (m, 1H), 6.50 (d, 1H), 1.62 (s, 9H).

Step 2. (3aS,7aR)-tert-Butyl octahydro-1H-pyrrolo[2,3-c]pyridine-1-carboxylate To a dry hydrogenation bottle, PtO$_2$ (13 g) was added under Ar atmosphere. A solution of tert-butyl 1H-pyrrolo[2,3-c]pyridine-1-carboxylate (135 g, 0.62 mol) in EtOH (3 L) was added and the resulting mixture was hydrogenated at 50 psi H$_2$ at 80° C. for 48 hours. TLC (petroleum ether/EtOAc, 1:1) showed starting material was consumed completely. The reaction mixture was filtered, and the filtrate was concentrated to give (3aS,7aR)-tert-butyl octahydro-1H-pyrrolo[2,3-c]pyridine-1-carboxylate (810 g, 96.4%) as a colorless oil. $^1$H NMR (400 MHz, MeOH-d$_4$) δ 1.27-1.43 (m, 9H) 1.49-1.95 (m, 4H) 2.18-2.48 (m, 2H) 2.53-2.77 (m, 2H) 3.09 (d, J=5.02 Hz, 2H) 3.19-3.42 (m, 2H) 3.62 (br s, 1H).

Step 3. (3aR,7aR)-Benzyl hexahydro-1H-pyrrolo[2,3-c]pyridine-6(2H)-carboxylate To a stirred solution of (3aS,7aR)-tert-butyl octahydro-1H-pyrrolo[2,3-c]pyridine-1-carboxylate (200 g, 0.885 mol)

and DIPEA (251 g, 1.95 mol) in DCM (2 L) at 0° C. was added dropwise Cbz-Cl (181 g, 1.06 mol) over a period of 45 min. After the addition, the resulting mixture was stirred at room temperature for 16 hours. TLC (DCM/MeOH, 10:1) showed the starting material was consumed completely. The reaction mixture was evaporated to dryness, and then partitioned between EtOAc (8 L) and water (3 L); the organic layer was washed with water (3 L) and brine (3 L), dried over anhydrous $Na_2SO_4$ and concentrated to give (3aS,7aR)-tert-butyl octahydro-1H-pyrrolo[2,3-c]pyridine-1-carboxylate (1147 g, 90%) as a colorless oil.

$^1$H NMR (400 MHz, $CDCl_3$) δ 1.15-1.48 (m, 9H) 1.51-1.65 (m, 1H) 1.68-1.90 (m, 2H) 2.32 (br s, 1H) 2.72 (t, J=11.04 Hz, 1H) 2.97 (br s, 1H) 3.13-3.56 (m, 3H) 3.73 (s, 2H) 3.85-4.28 (m, 1H) 4.91-5.14 (m, 2H) 7.12-7.38 (m, 5H).

Step 4, 5 and 6. (3aR,7aR)-Benzyl hexahydro-1H-pyrrolo[2,3-c]pyridine-6(2H)-carboxylate and (3aS,7aS)-benzyl hexahydro-1H-pyrrolo[2,3-c]pyridine-6(2H)-carboxylate To a 0° C. stirred solution of (3aS,7aR)-tert-butyl octahydro-1H-pyrrolo[2,3-c]pyridine-1-carboxylate (280 g, 0.68 mol) in DCM (600 mL) was added dropwise 4M HCl in dioxane (2.5 L) over a period of 1 hour. The reaction mixture was stirred at room temperature for 15 hours. TLC (petroleum ether/EtOAc, 2:1) showed the starting material was consumed completely. The reaction mixture was evaporated to dryness, and then partitioned between MTBE (6 L) and water $H_2O$ (4 L), the aqueous phase was then basified to pH 9-10 and extracted with DCM (3 L*4). The combined organic layers were concentrated to give rac-(3aR,7aR)-benzyl hexahydro-1H-pyrrolo[2,3-c]pyridine-6(2H)-carboxylate (687 g, 85%), which was separated by SFC to give (3aS,7aS)-benzyl hexahydro-1H-pyrrolo[2,3-c]pyridine-6(2H)-carboxylate (280 g, 42.2%) and (3aR,7aR)-benzyl hexahydro-1H-pyrrolo[2,3-c]pyridine-6(2H)-carboxylate (270, 39.3%) as yellow oil. (Peak 1 was (3aR,7aR)-benzyl hexahydro-1H-pyrrolo[2,3-c]pyridine-6(2H)-carboxylate, RT=9.81; peak 2 was (3aS,7aS)-benzyl hexahydro-1H-pyrrolo[2,3-c]pyridine-6(2H)-carboxylate, RT=10.63). $^1$H NMR (400 MHz, $CDCl_3$) δ 1.28-1.63 (m, 3H) 1.68-1.90 (m, 2H) 1.97-2.09 (m, 1H) 2.71-3.19 (m, 4H) 3.26-3.43 (m, 1H) 3.55-3.77 (m, 2H) 5.02 (br s, 2H) 7.10-7.35 (m, 5H). Separation conditions: Instrument: SFC 350; Column: AS 250 mm×50 mm, 10 μm; Mobile phase: A: Supercritical $CO_2$, B: EtOH (0.05% DEA), A:B=65:35 at 240 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.

Step 7. (3aS,7aS)-Benzyl 1-(2-chloro-7H-pyrrolo[2,3-d]pyrimidin-4-yl)hexahydro-1H-pyrrolo[2,3-c]pyridine-6(2H)-carboxylate A mixture of (3aS,7aS)-benzyl hexahydro-1H-pyrrolo[2,3-c]pyridine-6(2H)-carboxylate, peak 2(135 g, 0.52 mol), DIPEA (268 g, 2.1 mol) and 2,4-dichloro-7H-pyrrolo[2,3-d]pyrimidine (88.7 g, 0.47 mol) in n-BuOH (1 L) was heated to 80° C. for 3 hours, TLC (Petroleum ether/ether, 2:1) showed 2,4-dichloro-7H-pyrrolo[2,3-d]pyrimidine was consumed completely. The reaction mixture was cooled to room temperature and evaporated to dryness via oil pump at 45° C. The residue was partitioned between DCM (2 L) and water (1.5 L); the organic layer was washed with water (1 L) and brine (1 L), dried over $Na_2SO_4$ and concentrated to give (3aS,7aS)-benzyl 1-(2-chloro-7H-pyrrolo[2,3-d]pyrimidin-4-yl)hexahydro-1H-pyrrolo[2,3-c]pyridine-6(2H)-carboxylate (310 g, 80%) as a yellow solid. $^1$H NMR (400 MHz, DMSO-$d_6$) δ 1.58-2.35 (m, 5H) 2.90-3.28 (m, 2H) 3.58-4.07 (m, 3H) 4.35 (br s, 2H) 5.16 (br s, 2H) 6.46-6.85 (m, 1H) 7.12-7.57 (m, 6H) 11.87 (br s, 1H).

Step 8. 4-((3aR,7aS)-Octahydro-1H-pyrrolo[2,3-c]pyridin-1-yl)-7H-pyrrolo[2,3-d]pyrimidine To a dry Parr hydrogenation bottle, Pd/C (12 g) was added under Ar atmosphere. Then a solution of (3aS,7aS)-benzyl 1-(2-chloro-7H-pyrrolo[2,3-d]pyrimidin-4-yl)hexahydro-1H-pyrrolo[2,3-c]pyridine-6(2H)-carboxylate (62 g, 0.15 mol) in EtOH (1.2 L) was added and the resulting mixture was hydrogenated under 50 psi of $H_2$ at 65° C. for 48 hours, TLC (Petroleum ether/EtOAc, 1:1) showed the starting material was consumed completely; the reaction mixture was filtered and the filter cake was washed with warm MeOH and water (v/v 1:1, 500 mL×2); the combined filtrate was evaporated to give 4-((3aR,7aS)-octahydro-1H-pyrrolo[2,3-c]pyridin-1-yl)-7H-pyrrolo[2,3-d]pyrimidine (190 g, 90%) as a white solid.

Step 9. 1-((3aS,7aS)-1-(7H-Pyrrolo[2,3-d]pyrimidin-4-yl)hexahydro-1H-pyrrolo[2,3-c]pyridin-6(2H)-yl)prop-2-en-1-one To a solution of 4-((3aR,7aS)-octahydro-1H-pyrrolo[2,3-c]pyridin-1-yl)-7H-pyrrolo[2,3-d]pyrimidine (150 g, 0.54 mol) in aq Na—$HCO_3$ (150 g, 1.79 mol) in $H_2O$ (1.5 L) at 0° C. was added dropwise a solution of acryloyl chloride (53.3 g, 0.59 mol) in MeCN (150 mL) carefully. After the addition, the resulting mixture was stirred at room temperature for 2 hours. TLC (DCM/MeOH, 5:1) showed 4-((3aR,7aS)-octahydro-1H-pyrrolo[2,3-c]pyridin-1-yl)-7H-pyrrolo[2,3-d]pyrimidine was consumed completely. The reaction mixture was extracted with DCM (500 mL*4) and the combined organic layers were concentrated to give the crude product, which was purified by column chromatography to give 1-((3aS,7aS)-1-(7H-pyrrolo[2,3-d]pyrimidin-4-yl)hexahydro-1H-pyrrolo[2,3-c]pyridin-6(2H)-yl)prop-2-en-1-one (130 g, 81%) as a white solid. $^1$H NMR (400 MHz, DMSO-$d_6$): δ 11.58 (s, 1H) 8.09-8.07 (d, J=9.2 Hz, 1H) 7.115 (s, 1H), 6.82-6.78 (m, 1H), 6.51 (m, 1H), 6.05-6.01 (m, 1H), 5.69-5.85 (m, 1H), 4.69-4.68 (m, 0.5H), 4.27 (s, 1H), 3.90-3.74 (m, 3H), 3.13-3.24 (m, 2H), 2.74-2.71 (m, 0.5H), 2.19-1.74 (m, 4.5H).

Example 9: 1-((2S,5R)-5-((7H-pyrrolo[2,3-d]pyrimidin-4-yl)amino)-2-ethylpiperidin-1-yl)prop-2-en-1-one The racemic 5-((tert-butoxycarbonyl)amino)-2-ethylpiperidine-1-carboxylate was prepared using a process similar to the methyl intermediate. The racemic intermediate contained the cis-isomers as the major component as was the case for the methyl intermediate. The racemic mixture was separated into four optically pure isomers via chiral SFC, and the two cis-isomers were obtained as peak 3 and 4. SFC preparative separation conditions: Column: Chiralcel OJ-H 30×250 mm; Mobile phase: 95/5 $CO_2$/methanol; Flow rate: 120 mL/min; Wavelength: 210 nm; SFC analytical condition: Column: Chiralcel OJ-H 4.6×25 mm; Mobile phase: 5-60% $CO_2$/methanol; Flow rate: 3 mL/min; Wavelength: 210 nm.

Preparation of final analogs using the enantiomerically pure benzyl 5-((tertbutoxycarbonyl)amino)-2-ethylpiperidine-1-carboxylate followed protocols similar to other analogs (see Example 5). Thus 1-((2S,5R)-5-((7H-pyrrolo[2,3-d]pyrimidin-4-yl)amino)-2-ethylpiperidin-1-yl)prop-2-en-1-one was prepared from peak 3 of the chiral separation of the racemic 5-((tert-butoxycarbonyl)amino)-2-ethylpiperidine-1-carboxylate. $^1$H NMR (400 MHz, DMSO-$d_6$) δ 11.51 (br s, 1H), 8.11 (d, J=13.6 Hz, 1H), 7.26 (dd, J=6.6, 21.4 Hz, 1H), 7.08 (br s, 1H), 6.9-6.7 (m, 1H), 6.53 (s, 1H), 6.10 (d, J=16.8 Hz, 1H), 5.7-5.6 (m, 1H), 4.57 (br s, 1H), 4.07 (m, 2H), 2.90 (t, J=12.1 Hz, 1H), 1.92-1.5 (m, 6H), 0.81 (m, 3H). LCMS (acid, 3 min run): RT 0.76 min. LC/MS (M+H)=300.25.

Example 10: 1-((3R,5R)-3-((7H-pyrrolo[2,3-d]pyrimidin-4-yl)amino)-5-fluoropiperidin-1-yl)prop-2-en-1-one

Step 1. N-((3R,5R)-1-Benzyl-5-fluoropiperidin-3-yl)-2-chloro-7H-pyrrolo[2,3-d]pyrimidin-4-amine A mixture of (3R,5R)-1-benzyl-5-fluoropiperidin-3-amine (prepared as described in *Eur. J. Org. Chem.* 2012, 10, 2023 and *Org. Lett.* 2011, 13, 4442) (500 mg, 2.4 mmol), DIPEA (1.55 g, 12 mmol) and 2,4-dichloro-7H-pyrrolo[2,3-d]pyrimidine (495 mg, 2.64 mmol) in n-BuOH (35 mL) was heated to 130-140° C. overnight. LC-MS showed the reaction was completed. TLC (PE/EtOAc, 1:1) showed the starting material was consumed completely and the desired product was formed. The reaction mixture was cooled to room temperature and evaporated to dryness in vacuo at 45° C. The residue was treated with water (20 mL) and extracted with EtOAc (30 mL×2). The combined organic layers were washed with brine, dried over $Na_2SO_4$ and concentrated to give crude product, which was purified via chromatography to give N-((3R,5R)-1-benzyl-5-fluoropiperidin-3-yl)-2-chloro-7H-pyrrolo[2,3-d]pyrimidin-4-amine (760 mg, 88.0%) as an oil. LC/MS (M+H) 360.2.

Step 2. N-((3R,5R)-5-Fluoropiperidin-3-yl)-7H-pyrrolo[2,3-d]pyrimidin-4-amine To a dry Parr hydrogenation bottle, 10% dry Pd/C (160 mg) was added under Ar atmosphere followed by a solution of N-((3R,5R)-1-benzyl-5-fluoropiperidin-3-yl)-2-chloro-7H-pyrrolo[2,3-d]pyrimidin-4-amine (940 mg, 2.61 mmol) in MeOH (30 mL) and THF (6 mL). The resulting mixture was hydrogenated under 50 psi of $H_2$ at 35° C. for 72 hours. LC-MS showed most of the starting material was consumed completely and the desired product was formed. The reaction solution was filtered through a pad of Celite®, and the filter cake was washed with MeOH three times. The combined filtrate was concentrated to give N-((3R,5R)-5-fluoropiperidin-3-yl)-7H-pyrrolo[2,3-d]pyrimidin-4-amine (600 mg, 97.5%) as a white solid. $^1$H NMR (400 MHz, DMSO-$d_6$) δ 11.61 (br s, 1H), 9.50 (br s, 1H), 8.22-8.11 (m, 1H), 7.60 (d, J=7.8 Hz, 1H), 7.23-7.03 (m, 1H), 6.61 (d, J=1.8 Hz, 1H), 5.32-5.13 (m, 1H), 4.80-4.64 (m, 1H), 3.32-3.24 (m, 1H), 3.22-3.12 (m, 1H), 2.84 (t, J=11.5 Hz, 1H), 2.32 (br s, 1H), 2.05-1.85 (m, 1H), 1.37-0.82 (m, 1H).

Step 3. 1-((3R,5R)-3-((7H-Pyrrolo[2,3-d]pyrimidin-4-yl)amino)-5-fluoropiperidin-1-yl)prop-2-en-1-one To a stirred solution of N-((3R,5R)-5-fluoropiperidin-3-yl)-7H-pyrrolo[2,3-d]pyrimidin-4-amine (200 mg, 0.85 mmol) in THF (12 mL) and aq. $NaHCO_3$ solution (12 mL) at 0° C. was added acryl-Cl (85 mg, 0.93 mmol) dropwise.

The resulting mixture was stirred at 0° C. for 2 hours. TLC (DCM/MeOH, 10:1) showed starting material was consumed completely. The reaction mixture was diluted with $H_2O$ (20 mL) and extracted with EtOAc (30 mL×2); the combined organic layer was washed with brine, dried over $Na_2SO_4$ and concentrated to give crude product, which was further purified by column chromatography on silica gel (MeOH: DCM, 0-8%) to give 1-((3R,5R)-3-((7H-pyrrolo[2,3-d]pyrimidin-4-yl)amino)-5-fluoropiperidin-1-yl)prop-2-en-1-one (130 mg, 53.0%) as a white solid. $^1$H NMR (400 MHz, DMSO-$d_6$) δ 11.55 (br s, 1H), 8.13 (d, J=18.8 Hz, 1H), 7.41-7.27 (m, 1H), 7.10 (br s, 1H), 6.80 (dd, J=10.5, 16.8 Hz, 1H), 6.55 (br s, 1H), 6.13 (dd, J=2.3, 16.6 Hz, 1H), 5.70 (d, J=10.3 Hz, 1H), 5.17-4.91 (m, 1H), 4.71-4.18 (m, 3H), 3.40 (d, J=15.1 Hz, 0.5H), 3.19-2.98 (m, 1H), 2.61 (t, J=11.5 Hz, 0.5H), 2.29 (d, J=6.0 Hz, 1H), 2.05-1.74 (m, 1H).

Example 11: 1-((3R,4S)-3-((7H-pyrrolo[2,3-d]pyrimidin-4-yl)amino)-4-methylpiperidin-1-yl)prop-2-en-1-one

Step 1. rac-(3R,4S)-tert-Butyl 3-((2-chloro-7H-pyrrolo[2,3-d]pyrimidin-4-yl)amino)-4-methylpiperidine-1-carboxylate To a solution of rac-(3R,4S)-tert-butyl 3-amino-4-methylpiperidine-1-carboxylate (prepared as described in WO2011029046) (500 mg, 2.333 mmol) and 2,4-dichloro-7H-pyrrolo[2,3-d]pyrimidine (483 mg, 2.566 mmol, 1.1 eq.) in n-BuOH (15 mL) was added DIPEA (903 mg, 6.999 mmol, 3.0 eq.) at room temperature, and heated to 140° C. overnight. After LCMS indicated the reaction was complete, the reaction mixture was concentrated to dryness in vacuo. The residue was dissolved in EtOAc (50 mL) and diluted with water (50 mL). The layers were separated and the aqueous layer was extracted with EtOAc (50 mL×1), and the combined organic layers were washed with brine, dried with sodium sulfate. The solvent was removed under reduced pressure. The residue was purified by column chromatography (EtOAc/PE=8%-50%) to give rac-(3R,4S)-tert-butyl 3-((2-chloro-7H-pyrrolo[2,3-d]pyrimidin-4-yl)amino)-4-methylpiperidine-1-carboxylate (rac-trans, 563 mg, 66%) as a yellow solid. $^1$H NMR (400 MHz, $CDCl_3$) δ 11.92 (br s, 1H), 7.14 (br s, 1H), 6.46 (br s, 1H), 4.40 (d, J=9.3 Hz, 1H), 4.08-3.65 (m, 2H), 2.98-2.63 (m, 2H), 1.90-1.60 (m, 3H), 1.52-1.38 (m, 1H), 1.48 (s, 9H), 1.11-1.05 (m, 3H).

Step 2. Rac-(3R,4S)-tert-Butyl 3-((7H-pyrrolo[2,3-d]pyrimidin-4-yl)amino)-4-methylpiperidine-1-carboxylate To a dry Parr hydrogenation bottle, dry Pd/C (100 mg) was added under $N_2$ atmosphere. A solution of rac-(3R,4S)-tert-butyl 3-((2-chloro-7H-pyrrolo[2,3-d]pyrimidin-4-yl)amino)-4-methylpiperidine-1-carboxylate (560 mg, 1.531 mmol) in MeOH/THF (30 mL/10 mL) was added, and the resulting mixture was heated to 40° C. under 50 psi of $H_2$ for 2 days. After LCMS showed the reaction to be complete, the reaction mixture was filtered, and the filter cake was washed with MeOH. The combined filtrate was evaporated to give rac-(3R,4S)-tert-butyl 3-((7H-pyrrolo[2,3-d]pyrimidin-4-yl)amino)-4-methylpiperidine-1-carboxylate (520 mg, 93%) as a yellow solid. LC/MS (M+H)=332.2.

Step 3. Rac-N-((3R,4S)-4-Methylpiperidin-3-yl)-7H-pyrrolo[2,3-d]pyrimidin-4-amine To a solution of rac-(3R,4S)-tert-butyl 3-((7H-pyrrolo[2,3-d]pyrimidin-4-yl)amino)-4-methylpiperidine-1-carboxylate (520 mg, 1.531 mmol) in DCM (15 mL) at 0° C. was added 4.0 M HCl/dioxane (15 mL). The reaction mixture was allowed to warm to room temperature and stirred for 3 hours. After LCMS showed the reaction to be complete, the reaction mixture was concentrated to give rac-N-((3R,4S)-4-methylpiperidin-3-yl)-7H-pyrrolo[2,3-d]pyrimidin-4-amine (410 mg, 100%) as a solid. LC/MS (M+H)=232.2.

Step 4. rac-1-((3R,4S)-3-((7H-Pyrrolo[2,3-d]pyrimidin-4-yl)amino)-4-methylpiperidin-1-yl)prop-2-en-1-one To a solution of rac-N-((3R,4S)-4-methylpiperidin-3-yl)-7H-pyrrolo[2,3-d]pyrimidin-4-amine (410 mg, 1.530 mmol) in THF (20 mL) and saturated. NaHCO$_3$ (15 mL) at 0° C. was added acryloyl chloride (152 mg, 1.683 mmol, 1.1 eq.). The reaction mixture was stirred at 0° C. for 2 hours. After TLC (EtOAc/MeOH, 10:1) showed the reaction to be complete, the reaction mixture was diluted with water (50 mL), and extracted with EtOAc (50 mL×2). The combined organic layers were washed with brine, dried over Na$_2$SO$_4$ and concentrated. The residue was purified by flash column chromatography (MeOH/EtOAc, 2%~10%) and lyophilized to give rac-1-((3R,4S)-3-((7H-pyrrolo[2,3-d]pyrimidin-4-yl)amino)-4-methylpiperidin-1-yl)prop-2-en-1-one (150 mg, 34%) as a white solid. $^1$H NMR (400 MHz, DMSO-d$_6$) δ 11.53 (br s, 1H), 8.08 (d, J=15.1 Hz, 1H), 7.32-7.20 (m, 1H), 7.08 (br s, 1H), 6.81 (dt, J=10.5, 17.3 Hz, 1H), 6.59 (br s, 1H), 6.12 (d, J=14.8 Hz, 1H), 5.69 (d, J=10.3 Hz, 1H), 4.65-4.39 (m, 1H), 4.27-4.04 (m, 1H), 3.94-3.71 (m, 1H), 3.08-2.96 (m, 0.5H), 2.89-2.77 (m, 0.5H), 2.71-2.60 (m, 0.5H), 2.46-2.28 (m, 0.5H), 1.82 (d, J=12.3 Hz, 2H), 1.29-1.12 (m, 1H), 0.94 (dd, J=6.0, 12.3 Hz, 3H). LCMS (M+H)=286.1.

Step 5. 1-((3R,4S)-3-((7H-Pyrrolo[2,3-d]pyrimidin-4-yl)amino)-4-methylpiperidin-1-yl)prop-2-en-1-one (pk 1) and 1-((3S,4R)-3-((7H-pyrrolo[2,3-d]pyrimidin-4-yl)amino)-4-methylpiperidin-1-yl)prop-2-en-1-one (pk 2)

rac-1-((3R,4S)-3-((7H-Pyrrolo[2,3-d]pyrimidin-4-yl) amino)-4-methylpiperidin-1-yl)prop-2-en-1-one (120 mg) was separated by chiral SFC (Chiral Pak-AD (250×30 mm, 5 um), 30% EtOH (0.05% NH3 in H2O) in CO2) to give the pair of enantiomers, (peak 1, 47.8 mg) and (peak 2, 48.2 mg) as white solids, absolute stereochemistry arbitrarily assigned.

Peak 1 data: $^1$H NMR (400 MHz, DMSO-d$_6$) δ 11.53 (br s, 1H), 8.08 (d, J=15.1 Hz, 1H), 7.32-7.20 (m, 1H), 7.08 (br s, 1H), 6.81 (dt, J=10.5, 17.3 Hz, 1H), 6.59 (br s, 1H), 6.12 (d, J=14.8 Hz, 1H), 5.69 (d, J=10.3 Hz, 1H), 4.65-4.39 (m, 1H), 4.27-4.04 (m, 1H), 3.94-3.71 (m, 1H), 3.08-2.96 (m, 0.5H), 2.89-2.77 (m, 0.5H), 2.71-2.60 (m, 0.5H), 2.46-2.28 (m, 0.5H), 1.82 (d, J=12.3 Hz, 2H), 1.29-1.12 (m, 1H), 0.94 (dd, J=6.0, 12.3 Hz, 3H). LCMS (M+H)=285.9. Peak 2 data: $^1$H NMR (400 MHz, DMSO-d$_6$) δ 11.53 (br s, 1H), 8.08 (d, J=15.1 Hz, 1H), 7.32-7.20 (m, 1H), 7.08 (br s, 1H), 6.81 (dt, J=10.5, 17.3 Hz, 1H), 6.59 (br s, 1H), 6.12 (d, J=14.8 Hz, 1H), 5.69 (d, J=10.3 Hz, 1H), 4.65-4.39 (m, 1H), 4.27-4.04 (m, 1H), 3.94-3.71 (m, 1H), 3.08-2.96 (m, 0.5H), 2.89-2.77 (m, 0.5H), 2.71-2.60 (m, 0.5H), 2.46-2.28 (m, 0.5H), 1.82 (d, J=12.3 Hz, 2H), 1.29-1.12 (m, 1H), 0.94 (dd, J=6.0, 12.3 Hz, 3H). LCMS (M+H)=285.9.

Example 12: (R)-1-(3-((7H-Pyrrolo[2,3-d]pyrimidin-4-yl)amino)piperidin-1-yl)prop-2-en-1-one Step 1. (R)-tert-Butyl 3-((7-tosyl-7H-pyrrolo[2,3-d]pyrimidin-4-yl)amino)piperidine-1-carboxylate To a stirred solution of 4-chloro-7-tosyl-7H-pyrrolo[2,3-d]pyrimidine (8.73 g, 28.4 mmol) in n-Butanol (100 mL) was added DIPEA (6.0 mL, 1.2 eq) and (R)-3-amino piperidine-1-carboxylic acid tert-butyl ester (6.82 g, 1.2 eq). The reaction mixture was heated at 70° C. for overnight. The solvent was removed under reduced pressure and the crude residue was purified by column chromatography (100-200 mesh silica, 0-3% MeOH in DCM) to obtain (R)-tert-butyl 3-((7-tosyl-7H-pyrrolo[2,3-d]pyrimidin-4-yl)amino)piperidine-1-carboxylate (5.6 g, 42%). LC/MS (M+H)=472.2. $^1$H NMR (400 MHz, CDCl$_3$) δ ppm 1.09-1.30 (m, 4H) 1.33 (br s, 9H) 1.49-1.94 (m, 2H) 2.34 (s, 3H) 3.37 (br s, 2H) 3.67 (d, J=12.88 Hz, 1H) 4.09-4.21 (m, 1H) 6.39 (d, J=4.10 Hz, 1H) 7.10-7.29 (m, 2H) 7.42 (d, J=4.10 Hz, 1H) 7.92-8.07 (m, 2H) 8.39 (s, 1H).

Step 2. (R)-tert-Butyl 3-((7H-pyrrolo[2,3-d]pyrimidin-4-yl)amino)piperidine-1-carboxylate To a stirred solution of (R)-tert-butyl 3-((7-tosyl-7H-pyrrolo[2,3-d]pyrimidin-4-yl)amino)piperidine-1-carboxylate (29.4 g, 62 mmol) in MeOH (96 mL), THF (96 mL) and water (96 mL) was added LiOH.H$_2$O (2.99 g, 125 mmol, 2 eq). The mixture was heated at 60° C. for 1 hour. After the reaction mixture was cooled to room temperature, the organic solvent evaporated in vacuo. The aqueous mixture was made slightly acidic and then extracted with ethyl acetate (4×150 mL). The organic fractions were combined and washed with brine, dried over Na$_2$SO$_4$ and concentrated under reduced pressure. The crude material was purified by column chromatography (100-200 mesh silica, 0-2% MeOH in DCM) to provide 8.5 g (70%) of (R)-tert-butyl 3-((7H-pyrrolo[2,3-d]pyrimidin-4-yl)amino)piperidine-1-carboxylate as an off white solid. LC/MS (M+H) 318.2. $^1$H NMR (400 MHz, CDCl$_3$) δ 1.45 (br s, 9H) 1.58-1.87 (m, 3H) 2.04 (dd, J=8.39, 4.10 Hz, 1H) 3.35-3.56 (m, 2H) 3.75-3.91 (m, 2H) 4.22-4.38 (m, 1H) 5.18 (br s, 1H) 6.33-6.47 (m, 1H) 7.11 (d, J=2.34 Hz, 1H) 8.39 (s, 1H) 10.19 (br s, 1H).

Step 3. (R)—N-(Piperidin-3-yl)-7H-pyrrolo[2,3-d]pyrimidin-4-amine

To a stirred solution of (R)-tert-butyl 3-((7H-pyrrolo[2,3-d]pyrimidin-4-yl)amino)piperidine-1-carboxylate in dioxane (40 mL) was added 4M HCl in dioxane (60 mL) wise. The reaction was stirred for ~1 hr and then diluted with diethyl ether to form a solid, which was filtered and collected. The solid was dried on high vacuum to give (R)—N-(piperidin-3-yl)-7H-pyrrolo[2,3-d]pyrimidin-4-amine HCl salt (4.6 g, 92%). LC/MS (M+H)=218.2. $^1$H NMR (400 MHz, D$_2$O) δ 1.70-2.31 (m, 4H) 2.94-3.18 (m, 2H) 3.32-3.45 (m, 1H) 3.64 (dd, J=12.68, 4.10 Hz, 1H) 4.31-4.47 (m, 1H) 6.78 (d, J=3.51 Hz, 1H) 7.35 (d, J=3.90 Hz, 1H) 8.24-8.35 (m, 1H).

Step 4. (R)-1-(3-((7H-Pyrrolo[2,3-d]pyrimidin-4-yl)amino)piperidin-1-yl)prop-2-en-1-one To a round bottom flask containing (R)—N-(piperidin-3-yl)-7H-pyrrolo[2,3-d]pyrimidin-4-amine HCl salt (1.0 g, 3.44 mmol) was added DCM (30 mL), EtOH (3 mL) and TEA (2.11 mL, 4.4 eq). After 30 min, acrylolyl chloride in 20 ml of DCM was added dropwise and the reaction stirred at rt for 2 hrs. The mixture was poured into water and the layers separated. The organic layer was dried ($Na_2SO_4$) and the solvent removed to give crude product (~900 mg). The material was purified by chromatography (silica, DCM/ MEOH) to give (R)-1-(3-((7H-pyrrolo[2,3-d]pyrimidin-4-yl)amino)piperidin-1-yl)prop-2-en-1-one (310 mg, 33%). LC/MS (M+H)=272.1. $^1$H NMR (400 MHz, DMSO-$d_6$) δ 1.40-2.12 (m, 3H) 2.61-2.76 (m, 1H) 2.89-3.18 (m, 2H) 3.92-4.22 (m, 2H) 4.55 (d, J=12.10 Hz, 1H) 5.47-5.75 (m, 1H) 5.97-6.20 (m, 1H) 6.60 (br s, 1H) 6.65-6.90 (m, 1H) 7.00-7.13 (m, 1H) 7.25 (d, J=6.63 Hz, 1H) 8.12 (d, J=14.44 Hz, 1H) 11.50 (br s, 1H).

Example 13: 1-((2S,5R)-5-((5-(2-Methoxyethyl)-7H-pyrrolo[2,3-d]pyrimidin-4-yl)amino)-2-methylpiperidin-1-yl)prop-2-en-1-one Step 1. (+)-(2S,5R)-Benzyl 5-amino-2-methylpiperidine-1-carboxylate and (−)-(2R,5S)-benzyl 5-amino-2-methylpiperidine-1-carboxylate Racemic (2S,5R)-benzyl 5-amino-2-methylpiperidine-1-carboxylate (Example 5, step 5, 10 g) was purified by chiral SFC (cellulose-2; $CO_2$/MeOH-0.2% $NH_3$/EtOH) to give pk 1: (2R,5S)-benzyl 5-amino-2-methylpiperidine-1-carboxylate, [a]d20=−7.09 (c=1.1, MeOH). $^1$H NMR (400 MHz, DMSO-$d_6$) δ 8.37 (br s, 3H), 7.24-7.49 (m, 5H), 5.09 (s, 2H), 4.32 (m, 1H), 4.16 (d, J=8.28 Hz, 1H), 3.00 (br s, 2H), 1.83 (m, 2H), 1.59 (m, 2H), 1.11 (d, J=7.03 Hz, 3H). pk2: (2S,5R)-benzyl 5-amino-2-methylpiperidine-1-carboxylate, [a]d20=+7.09 (c=1.1, MeOH). $^1$H NMR (400 MHz, DMSO-$d_6$) δ 8.37 (br s, 3H), 7.24-7.49 (m, 5H), 5.09 (s, 2H), 4.32 (m, 1H), 4.16 (d, J=8.28 Hz, 1H), 3.00 (br s, 2H), 1.83 (m, 2H), 1.59 (m, 2H), 1.11 (d, J=7.03 Hz, 3H).

Step 2. (2S,5R)-Benzyl 5-((5-(2-methoxyethyl)-7-tosyl-7H-pyrrolo[2,3-d]pyrimidin-4-yl)amino)-2-methylpiperidine-1-carboxylate A mixture of 4-chloro-5-(2-methoxyethyl)-7-tosyl-7H-pyrrolo[2,3-d]pyrimidine, (+)-(2S,5R)-benzyl 5-amino-2-methylpiperidine-1-carboxylate and Hunig's base in n-BuOH were combined and heated to 90° C. overnight. The mixture was removed from heat and concentrated. The residue was purified by CombiFlash® (24 g gold column, 0 to 50% EA in Hept) to give 264 mg of (2S,5R)-benzyl 5-((5-(2-methoxyethyl)-7-tosyl-7H-pyrrolo[2,3-d]pyrimidin-4-yl)amino)-2-methylpiperidine-1-carboxylate. LC/MS (M+H) 578.5.

Step 3. 5-(2-Methoxyethyl)-N-((3R,6S)-6-methylpiperidin-3-yl)-7-tosyl-7H-pyrrolo[2,3-d]pyrimidin-4-amine To a Parr reactor bottle was added (2S,5R)-benzyl 5-((5-(2-methoxyethyl)-7-tosyl-7H-pyrrolo[2,3-d]pyrimidin-4-yl)amino)-2-methylpiperidine-1-carboxylate (in 10 mL of EtOH) and Pd(OH)$_2$ (126 mg). The reaction was stirred at 25 psi $H_2$ overnight at rt. The mixture was filtered through Celite® and the solvent removed to give 190 mg 5-(2-methoxyethyl)-N-((3R,6S)-6-methylpiperidin-3-yl)-7-tosyl-7H-pyrrolo[2,3-d]pyrimidin-4-amine as a white foam. LC/MS (M+H): 444.4.

Step 4. 1-((2S,5R)-5-((5-(2-Methoxyethyl)-7-tosyl-7H-pyrrolo[2,3-d]pyrimidin-4-yl)amino)-2-methylpiperidin-1-yl)prop-2-en-1-one To a solution of 5-(2-methoxyethyl)-N-((3R,6S)-6-methylpiperidin-3-yl)-7-tosyl-7H-pyrrolo[2, 3-d]pyrimidin-4-amine chloroform (5 mL)) was added Hunig's base. The solution was cooled to 0° C. and acryloyl chloride was added. After 30 min, the reaction was determined to be complete by LC/MS, and $NaHCO_3$ was added. The reaction was stirred for 30 min. The organic layer was separated and concentrated. The residue was purified by CombiFlash® (20 to 100 EA in heptane) to give 210 mg 1-((2S,5R)-5-((5-(2-methoxyethyl)-7-tosyl-7H-pyrrolo[2,3-d]pyrimidin-4-yl)amino)-2-methylpiperidin-1-yl)prop-2-en-1-one. LC/MS (M+H): 498.4.

Step 5. 1-((2S,5R)-5-((5-(2-Methoxyethyl)-7H-pyrrolo[2,3-d]pyrimidin-4-yl)amino)-2-methylpiperidin-1-yl)prop-2-en-1-one 1-((2S,5R)-5-((5-(2-Methoxyethyl)-7-tosyl-7H-pyrrolo [2,3-d]pyrimidin-4-yl)amino)-2-methylpiperidin-1-yl)prop-2-en-1-one (200 mg) was dissolved in 3 mL of THF. A solution of TBAF (1 M in THF, 0.804 mL, 2 eq) was added. The reaction mixture was heated to 60° C. and stirred overnight. The reaction was cooled to rt and diluted with 10 mL of EtOAc. The solution was washed with $NH_4Cl$ (10%), brine and dried ($Na_2SO_4$). The mixture was filtered and concentrated. The residue was purified by CombiFlash® (12 g gold column, 0 to 10% MeOH in DCM) to give 100 mg of 1-((2S,5R)-5-((5-(2-methoxyethyl)-7H-pyrrolo[2,3-d]pyrimidin-4-yl)amino)-2-methylpiperidin-1-yl)prop-2-en-1-one. LC/MS (M+H)=344.3. $^1$H NMR (400 MHz, DMSO-$d_6$) δ 8.21 (s, 1H), 7.18 (br s, 1H), 7.08 (s, 1H), 6.82-6.77 (m, 1H), 6.10-6.07 (m, 1H) 5.68-5.66 (m, 1H) 3.61-3.57 (m, 2H), 3.30 (s, 3H), 3.05-3.00 (m, 2H), 2.49-2.48 (m, 3H), 1.87-1.56 (m, 5H), 1.22-1.18 (m, 3H).

Example 14: 1-((3R,5S)-3-(7H-Pyrrolo[2,3-d]pyrimidin-4-ylamino)-5-methylpiperidin-1-yl)prop-2-en-1-one (chiral and rac-cis Step 1: tert-Butyl(5-methylpyridin-3-yl)carbamate A solution of 5-methylpyridin-3-amine (20 g, 185 mmol) and (Boc)$_2$O (44.4 g, 203.5 mmol) in THF (360 mL) was stirred at room temperature for 5 h. TLC (PE/EtOAc, 1:1) showed the reaction was completed. The reaction mixture was concentrated, and triturated with MTBE to give tert-butyl(5-methylpyridin-3-yl)carbamate (26.4 g, 69%) as a white solid. $^1$H NMR (400 MHz, CDCl$_3$) δ 8.21 (d, J=2.3 Hz, 1H), 8.15-8.10 (m, 1H), 7.88 (br s, 1H), 6.66 (br s, 1H), 2.33 (s, 3H), 1.53 (s, 9H), Step 2. rac-cis/trans-tert-Butyl(5-methylpiperidin-3-yl)carbamate To a dry hydrogenation bottle, PtO$_2$ (3.0 g) was added under $N_2$ atmosphere. A solution of compound 2 (26.4 g, 127 mmol) in CH$_3$COOH (300 mL) was added, and the resulting mixture was heated to 50° C. under 55 psi of $H_2$ for 5 days. $^1$H NMR showed most of starting material was consumed. The reaction mixture was filtered and the filter cake was washed with MeOH. The combined filtrate was evaporated under high vacuum to give rac-cis/trans-tert-butyl(5-methylpiperidin-3-yl)carbamate (27.3 g, 100%) as a yellow oil. LC/MS (M+H) 214.2

Step 3. rac-cis/trans-Benzyl 3-((tert-butoxycarbonyl)amino)-5-methylpiperidine-1-carboxylate To a solution of rac-cis/trans-tert-butyl(5-methylpiperidin-3-yl)carbamate (27.3 g, 127 mmol) in THF (200 mL) and $H_2O$ (100 mL) was added $NaHCO_3$ (40.53 g, 482 mmol, 3.8 eq.) at room temperature, and stirred at room temperature for 1 h. CbzCl (26 g, 152 mmol, 1.2 eq.) was added dropwise, and stirred at room temperature for 8 h. TLC (PE/EtOAc, 2:1) showed the reaction to be complete. The reaction mixture was extracted with EtOAc (200 mL×3). The combined organic layers were washed with brine (100 mL), dried over $Na_2SO_4$ and concentrated. The residue was purified by column chromatography (PE/EtOAc, 8:1-4:1) to give rac-cis/trans-benzyl 3-((tert-butoxycarbonyl)amino)-5-methylpiperidine-1-carboxylate (20 g, 45%, containing some benzyl alcohol) as a white solid. LC/MS (M+H) 348.2.

Step 4. rac-cis/trans-Benzyl 3-amino-5-methylpiperidine-1-carboxylate

To a solution of rac-cis/trans-benzyl 3-((tert-butoxycarbonyl)amino)-5-methylpiperidine-1-carboxylate (20 g, 57.4 mmol) in DCM (40 mL) was added HCl (g)/dioxane (50 mL, 4M) dropwise at room temperature, and stirred at room temperature for 6 hrs. LCMS showed the reaction to be complete. The reaction mixture was concentrated, and filtered, and then triturated with MTBE to give rac-cis/trans-benzyl 3-amino-5-methylpiperidine-1-carboxylate (5.8 g, 43%, 0.817 mol HCl) as a gray solid. $^1$H NMR (400 MHz, MeOD) δ 7.43-7.27 (m, 5H), 5.14 (s, 2H), 4.50-4.39 (m, 1H), 4.12 (d, J=10.3 Hz, 1H), 4.04-3.90 (m, 1H), 3.74-3.43 (m, 1H), 3.23-3.10 (m, 1H), 2.82-2.59 (m, 1H), 2.40 (s, 1H), 2.26-2.05 (m, 1H), 1.92 (d, J=11.3 Hz, 1H), 1.78-1.58 (m, 1H), 1.30 (s, 1H), 1.25-1.05 (m, 2H), 1.01-0.93 (m, 3H). LCMS (M+H)=248.9.

Step 5. rac-cis-(3R,5S)-Benzyl 3-((2-chloro-7H-pyrrolo[2,3-d]pyrimidin-4-yl)amino)-5-methylpiperidine-1-carboxylate and rac-trans-(3R,5R)-benzyl 3-((2-chloro-7H-pyrrolo[2,3-d]pyrimidin-4-yl)amino)-5-methylpiperidine-1-carboxylate To a mixture of rac-cis/trans-benzyl 3-((tert-butoxycarbonyl)amino)-5-methylpiperidine-1-carboxylate (prepared similarly as described in WO201102904)) (4 g, 14.046 mmol) and 2,4-dichloro-7H-pyrrolo[2,3-d]pyrimidine (2.9 g, 15.451 mmol, 1.1 eq.) in n-BuOH (70 mL) at room temperature was added DIPEA (7.248 g, 56.184 mmol, 4.0 eq.). The reaction mixture was heated to 140° C. for 30 h. After LCMS showed the reaction to be complete, the reaction mixture was concentrated to dryness in vacuo. The residue was dissolved in EtOAc (150 mL), and diluted with water (150 mL) and the the organic layer was separated. The aqueous layer was extracted with EtOAc (150 mL×2), and the combined organic layers were washed with brine, dried with sodium sulfate. The solvent was removed under reduced pressure. The residue was purified by column chromatography (PE/EtOAc, 6:1 to 2:1) to give rac-cis-(3R,5S)-benzyl 3-((2-chloro-7H-pyrrolo[2,3-d]pyrimidin-4-yl)amino)-5-methylpiperidine-1-carboxylate (rac-cis, spot 2 on the TLC plate-high polarity, 1.934 g, 34%) and rac-trans-(3R,5R)-benzyl 3-((2-chloro-7H-pyrrolo[2,3-d]pyrimidin-4-yl)amino)-5-methylpiperidine-1-carboxylate (rac-trans, spot 1 on the TLC plate-low polarity, 559 mg, 10%) as a yellow solid. Pk2: rac-cis-(3R,5S)-benzyl 3-((2-chloro-7H-pyrrolo[2,3-d]pyrimidin-4-yl)amino)-5-methylpiperidine-1-carboxylate (rac-cis): $^1$H NMR (400 MHz, DMSO-$d_6$) δ 11.70 (br s, 1H), 7.70 (d, J=7.5 Hz, 1H), 7.45-7.24 (m, 5H), 7.09 (br s, 1H), 6.58 (br s, 1H), 5.21-5.01 (m, 2H), 4.33 (br s, 1H), 4.07-3.96 (m, 2H), 3.17 (d, J=5.3 Hz, 1H), 2.61-2.53 (m, 1H), 2.33 (br s, 1H), 2.06-1.94 (m, 1H), 1.67 (br s, 1H), 1.29-1.13 (m, 1H), 0.91 (d, J=6.5 Hz, 3H).

Pk1: rac-trans-(3R,5R)-benzyl 3-((2-chloro-7H-pyrrolo[2,3-d]pyrimidin-4-yl)amino)-5-methylpiperidine-1-carboxylate (rac-trans): $^1$H NMR (400 MHz, DMSO-$d_6$) δ 11.69 (br s, 1H), 7.63-6.59 (m, 8H), 5.05 (d, J=16.8 Hz, 1H), 4.87 (br s, 1H), 4.35-3.95 (m, 2H), 3.86-3.51 (m, 2H), 3.11-2.64 (m, 1H), 2.19 (br s, 1H), 1.90-1.72 (m, 2H), 1.56 (br s, 1H), 0.91 (d, J=6.5 Hz, 3H), Step 6. rac-cis-N-((3R,5S)-5-Methylpiperidin-3-yl)-7H-pyrrolo[2,3-d]pyrimidin-4-amine To a dry Parr hydrogenation bottle, dry Pd/C (500 mg) was added under $N_2$ atmosphere. Then, a solution of rac-cis-(3R,5S)-benzyl 3-((2-chloro-7H-pyrrolo[2,3-d]pyrimidin-4-yl)amino)-5-methylpiperidine-1-carboxylate (rac-cis, 1.934 g, 4.835 mmol) in $CH_3OH$/THF (60 mL/20 mL) was added. The resulting mixture was heated to 40° C. under 50 psi of $H_2$ for 3 days. After LCMS showed the reaction to be complete and Cl atom was removed, the reaction mixture was filtered, and the filter cake was washed with MeOH. The combined filtrate was evaporated to give rac-cis-N-((3R,5S)-5-methylpiperidin-3-yl)-7H-pyrrolo[2,3-d]pyrimidin-4-amine (rac-cis, 1.4 g, 100%) as a pink solid. LC/MS (M+H) =231.2.

Step 7. rac-cis-1-((3R,5S)-3-((7H-Pyrrolo[2,3-d]pyrimidin-4-yl)amino)-5-methylpiperidin-1-yl)prop-2-en-1-one To a solution of rac-cis-N-((3R,5S)-5-methylpiperidin-3-yl)-7H-pyrrolo[2,3-d]pyrimidin-4-amine (400 mg, 1.494 mmol) in THF (20 mL) was added saturated aq.$NaHCO_3$ (15 mL) at 0° C. was added acryloyl chloride (149 mg, 1.643 mmol, 1.1 eq.) slowly. The reaction was stirred at 0° C. for 2 hours. After TLC (EtOAc/MeOH, 10:1) showed the reaction to be complete, the reaction mixture was diluted with water (80 mL), and extracted with EtOAc (80 mL×2). The combined organic layers were washed with brine, dried over $Na_2SO_4$ and concentrated. The residue was purified by flash column chromatography (EtOAc/MeOH, 10:1) to give rac-cis-1-((3R,5S)-3-((7H-pyrrolo[2,3-d]pyrimidin-4-yl)amino)-5-methylpiperidin-1-yl)prop-2-en-1-one (300 mg, 71%) as a white solid. $^1$H NMR (400 MHz, DMSO-$d_6$) δ 11.52 (br s, 1H), 8.10 (d, J=14.3 Hz, 1H), 7.39-7.22 (m, 1H), 7.07 (br s, 1H), 6.94-6.78 (m, 1H), 6.56 (br s, 1H), 6.12 (dd, J=8.9, 16.2 Hz, 1H), 5.69 (t, J=10.4 Hz, 1H), 4.71 (d, J=10.0 Hz, 1H), 4.47-4.29 (m, 1H), 4.03 (d, J=11.0 Hz, 2H), 2.73 (t, J=11.5 Hz, 1H), 2.58 (t, J=12.3 Hz, 1H), 2.40-2.30 (m, 1H), 2.19 (t, J=11.5 Hz, 1H), 2.05 (d, J=11.8 Hz, 1H), 1.36-1.17 (m, 1H), 0.97-0.89 (m, 3H). LCMS (M+H) 285.9.

Step 8. 1-((3R,5S)-3-((7H-Pyrrolo[2,3-d]pyrimidin-4-yl)amino)-5-methylpiperidin-1-yl)prop-2-en-1-one and 1-((3S,5R)-3-((7H-pyrrolo[2,3-d]pyrimidin-4-yl)amino)-5-methylpiperidin-1-yl)prop-2-en-1-one rac-cis-1-((3R,5S)-3-((7H-Pyrrolo[2,3-d]pyrimidin-4-yl)amino)-5-methylpiperidin-1-yl)prop-2-en-1-one was separated by chiral SFC (AD, 250 mm×30 mm, 20 µm, 35% MeOH/NH4OH, 80 ml/min) to give 1-((3R,5S)-3-((7H-pyrrolo[2,3-d]pyrimidin-4-yl)amino)-5-methylpiperidin-1-yl)prop-2-en-1-one (pk1) and 1-((3S,5R)-3-((7H-pyrrolo[2,3-d]pyrimidin-4-yl)amino)-5-methylpiperidin-1-yl)prop-2-en-1-one (pk 2).

Peak 1: $^1$H NMR (400 MHz, DMSO-d$_6$) δ 11.53 (br s, 1H), 8.10 (d, J=14.3 Hz, 1H), 7.42-7.23 (m, 1H), 7.08 (br s, 1H), 6.86 (td, J=11.4, 16.4 Hz, 1H), 6.57 (br s, 1H), 6.18-6.06 (m, 1H), 5.70 (t, J=10.2 Hz, 1H), 4.71 (d, J=9.8 Hz, 1H), 4.48-4.30 (m, 1H), 4.03 (d, J=11.8 Hz, 1H), 2.79-2.54 (m, 1H), 2.42-2.14 (m, 1H), 2.06 (d, J=12.5 Hz, 1H), 1.63 (br s, 1H), 1.39-1.17 (m, 1H), 0.99-0.87 (m, 3H). LCMS (M+H)=285.9. Peak 2: $^1$H NMR (400 MHz, DMSO-d$_6$) δ 11.53 (br s, 1H), 8.10 (d, J=14.6 Hz, 1H), 7.38-7.23 (m, 1H), 7.08 (br s, 1H), 6.94-6.79 (m, 1H), 6.56 (br s, 1H), 6.12 (dd, J=7.8, 16.8 Hz, 1H), 5.75-5.64 (m, 1H), 4.71 (d, J=11.8 Hz, 1H), 4.49-4.30 (m, 1H), 4.03 (d, J=11.5 Hz, 1H), 2.81-2.54 (m, 1H), 2.42-2.15 (m, 1H), 2.06 (d, J=12.3 Hz, 1H), 1.62 (br s, 1H), 1.38-1.18 (m, 1H), 0.99-0.88 (m, 3H). LCMS (M+H) 285.9.

Example 15: 1-((3R,5S)-3-((7H-Pyrrolo[2,3-d]pyrimidin-4-yl)amino)-5-fluoropiperidin-1-yl)prop-2-en-1-one Step 1. (2S,4R)-Methyl 1-benzyl-4-hydroxypyrrolidine-2-carboxylate To a stirred solution of (2S,4R)-methyl 4-hydroxypyrrolidine-2-carboxylate (35 g, 193 mmol, 1 eq.) in DCM (300 mL) was added Et$_3$N (78 g, 772 mmol, 4 eq.) and BnBr (39.5 g, 231 mmol, 1.2 eq.) in turns at 0° C. The reaction mixture was stirred at room temperature for 12 hours. After TLC (DCM/MeOH, 10:1) showed the reaction complete, the reaction mixture was diluted with saturated sodium carbonate (200 ml). The organic layer was washed with brine (200 mL), dried over Na$_2$SO$_4$ and concentrated to dryness, the crude product was purified by chromatography (MeOH/EtOAc, 0% to 10%) to give (2S,4R)-methyl 1-benzyl-4-hydroxypyrrolidine-2-carboxylate (30 g, 66%) as a yellow oil. $^1$H NMR (400 MHz, CDCl$_3$) δ ppm 2.16-2.39 (m, 1H) 2.42-2.65 (m, 2H) 3.18-3.37 (m, 2H) 3.60 (d, J=13.05 Hz, 1H) 3.71 (s, 3H) 4.03 (d, J=13.05 Hz, 1H) 4.97-5.23 (m, 1H) 7.22-7.39 (m, 5H).

Step 2. (2S,4S)-Methyl 1-benzyl-4-fluoropyrrolidine-2-carboxylate

To a stirred solution of (2S,4R)-methyl 1-benzyl-4-hydroxypyrrolidine-2-carboxylate (6 g, 25.37 mmol, 1 eq.) in anhydrous DCM (100 mL) was added DAST (10.2 g, 63.4 mmol, 2.5 eq.) at −78° C. under N$_2$. The reaction mixture was stirred at −78° C. for 0.5 hours and then warm to room temperature for 2 hours. After TLC (petroleum ether/ethyl acetate, 1:1) showed starting material to be consumed, the reaction mixture was quenched with saturated sodium carbonate (200 ml). The organic layer was separated out and the aqueous layer was extracted with CH$_2$Cl$_2$ again. The combined organic layers were washed with brine (200 mL), dried over Na$_2$SO$_4$ and concentrated to dryness, the crude product was purified by sp1 (EtOAc/petroleum ether, 10% to 80%) to give (2S,4S)-methyl 1-benzyl-4-fluoropyrrolidine-2-carboxylate (2 g, 34%) as a yellow oil. $^1$H NMR (400 MHz, CDCl$_3$) δ 2.20-2.37 (m, 1H) 2.43-2.67 (m, 2H) 3.22-3.35 (m, 2H) 3.60 (d, J=13.30 Hz, 1H) 3.67-3.75 (m, 3H) 4.03 (d, J=13.05 Hz, 1H) 4.99-5.22 (m, 1H) 7.22-7.38 (m, 5H).

Step 3. ((2S,4S)-1-Benzyl-4-fluoropyrrolidin-2-yl)methanol

To a stirred solution of LiAlH4 (1.28 g, 33.7 mmol, 1 eq.) in anhydrous THF (50 mL) was added dropwise a solution of (2S,4S)-methyl 1-benzyl-4-fluoropyrrolidine-2-carboxylate (8 g, 33.7 mmol, 1 eq.) in anhydrous THF (50 mL) at 0° C. The reaction mixture was stirred at room temperature for 10 hours. After TLC (petroleum ether/ethyl acetate, 4:1) showed starting material to be consumed, the reaction mixture was cooled to 0° C. and sequentially quenched with water (1.3 ml), 15% NaOH solution (1.3 ml) and water (3.9 ml). MgSO$_4$ (5 g) was added and the mixture was warmed to room temperature and stirred for 0.5 hours. The mixture was filtered and concentrated in vacuum to give the crude product, which was purified by sp1 (EtOAc/petroleum ether, 40% to 100%) to give (2S,4S)-1-benzyl-4-fluoropyrrolidin-2-yl)methanol (6 g, 70%) as a yellow oil. $^1$H NMR (400 MHz, CDCl$_3$) δ 2.09-2.51 (m, 3H) 2.62 (d, J=9.03 Hz, 1H) 2.80 (t, J=6.53 Hz, 1H) 3.13-3.35 (m, 2H) 3.49 (t, J=9.79 Hz, 1H) 3.77 (dd, J=11.04, 3.01 Hz, 1H) 4.05 (d, J=13.05 Hz, 1H) 4.94-5.16 (m, 1H) 7.22-7.39 (m, 5H).

Step 4. (3R,5S)-3-Azido-1-benzyl-5-fluoropiperidine and (2S,4S)-2-(azidomethyl)-1-benzyl-4-fluoropyrrolidine To a stirred solution of (2S,4S)-1-benzyl-4-fluoropyrrolidin-2-yl)methanol (4 g, 19 mmol, 1 eq.) in anhydrous DCM (200 mL) was added n-Bu$_4$NN$_3$ (5.96 g, 21 mmol, 1.1 eq.) and XtalFluor® (4.8 g, 21 mmol, 1.1 eq.) at −78° C. under N$_2$ protection. The reaction mixture was stirred at −78° C. for 6 hours. After TLC (petroleum ether/ethyl acetate, 4:1) showed starting material to be consumed, the reaction mixture was quenched with 15% NaOH solution (30 ml), and concentrated to dryness. The residue was purified by chromatography (EtOAc/petroleum ether, 0% to 20%) to give a mixture of (3R,5S)-3-azido-1-benzyl-5-fluoropiperidine and (2S,4S)-2-(azidomethyl)-1-benzyl-4-fluoropyrrolidine (2.2 g, 50%) as a yellow oil. The mixture was separated via SFC (ChiralPak AD, 300×50 mm, 10 µm, 15% MeOH/NH$_4$OH, 180 mL/min) to give (3R,5S)-3-azido-1-benzyl-5-fluoropiperidine (1.2 g) and (2S,4S)-2-(azidomethyl)-1-benzyl-4-fluoropyrrolidine (1 g) as yellow oil. (3R,5S)-3-azido-1-benzyl-5-fluoropiperidine: $^1$H NMR (400 MHz, CDCl$_3$) δ 1.48-1.67 (m, 1H) 2.04-2.22 (m, 2H) 2.34 (br s, 4H) 2.58-2.90 (m, 2H) 2.97-3.10 (m, 1H) 3.50-3.65 (m, 2H) 4.55-4.82 (m, 1H) 7.19-7.41 (m, 5H).

Step 5. (3R,5S)-1-Benzyl-5-fluoropiperidin-3-amine

To a solution of (3R,5S)-3-azido-1-benzyl-5-fluoropiperidine (1.4 g, 5.9 mmol, 1 eq.) in THF (50 mL) was added PPh$_3$ (2.35 g, 90 mmol, 1.5 eq.) in portions at room temperature. The reaction mixture was stirred at rt for 3 hours. Then water (0.7 ml) was added dropwise to the mixture and heated to 60° C. for 10 hours. After TLC (petroleum ether/ethyl acetate, 4:1) showed starting material to be consumed, the reaction mixture was concentrated to dryness, and purified by sp1 (MeOH/CH$_2$Cl$_2$ 0% to 10%) to give (3R,5S)-1-benzyl-5-fluoropiperidin-3-amine (1.1 g, 80%) as a colorless oil. LC/MS (M+H)=209.2. $^1$H NMR (400 MHz, CDCl$_3$) δ 1.37-1.53 (m, 1H) 1.99 (t, J=9.41 Hz, 1H) 2.12-

2.36 (m, 2H) 2.70 (d, J=10.29 Hz, 1H) 2.82-3.01 (m, 2H) 3.53-3.62 (m, 2H) 4.55-4.77 (m, 1H) 7.22-7.37 (m, 5H).

Step 6. N-((3R,5S)-1-Benzyl-5-fluoropiperidin-3-yl)-2-chloro-7H-pyrrolo[2,3-d]pyrimidin-4-amine A mixture of (3R,5S)-1-benzyl-5-fluoropiperidin-3-amine (300 mg, 1.44 mmol), DIPEA (929 mg, 7.2 mmol) and 2,4-dichloro-7H-pyrrolo[2,3-d]pyrimidine (297 mg, 1.59 mmol) in n-BuOH (10 mL) was heated to 130-140° C. overnight. After LC-MS showed the reaction to be complete, the reaction mixture was cooled to room temperature and evaporated to dryness in vacuo at 45° C. The residue was diluted with EtOAc (30 mL) and washed with water (20 mL). The aqueous layer was extracted with EtOAc (30 mL). The combined organic layers were washed with water and brine, dried over $Na_2SO_4$ and concentrated to give crude product, which was purified via chromatography (EtOAc/petroleum ether, 10% to 80%) to give N-((3R,5S)-1-benzyl-5-fluoropiperidin-3-yl)-2-chloro-7H-pyrrolo[2,3-d]pyrimidin-4-amine (300 mg, 65%) as a yellow solid. LC/MS (M+H)=359.2.

Step 7. N-((3R,5S)-5-Fluoropiperidin-3-yl)-7H-pyrrolo[2,3-d]pyrimidin-4-amine To a dry Parr hydrogenation bottle, 10% dry Pd/C (50 mg) was added under Ar atmosphere. A solution of N-((3R,5S)-1-benzyl-5-fluoropiperidin-3-yl)-2-chloro-7H-pyrrolo[2,3-d]pyrimidin-4-amine (300 mg, 0.84 mmol) in MeOH (20 mL) was added and the resulting mixture was hydrogenated under 50 psi of $H_2$ at 35° C. for 72 hours. The reaction mixture was filtered through a pad of Celite®, and the filter cake was washed with MeOH three times. The combined filtrate was concentrated to give N-((3R,5S)-5-fluoropiperidin-3-yl)-7H-pyrrolo[2,3-d]pyrimidin-4-amine (200 mg, 100%) as a white solid. $^1$H NMR (400 MHz, DMSO-$d_6$) δ 0.74-1.28 (m, 1H) 1.94-2.11 (m, 1H) 2.31-2.46 (m, 1H) 2.96 (dd, J=12.17, 8.41 Hz, 1H) 3.43-3.56 (m, 2H) 4.12 (br s, 1H) 4.57 (br s, 1H) 4.86-5.12 (m, 1H) 6.62 (d, J=2.01 Hz, 1H) 7.12 (br s, 1H) 7.53 (d, J=7.53 Hz, 1H) 8.06-8.19 (m, 1H) 11.61 (br s, 1H).

Step 8. 1-((3R,5S)-3-((7H-Pyrrolo[2,3-d]pyrimidin-4-yl)amino)-5-fluoropiperidin-1-yl)prop-2-en-1-one To a solution of N-((3R,5S)-5-fluoropiperidin-3-yl)-7H-pyrrolo[2,3-d]pyrimidin-4-amine (100 mg, 0.424 mmol) in THF (3 mL) and aq. NaHCO$_3$ solution (3 mL) at 0° C. was added acryloyl chloride (42 mg, 0.468 mmol) dropwise at 0° C. carefully. The resulting mixture was stirred at 0° C. for 2 hours. After TLC (DCM/MeOH, 10:1) showed starting material to be consumed, the reaction mixture was diluted with water (20 mL) and extracted with EtOAc (30 mL×2); the combined organic layers were washed with brine, dried over Na$_2$SO$_4$ and concentrated to give crude product, which was further purified by column chromatography on silica gel (MeOH/DCM, 0% to 8%) to give 1-((3R,5S)-3-((7H-pyrrolo[2,3-d]pyrimidin-4-yl)amino)-5-fluoropiperidin-1-yl)prop-2-en-1-one (60 mg, 50%) as a white solid. The solid was further purified by RP-HPLC to give pure product (25.7 mg). HPLC: Column: DIKMA Diamonsil(2) C18 200×20 mm*5 μm; Mobile phase: 0% MeCN (0.225% FA) in water (0.225% FA) to 10% MeCN (0.225% FA) in water (0.225% FA). $^1$H NMR (400 MHz, DMSO-$d_6$) δ 1.75-2.13 (m, 1H) 1.82-2.12 (m, 1H) 2.36-2.48 (m, 1H) 3.25 (br s, 1H) 4.27 (br s, 3H) 4.61-4.88 (m, 1H) 5.67 (d, J=9.03 Hz, 1H) 6.10 (dd, J=16.81, 2.26 Hz, 1H) 6.52 (d, J=2.51 Hz, 1H) 6.64-6.82 (m, 1H) 6.90 (d, J=7.03 Hz, 1H) 7.08 (br s, 1H) 8.15 (s, 1H) 11.35 (br s, 1H).

Example 16: 1-((1R,2R,5R)-2-((7H-Pyrrolo[2,3-d]pyrimidin-4-yl)amino)-8-azabicyclo[3.2.1]octan-8-yl)prop-2-en-1-one

Step 1. Rac-N-(8-Methyl-8-azabicyclo[3.2.1]octan-2-yl)-7-tosyl-7H-pyrrolo[2,3-d]pyrimidin-4-amine A solution of the 4-chloro-7-tosyl-7H-pyrrolo[2,3-d]pyrimidine, 8-methyl-8-azabicyclo[3.2.1]octan-2-amine (Pharmablock), and DIEA in 1-butanol (30 mL) was heated to 80° C. overnight. LCMS showed the pyrrolopyrimidine was consumed, and ionization consistent with the desired product. The reaction was concentrated in vacuo, and the crude material was partitioned between ethyl acetate (10 mL) and water (20 mL). The mixture was filtered and the solid was washed with ether to give 6 g of rac-N-(8-methyl-8-azabicyclo[3.2.1]octan-2-yl)-7-tosyl-7H-pyrrolo[2,3-d]pyrimidin-4-amine. LC/MS (M+H)=412.1.

Step 2. N-((1R,2R,5S)-8-Azabicyclo[3.2.1]octan-2-yl)-7-tosyl-7H-pyrrolo[2,3-d]pyrimidin-4-amine To a solution of rac-N-(8-methyl-8-azabicyclo[3.2.1]octan-2-yl)-7-tosyl-7H-pyrrolo[2,3-d]pyrimidin-4-amine (4.0 g, 9.72 mmol) in DCE (50 mL) at 0° C. was added NaHCO$_3$ (10 eq, 97.2 mmol, 8.25 g mg) in DCE (50 mL) followed by 1-chloroethyl chloroformate (10 eq, 10.6 mL, 97.2 mmol). After 10 min, the reaction was allowed to warm to room temperature. The resulting mixture was heated to 50° C. for 4 hrs. After cooling to room temperature, the reaction mixture was poured into Na$_2$CO$_3$ (2N) and the organic layers were separated. The aqueous layer was extracted with DCM. The combined organic layer was evaporated to dryness. The residue was dissolved in EtOH (120 mL) and refluxed for 4 h. All volatiles were removed in vacuo. The residue was treated with DCM and Na$_2$CO$_3$ (aq). The organic layer was separated and the aqueous layer was extracted with DCM. The combined organic extracts were dried (Na$_2$SO$_4$) and solvent was removed to give 4.0 g of crude product. The crude product was purified by CombiFlash® (40 g gold column, 0 to 10% 2M NH3 in MeOH in DCM) to give 2 g of racemic N-((1R,2R,5S)-8-azabicyclo[3.2.1]oc-tan-2-yl)-7-tosyl-7H-pyrrolo[2,3-d]pyrimidin-4-amine. LC/MS (M+H)=398.1 (M+H). $^1$H NMR (400 MHz, CDCl$_3$) δ 8.42 (s, 1H), 8.08-8.02 (m, 2H), 7.46-7.48 (m, 1H), 7.33-7.27 (m, 2H), 6.57-6.52 (m, 1H), 5.03-4.91 (m, 1H), 4.33-4.26 (m, 1H), 3.76 (bs, 1H), 3.60 (bs, 1H), 2.37 (s, 3H), 2.03-1.26 (m, 9H). racemic N-((1R,2R,5S)-8-azabicyclo[3.2.1]octan-2-yl)-7-tosyl-7H-pyrrolo[2,3-d]pyrimidin-4-amine (1 g) was purified by chiral SFC to provide 400 mg of two peaks: enantiomer 1 (pk1): N-((1R,2R,5S)-8-azabicyclo[3.2.1]oc-tan-2-yl)-7-tosyl-7H-pyrrolo[2,3-d]pyrimidin-4-amine and enantiomer 2 (pk 2): N-((1S,2S,5R)-8-azabicyclo[3.2.1]oc-tan-2-yl)-7-tosyl-7H-pyrrolo[2,3-d]pyrimidin-4-amine. Column: Chiral Tech AS-H 250 mm×21.2 mm 5 um Isocratic Conditions: Mobile Phase A: 80% CO2; Mobile Phase B: 20%; Methanol+0.2% NH4OH; Detection 210 nM; Flow: 80.0 mL/min; Backpressure: 120 Bar.

Step 3. 1-((1R,2R,5R)-2-((7-Tosyl-7H-pyrrolo[2,3-d]pyrimidin-4-yl)amino)-8-azabicyclo[3.2.1]octan-8-yl)prop-2-en-1-one To a solution N-((1R,2R,5S)-8-azabicyclo[3.2.1]octan-2-yl)-7-tosyl-7H-pyrrolo[2,3-d]pyrimidin-4-amine (pk1) in chloroform (10 mL) was added DIPEA. The solution was cooled to 0° C. and acryloyl chloride (in 1 mL of CHCl$_3$) was added over 5 min. The reaction was stirred for 30 minutes. Na$_2$CO$_3$ (10%; 5 mL) was added. The reaction was stirred at 0° C. for 0.5 hr and the organic phase was separated and the solvent was evaporated. The residue (300 mg) was purified by CombiFlash®(12 g gold column, 20 to 100% EA in Hept) to give 208 mg of 1-((1R,2R,5R)-2-((7-Tosyl-7H-pyrrolo[2,3-d]pyrimidin-4-yl)amino)-8-azabicyclo[3.2.1]octan-8-yl)prop-2-en-1-one. LC/MS (M+H): 452.2. $^1$H NMR (400 MHz, CDCl$_3$) δ 8.44 (s, 1H), 8.08-8.02 (m, 2H), 7.50-7.45 (m, 1H), 7.31-7.25 (m, 2H), 6.92-6.83 (m, 1H), 6.50-6.41 (m, 2H), 5.80-5.71 m, 1H), 5.01-4.97 (m, 1H), 4.78-4.73 (m, 1H), 4.69-4.60 (br s, 1H), 4.26-4.16 (m, 1H), 2.40 (s, 3H), 2.01-1.53 (m, 8H).

Step 4. 1-((1R,2R,5R)-2-((7H-Pyrrolo[2,3-d]pyrimidin-4-yl)amino)-8-azabicyclo[3.2.1]octan-8-yl)prop-2-en-1-one 1-((1R,2R,5R)-2-((7-Tosyl-7H-pyrrolo[2,3-d]pyrimidin-4-yl)amino)-8-azabicyclo[3.2.1]octan-8-yl)prop-2-en-1-one (200 mg) was dissolved in 5 mL of THF. TBAF (1M in THF, 1.9 mL) was added. The reaction was heated to 60° C. for 48 hrs. The solvent was removed in vacuo and the residue was treated with EtOAc and NH$_4$Cl (10%) (5 mL each). The layers were separated and the organic layer collected, washed with NH$_4$Cl (10%) and satd. Na—HCO$_3$ and brine. The organic fraction was collected, dried (Na$_2$SO$_4$) and the solvent removed to give 200 mg of crude product, which was purified by RP-HPLC to provide 90 mg of product. The product was further purified by CombiFlash® (12 g gold column, 0 to 10% MeOH in DCM) give 55 mg of 1-((1R,2R,5R)-2-((7H-pyrrolo[2,3-d]pyrimidin-4-yl)amino)-8-azabicyclo[3.2.1]octan-8-yl)prop-2-en-1-one. LC/MS (M+H) 298.3. $^1$H NMR (400 MHz, CDCl$_3$) δ 11.58-11.47 (m, 1H) 8.44-8.34 (m, 1H), 7.20-7.15 (m, 1H), 7.04-7.00 (m, 2H), 6.61-6.42 (m, 2H), 5.84-5.76 (m, 1H) 5.11-5.04 (m, 1H) 4.84-4.82 (m, 1H), 4.48-4.30 (m, 1H), 2.17-1.69 (m, 8H).

Example 17: 1-((3R,5S)-3-(7H-Pyrrolo[2,3-d]pyrimidin-4-ylamino)-5-hydroxypiperidin-1-yl)prop-2-en-1-one Step 1. (3S,5S)-5-((tert-Butyldimethylsilyl)oxy)piperidin-3-ol (3S,5S)-1-benzyl-5-((tert-butyldimethylsilyl)oxy)piperidin-3-ol (3.6 g, 11.196 mmol) was taken up in EtOH (30 ml) and the ethanol solution was degassed with argon for 15 mins after which 10% Pd/C (400 mg) was added and the resultant mixture was hydrogenated using a hydrogen bladder for 16 h. After TLC (5% MeOH in DCM) showed starting material to be consumed, the reaction mixture was filtered through a Celite® bed, and the filtrate was concentrated to obtain 3 g crude (3S,5S)-5-((tertbutyldimethylsilyl)oxy)piperidin-3-ol as light yellow oil. Crude (3S,5S)-5-((tertbutyldimethylsilyl)oxy)piperidin-3-ol was directly used for the next step.

Step 2. (3S,5S)-tert-Butyl 3-((tert-butyldimethylsilyl)oxy)-5-hydroxypiperidine-1-carboxylate To a stirred solution of (3S,5S)-5-((tert-butyldimethylsilyl)oxy)piperidin-3-ol (2.59 g, 11.192 mmol) in DCM (19 ml) at 0° C. was added TEA (3.12 ml, 22.385 mmol) and Boc$_2$O (3.086 ml, 13.431 mmol in a DCM (4 ml) solution). The reaction mixture was allowed to warm to room temperature over 45 min. After TLC (70% EtOAc in hexane) indicated starting material to be consumed, the reaction mixture was quenched with water (20 ml) and extracted with DCM (2×50 ml). The organic layers were combined and dried over Na$_2$SO$_4$ and concentrated to provide the crude product, which was purified by CombiFlash® (EtOAc/hexane, 100% hexane to 35% EtOAc in hexane) to afford 3.2 g (86%) (3S,5S)-tert-butyl 3-((tertbutyldimethylsilyl)oxy)-5-hydroxypiperidine-1-carboxylate as a light brown oil. $^1$H NMR (400 MHz, CDCl$_3$) δ 0.03-0.10 (m, 6H) 0.87 (s, 9H) 1.45 (s, 9H) 1.68 (br s, 1H) 1.78-1.88 (m, 1H) 3.08 (br s, 1H) 3.39 (br s, 2H) 3.57 (dd, J=13.69, 3.42 Hz, 1H) 3.87-4.11 (m, 2H).

Step 3. (3S,5S)-tert-Butyl 3-((tert-butyldimethylsilyl)oxy)-5-((methylsulfonyl)oxy)piperidine-1-carboxylate To a stirred solution of (3S,5S)-tert-butyl 3-((tert-butyldimethylsilyl)oxy)-5-hydroxypiperidine-1-carboxylate (3.5 g, 10.557 mmol) in DCM (25 ml) at 0° C. was added TEA (4.414 ml, 31.671 mmol) followed by mesyl chloride (1.06 ml, 13.724 mmol). The reaction mixture was allowed to stir for 4 h. After TLC (30% EtOAc in hexane) indicated clean conversion, the reaction mixture was quenched with water and extracted with DCM (2×75 ml). The combined organic fractions were dried over Na$_2$SO$_4$ and concentrated to provide 4.5 g crude (3S,5S)-tert-butyl 3-((tert-butyldimethylsilyl)oxy)-5-((methylsulfonyl)oxy)piperidine-1-carboxylate as light yellow oil, which was used for the next step directly. $^1$H NMR (400 MHz, CDCl$_3$) δ 0.08 (d, J=1.47 Hz, 6H) 0.88 (s, 9H) 1.33-1.49 (m, 9H) 1.85 (br s, 1H) 2.09 (br s, 1H) 2.90-3.08 (m, 4H) 3.40 (br s, 1H) 3.59-3.86 (m, 2H) 3.95 (br s, 1H) 4.94 (br s, 1H).

Step 4. (3R,5S)-tert-Butyl 3-azido-5-((tert-butyldimethylsilyl)oxy)piperidine-1-carboxylate To a stirred solution of (3S,5S)-tert-butyl 3-((tert-butyldimethylsilyl)oxy)-5-((methylsulfonyl)oxy)piperidine-1-carboxylate (4.32 g, 10.546 mmol) in DMF (35 ml) was added NaN$_3$ (2.057 g, 31.639 mmol). The reaction mixture was heated to 100° C. for 16 h. The reaction mixture was concentrated to remove DMF and the residue was taken up into EtOAc (200 ml) and washed with water (3×50 ml). The organic fractions were dried over Na$_2$SO$_4$ and concentrated to provide crude material, which after CombiFlash® (EtOAc/hexane, 100% hexane to 20% EtOAc in hexane) afforded 1.9 g (51%) (3R,5S)-tert-butyl 3-azido-5-((tert-butyldimethylsilyl)oxy)piperidine-1-carboxylate as a light yellow oil. $^1$H NMR (400 MHz, CDCl$_3$) δ 0.04-0.10 (m, 6H) 0.88 (s, 9H) 1.40-1.46 (m, 9H) 1.48-1.45 (m, 1H) 2.26 (d, J=12.23 Hz, 1H) 2.36-2.60 (m, 2H) 3.24-3.40 (m, 1H) 3.49-3.65 (m, 1H) 3.88-4.36 (m, 2H).

Step 5. (3R,5S)-tert-Butyl 3-amino-5-((tert-butyldimethylsilyl)oxy)piperidine-1-carboxylate To a stirred solution of (3R,5S)-tert-butyl 3-azido-5-((tert-butyldimethylsilyl)oxy)piperidine-1-carboxylate (1.9 g, 5.329 mmol) in THF (100 ml) was added H$_2$O (0.671 ml, 37.303 mmol) and PPh$_3$ (2.097 g, 7.993 mmol). The reaction mixture was refluxed for 16 h. The volatiles were removed under reduced pressure, and the crude product was purified by column chromatography using 100-200 silica and MeOH/DCM as eluent (100% DCM to 5% MeOH in DCM) to afford 1.52 g (86%) of (3R,5S)-tert-butyl 3-amino-5-((tert-butyldimethylsilyl)oxy)piperidine-1-carboxylate as a light yellow oil. $^1$H NMR (400 MHz, CDCl$_3$) δ 0.07 (d, J=0.98 Hz, 6H) 0.88 (s, 9H) 1.20-1.31 (m, 1H) 1.44 (s, 9H) 2.07 (s, 1H) 2.43-2.55 (m, 1H) 2.60-2.71 (m, 1H) 2.81 (m, J=9.30, 9.30 Hz, 1H) 3.53-3.69 (m, 1H) 3.78-3.97 (m, 2H).

Step 6. (3S,5R)-tert-Butyl 3-((tert-butyldimethylsilyl)oxy)-5-((7-tosyl-7H-pyrrolo[2,3-d]pyrimidin-4-yl)amino)piperidine-1-carboxylate To a stirred solution of (3R,5S)-tert-butyl 3-amino-5-((tert-butyldimethylsilyl)oxy)piperidine-1-carboxylate (1.52 g, 4.598 mmol) in n-butanol (10 ml) was added 4-chloro-7-tosyl-7H-pyrrolo[2,3-d]pyrimidine (1.698 g, 5.518 mmol) and DIPEA (1.642 ml, 9.197 mmol). The resulting mixture was refluxed for 36 h, and then the volatiles were removed under reduced pressure. The crude material was purified by CombiFlash® (EtOAc/hexane as eluent, 100% hexane to 60% EtOAc in hexane) to afford 2 g (72%) (3S,5R)-tert-butyl 3-((tertbutyldimethylsilyl)oxy)-5-((7-tosyl-7H-pyrrolo[2,3-d]pyrimidin-4-yl)amino)piperidine-1-carboxylate as a light yellow solid. $^1$H NMR (400 MHz, DMSO-d$_6$) δ ppm 0.09 (s, 6H) 0.87 (s, 9H) 1.12-1.58 (m, 10H) 2.13 (d, J=10.76 Hz, 1H) 2.33 (br s, 3H) 2.80-3.00 (m, 1H) 3.53-3.92 (m, 3H) 3.98-4.13 (m, 2H) 6.61-6.88 (m, 1H) 7.43 (d, J=8.31 Hz, 2H) 7.59 (br s, 2H) 7.96 (d, J=8.31 Hz, 2H) 8.25 (s, 1H).

Step 7. N-((3R,5S)-5-((tert-Butyldimethylsilyl)oxy)piperidin-3-yl)-7-tosyl-7H-pyrrolo[2,3-d]pyrimidin-4-amine To a stirred solution of (3S,5R)-tert-butyl 3-((tert-butyldimethylsilyl)oxy)-5-((7-tosyl-7H-pyrrolo[2,3-d]pyrimidin-4-yl)amino)piperidine-1-carboxylate (1 g, 1.662 mmol) in DCM (10 ml) at 0° C. was added TFA (0.763 ml, 9.969 mmol). The reaction mixture was allowed to come to ambient temp and stirred for 16 h. The reaction mixture was quenched with aq NaHCO$_3$ solution (10 ml) and extracted with DCM (2×30 ml). The organic fractions were dried over Na$_2$SO$_4$ and concentrated to provide crude material. The crude material was purified by CombiFlash® using (MeOH/DCM, 100% DCM to 8% MeOH in DCM) to afford 520 mg (62%) N-((3R,5S)-5-((tert-butyldimethylsilyl)oxy)piperidin-3-yl)-7-tosyl-7H-pyrrolo[2,3-d]pyrimidin-4-amine as light yellow solid. $^1$H NMR (400 MHz, DMSO-d$_6$) δ ppm 0.03 (s, 6H) 0.84 (s, 9H) 1.25 (br s, 2H) 1.32-1.43 (m, 1H) 2.01-2.20 (m, 2H) 2.35 (s, 3H) 2.80-3.05 (m, 2H) 3.53-3.70 (m, 1H) 4.05 (m, 1H) 6.88 (d, 1H) 7.43 (d, 2H) 7.50-7.62 (m, 2H) 7.96 (s, 2H) 8.21 (s, 1H).

Step 8. 1-((3S,5R)-3-((tert-Butyldimethylsilyl)oxy)-5-((7-tosyl-7H-pyrrolo[2,3-d]pyrimidin-4-yl)amino)piperidin-1-yl)prop-2-en-1-one To a stirred solution of N-((3R,5S)-5-((tert-butyldimethyl-silyl)oxy)piper-idin-3-yl)-7-tosyl-7H-pyrrolo[2,3-d]pyrimidin-4-amine (520 mg, 1.036 mmol) in DCM (20 ml) at 0° C. was added TEA (0.437 ml, 3.109 mmol) and Acryloyl chloride (0.084 ml, 1.036 mmol). The reaction mixture was allowed to stir at 0° C. for 30 minutes. The reaction was quenched with water (10 ml) and extracted with DCM (2×50 ml). The organic fractions were dried over Na$_2$SO$_4$ and concentrated to provide crude material, which was purified by CombiFlash® (EtOAc/hexane, 100% hexane to 70% EtOAc in hexane) to afford 450 mg 1-((3S,5R)-3-((tert-butyldimethylsilyl)oxy)-5-((7-tosyl-7H-pyrrolo[2,3-d]pyrimidin-4-yl)amino)piperidin-1-yl)prop-2-en-1-one as off white solid. $^1$H NMR (400 MHz, DMSO-d$_6$) δ ppm 0.08 (br s, 6H) 0.81-0.91 (m, 9H) 1.53-1.66 (m, 1H) 2.13-2.23 (m, 1H) 2.35 (s, 3H) 2.69-2.98 (m, 1H) 3.60-3.81 (m, 1H) 3.86-4.07 (m, 1H) 4.10-4.25 (m, 1H) 4.35-4.50 (m, 1H) 5.59-5.74 (m, 1H) 6.00-6.15 (m, 1H) 6.67-6.80 (m, 1H) 6.86 (m, 1H) 7.43 (d, 2H) 7.58 (d, J=3.91 Hz, 1H) 7.61-7.79 (m, 1H) 7.96 (d, J=8.31 Hz, 2H) 8.21-8.30 (m, 1H).

Step 9. 1-((3S,5R)-3-Hydroxy-5-((7-tosyl-7H-pyrrolo[2,3-d]pyrimidin-4-yl)amino)piperidin-1-yl)prop-2-en-1-one To a stirred solution of 1-((3S,5R)-3-((tert-butyldimethylsilyl)oxy)-5-((7-tosyl-7H-pyrrolo[2,3-d]pyrimidin-4-yl)amino)piperidin-1-yl)prop-2-en-1-one (450 mg, 0.81 mmol) in THF (5 ml) at 0° C. was added 1M TBAF in THF (1.21 ml, 1.21 mmol). The reaction mixture was allowed to come to ambient temp and stirred for 4 h. The reaction mixture was quenched with water (10 ml) and extracted with EtOAc (3×30 ml). The combined organic fractions were dried over Na$_2$SO$_4$ and concentrated to provide 300 mg of 1-((3S,5R)-3-hydroxy-5-((7-tosyl-7H-pyrrolo[2,3-d]pyrimidin-4-yl)amino)piperidin-1-yl)prop-2-en-1-one (crude) which was used for the next step without further purification. LC/MS (M+H)=442.2.

Step 10. 1-((3R,5S)-3-((7H-Pyrrolo[2,3-d]pyrimidin-4-yl)amino)-5-hydroxypiperidin-1-yl)prop-2-en-1-one To a solution of 1-((3S,5R)-3-hydroxy-5-((7-tosyl-7H-pyrrolo[2,3-d]pyrimidin-4-yl)amino)piperidin-1-yl)prop-2-en-1-one (300 mg, 0.679 mmol) in MeOH (5 ml) at 0° C. was added H$_2$O (1 ml) and K$_2$CO$_3$ (132.724 mg, 1.019 mmol). The reaction mixture was allowed to come to ambient temperature and stirred for 16 h. The volatiles were removed in vacuo and the crude material was taken up in EtOAc (50 ml) and washed with water (2×20 ml). The organic fractions were dried over Na$_2$SO$_4$ and concentrated to provide crude material, which after purification by preparative HPLC afforded 30 mg of 1-((3R,5S)-3-((7H-pyrrolo[2,3-d]pyrimidin-4-yl)amino)-5-hydroxypiperidin-1-yl)prop-2-en-1-one as white solid.

Prep-HPLC: Instrument: Waters auto purification instrument; Column: Zorbax SB-C18 (250×21.2 mm); Mobile Phase: Gradient of Methanol and 0.05% TFA in H2O; Detector: PDA. LC/MS (M+H)=288.

$^1$H NMR (400 MHz, MeOH-d$_4$) δ ppm 1.17-1.35 (m, 2H) 1.67-1.90 (m, 1H) 2.32 (d, J=12.72 Hz, 1H) 3.38-3.49 (m, 1H) 3.77-3.96 (m, 1H) 3.99-4.19 (m, 1H) 4.23-4.44 (m, 1H) 5.47-5.81 (m, 1H) 6.00-6.21 (m, 1H) 6.48 (d, J=2.93 Hz, 1H) 6.56-6.89 (m, 1H) 7.08 (br s, 1H) 8.04-8.20 (m, 1H).

Example 18: 1-((2S,5R)-5-((5-Chloro-7H-pyrrolo[2,3-d]pyrimidin-4-yl)amino)-2-methylpiperidin-1-yl)prop-2-en-1-one

Step 1. (2S,5R)-Benzyl 5-((5-chloro-7H-pyrrolo[2,3-d]pyrimidin-4-yl)amino)-2-methylpiperidine-1-carboxylate Prepared as in Example 13: (2S,5R)-benzyl 5-((5-chloro-7H-pyrrolo[2,3-d]pyrimidin-4-yl)amino)-2-methylpiperidine-1-carboxylate (190 mg, 56%). LC/MS (M+H)=400.1.

Step 2. 5-Chloro-N-((3R,6S)-6-methylpiperidin-3-yl)-7H-pyrrolo[2,3-d]pyrimidin-4-amine To a flask containing (2S,5R)-benzyl 5-((5-chloro-7H-pyrrolo[2,3-d]pyrimidin-4-yl)amino)-2-methylpiperidine-1-carboxylate (190 mg, 0.47 mmol) was added DCM (5 mL) and HBr/AcOH (5 mL). After stirring at 25° C. for 3 hrs, 50 mL of diethyl ether was added and the reaction stirred for 15 min and filtered. The solid was dried to give 5-chloro-N-((3R,6S)-6-methylpiperidin-3-yl)-7H-pyrrolo[2,3-d]pyrimidin-4-amine as the HBr salt (170 mg, 83%) LC/MS (M+H)=266.1

Step 3. Prep of 1-((2S,5R)-5-((5-chloro-7H-pyrrolo[2,3-d]pyrimidin-4-yl)amino)-2-methylpiperidin-1-yl)prop-2-en-1-one To a flask containing 5-chloro-N-((3R,6S)-6-methylpiperidin-3-yl)-7H-pyrrolo[2,3-d]pyrimidin-4-amine-HBr (170 mg, 0.49 mmol) salt was added DCM (5 mL) and Hunigs base (0.24 mL, 2.8 mL). The mixture was cooled to 0° C. and then acryloyl chloride in DCM (0.04 mL in 2 mL DCM) was added dropwise. After the addition, the reaction was stirred at rt for 1 hr and then poured into water. The layers were separated and the organic layer collected, dried ($Na_2SO_4$) and the solvent removed to give a yellow solid, which was purified by RP-HPLC to give 1-((2S,5R)-5-((5-chloro-7H-pyrrolo[2,3-d]pyrimidin-4-yl)amino)-2-methylpiperidin-1-yl)prop-2-en-1-one (33 mg, 21%). LC/MS (M+H)=320.1. $^1$H NMR (400 MHz, MeOH-$d_4$) d ppm 1.24-1.45 (m, 3H) 1.77-1.98 (m, 2H) 2.01-2.16 (m, 2H) 3.03-3.23 (m, 1H) 4.12 (br s, 1H) 4.45-4.74 (m, 2H) 5.80 (dd, 1H) 6.25 (dd, 1H) 6.85 (dd, 1H) 7.37 (s, 1H) 8.32 (s, 1H).

Example 19: 1-((3R,5S)-3-((7H-Pyrrolo[2,3-d]pyrimidin-4-yl)amino)-5-methoxypiperidin-1-yl)prop-2-en-1-one

Step 1. (3S,5R)-tert-Butyl 3-((tert-butyldimethylsilyl)oxy)-5-((7-trityl-7H-pyrrolo[2,3-d]pyrimidin-4-yl)amino)piperidine-1-carboxylate To a solution of (3R,5S)-tert-butyl 3-amino-5-((tert-butyldimethyl-silyl)oxy)piperidine-1-carboxylate (from ex 17:step 6) (700 mg, 2.117 mmol) in n-BuOH (10 mL) was added 4-chloro-7-trityl-7H-pyrrolo[2,3-d]pyrimidine (1.257 g, 3.176 mmol), followed by DIPEA (802 mg, 6.351 mmol) at room temperature. The resultant mixture was heated to 120° C. overnight. After TLC (Petroleum ether: EtOAc, 2:1) showed the starting material to be consumed, the mixture was concentrated to dryness to give crude product which was purified by column chromatography (silica, EtOAc/Petroleum ether, 0-45%) to give (3S,5R)-tert-butyl 3-((tert-butyldimethylsilyl)oxy)-5-((7-trityl-7H-pyrrolo[2,3-d]pyrimidin-4-yl)amino)piperidine-1-carboxylate (708 mg, 48%) as a white solid. LC/MS (M+H) 690.9.

Step 2. (3S,5R)-tert-Butyl 3-hydroxy-5-((7-trityl-7H-pyrrolo[2,3-d]pyrimidin-4-yl)amino)piperidine-1-carboxylate To a solution of (3S,5R)-tert-butyl 3-((tertbutyldimethylsilyl)oxy)-5-((7-trityl-7H-pyrrolo[2,3-d]pyrimidin-4-yl)amino)piperidine-1-carboxylate (708 mg, 1.026 mmol) in THF (15 mL) was added TBAF (536.5 mg, 2.052 mmol) at room temperature. The resulting solution was warmed and stirred at 40° C. overnight. After TLC (EtOAc) showed the starting material to be consumed, the reaction mixture was separated between EtOAc (20 mL) and $H_2O$ (20 mL). The organic layer was washed with brine, dried over $Na_2SO_4$ and concentrated to dryness to give crude (3S,5R)-tert-butyl 3-hydroxy-5-((7-trityl-7H-pyrrolo[2,3-d]pyrimidin-4-yl)amino)piperidine-1-carboxylate (550 mg, 93%) as a white solid, which was directly used to next step without further purification. LC/MS (M+H) 576.3.

Step 3. (3S,5R)-tert-Butyl 3-methoxy-5-((7-trityl-7H-pyrrolo[2,3-d]pyrimidin-4-yl)amino)piperidine-1-carboxylate To a solution of (3S,5R)-tert-butyl 3-hydroxy-5-((7-trityl-7H-pyrrolo[2, 3-d]pyrimidin-4-yl)amino)piperidine-1-carboxylate (550 mg, 0.955 mmol)) in anhydrous THF (10 mL) was added NaH (84 mg, 2.101 mmol) at 0° C. under $N_2$. The resultant suspension was stirred at 0° C. for 10 min. MeI (162.8 mg, 1.146 mmol) in anhydrous THF (40 mL) was the added. The resultant mixture was stirred at room temperature overnight. After TLC (EtOAc) showed the starting material to be consumed, the reaction mixture was quenched with water, and extracted with EtOAc (10 mL×2). The combined organic layers were washed with brine, dried over $Na_2SO_4$ and concentrated to dryness to give crude product which was purified by column chromatography (silica, EtOAc: Petroleum ether, 0-60%) to give (3S,5R)-tert-butyl 3-methoxy-5-((7-trityl-7H-pyrrolo[2,3-d]pyrimidin-4-yl)amino)piperidine-1-carboxylate (400 mg, 71%) as a white solid. LC/MS (M+H)=590.3.

Step 4. N-((3R,5S)-5-Methoxypiperidin-3-yl)-7-trityl-7H-pyrrolo[2,3-d]pyrimidin-4-amine To a solution of (3S,5R)-tert-butyl 3-methoxy-5-((7-trityl-7H-pyrrolo[2,3-d]pyrimidin-4-yl)amino)piperidine-1-carboxylate (400 mg, 0.68 mmol) in anhydrous DCM (4 mL) was added 4M HCl/dioxane (4 mL) dropwise at 0° C. The resulting solution was stirred at 0° C. for 1 h. After TLC (EtOAc) showed the starting material to be consumed, the mixture was concentrated to dryness to give N-((3R,5S)-5-methoxypiperidin-3-yl)-7-trityl-7H-pyrrolo[2,3-d]pyrimidin-4-amine (356 mg, 100%) as a white solid.

Step 5. 1-((3S,5R)-3-Methoxy-5-((7-trityl-7H-pyrrolo[2,3-d]pyrimidin-4-yl)amino)piperidin-1-yl)prop-2-en-1-one To a solution of N-((3R,5S)-5-methoxypiperidin-3-yl)-7-trityl-7H-pyrrolo[2,3-d]pyrimidin-4-amine (356 mg, 0.68 mmol) in THF (10 mL) and sat. $NaHCO_3$ (aq) (10 mL) was added acryl-Cl (73.3 mg, 0.815 mmol) at 0° C. The resultant mixture was stirred at 0° C. for 1 h. TLC (EtOAc) showed the starting material was consumed completely. The reaction mixture was separated between THF and water. The aqueous layer was extracted with EtOAc (10 mL×2). The combined organic layers were washed with brine, dried over $Na_2SO_4$ and concentrated to dryness to give crude 1-((3S,5R)-3-methoxy-5-((7-trityl-7H-pyrrolo[2,3-d]pyrimidin-4-yl)amino)piperidin-1-yl)prop-2-en-1-one (348 mg, 100%) as a white solid. which was directly used to the next step without further purification. LC/MS (M+H)=544.0.

Step 6. 1-((3R,5S)-3-((7H-Pyrrolo[2,3-d]pyrimidin-4-yl)amino)-5-methoxypiperidin-1-yl)prop-2-en-1-one A solution of 1-((3S,5R)-3-methoxy-5-((7-trityl-7H-pyrrolo[2,3-d]pyrimidin-4-yl)amino)piperidin-1-yl)prop-2-en- 1-one (348 mg, 0.64 mmol) in TFA (5 mL) was stirred at 40° C. overnight. TLC (EtOAc) showed the starting material was consumed completely. The mixture was diluted with THF and concentrated to dryness to give crude product which was purified by column chromatography (silica, MeOH: EtOAc=0-33%) and RP-HPLC to give 1-((3R,5S)-3-((7H-pyrrolo[2,3-d]pyrimidin-4-yl)amino)-5-methoxypiperidin-1-yl)prop-2-en-1-one (12.1 mg, 6.3%) as a white solid. LC/MS (M+H)=302.1. $^1$H NMR (400 MHz, DMSO-d$_6$) δ 1.43-1.66 (m, 1H) 2.36 (d, 1H) 2.57-3.05 (m, 2H) 3.19-3.35 (m, 3H) 4.18 (d, 2H) 4.45 (d, 1H) 5.61-5.76 (m, 1H) 6.02-6.17 (m, 1H) 6.51 (d, 1H) 6.63-6.97 (m, 1H) 7.10 (d, 1H) 7.19-7.33 (m, 1H) 8.05-8.17 (m, 1H) 11.56 (br s, 1H).

Example 20: (R)-2-(4-((1-Acryloylpiperidin-3-yl)amino)-7H-pyrrolo[2,3-d]pyrimidin-5-yl)acetonitrile Similar to preparation of Example 12, except using Het-Cl as 2-(4-chloro-7H-pyrrolo[2,3-d]pyrimidin-5-yl)acetonitrile. LC/MS (M+H)=311.1.

Example 21: rac-1-((3aR,7aR)-1-(7H-Pyrrolo[2,3-d]pyrimidin-4-yl)hexahydro-1H-pyrrolo[2,3-c]pyridin-6(2H)-yl)prop-2-en-1-one Similar to preparation of rac-1-((3aS,7aS)-1-(7H-pyrrolo[2,3-d]pyrimidin-4-yl)hexahydro-1H-pyrrolo[2,3-c]pyridin-6(2H)-yl)prop-2-en-1-one (ex 8), except using rac-(3aR,7aR)-benzyl hexahydro-1H-pyrrolo[2,3-c]pyridine-6(2H)-carboxylate through the synthetic sequence. LC/MS (M+H)=298.1. $^1$H NMR (400 MHz, DMSO-d$_6$) δ 11.583 (s, 1H) ?8.09-8.07 (d, J=9.2 Hz, 1H) 7.11 (s, 1H), 6.82-6.78 (m, 1H), 6.510 (m, 1H), 6.05-6.01 (m, 1H), 5.695-5.851 (m, 1H), 4.69-4.68 (m, 0.5H), 4.27 (s, 1H), 3.90-3.74 (m, 3H), 3.13-3.24 (m, 2H), 2.74-2.71 (m, 0.5H), 2.19-1.74 (m, 4.5H).

Example 22: rac-cis-1-((3R,5S)-3-((7H-Pyrrolo[2,3-d]pyrimidin-4-yl)amino)-5-methylpiperidin-1-yl)prop-2-en-1-one See Example 14 (step 7). To a solution of rac-cis-N-((3R,5S)-5-methylpiperidin-3-yl)-7H-pyrrolo[2,3-d]pyrimidin-4-amine (400 mg, 1.494 mmol) in THF (20 mL) was added saturated aq.NaHCO3 (15 mL) at 0° C. was added acryloyl chloride (149 mg, 1.643 mmol, 1.1 eq.) slowly. The reaction was stirred at 0° C. for 2 hours. After TLC (EtOAc:MeOH=10:1) showed the reaction to be complete, the reaction mixture was diluted with water (80 mL), and extracted with EtOAc (80 mL×2). The combined organic layers were washed with brine, dried over Na$_2$SO$_4$ and concentrated. The residue was purified by flash column chromatography (EtOAc/MeOH, 10:1) to give rac-cis-1-((3R,5S)-3-((7H-pyrrolo[2,3-d]pyrimidin-4-yl)amino)-5-methylpiperidin-1-yl)prop-2-en-1-one (300 mg, 71%) as a white solid. $^1$H NMR (400 MHz, DMSO-d$_6$) δ 11.52 (br s, 1H), 8.10 (d, J=14.3 Hz, 1H), 7.39-7.22 (m, 1H), 7.07 (br s, 1H), 6.94-6.78 (m, 1H), 6.56 (br s, 1H), 6.12 (dd, J=8.9, 16.2 Hz, 1H), 5.69 (t, J=10.4 Hz, 1H), 4.71 (d, J=10.0 Hz, 1H), 4.47-4.29 (m, 1H), 4.03 (d, J=11.0 Hz, 2H), 2.73 (t, J=11.5 Hz, 1H), 2.58 (t, J=12.3 Hz, 1H), 2.40-2.30 (m, 1H), 2.19 (t, J=11.5 Hz, 1H), 2.05 (d, J=11.8 Hz, 1H), 1.36-1.17 (m, 1H), 0.97-0.89 (m, 3H). LCMS (M+H) 285.9.

Examples 23-40

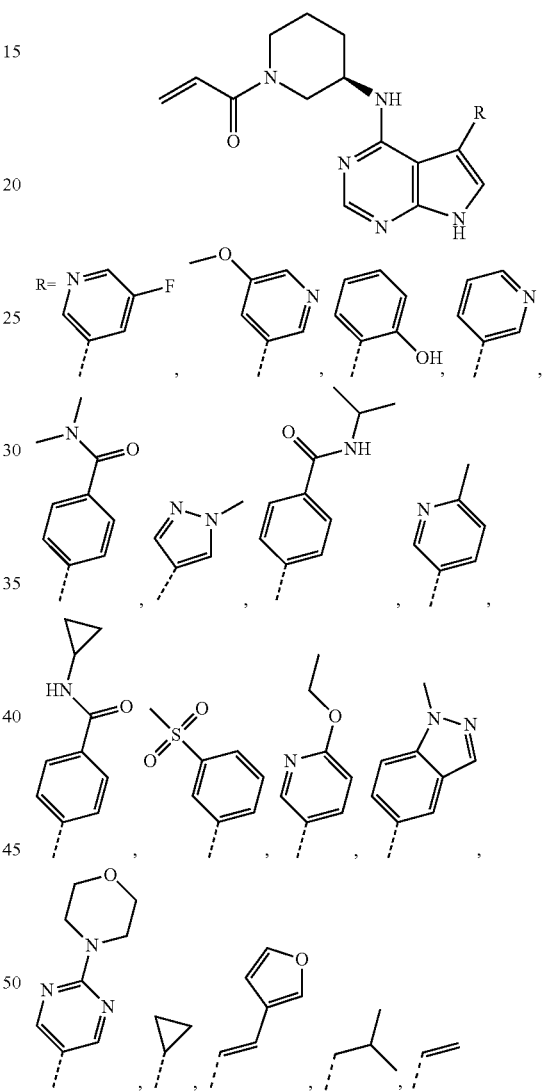

| Example | LC/MS | IUPAC NAME |
|---|---|---|
| 23 | 367 | 1-[(3R)-3-{[5-(5-fluoropyridin-3-yl)-7H-pyrrolo[2,3-d]pyrimidin-4-yl]amino}piperidin-1-yl]prop-2-en-1-one |
| 24 | 379 | 1-[(3R)-3-{[5-(5-methoxypyridin-3-yl)-7H-pyrrolo[2,3-d]pyrimidin-4-yl]amino}piperidin-1-yl]prop-2-en-1-one |
| 25 | 364 | 1-[(3R)-3-{[5-(2-hydroxyphenyl)-7H-pyrrolo[2,3-d]pyrimidin-4-yl]amino}piperidin-1-yl]prop-2-en-1-one |
| 26 | 349 | 1-[(3R)-3-{[5-(pyridin-3-yl)-7H-pyrrolo[2,3-d]pyrimidin-4-yl]amino}piperidin-1-yl]prop-2-en-1-one |

| Example | LC/MS | IUPAC NAME |
|---|---|---|
| 27 | 419 | 4-(4-{[(3R)-1-acryloylpiperidin-3-yl]amino}-7H-pyrrolo[2,3-d]pyrimidin-5-yl)-N,N-dimethylbenzamide |
| 28 | 352 | 1-[(3R)-3-{[5-(1-methyl-1H-pyrazol-4-yl)-7H-pyrrolo[2,3-d]pyrimidin-4-yl]amino}piperidin-1-yl]prop-2-en-1-one |
| 29 | 434 | 4-(4-{[(3R)-1-acryloylpiperidin-3-yl]amino}-7H-pyrrolo[2,3-d]pyrimidin-5-yl)-N-(propan-2-yl)benzamide |
| 30 | 363 | 1-[(3R)-3-{[5-(6-methylpyridin-3-yl)-7H-pyrrolo[2,3-d]pyrimidin-4-yl]amino}piperidin-1-yl]prop-2-en-1-one |
| 66 | 363 | (R)-1-(3-((5-(6-methylpyridin-3-yl)-7H-pyrrolo[2,3-d]pyrimidin-4-yl)amino)piperidin-1-yl)prop-2-en-1-one |
| 31 | 466 | 4-(4-{[(3R)-1-acryloylpiperidin-3-yl]amino}-7H-pyrrolo[2,3-d]pyrimidin-5-yl)-2-chloro-N-cyclopropylbenzamide |
| 32 | 427 | 1-[(3R)-3-({5-[3-(methylsulfonyl)phenyl]-7H-pyrrolo[2,3-d]pyrimidin-4-yl}amino)piperidin-1-yl]prop-2-en-1-one |
| 33 | 393 | 1-[(3R)-3-{[5-(6-ethoxypyridin-3-yl)-7H-pyrrolo[2,3-d]pyrimidin-4-yl]amino}piperidin-1-yl]prop-2-en-1-one |
| 34 | 402 | 1-[(3R)-3-{[5-(1-methyl-1H-indazol-5-yl)-7H-pyrrolo[2,3-d]pyrimidin-4-yl]amino}piperidin-1-yl]prop-2-en-1-one |
| 35 | 435 | 1-[(3R)-3-({5-[2-(morpholin-4-yl)pyrimidin-5-yl]-7H-pyrrolo[2,3-d]pyrimidin-4-yl}amino)piperidin-1-yl]prop-2-en-1-one |
| 36 | 435 | 1-[(3R)-3-({5-[6-(morpholin-4-yl)pyridin-3-yl]-7H-pyrrolo[2,3-d]pyrimidin-4-yl}amino)piperidin-1-yl]prop-2-en-1-one |
| 37 | 312 | 1-{(3R)-3-[(5-cyclopropyl-7H-pyrrolo[2,3-d]pyrimidin-4-yl)amino]piperidin-1-yl}prop-2-en-1-one |
| 38 | 364 | 1-[(3R)-3-({5-[(E)-2-(furan-3-yl)ethenyl]-7H-pyrrolo[2,3-d]pyrimidin-4-yl}amino)piperidin-1-yl]prop-2-en-1-one |
| 39 | 328 | 1-[(3R)-3-{[5-(2-methylpropyl)-7H-pyrrolo[2,3-d]pyrimidin-4-yl]amino}piperidin-1-yl]prop-2-en-1-one |
| 40 | 298 | 1-{(3R)-3-[(5-ethenyl-7H-pyrrolo[2,3-d]pyrimidin-4-yl)amino]piperidin-1-yl}prop-2-en-1-one |

Examples 23-40 were prepared as described in the scheme below using parallel methods known to those of ordinary skill in the art, and in light of the description herein.

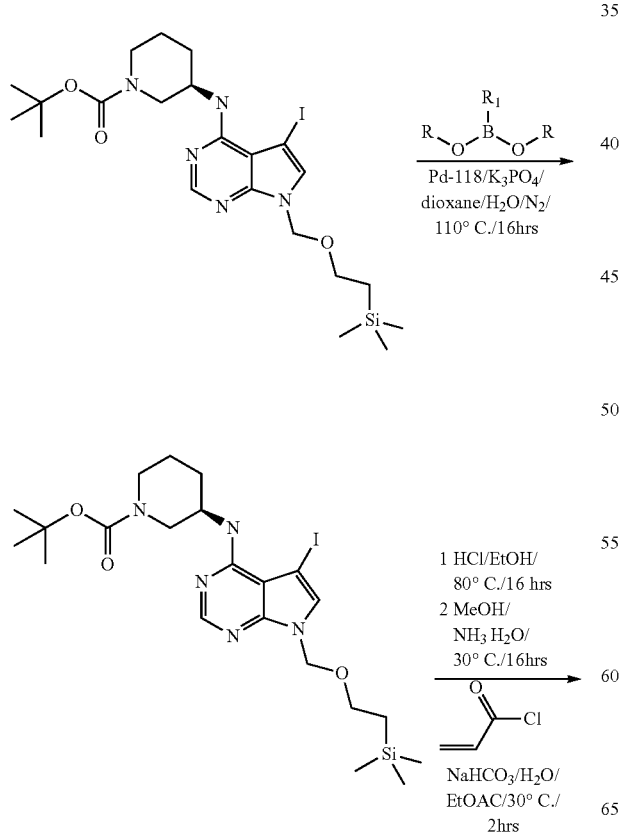

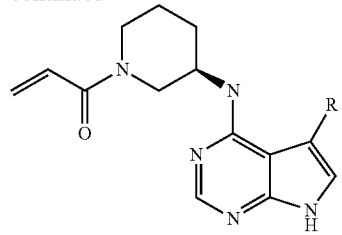

Step 1: Suzuki Coupling. A 0.16 M solution of (R)-tert-butyl 3-((5-iodo-7-((2-(trimethylsilyl)ethoxy)methyl)-7H-pyrrolo[2,3-d]pyrimidin-4-yl)amino)piperidine-1-carboxylate in dioxane is prepared. A 0.63 M solution of $K_3PO_4$ in $H_2O$ is prepared. A monomer boronate/boronic acid (225 μmol, 1.8 eq) is dispensed to 8 ml reaction vials. A volume of 800 μL of (R)-tert-butyl 3-((5-iodo-7-((2-(trimethylsilyl)ethoxy)methyl)-7H-pyrrolo[2,3-d]pyrimidin-4-yl)amino)piperidine-1-carboxylate (125 μmol, 1.0 eq) solution is then dispensed to the vial, followed by 400 μL of $K_3PO_4$ (250 μmol, 2.0 eq) solution and then Pd-118 ((1,1'-bis(di-tert-butylphosphino) ferrocene palladium dichloride) (4.9 mg, 7.5 μmol, 0.06 eq), all under $N_2$ atmosphere. The vials are capped and shaken at 110° C. for 16 hrs. Reaction progress is checked by LC-MS. Upon completion, each reaction mixture is filtered and concentrated by Speedvac®. The residue is washed with $H_2O$ and extracted with EtOAc (1 ml×3). The organic layers were collected, dried over anhydrous $Na_2SO_4$, filtered and concentrated by Speedvac® to give a crude intermediate, which was used in the next step directly.

Step 2: De-protection. A mixed solution of conc. HCl (37% aqueous solution) in EtOH (v/v 1:6) is prepared. One ml of the HCl solution is dispensed to 8 ml vials containing the crude intermediate from Step 1. The vials are capped and shaken at 80° C. for 16 hrs. Solvent is evaporated by Speedvac®. A mixed solution of NH₃H₂O in MeOH (v/v 1:4) is prepared, and 1 ml is dispensed to each vial. The vial is capped and shaken at 30° C. for 16 hrs. Reaction progress is checked by LC-MS. Upon completion, the reaction is filtered and concentrated to give the crude intermediate, which was used for final step directly.

Step 3: Acylation. A saturated solution of NaHCO₃ in H₂O is prepared and one ml is dispensed to the vials containing the product of step 2. One ml of EtOAc is then dispensed to each vial, followed by acryloyl chloride (250 μmol, 2.0 eq). The vials are capped and shaken at 30° C. for 2 hours. Reaction progress is checked by LC-MS. Upon completion, the mixture is concentrated. The residue is purified by preparative HPLC to give the final product.

Example 41: 1-((3aS,7aS)-1-(7H-Pyrrolo[2,3-d]pyrimidin-4-yl)hexahydro-1H-pyrrolo[2,3-c]pyridin-6(2H)-yl)-2-(trifluoromethyl)prop-2-en-1-one Step 1. 1-((3aS,7aS)-1-(7H-Pyrrolo[2,3-d]pyrimidin-4-yl)hexahydro-1H-pyrrolo[2,3-c]pyridin-6(2H)-yl)-2-(trifluoromethyl)prop-2-en-1-one To a round bottom flask containing the amine (Example 8; 4-((3aR,7aS)-octahydro-1H-pyrrolo[2,3-c]pyridin-1-yl)-7H-pyrrolo[2,3-d]pyrimidine, 150 mg, 0.47 mmol) was added DCM (5 ml) and DIPEA (0.33 mL, 1.90 mmol). The reaction mixture was cooled to 0° C. and BOP (238 mg, 0.52 mmol) and 2-(trifluoromethyl)acrylic acid (73.0 mg, 0.52 mmol) were added. After 1 hr, the reaction was poured into water/ethyl acetate and the layers separated. The organic layer was dried (Na₂SO₄), filtered and solvent removed to give an oil, which was purified by column chromatography (silica, DCM/MeOH, 25 g) to give a major fraction. This was further purified by RP-HPLC to give pure 1-((3aS,7aS)-1-(7H-pyrrolo[2,3-d]pyrimidin-4-yl)hexahydro-1H-pyrrolo[2,3-c]pyridin-6(2H)-yl)-2-(trifluoromethyl)prop-2-en-1-one (114 mg, 65%). LC/MS (M+H) 366.2.

Example 42-46

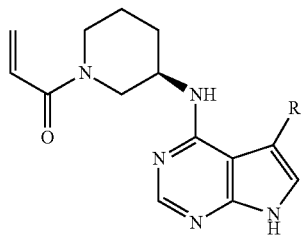

wherein R=F, Me, Et, CN, CH₂CH₂OMe

Examples 42-46 were prepared as described in Examples 1-3, but using Het-Cl=4-chloro-5-fluoro-7H-pyrrolo[2,3-d]pyrimidine or 4-chloro-5-methyl-7H-pyrrolo[2,3-d]pyrimidine or 4-chloro-5-ethyl-7H-pyrrolo[2,3-d]pyrimidine or 4-chloro-5-(2-methoxyethyl)-7H-pyrrolo[2,3-d]pyrimidine.

| Example | LC/MS (M + H) | IUPAC Name |
|---|---|---|
| 42 | 290 | 1-{(3R)-3-[(5-fluoro-7H-pyrrolo[2,3-d]pyrimidin-4-yl)amino]piperidin-1-yl}prop-2-en-1-one |

-continued

| Example | LC/MS (M + H) | IUPAC Name |
|---|---|---|
| 43 | 286 | 1-{(3R)-3-[(5-methyl-7H-pyrrolo[2,3-d]pyrimidin-4-yl)amino]piperidin-1-yl}prop-2-en-1-one |
| 44 | 300 | 1-{(3R)-3-[(5-ethyl-7H-pyrrolo[2,3-d]pyrimidin-4-yl)amino]piperidin-1-yl}prop-2-en-1-one |
| 45 | 297 | 4-{[(3R)-1-acryloylpiperidin-3-yl]amino}-7H-pyrrolo[2,3-d]pyrimidine-5-carbonitrile |
| 46 | 330 | 1-[(3R)-3-{[5-(2-methoxyethyl)-7H-pyrrolo[2,3-d]pyrimidin-4-yl]amino}piperidin-1-yl]prop-2-en-1-one |

Example 47: 1-{(3R)-3-[(3-methyl-1H-pyrrolo[2,3-b]pyridin-4-yl)amino]piperidin-1-yl}prop-2-en-1-one. LC/MS (M+H) 285

Example 48: 1-[(3aS,7aS)-1-(5-ethynyl-7H-pyrrolo[2,3-d]pyrimidin-4-yl)octahydro-6H-pyrrolo[2,3-c]pyridin-6-yl]prop-2-en-1-one Step 1. (3aS,7aS)-Benzyl 1-(2,2,2-trifluoroacetyl)hexahydro-1H-pyrrolo[2,3-c]pyridine-6(2H)-carboxylate To a solution of (−)-(3aS,7aS)-benzyl hexahydro-1H-pyrrolo[2,3-c]pyridine-6(2H)-carboxylate (3.85 g, 14.8 mmol) in DCM (15 mL) at 0° C. was added DIPEA (5.72 mL, 32.5 mmol) followed by trifluoroacetic anhydride (2.2 mL, 15.5 mmol). The reaction mixture was stirred at rt for 2 hrs and then poured into saturated NaHCO₃/DCM. The layers were separated and the organic layer dried (Na₂SO₄) and the solvent removed to give the crude (3aS,7aS)-benzyl 1-(2,2,2-trifluoroacetyl)hexahydro-1H-pyrrolo[2,3-c]pyridine-6(2H)-carboxylate, which was used without purification in the next step. LC/MS (M+H) 357.1.

Step 2. 2,2,2-Trifluoro-1-((3aR,7aS)-octahydro-1H-pyrrolo[2,3-c]pyridin-1-yl)ethanone To a Parr bottle was added 3aS,7aS)-benzyl 1-(2,2,2-trifluoroacetyl)hexahydro-1H-pyrrolo[2,3-c]pyridine-6(2H)-carboxylate (5.27 g, 14.8 mmol), ethanol (30 mL) and 5% Pd/C (500 mg). The mixture was shaken overnight at 40 psi at 25° C. The reaction mixture was filtered through Celite® and the solvent removed to give 2,2,2-trifluoro-1-((3aR,7aS)-octahydro-1H-pyrrolo[2,3-c]pyridin-1-yl)ethanone. The material was used in the next step without further purification. LC/MS (M+H) 223.1.

Step 3. (3aS,7aS)-2-(Trimethylsilyl)ethyl hexahydro-1H-pyrrolo[2,3-c]pyridine-6(2H)-carboxylate To a flask containing 2,2,2-trifluoro-1-((3aR,7aS)-octahydro-1H-pyrrolo[2,3-c]pyridin-1-yl)ethanone (3.29, 14.8 mmol) was added DCM (30 mL), TEA (10.3 mL, 73.9 mmol) and Teoc-OSuc (4.19 g, 16.3 mmol). The reaction mixture was stirred at 25° C. overnight and then poured into saturated NaHCO₃/DCM. The layers were separated and the organic layer dried (Na₂SO₄) and the solvent removed to give (3aS,7aS)-2-(trimethylsilyl)ethyl hexahydro-1H-pyrrolo[2,3-c]pyridine-6(2H)-carboxylate. To (3aS,7aS)-2-(trimethylsilyl)ethyl hexahydro-1H-pyrrolo[2,3-c]pyridine-6(2H)-carboxylate (5.42 g, 14.8 mmol) was added MeOH (25 mL) and K₂CO₃ (4.09 g, 29.6 mmol). The mixture was stirred at rt for 4 hrs and then filtered and concentrated. The residue was taken up into DCM and washed with saturated NaHCO$_3$ and brine. The organic extract was dried (Na$_2$SO$_4$) and the solvent removed to give the desired product (3.2 g, 80%). LC/MS (M+H) 271.2. $^1$H NMR (400 MHz, CDCl$_3$) δ −0.17-0.03 (m, 9H) 0.80-1.00 (m, 2H) 1.26 (dd, 1H) 1.33-1.72 (m, 4H) 1.77-1.94 (m, 1H) 1.99-2.16 (m, 1H) 2.80-3.14 (m, 3H) 3.34 (dd, 1H) 3.56-3.76 (m, 2H) 4.04-4.21 (m, 2H) 5.27 (s, 1H).

Step 4. 4-Chloro-5-((trimethylsilyl)ethynyl)-7H-pyrrolo[2,3-d]pyrimidine

To a flask was added 4-chloro-5-iodo-7H-pyrrolo[2,3-d]pyrimidine (5.0 g, 17.89 mmol), CuI (681 mg, 3.58 mmol), TMS-acetylene (3.79 mL, 26.8 mmol), Pd(PPh$_3$)$_4$ (1.06 g, 0.89 mmol), THF (100 ml), DMF (33 mL) and TEA (1.28 mL). The reaction was stirred at rt for 16 hrs. The solvent was removed in vacuo and the residue taken up into DCM (300 mL). The mixture was washed with water (3×75 mL), dried (Na$_2$SO$_4$) and the solvent removed to give an oil, which after chromatography (silica, 70% EtOAc/Hep) gave the desired product (3.8 g, 85%). LC/MS (M+H) 250.0. $^1$H NMR (400 MHz, DMSO-d$_6$) δ 0.26 (br s, 9H), 8.09 (d, J=2.34 Hz, 1H), 8.64 (s, 1H).

Step 5. (3aS,7aS)-2-(Trimethylsilyl)ethyl 1-(5-((trimethylsilyl)ethynyl)-7H-pyrrolo[2,3-d]pyrimidin-4-yl)hexahydro-1H-pyrrolo[2,3-c]pyridine-6(2H)-carboxylate To a round bottom flask containing (3aS,7aS)-2-(trimethylsilyl)ethyl hexahydro-1H-pyrrolo[2,3-c]pyridine-6(2H)-carboxylate (1.94 g, 7.17 mmol) was added i-PrOH (20 ml), DIPEA (1.89 mL, 10.8 mmol) and 4-chloro-5-((trimethylsilyl)ethynyl)-7H-pyrrolo[2,3-d]pyrimidine (1.79 g, 7.17 mmol). The reaction mixture was heated to 80° C. for 2 hrs (LC/MS shows desired product; tms intact). The solvent was removed in vacuo and the residue diluted with DCM/H$_2$O. The layers were separated and the organic layer collected, dried (Na$_2$SO$_4$) and the solvent removed to give the crude, which was purified by chromatography (silica, EtOAc/MeOH) to give (3aS,7aS)-2-(trimethylsilyl)ethyl 1-(5-((trimethylsilyl)ethynyl)-7H-pyrrolo[2,3-d]pyrimidin-4-yl)hexahydro-1H-pyrrolo[2,3-c]pyridine-6(2H)-carboxylate (1.3 g, 38%). LC/MS (M+H) 484.2. $^1$H NMR (400 MHz, CDCl$_3$) δ −0.07 (s, 9H) 0.42 (s, 9H) 0.63-1.11 (m, 2H) 1.19-1.36 (m, 1H) 1.60-2.15 (m, 4H) 2.38-2.63 (m, 1H) 3.25-3.73 (m, 2H) 3.90-4.22 (m, 4H) 4.26-4.48 (m, 1H) 4.51-4.76 (m, 1H) 7.48 (s, 1H) 8.33 (s, 1H) 11.86 (br s, 1H).

Step 6. 5-Ethynyl-4-((3aR,7aS)-octahydro-1H-pyrrolo[2,3-c]pyridin-1-yl)-7H-pyrrolo[2,3-d]pyrimidine To a flask containing (3aS,7aS)-2-(trimethylsilyl)ethyl 1-(5-((trimethylsilyl)ethynyl)-7H-pyrrolo[2,3-d]pyrimidin-4-yl)hexahydro-1H-pyrrolo[2,3-c]pyridine-6(2H)-carboxylate (800 mg, 1.65 mmol) was added THF (10 mL) and TBAF (3.64 mL, 1M in THF). After stirring at rt for 48 hrs the reaction was poured into water and the mixture extracted with ethyl acetate. The organic extracts were collected, dried (Na$_2$SO$_4$) and the solvent removed to give an oil (not product). The aqueous layer was adjusted to pH-10 and then extracted with DCM. The organic extracts were combined, dried (Na$_2$SO$_4$) and the solvent removed to give crude 1-((3aS,7aS)-1-(5-ethynyl-7H-pyrrolo[2,3-d]pyrimidin-4-yl)hexahydro-1H-pyrrolo[2,3-c]pyridin-6(2H)-yl)prop-2-en-1-one (442 mg), which was used in the next step without purification.

Step 7. 1-((3aS,7aS)-1-(5-Ethynyl-7H-pyrrolo[2,3-d]pyrimidin-4-yl)hexahydro-1H-pyrrolo[2,3-c]pyridin-6(2H)-yl)prop-2-en-1-one To flask containing 5-ethynyl-4-((3aR,7aS)-octahydro-1H-pyrrolo[2,3-c]pyridin-1-yl)-7H-pyrrolo[2,3-d]pyrimidine (442 mg, 1.65 mmol) was added DCM (7 mL) and TEA (0.51 mL, 3.64 mmol). The flask was cooled to 0° C. and acryloyl chloride (189 mg in 5 mL DCM) was added dropwise over 5 minutes. After addition was complete the reaction was stirred for 30 min. The reaction mixture was poured into water and the layers separated. The organic layer was collected, washed with brine, dried (Na$_2$SO$_4$) and the solvent removed to give an oil, which was purified by RP-HPLC to give 1-((3aS,7aS)-1-(5-ethynyl-7H-pyrrolo[2,3-d]pyrimidin-4-yl)hexahydro-1H-pyrrolo[2,3-c]pyridin-6(2H)-yl)prop-2-en-1-one (197 mg, 37%). LC/MS (M+H) 322.1. $^1$H NMR (400 MHz, DMSO-d$_6$) δ 1.49-2.03 (m, 4H) 3.40-3.93 (m, 4H) 4.05 (s, 1H) 4.15-4.59 (m, 3H) 5.42 (d, 1H) 5.97-6.19 (m, 1H) 6.39 (dd, 1H) 6.80 (dd, 1H) 7.66 (d, 1H) 8.10-8.27 (m, 1H) 12.13 (br s, 1H).

Example 49: 1-[(3aS,7aR)-1-(7H-Pyrrolo[2,3-d]pyrimidin-4-yl)octahydro-6H-pyrrolo[2,3-c]pyridin-6-yl]prop-2-en-1-one Step 1. Dimethyl 3-(cyano((diphenylmethyl)amino)methyl)pentanedioate To a flask containing 2-((diphenylmethylene)amino)acetonitrile (4.0 g, 18.16 mmol) in THF at −78° C. was added DBU (1.6 mL, 9.08 mmol) and (E)-dimethyl pent-2-enedioate. The mixture was stirred at −78° C. overnight and then rt for 24 hrs. The solvent was removed in vacuo and the crude material purified by chromatography (silica, EtOAc/Hep, 0 to 30%) to give 3.9 g of dimethyl 3-(cyano((diphenylmethylene)amino)methyl)pent-anedioate. GC/MS 378. $^1$H NMR (400 MHz, CDCl$_3$) δ 2.48-2.57 (m, 1H) 2.66 (d, J=6.25 Hz, 2H) 2.78-2.89 (m, 2H) 3.59 (s, 6H) 4.51 (d, J=4.49 Hz, 1H) 7.17-7.22 (m, 2H) 7.30-7.37 (m, 2H) 7.40-7.46 (m, 1H) 7.47-7.53 (m, 3H) 7.58-7.63 (m, 2H).

Step 2. Methyl 2-(1-benzhydryl-2-cyano-5-oxopyrrolidin-3-yl)acetate

To a flask containing dimethyl 3-(cyano((diphenylmethylene)amino)methyl)pentanedioate was added HOAc (5.0 mL) and Na(OAc)$_3$BH (5.3 g, 24 mmol). The reaction mixture was stirred overnight and then concentrated and diluted with saturated NaHCO$_3$/EtOAc. The layers were separated and the organic layer washed with water, brine and dried (MgSO$_4$). The solvent was removed to give crude material, which after chromatography (silica, EtOAc/Hep, 0 to 50%) gave methyl 2-(1-benzhydryl-2-cyano-5-oxopyrrolidin-3-yl)acetate (2.5 g, 73%). LC/MS (M+H) 349.2. $^1$H NMR (400 MHz, CDCl$_3$) δ 2.34-2.46 (m, 2H) 2.64-2.77 (m, 2H) 2.89-3.10 (m, 2H) 3.64 (s, 3H) 3.88 (d, J=3.12 Hz, 1H) 4.53 (d, J=7.61 Hz, 1H) 6.54 (d, J=13.27 Hz, 1H) 7.05-7.17 (m, 1H) 7.25-7.43 (m, 8H).

Step 3. 1-Benzhydryltetrahydro-1H-pyrrolo[2,3-c]pyridine-2,5(3H,6H)-dione

To a Parr bottle was added methyl 2-(1-benzhydryl-2-cyano-5-oxopyrrolidin-3-yl)acetate (2.5 g, 7.2 mmol), MeOH (10 mL) and PtO₂ (200 mg). The reaction was shaken overnight at 40 psi H₂, 60° C. for 30 hrs. The reaction mixture was filtered through Celite® and the solvent removed in vacuo to give crude 1-benzhydryltetrahydro-1H-pyrrolo[2,3-c]pyridine-2,5(3H,6H)-dione (2.2 g, 96%), which was used without further purification.
LC/MS (M+H) 321.2.

Step 4. 1-Benzhydryloctahydro-1H-pyrrolo[2,3-c]pyridine

To a flask containing 1-benzhydryltetrahydro-1H-pyrrolo[2,3-c]pyridine-2,5(3H,6H)-dione (1.0 g, 3.1 mmol) was added THF (5 mL) and LAH (474 mg, 12.5 mmol). The reaction was stirred at 60° C. overnight. The reaction mixture was worked up using a Fisher workup. The reaction mixture was filtered through Celite® and washed with methanol. The solvent was concentrated to give crude 1-benzhydryloctahydro-1H-pyrrolo[2,3-c]pyridine (900 mg, 98%), which was used without further purification. LC/MS (M+H) 293.2.

Step 5. 1-Benzhydryl-6-tosyloctahydro-1H-pyrrolo[2,3-c]pyridine

To a flask containing 1-benzhydryl-6-tosyloctahydro-1H-pyrrolo[2,3-c]pyridine (900 mg, 3.08 mmol) was added DCM (10 mL), TEA (0.89 mL, 6.16 mmol) and TsCl (719 mg, 3.69 mmol). The reaction was stirred at rt overnight and the poured into DCM/water. The layers were separated and organic layer collected, dried (Na₂SO₄). The solvent was removed to give crude, which was purified by chromatography to give 1-benzhydryl-6-tosyloctahydro-1H-pyrrolo[2,3-c]pyridine (400 mg, 29%). LC/MS (M+H) 447.2.

Step 6. 1-Benzhydryl-6-tosyloctahydro-1H-pyrrolo[2,3-c]pyridine

To a Parr bottle containing 1-benzhydryl-6-tosyloctahydro-1H-pyrrolo[2,3-c]pyridine (400 mg, 0.89 mmol) in ethanol/acetic acid (10 mL/1 mL) was added Pd(OH)₂ (60 mg). The reaction was shaken at 40 psi H₂ overnight. The reaction mixture was filtered through Celite® and the solvent removed to give crude 1-benzhydryl-6-tosyloctahydro-1H-pyrrolo[2,3-c]pyridine, which was used without further purification. LC/MS (M+H) 281.1.

Step 7. 7-Tosyl-4-((3aS,7aR)-6-tosyloctahydro-1H-pyrrolo[2,3-c]pyridin-1-yl)-7H-pyrrolo[2,3-d]pyrimidine To a flask containing 4-chloro-7-tosyl-7H-pyrrolo[2,3-d]pyrimidine (276 mg, 0.89 mmol) was added n-BuOH (5 mL), 1-benzhydryl-6-tosyloctahydro-1H-pyrrolo[2,3-c]pyridine (251 mg, 0.89 mmol) and DIPEA (1.14 mL, 6.53 mmol). The reaction was heated to 80° C. for 4 hrs and then diluted with water/ethyl acetate. The layers were separated and the organic extract collected and dried (Na₂SO₄). The solvent was removed to give the crude, which was purified by chromatography (silica, EtOAc/Hep, 0 to 40%) to give two peaks with same molecular weight. Pk1 (cis-isomer, 25 mg), compared to Example 8, Step 8 material treated with TsCl. LC/MS (M+H) 552.0. Pk2 (trans-isomer, 85 mg): LC/MS (M+H) 552.1.

Step 8. 4-((3aR,7aR)-Octahydro-1H-pyrrolo[2,3-c]pyridin-1-yl)-7H-pyrrolo[2,3-d]pyrimidine To a flask containing 7-tosyl-4-((3aS,7aR)-6-tosyloctahydro-1H-pyrrolo[2,3-c]pyridin-1-yl)-7H-pyrrolo[2,3-d]pyramid-ine pk2 (100 mg, 0.18 mmol) in MeOH (5 mL) was added NaHPO₄ (109 mg, 0.90 mmol) and Na/Hg (20-30 beads). The reaction mixture was stirred at rt overnight and then filtered through Celite®. The solvent was removed and the crude material diluted with ethyl acetate/water. The pH of aqueous layer was adjusted to pH-9 and then extracted with ethyl acetate (3×). The organic extracts were combined and washed with water, brine and dried (Na₂SO₄). The solvent was removed to give 4-((3aR,7aR)-octahydro-1H-pyrrolo[2,3-c]pyridin-1-yl)-7H-pyrrolo[2,3-d]pyrimidine (35 mg, 80%). LC/MS (M+H) 244.2.

Step 9. 1-((3aS,7aR)-1-(7H-Pyrrolo[2,3-d]pyrimidin-4-yl)hexahydro-1H-pyrrolo[2,3-c]pyridin-6(2H)-yl)prop-2-en-1-one To a flask containing 4-((3aR,7aR)-octahydro-1H-pyrrolo[2,3-c]pyridin-1-yl)-7H-pyrrolo[2,3-d]pyrimidine (20 mg, 0.08 mmol) in DCM at 0° C. was added DIPEA (0.06 mL, 0.33 mmol) and acryloyl chloride (8.0 mg, 0.08 mmol). The mixture was stirred for 3 hrs at 0° C. and then diluted with water/DCM. The layers were separated and the organic layer collected and dried (Na₂SO₄). The solvent was removed to give crude material, which after chromatography (silica, MeOH/DCM, 0 to 10%) gave 1-((3aS,7aR)-1-(7H-pyrrolo[2,3-d]pyrimidin-4-yl)hexahydro-1H-pyrrolo[2,3-c]pyridin-6(2H)-yl)prop-2-en-1-one (6.5 mg, 27%). LC/MS (M+H) 298.2.

Example 50: 1-[(3R,4S)-4-methyl-3-(7H-pyrrolo[2,3-d]pyrimidin-4-ylamino)piperidin-1-yl]prop-2-en-1-one Preparation of rac-1-((3R,4S)-3-((7H-pyrrolo[2,3-d]pyrimidin-4-yl)amino)-4-methylpiperidin-1-yl)prop-2-en-1-one (from Example 11, Step 4). To a solution of N-((3R,4S)-4-methylpiperidin-3-yl)-7H-pyrrolo[2,3-d]pyrimidin-4-amine (410 mg, 1.530 mmol) in THF (20 mL) and aq.NaHCO₃ (15 mL) at 0° C. was added acryloyl chloride (152 mg, 1.683 mmol, 1.1 eq.). The reaction mixture was stirred at 0° C. for 2 hours. After TLC (EtOAc/MeOH, 10:1) showed the reaction to be complete, the reaction mixture was diluted with water (50 mL), and extracted with EtOAc (50 mL×2). The combined organic layers were washed with brine, dried over Na₂SO₄ and concentrated. The residue was purified by flash column chromatography (MeOH/EtOAc, 2%-10%) and lyophilized to give rac-1-((3R,4S)-3-((7H-pyrrolo[2,3-d]pyrimidin-4-yl)amino)-4-methylpiperidin-1-yl)prop-2-en-1-one (150 mg, 34%) as a white solid. ¹H NMR (400 MHz, DMSO-d₆) δ 11.53 (br s, 1H), 8.08 (d, J=15.1 Hz, 1H), 7.32-7.20 (m, 1H), 7.08 (br s, 1H), 6.81 (dt, J=10.5, 17.3 Hz, 1H), 6.59 (br s, 1H), 6.12 (d, J=14.8 Hz, 1H), 5.69 (d, J=10.3 Hz, 1H), 4.65-4.39 (m, 1H), 4.27-4.04 (m, 1H), 3.94-3.71 (m, 1H), 3.16 (d, J=5.3 Hz, 1H), 3.08-2.96 (m, 1H), 2.89-2.77 (m, 1H), 2.71-2.60 (m, 1H), 2.46-2.28 (m, 1H), 1.82 (d, J=12.3 Hz, 2H), 1.29-1.12 (m, 1H), 0.94 (dd, J=6.0, 12.3 Hz, 3H). LCMS (M+H) 286.1.

Example 51: rac-1-[(3aR,7aR)-1-(7H-Pyrrolo[2,3-d]pyrimidin-4-yl)octahydro-6H-pyrrolo[2,3-c]pyridin-6-yl]prop-2-en-1-one Prepared as in Example 8, except using rac-(3aR,7aR)-benzyl hexahydro-1H-pyrrolo[2,3-c]pyridine-6(2H)-carboxylate instead of optically active material in Step 7.
LC/MS (M+H) 298.2. ¹H NMR (400 MHz, DMSO-d₆) δ 11.58 (s, 1H) 8.09-8.07 (d, J=9.2 Hz, 1H) 7.115 (s, 1H), 6.82-6.78 (m, 1H), 6.51 (m, 1H), 6.05-6.01 (m, 1H), 5.69-5.85 (m, 1H), 4.69-4.68 (m, 0.5H), 4.27 (s, 1H), 3.90-3.74 (m, 3H), 3.13-3.24 (m, 2H), 2.74-2.71 (m, 0.5H), 2.19-1.74 (m, 4.5H).

Example 52: 1-[2-(Hydroxymethyl)-5-(7H-pyrrolo[2,3-d]pyrimidin-4-ylamino)piperidin-1-yl]prop-2-en-1-one (rac-cis/trans)

Prepared as in Example 7, except no separation of diastereomers or enantiomers is carried out. LC/MS (M+H) 302.2.

Example 53: (R)(-1-(3-((5-(2-hydroxy-2-methylpropyl)-7H-pyrrolo[2,3-d]pyrimidin-4-yl)amino)piperidin-1-yl)prop-2-en-1-one Step 1. 1-(4-Chloro-7H-pyrrolo[2,3-d]pyrimidin-5-yl)-2-methylpropan-2-ol To a solution of NaH (343 mg, 8.57 mmol) in 20 mL of THF cooled with ice bath, was added 5-bromo-4-chloro-7H-pyrrolo[2,3-d]pyrimidine (1000 mg, 4.32 mmol). After 10 min, the reaction was cooled with dry ice/acetone bath. BuLi (1.6M; 4.02 mL, 6.43 mmol) was added. After 30 min, 2,2-dimethyloxirane (927 mg, 12.9 mmol) was added slowly. The reaction was allowed to warm to rt slowly then it was stirred at rt overnight. NH$_4$Cl (10%, 20 mL) was added slowly. The reaction was stirred for 15 min. The mixture was concentrated under vacuum to remove organic solvent. The aqueous solution was extracted with ethyl acetate (2×10 mL). The combined organic layer was dried and concentrated. The residue was purified by CombiFlash® (40 g column, 10 to 100% EA in heptane) to give 549 mg of 1-(4-chloro-7H-pyrrolo[2,3-d]pyrimidin-5-yl)-2-methylpropan-2-ol (56.5%). LC/MS (M+H) 226.2. 1H NMR (400 MHz, CDCl$_3$) δ 10.63 (br, 1H), 8.59 (s, 1H), 7.33 (s, 1H), 3.14 (s, 2H), 1.29 (s, 6H).

Step 2. (R)-tert-Butyl 3-((5-(2-hydroxy-2-methylpropyl)-7H-pyrrolo[2,3-d]pyrimidin-4-yl)amino)piperidine-1-carboxylate To a solution of the pyrrolopyrimidine 1-(4-chloro-7H-pyrrolo[2,3-d]pyrimidin-5-yl)-2-methylpropan-2-ol (140 mg, 0.62 mmol) in 5 mL of dioxane/H$_2$O (8:4) was added (R)-tert-butyl 3-aminopiperidine-1-carboxylate (124 mg, 0.62 mmol) and potassium carbonate (172 mg, 1.24 mmol). The resultant reaction mixture was heated to 110° C. for 5 days. After cooling, the reaction mixture was concentrated. The aqueous mixture was diluted with 5 ml of water and extracted with EtOAc (3×). The combined organic layer was washed with water (4×), brine and dried (Na$_2$SO$_4$) then filtered and concentrated. The residue was purified by silica gel column chromatography (0-100% EtOAc in heptane) to give (R)-tert-butyl 3-((5-(2-hydroxy-2-methylpropyl)-7H-pyrrolo[2,3-d]pyrimidin-4-yl)amino)piperidine-1-carboxylate (85 mg, 35% yield)). LC/MS (M+H) 390.4.

Step 3. (R)-2-Methyl-1-(4-(piperidin-3-ylamino)-7H-pyrrolo[2,3-d]pyrimidin-5-yl)propan-2-ol To a solution of (R)-tert-butyl 3-((5-(2-hydroxy-2-methylpropyl)-7H-pyrrolo[2,3-d]pyrimidin-4-yl)amino)piperidine-1-carboxylate (85 mg, 0.22 mmol) in 5 mL of THF was added HCl (4M in dioxane) (5 mL) and the resulting mixture stirred at RT for 3 h. The reaction was concentrated. The residue was dissolved in DCM and concentrated. The process was repeated 3 times to give 65 mg of (R)-2-methyl-1-(4-(piperidin-3-ylamino)-7H-pyrrolo[2,3-d]pyrimidin-5-yl)propan-2-ol as an HCl salt. LC/MS (M+H) 290.3.

Step 4. (R)-1-(3-((5-(2-Hydroxy-2-methylpropyl)-7H-pyrrolo[2,3-d]pyrimidin-4-yl)amino)piperidin-1-yl)prop-2-en-1-one To a flask containing (R)-2-methyl-1-(4-(piperidin-3-ylamino)-7H-pyrrolo[2,3-d]pyrimidin-5-yl)propan-2-ol (65 mg, 0.2 mmol), DIPEA (10 eq needed to get the salt neutralized and homogenous) and DCM (5 mL) at 0° C. was added acryloyl chloride (18 mg, 0.200 mmol solution in 1 mL of DCM) was added. After 45 mins, the reaction mixture was quenched with a saturated solution of NaHCO3 (5 mL) and the layers were partitioned. The aqueous layer was extracted (2×) with DCM and the combined organic layers were concentrated to afford the crude product as a white solid. The solid was purified by reverse phase HPLC to give 15 mg of desired product. LC/MS (M+H) 344.2. $^1$H NMR (400 MHz, MeOH-d$_4$) δ 8.19 (s, 1H), 7.12 (s, 1H), 6.88-6.76 (m, 1H), 6.22-6.14 (m, 1H), 5.78-5.73 (m, 1H), 4.15-3.99 (m, 1H), 3.92-3.84 (m, 1H) 3.79-3.50 (3H), 2.89-2.74 (m, 2H), 2.20-2.05 (m, 1H), 2.00-1.769 (m, 2H), 1.73-1.58 (m, 1H), 1.30-1.15 (m, 3H), 1.18-1.149 (m, 3H).

Example 54: 1-((3S,4R)-3-((7H-Pyrrolo[2,3-d]pyrimidin-4-yl)amino)-4-fluoropiperidin-1-yl)prop-2-en-1-one Step 1. (3S,4R)-Benzyl 4-fluoro-3-((7-trityl-7H-pyrrolo[2,3-d]pyrimidin-4-yl)amino)piperidine-1-carboxylate To a solution of 4-chloro-7-trityl-7H-pyrrolo[2,3-d]pyrimidine (308 mg, 0.779 mmol) and cesium fluoride (474 mg, 3.12 mmol) in DMSO (3.0 mL) was added (3S,4R)-benzyl 3-amino-4-fluoropiperidine-1-carboxylate (prepared according to WO2010/16005 and WO2011/101161) (225 mg, 0.779 mmol). The reaction mixture was heated to 120° C. for 16 hours. After LCMS showed that 4-chloro-7-trityl-7H-pyrrolo[2,3-d]pyrimidine was consumed completely, the reaction mixture was diluted with a 1:1 mixture of DCM/water (200 mL). The organic layer was extracted and the aqueous layer was back extracted with DCM (2×50 mL). The organic extracts were combined, washed with brine (2×100 mL), dried over sodium sulfate, filtered, and concentrated in vacuo to yield crude product which was dry loaded with Celite® onto a Silicycle® 80 g HP column and purified via normal phase column chromatography (25-75% EtOAc/heptanes over 10 column volumes) to afford (3S,4R)-benzyl 4-fluoro-3-((7-trityl-7H-pyrrolo[2,3-d]pyrimidin-4-yl)amino)piperidine-1-carboxylate (400.0 mg, 84%) as a colorless solid. LCMS (M+H) 532.56.

Step 2. N-((3S,4R)-4-Fluoropiperidin-3-yl)-7-trityl-7H-pyrrolo[2,3-d]pyrimidin-4-amine To a dry hydrogenation bottle, 10% Pd/C (175 mg) was added under nitrogen atmosphere. A solution of (3S,4R)-benzyl 4-fluoro-3-((7-trityl-7H-pyrrolo[2,3-d]pyrimidin-4-yl)amino)piperidine-1-carboxylate (400 mg, 0.654 mmol) in anhydrous ethanol (13.0 mL) was added and the resulting mixture was hydrogenated under 50 psi of H$_2$ at ambient temperature for 3 hours. After LCMS showed the starting material to be consumed completely, the reaction mixture was filtered through a thin pad of Celite® and the filter cake was washed with ethanol. The combined filtrate was evaporated, azeotroped with toluene (5×) at 75° C. to afford compound N-((3S,4R)-4-fluoropiperidin-3-yl)-7-trityl-7H-pyrrolo[2,3-d]pyrimidin-4-amine (312 mg, 100%) as a colorless solid, which was used directly to next step without further purification.

Step 3. 1-((3S,4R)-4-Fluoro-3-((7-trityl-7H-pyrrolo[2,3-d]pyrimidin-4-yl)amino)piperidin-1-yl)prop-2-en-1-one To a solution of N-((3S,4R)-4-fluoropiperidin-3-yl)-7-trityl-7H-pyrrolo[2,3-d]pyrimidin-4-amine (312 mg, 0.653 mmol) in anhydrous CHCl$_3$ (15.0 mL) is added Hunig's base (0.6 mL, 4.0 mmol). The reaction mixture was cooled to 2° C., and then treated dropwise with a solution of acrylic chloride (0.053 mL, 0.653 mmol) in anhydrous CHCl$_3$ (3.0 mL). The reaction mixture was allowed to warm to ambient temperature and after 35 minutes, LCMS showed compound N-((3S,4R)-4-fluoropiperidin-3-yl)-7-trityl-7H-pyrrolo[2,3-d]pyrimidin-4-amine was consumed completely. The reaction mixture was cooled to 2° C. and quenched with 10% aqueous sodium bicarbonate (15 mL). The organic layer was extracted and the aqueous layer was back extracted with chloroform (2×10 mL). The organic extracts were combined, dried over magnesium sulfate, filtered, and concentrated in vacuo to yield crude product which was dry loaded with Celite® onto a Silicycle® 80 g HP column and purified via normal phase column chromatography (50-85% EtOAc/heptanes over 10 column volumes) to afford 1-((3S,4R)-4-fluoro-3-((7-trityl-7H-pyrrolo[2,3-d]pyrimidin-4-yl)amino)piperidin-1-yl)prop-2-en-1-one (280.0 mg, 81%) as a colorless solid. LCMS (M+H) 532.56.

Step 4. 1-((3S,4R)-3-((7H-Pyrrolo[2,3-d]pyrimidin-4-yl)amino)-4-fluoropiperidin-1-yl)prop-2-en-1-one A solution of 1-((3S,4R)-4-fluoro-3-((7-trityl-7H-pyrrolo[2,3-d]pyrimidin-4-yl)amino)piperidin-1-yl)prop-2-en-1-one (270.0 mg, 0.508 mmol) in trifluoroacetic acid (5.00 mL) was stirred at ambient temperature for 19 hours. The reaction mixture was concentrated in vacuo and dry loaded with Celite® onto a Silicycle® 80 g HP column and purified via normal phase column chromatography (0-20% MeOH/DCM over 10 column volumes) to afford 1-((3S,4R)-3-((7H-pyrrolo[2,3-d]pyrimidin-4-yl)amino)-4-fluoropiperidin-1-yl)prop-2-en-1-one (146.0 mg, 99%) as a colorless solid. LCMS (M+H) 290.41. $^1$H NMR (400 MHz, DMSO-d$_6$) δ 11.58 (S, 1H), 8.13 (s, 1H), 7.47 (s, 1H), 7.11 (s, 1H), 6.91-6.70 (m, 2H), 6.12 (t, J=20 Hz, 1H), 5.78-5.61 (m, 2H), 5.16-4.98 (m, 1H), 4.51-4.36 (m, 1H), 4.21-2.97 (m, 5H).

Example 55: (R)-1-(3-((5-(2-Hydroxyethyl)-7H-pyrrolo[2,3-d]pyrimidin-4-yl)amino)piperidin-1-yl)prop-2-en-1-one Prepared as in Examples 1-3, except using 5-(2-((tert-butyldimethylsilyl)oxy)ethyl)-4-chloro-7-tosyl-7H-pyrrolo[2,3-d]pyrimidine as the Het-Cl partner. LC/MS (M+H) 316.3. $^1$H NMR (400 MHz, DMSO-d$_6$) δ 1.31-2.06 (m, 4H) 2.78 (d, J=11.13 Hz, 2H) 2.94-3.18 (m, 1H) 3.47-3.87 (m, 3H) 3.96-4.21 (m, 2H) 5.11-5.67 (m, 2H) 5.90-6.14 (m, 1H) 6.50-6.90 (m, 2H) 7.02-7.38 (m, 1H) 8.03 (d, J=13.08 Hz, 1H) 11.25 (br s, 1H).

Example 56: 1-(2-((7H-Pyrrolo[2,3-d]pyrimidin-4-yl)amino)-8-azabicyclo[3.2.1]octan-8-yl)prop-2-en-1-one Prepared as described in Example 16, except no chiral SFC performed.

Example 57: 1-((3R,5S)-3-((7H-Pyrrolo[2,3-d]pyrimidin-4-yl)amino)-5-(dimethylamino)piperidin-1-yl)prop-2-en-1-one Step 1. (R)-tert-Butyl 3-oxo-5-((7-trityl-7H-pyrrolo[2,3-d]pyrimidin-4-yl)amino)piperidine-1-carboxylate To a solution of (3S,5R)-tert-butyl 3-hydroxy-5-((7-trityl-7H-pyrrolo[2,3-d]pyrimidin-4-yl)amino)piperidine-1-carboxylate (5.0 g, 8.68 mmol) in DCM (100 mL) was added Dess-Martin periodinane (4.0 g, 9.55 mmol), then the mixture was stirred at room temperature for 18 hours. After TLC (DCM/MeOH, 10:1) showed starting material to be consumed completely, the reaction mixture was concentrated to give crude product (7.8 g) as yellow solid, which was purified by prep-HPLC to give (R)-tert-butyl 3-oxo-5-((7-trityl-7H-pyrrolo[2,3-d]pyrimidin-4-yl)amino)piperidine-1-carboxylate (3.7 g, 74%) as a white solid. LC/MS (M+H) 574.5.

Step 2. (3S,5R)-tert-Butyl 3-(dimethylamino)-5-((7-trityl-7H-pyrrolo[2,3-d]pyrimidin-4-yl)amino)piperidine-1-carboxylate To a dry hydrogenation bottle, 10% dry Pd/C (300 mg) was added under Ar atmosphere. A solution of (R)-tert-butyl 3-oxo-5-((7-trityl-7H-pyrrolo[2,3-d]pyrimidin-4-yl)amino)piperidine-1-carboxylate (600 mg, 1.05 mmol) in 2M NHMe2/MeOH (20 mL) was added and the resulting mixture was hydrogenated at 45 psi H2 at 20° C. overnight. After TLC (DCM/MeOH/NH$_3$OH=10:1:1) indicated starting material to be consumed completely, and two new spots were formed, the reaction solution was filtered through a pad of Celite® and the cake was washed with MeOH three times. The combined filtrate was concentrated to give crude product, which was purified by column chromatography (silica, MeOH/NH$_3$/DCM, 0-8%) to provide (3S,5R)-tert-butyl 3-(dimethylamino)-5-((7-trityl-7H-pyrrolo[2,3-d]pyrimidin-4-yl)amino)pip-eridine-1-carboxylate (100 mg, 15.8%) as an oil and (3S,5S)-tert-butyl 3-(dimethylamino)-5-((7-trityl-7H-pyrrolo[2,3-d]pyrimidin-4-yl)amino)piperidine-1-carboxylate (300 mg, 47.6%) as a white solid. LC/MS (M+H) 603.5 (pk1); LC/MS (M+H) 603.5 (pk2).

Step 3. (3S,5R)—N3,N3-Dimethyl-N5-(7-trityl-7H-pyrrolo[2,3-d]pyrimidin-4-yl)piperidine-3,5-diamine To a solution of (3S,5R)-tert-butyl 3-(dimethylamino)-5-((7-trityl-7H-pyrrolo[2,3-d]pyrimidin-4-yl)amino) piperidine-1-carboxylate (100 mg, 0.660 mmol) in dioxane (10 mL) was added 4N HCl/dioxane (6 mL) dropwise at 0° C. and stirred at rt for 4 h. After TLC (DCM/MeOH, 10:1) indicated the reaction to be complete, the reaction mixture was concentrated to give crude product, which was purified by column chromatography (silica, MeOH/DCM, 0-10%) to give (3S,5R)—N3,N3-dimethyl-N5-(7-trityl-7H-pyrrolo[2,3-d]pyrimidin-4-yl)piperidine-3,5-diamine (100 mg, 100%) as a white solid. LC/MS (M+H) 503.5.

Step 4. 1-((3S,5R)-3-(Dimethylamino)-5-((7-trityl-7H-pyrrolo[2,3-d]pyrimidin-4-yl)amino)piperidin-1-yl)prop-2-en-1-one To a stirred solution of (3S,5R)—N3,N3-dimethyl-N5-(7-trityl-7H-pyrrolo[2,3-d]pyrimidin-4-yl)piperidine-3,5-diamine (100 mg, 0.199 mmol) in THF (10 mL)/aq. NaHCO$_3$ solution (10 mL) was added acryloyl chloride (19.8 mg, 0.219 mmol) dropwise at 0° C. After addition, the resulting mixture was stirred at 0° C. for 2 hours. After TLC (DCM/MeOH, 10:1) showed starting material to be consumed completely, the reaction mixture was diluted with H$_2$O (10 mL) and extracted with EtOAc (20 mL×2). The combined organic layers were washed with brine, dried over Na$_2$SO$_4$ and concentrated to give crude product, which was used to next step directly without further purification. LC/MS (M+H) 557.5.

Step 5. 1-((3R,5S)-3-((7H-Pyrrolo[2,3-d]pyrimidin-4-yl)amino)-5-(dimethylamino)piperidin-1-yl)prop-2-en-1-one 1-((3S,5R)-3-(Dimethylamino)-5-((7-trityl-7H-pyrrolo[2,3-d]pyrimidin-4-yl)amino)piperidin-1-yl)prop-2-en-1-one (50 mg, 0.089 mmol) in TFA (3 mL) was stirred at 30° C. overnight. After TLC (DCM/MeOH/NH$_4$OH, 10:1:1) indicated starting material was consumed completely, the reaction mixture was concentrated under vacuum to give crude product, which was purified by chromatography (silica, MeOH/NH$_3$/DCM, 0-10%) and further purified via prep-HPLC to give 1-((3R,5S)-3-((7H-pyrrolo[2,3-d]pyrimidin-4-yl)amino)-5-(dimethylamino)piperidin-1-yl)prop-2-en-1-one (17 mg, 30.3%) as a white solid. LC/MS (M+H) 315.2. $^1$H NMR (400 MHz, DMSO-d$_6$) δ 11.53 (br s, 1H), 8.16-8.07 (m, 1H), 7.49-7.31 (m, 1H), 7.12-7.06 (m, 1H), 6.81 (dd, J=10.5, 16.8 Hz, 1H), 6.55 (br s, 1H), 6.13 (d, J=16.8 Hz, 1H), 5.71 (d, J=10.8 Hz, 1H), 4.68-4.49 (m, 1H), 4.27 (d, J=12.0 Hz, 0.69H), 4.11 (br s, 1.51H), 2.98-2.81 (m, 1H), 2.64 (t, J=11.5 Hz, 1H), 2.44 (d, J=12.5 Hz, 1H), 2.36-2.16 (m, 6H), 1.72-1.50 (m, 1H).

Example 58: (3S,5R)-5-((7H-pyrrolo[2,3-d]pyrimidin-4-yl)amino)-1-acryloylpiperidine-3-carbonitrile

Step 1. (5R)-tert-Butyl 3-cyano-5-((7-trityl-7H-pyrrolo[2,3-d]pyrimidin-4-yl)amino)piperidine-1-carboxylate To a mixture of (R)-tert-butyl 3-oxo-5-((7-trityl-7H-pyrrolo[2,3-d]pyrimidin-4-yl)amino)piperidine-1-carboxylate (see Example 57) (1.0 g, 1.74 mmol) and TOSMIC (693.7 mg, 3.83 mmol) in DME (30 ml) at 0° C. was added t-BuOK (624.4 mg, 5.58 mmol) and EtOH (176.3 mg, 3.83 mmol) portionwise. The resulting mixture was stirred at 0° C. for 0.5 hour, then the mixture was warmed to room temperature and stirred for 2 hours. After TLC (DCM/MeOH, 10:1) indicated the reaction to be complete, the reaction solution was filtered, and concentrated to dryness to afford a crude product which purified by prep-TLC (Petroleum ether/EtOAC, 2:1) to afford (5R)-tert-butyl 3-cyano-5-((7-trityl-7H-pyrrolo[2,3-d]pyrimidin-4-yl)amino)piperidine-1-carboxylate (200 mg, 20%) as a yellow solid. LC/MS (M+H) 585.7.

Step 2. (5R)-5-((7-Trityl-7H-pyrrolo[2,3-d]pyrimidin-4-yl)amino)piperidine-3-carbonitrile To a solution of (5R)-tert-butyl 3-cyano-5-((7-trityl-7H-pyrrolo[2,3-d]pyrimidin-4-yl)amino)piperidine-1-carboxylate (235 mg, 0.41 mmol) in DCM (1.5 ml) at 0° C. was added TFA (229.0 mg, 2.0 mmol). The reaction was stirred at rt for 12 hours. After TLC (Petroleum ether/EtOAC, 1:1) indicated the reaction to be complete, the reaction mixture was concentrated in vacuo to give (5R)-5-((7-trityl-7H-pyrrolo[2,3-d]pyrimidin-4-yl)amino)piper-idine-3-carbonitrile (235 mg, 100%) as a yellow solid. LC/MS (M+H) 485.2.

Step 3. (5R)-1-Acryloyl-5-((7-trityl-7H-pyrrolo[2,3-d]pyrimidin-4-yl)amino)piperidine-3-carbonitrile To a stirred solution of (5R)-5-((7-trityl-7H-pyrrolo[2,3-d]pyrimidin-4-yl)amino)piperidine-3-carbonitrile (100 mg, 0.206 mmol) in THF (3 mL)/aq. NaHCO$_3$ solution (2.5 mL) at 0° C. was added acryloyl chloride (22.4 mg, 0.247 mmol) dropwise. The resulting mixture was stirred at 0° C. for 2 hours. After TLC (DCM/MeOH, 20:1) indicated the reaction to be complete, the reaction mixture was diluted with H$_2$O (20 mL) and extracted with EtOAc (30 mL×2), the combined organic extracts were washed with brine, dried (Na$_2$SO$_4$) and concentrated to give crude product, which was further purified by prep. TLC (Petroleum ether/EtOAC, 1:1) to give (5R)-1-acryloyl-5-((7-trityl-7H-pyrrolo[2,3-d]pyrimidin-4-yl)amino)piperidine-3-carbonitrile (80 mg, 72%) as yellow solid. LC/MS (M+H) 539.2.

Step 4. (3S,5R)-5-((7H-Pyrrolo[2,3-d]pyrimidin-4-yl)amino)-1-acryloylpiperidine-3-carbonitrile A solution of (5R)-1-acryloyl-5-((7-trityl-7H-pyrrolo[2,3-d]pyrimidin-4-yl)amino)piperidine-3-carbonitrile (80 mg, 0.272 mmol) in TFA (1 mL) was stirred at room temperature for 12 hours. After TLC (Petroleum ether/EtOAC, 1:1) indicated 20% starting material to be remaining, the reaction was heated to 30° C. for another 5 h. After LCMS indicated completion, the reaction mixture was concentrated to give crude product, which was further purified by prep. TLC (Petroleum ether/EtOAc, 1:1) to give (5R)-5-((7H-pyrrolo[2,3-d]pyrimidin-4-yl)amino)-1-acryloylpiperidine-3-carbonitrile (12 mg, 10% for 3 steps) as a white solid. Chiral HPLC showed it was a mixture of trans/cis, which was purified by SFC affording 1.4 mg of peak1 (trans) and 3.3 mg of peak2 (cis): SFC separation conditions: Column: ChiralPak AD (250 mm×30 mm, 20 μm), Mobile phase: 50% EtOH+NH$_3$H$_2$O, 80 mL/min. SFC analytical conditions: Column: Chiralpak AD-H 250×4.6 mm I.D., 5 μm Mobile phase: ethanol (0.05% DEA) in CO$_2$ from 5% to 40%; Flow rate: 2.35 mL/min; Wavelength: 220 nm. Peak 2: $^1$H NMR (400 MHz, MeOH-d$_4$) δ 8.20 (br s, 1H), 7.09 (d, J=3.5 Hz, 1H), 6.90-6.54 (m, 2H), 6.32-6.07 (m, 1H), 5.90-5.57 (m, 1H), 4.71-4.41 (m, 2H), 4.40-4.01 (m, 2H), 3.71-3.40 (m, 2H), 2.39 (br s, 1H), 2.17 (d, J=9.0 Hz, 1H). LC/MS (M+H) 297.1.

Example 59: 1-((3aS,7aS)-3a-Methyl-1-(7H-pyrrolo[2,3-d]pyrimidin-4-yl)hexahydro-1H-pyrrolo[2,3-c]pyridin-6(2H)-yl)prop-2-en-1-one (racemic-cis)

Step 1. rac-(3aS,7aS)-6-Benzyl-3a-methylhexahydro-1H-pyrrolo[2,3-c]pyridin-7(7aH)-one To a mixture of (3aS,7aS)-1,6-dibenzyl-3a-methylhexahydro-1H-pyrrolo[2,3-c]pyridin-7(7aH)-one (975 mg, 2.92 mmol), cyclohexene (7.5 mL, 73 mmol) and 10% Pd/C (175 mg, 0.16 mmol) in ethanol (14 mL) was stirred at reflux for 1.5 h. After TLC indicated complete conversion of starting material, the reaction was cooled, diluted with ethyl acetate and filtered through Celite®. The filtrate was concentrated under reduced pressure, giving (3aS,7aS)-6-benzyl-3a-methylhexahydro-1H-pyrrolo[2,3-c]pyridin-7(7aH)-one (683 mg, 95%) as a cloudy oil. LC/MS (M+Na) 267.2.

Step 2. rac-(3aS,7aS)-6-Benzyl-3a-methyloctahydro-1H-pyrrolo[2,3-c]pyridine

To a flask containing 3aS,7aS)-6-benzyl-3a-methylhexahydro-1H-pyrrolo[2,3-c]pyridin-7(7aH)-one (677 mg, 2.77 mmol) in THF (10 mL) at 0° C. was added LAH (150 mg, 3.95 mmol). The reaction was heated to reflux for 1 h. The reaction was cooled and quenched by the addition of water (0.15 mL), 15% NaOH (0.15 mL) and water (0.45 mL). The suspension was diluted with ethyl acetate and filtered through Celite®. Concentration under reduced pressure gave (3aS,7aS)-6-benzyl-3a-methyloctahydro-1H-pyrrolo[2,3-c]pyridine (607 mg, 95%) as a yellow oil. LC/MS (M+H) 231.2.

Step 3. rac-4-((3aS,7aR)-6-Benzyl-3a-methyloctahydro-1H-pyrrolo[2,3-c]pyridin-1-yl)-7-tosyl-7H-pyrrolo[2,3-d]pyrimidine To a flask containing (3aS,7aS)-6-benzyl-3a-methyloctahydro-1H-pyrrolo[2,3-c]pyridine (607 mg, 2.64 mmol) was added n-butanol (8.5 mL) 4-chloro-7-tosyl-7H-pyrrolo[2,3-d]pyrimidine (815 mg, 2.65 mmol) and DIPEA (3.8 mL, 22 mmol). The reaction mixture was stirred at 85° C. for 16 h. The reaction was cooled to rt and the solvent removed in vacuo. The crude material was purified by chromatography (silica, EtOAc/Heptane) to give 4-((3aS,7aR)-6-benzyl-3a-methyloctahydro-1H-pyrrolo[2,3-c]pyridin-1-yl)-7-tosyl-7H-pyrrolo[2,3-d]pyrimidine (913 mg, 69%) as an off-white solid. LC/MS (M+H) 502.2.

Step 4. rac-4-((3aS,7aR)-6-Benzyl-3a-methyloctahydro-1H-pyrrolo[2,3-c]pyridin-1-yl)-7H-pyrrolo[2,3-d]pyrimidine To a flask containing 4-((3aS,7aR)-6-benzyl-3a-methyloctahydro-1H-pyrrolo[2,3-c]pyridin-1-yl)-7-tosyl-7H-pyrrolo[2,3-d]pyrimidine (908 mg, 1.81 mmol) was added MeOH (14.4 mL), water (4.0 mL) and LiOH (124 mg, 5.1 mmol). The reaction was stirred at 60° C. for 1 h. The reaction was diluted with water (30 mL) and dichloromethane (30 mL) and the pH was adjusted to ~5 with 1M HCl. The layers were separated and the aqueous solution was extracted with dichloromethane (20 mL×2). The combined organic extracts were washed with brine (50 mL), dried (Na2SO4), filtered and concentrated under reduced pressure to give 4-((3aS,7aR)-6-benzyl-3a-methyloctahydro-1H-pyrrolo[2,3-c]pyridin-1-yl)-7H-pyrrolo[2,3-d]pyrimidine (628 mg) as a pale yellow solid. LC/MS (M+H) 348.2.

Step 5. Chiral separation of rac-4-((3aS,7aR)-6-benzyl-3a-methyloctahydro-1H-pyrrolo[2,3-c]pyridin-1-yl)-7H-pyrrolo[2,3-d]pyrimidine 4-((3aS,7aR)-6-Benzyl-3a-methyloctahydro-1H-pyrrolo[2,3-c]pyridin-1-yl)-7H-pyrrolo[2,3-d]pyrimidine racemate (622 mg) was purified by chiral SFC (Chiralpak AD-H, 60/40 $CO_2$/MeOH, 0.2% i-PrNH2) to give two peaks, pk1 assigned as (4-((3aS,7aR)-6-benzyl-3a-methyloctahydro-1H-pyrrolo[2,3-c]pyridin-1-yl)-7H-pyrrolo[2,3-d]pyrimidine, 263 mg, Rt=3.97 min) and pk 2 assigned as (4-((3aR,7aS)-6-benzyl-3a-methyloctahydro-1H-pyrrolo[2,3-c]pyridin-1-yl)-7H-pyrrolo[2,3-d]pyrimidine, 233 mg. Rt=5.31 min).

Step 6. 4-((3aR,7aS)-3a-Methyloctahydro-1H-pyrrolo[2,3-c]pyridin-1-yl)-7H-pyrrolo[2,3-d]pyrimidine To a flask containing (4-((3aR,7aS)-6-benzyl-3a-methyloctahydro-1H-pyrrolo[2,3-c]pyridin-1-yl)-7H-pyrrolo[2,3-d]pyrimidine was added ethanol (8.0 mL), cyclohexene (2.0 mL, 20 mmol) and Pd(OH)2 on carbon (263 mg, 0.38 mmol). The reaction was stirred at reflux for 1.5 h. The reaction was cooled, diluted with methanol and filtered through Celite®. The filtrate was concentrated and the product precipitated from ethyl acetate to give 4-((3aR,7aS)-3a-methyloctahydro-1H-pyrrolo[2,3-c]pyridin-1-yl)-7H-pyrrolo[2,3-d]pyrimidine (184 mg, 96%) as a colorless solid. LC/MS (M+H) 258.2.

Step 7. 1-((3aS,7aS)-3a-Methyl-1-(7H-pyrrolo[2,3-d]pyrimidin-4-yl)hexahydro-1H-pyrrolo[2,3-c]pyridin-6(2H)-yl)prop-2-en-1-one To a flask containing 4-((3aR,7aS)-3a-methyloctahydro-1H-pyrrolo[2,3-c]pyridin-1-yl)-7H-pyrrolo[2,3-d]pyrimidine (50 mg, 0.19 mmol) in DCM (3.0 mL) at 0° C. was added DIPEA (0.2 mL, 0.96 mL) and acryloyl chloride (19 mg, 0.20 mmol). The reaction was stirred at 0° C. for 3 h and then diluted with water/DCM (25/25 mL). The pH was adjusted to pH-5 and the layers separated. The organic extract was combined, dried (Na2SO4) and the solvent removed to give the crude product. The product was precipitated with ethyl acetate/heptanes to give 1-((3aS,7aS)-3a-methyl-1-(7H-pyrrolo[2,3-d]pyrimidin-4-yl)hexahydro-1H-pyrrolo[2,3-c]pyridin-6(2H)-yl)prop-2-en-1-one (49.6 mg, 83%) as a colorless solid. LC/MS (M+H) 312.2.

Example 60: 1-((3R,5R)-3-((7H-Pyrrolo[2,3-d]pyrimidin-4-yl)amino)-5-hydroxypiperidin-1-yl)prop-2-en-1-one

Step 1. N-((3R,5R)-1-Benzyl-5-((tert-butyldimethylsilyl)oxy)piperidin-3-yl)-7-tosyl-7H-pyrrolo[2,3-d]pyrimidin-4-amine To a stirred solution of (3R,5R)-1-benzyl-5-((tert-butyldimethylsilyl)oxy)piperidin-3-amine (4 g, 12.479 mmol) in n-butanol (25 ml) was added 4-chloro-7-tosyl-7H-pyrrolo[2,3-d]pyrimidine (4.608 g, 14.974 mmol) and DIPEA (4.443 ml, 24.957 mmol). The resulting mixture was heated to reflux for 24 h. The reaction mixture was cooled to ambient temp. After TLC (70% EtOAc in hexane) indicated starting material to be consumed, the solvent was removed in vacuo to provide the crude compound, which was purified by chromatography (silica, EtOAc/hexane 0-20%) to afford 5 g (68%) of N-((3R,5R)-1-benzyl-5-((tert-butyldimethylsilyl)oxy)piperidin-3-yl)-7-tosyl-7H-pyrrolo[2,3-d]pyrimidin-4-amine as a light yellow solid. LC/MS (M+H) 592.0. $^1$H NMR (400 MHz, $CDCl_3$) δ −0.07 (s, 6H) 0.87 (s, 9H) 1.44 (d, J=18.10 Hz, 1H) 1.93-2.31 (m, 3H) 2.37 (s, 3H) 2.65 (d, J=10.76 Hz, 1H) 2.94 (br s, 1H) 3.36-3.71 (m, 2H) 3.81-3.98 (m, 1H) 4.43 (br s, 1H) 5.63 (br s, 1H) 6.43 (d, J=3.91 Hz, 1H) 7.13-7.35 (m, 7H) 7.47 (d, J=3.91 Hz, 1H) 8.06 (d, J=8.31 Hz, 2H) 8.39 (s, 1H).

Step 2. N-((3R,5R)-1-Benzyl-5-((tert-butyldimethylsilyl)oxy)piperidin-3-yl)-7H-pyrrolo[2,3-d]pyrimidin-4-amine To a stirred solution of N-((3R,5R)-1-benzyl-5-((tert-butyldimethylsilyl)oxy)piperidin-3-yl)-7-tosyl-7H-pyrrolo[2,3-d]pyrimidin-4-amine (3 g, 5.069 mmol) in MeOH (15 ml) at 0° C. was added H$_2$O (3 ml) and K$_2$CO$_3$ (1.053 g, 7.603 mmol. The reaction was allowed to warm to rt and stirred for 16 h. After TLC (70% EtOAc in hexane) indicated starting material to be consumed completely, the solvent was removed in vacuo and the crude was purified by chromatography (silica, EtOAc/hexane, 0 to 70%) to afford 1.5 g (68%) N-((3R,5R)-1-benzyl-5-((tert-butyldimethylsilyl)oxy)piperidin-3-yl)-7H-pyrrolo[2,3-d]pyrimidin-4-amine as white solid. LC/MS (M+H) 437.8. $^1$H NMR (400 MHz, DMSO-d$_6$) δ −0.01 (s, 6H) 0.86 (s, 9H) 1.74 (d, J=4.89 Hz, 2H) 2.11-2.45 (m, 3H) 2.80 (d, J=8.31 Hz, 1H) 3.38-3.70 (m, 2H) 4.11 (br s, 1H). 4.62 (br s, 1H) 6.60 (br s, 1H) 6.94 (d, J=8.31 Hz, 1H) 7.07 (t, J=2.69 Hz, 1H) 7.15-7.40 (m, 5H) 8.06 (s, 1H) 11.47 (br s, 1H).

Step 3. N-((3R,5R)-5-((tert-Butyldimethylsilyl)oxy)piperidin-3-yl)-7H-pyrrolo[2,3-d]pyrimidin-4-amine A solution of N-((3R,5R)-1-benzyl-5-((tert-butyldimethylsilyl)oxy)piperidin-3-yl)-7H-pyrrolo[2,3-d]pyrimidin-4-amine (600 mg, 1.371 mmol) in ethanol was degassed with argon for 15 min and then charged with 10% Pd/C (60 mg). The mixture was hydrogenated using a hydrogen balloon for 16 h. After TLC (10% MeOH/DCM) indicated no starting material to be present, the reaction mixture was filtered through Celite®, and the filtrate was concentrated to give the crude material. The crude material was purified by column chromatography (100-200 silica, MeOH/DCM, 0 to 8%) to afford 380 mg (80%) N-((3R,5R)-5-((tert-butyldimethylsilyl)oxy)piperidin-3-yl)-7H-pyrrolo[2,3-d]pyrimidin-4-amine as a white solid.

$^1$H NMR (400 MHz, DMSO-d$_6$) δ 0.00 (br s, 6H) 0.82 (s, 9H) 1.65-1.88 (m, 2H) 2.56-2.42 (m, 3H) 2.70 (d, J=11.74 Hz, 1H) 2.91-3.06 (m, 1H) 3.96 (br s, 1H) 4.40 (br s, 1H) 6.57 (d, J=1.47 Hz, 1H) 6.88-7.12 (m, 2H) 8.06 (s, 1H) 11.46 (br s, 1H).

Step 4. 1-((3R,5R)-3-((7H-Pyrrolo[2,3-d]pyrimidin-4-yl)amino)-5-((tert-butyldimethylsilyl)oxy)piperidin-1-yl)prop-2-en-1-one To a stirred solution of N-((3R,5R)-5-((tert-butyldimethylsilyl)oxy) piperidin-3-yl)-7H-pyrrolo[2,3-d]pyrimidin-4-amine (400 mg, 1.151 mmol) in DCM (10 ml) at 0° C. was added TEA (0.481 ml, 3.453 mmol), followed by acryloyl chloride (0.093 ml, 1.15 mmol). The reaction mixture was stirred at 0° C. for 30 minutes. After TLC (10% MeOH/DCM) indicated starting material to be consumed, the reaction mixture was quenched with water (10 ml) and extracted with DCM (2×50 ml). The combined organics were washed with aq. NaHCO$_3$ (10 ml) and then with brine, dried (Na$_2$SO$_4$) and concentrated to provide the crude material, which was purified by chromatography (silica, MeOH/DCM 0 to 5%) to afford 180 mg (39%) 1-((3R,5R)-3-((7H-pyrrolo[2,3-d]pyrimidin-4-yl)amino)-5-((tert-butyldimethylsilyl)oxy)piperidin-1-yl)prop-2-en-1-one as light yellow solid. LC/MS (M+H) 401.8. 1H NMR (400 MHz, DMSO-d$_6$) δ −0.11-0.18 (m, 6H) 0.76-0.92 (m, 9H) 1.64-2.07 (m, 2H) 2.55-2.63 (m, 1H) 3.06-3.28 (m, 1H) 3.77-4.26 (m, 3H) 4.44 (br s, 1H) 4.64 (d, J=11.25 Hz, 1H) 5.50-5.74 (m, 1H) 5.96-6.15 (m, 1H) 6.57 (d, J=10.27 Hz, 1H) 6.71 (td, J=16.51, 10.51 Hz, 1H) 7.08 (br s, 1H) 7.13-7.30 (m, 1H) 7.99-8.19 (m, 1H) 11.51 (br s, 1H)

Step 5. 1-((3R,5R)-3-((7H-Pyrrolo[2,3-d]pyrimidin-4-yl)amino)-5-hydroxypiperidin-1-yl)prop-2-en-1-one To a stirred solution of 1-((3R,5R)-3-((7H-pyrrolo[2,3-d]pyrimidin-4-yl)amino)-5-((tert-butyldimethyl-silyl)oxy)piperidin-1-yl)prop-2-en-1-one (100 mg, 0.249 mmol) in THF (1 ml) was added 6N HCl (1 ml) at 0° C. The resultant mixture was allowed to come to ambient temperature, and stirred for 4 h. After TLC (10% MeOH/DCM) indicated starting material to be consumed, the reaction mixture was basified with saturated aq. NaHCO$_3$ solution and extracted with 20% IPA in DCM (5×30 ml). The organic extracts were dried (Na$_2$SO$_4$) and filtered. The solvent removed to provide the crude compound, which was purified by. RP-HPLC to give 25 mg of 1-((3R,5R)-3-((7H-pyrrolo[2,3-d]pyrimidin-4-yl)amino)-5-hydroxypiperidin-1-yl)prop-2-en-1-one as a white solid. LC/MS (M+H)=288.0. $^1$H NMR (400 MHz, MeOH-d$_4$) δ 1.78-2.28 (m, 3H) 2.83-3.01 (m, 1H) 3.33-3.63 (m, 2H) 3.76-3.97 (m, 1H) 4.00-4.22 (m, 2H) 4.45-4.67 (m, 1H) 5.46-5.79 (m, 1H) 5.97-6.26 (m, 1H) 6.46-6.70 (m, 2H) 6.78 (dd, J=16.87, 10.51 Hz, 1H) 7.06 (t, J=3.18 Hz, 1H) 8.06-8.23 (m, 1H).

Example 61: 1-[(5R)-2,2-Dimethyl-5-(7H-pyrrolo[2,3-d]pyrimidin-4-ylamino)piperidin-1-yl]prop-2-en-1-one

Step 1. N-(1-Benzyl-6,6-dimethylpiperidin-3-yl)-7-tosyl-7H-pyrrolo[2,3-d]pyrimidin-4-amine A flask containing 4-chloro-7-tosyl-7H-pyrrolo[2,3-d]pyrimidine (212 mg 0.688 mmol), 1-benzyl-6,6-dimethyl-piperidin-3-amine (200 mg, 0.688 mmol), DIEA (1.22 mL, 6.88 mmol) and n-BuOH (2.5 mL) were heated to 110° C. overnight. The mixture was concentrated under reduced pressure, and the residue was purified via flash chromatography (CombiFlash®, 12 g gold column, 10 to 50% EA in heptane) to give 140 mg (41.6%) of N-(1-benzyl-6,6-dimethylpiperidin-3-yl)-7-tosyl-7H-pyrrolo[2,3-d]pyrimidin-4-amine.

LC/MS (M+H) 490.1.

Step 2. N-(6,6-Dimethylpiperidin-3-yl)-7-tosyl-7H-pyrrolo[2,3-d]pyrimidin-4-amine To a solution of N-(1-benzyl-6,6-dimethylpiperidin-3-yl)-7-tosyl-7H-pyrrolo[2,3-d]pyrimidin-4-amine (100 mg, 0.204 mmol) in 5 mL of EtOH was added 20 mg of Pd/C (5%, 50% water) followed by HCOONH$_4$ (64.4 mg, 1.02 mmol). The reaction was heated to reflux for 24 hrs. The reaction was allowed to cool to rt and filtered. The filtrate was concentrated. The residue was dissolved in DCM and washed with water. The organic layer was separated and concentrated to give 70 mg of N-(6,6-dimethylpiperidin-3-yl)-7-tosyl-7H-pyrrolo[2,3-d]pyrimidin-4-amine. LC/MS (M+H) 400.1.

Step 3. 1-(2,2-Dimethyl-5-((7-tosyl-7H-pyrrolo[2,3-d]pyrimidin-4-yl)amino)piperidin-1-yl)prop-2-en-1-one To a solution N-(6,6-dimethylpiperidin-3-yl)-7-tosyl-7H-pyrrolo[2,3-d]pyrimidin-4-amine (70 mg, 0.18 mmol) in chloroform (5 mL)) was added DIPEA (0.124 mL, 0.700 mmol). The solution was cooled to 0° C. and acryloyl chloride (23.7 mg, 0.26 mmol) in 1 mL of CHCl$_3$ was added. After 30 min, saturated NaHCO$_3$ (5 mL) was added and the reaction mixture was stirred for 30 min. The organic layer was separated and concentrated to give 80 mg of 1-(2,2-dimethyl-5-((7-tosyl-7H-pyrrolo[2,3-d]pyrimidin-4-yl)amino)piperidin-1-yl)prop-2-en-1-one. $^1$H NMR (400 MHz, CDCl$_3$) δ 8.38 (s, 1H), 8.00 (d, 2H), 7.41 (d, 1H), 7.22 (d, 2H), 6.36 (d, 1H), 6.35-6.28 (m, 1H), 6.07-6.02 (m, 1H), 5.42-5.39 (m, 1H), 5.04-5.02 (m, 1H), 4.31-4.27 (m, 1H), 3.71-3.67 (m, 1H), 3.30-3.25 (m, 1H), 2.30 (s, 3H), 2.06-2.03 (m, 1H), 1.61-1.58 (m, 2H), 1.45 (d, 6H); m/z 454.1 (M+H).

Step 4. (R)-1-(5-((7H-Pyrrolo[2,3-d]pyrimidin-4-yl)amino)-2,2-dimethylpiperidin-1-yl)prop-2-en-1-one To a flask containing 1-(2,2-dimethyl-5-((7-tosyl-7H-pyrrolo[2,3-d]pyrimidin-4-yl)amino)piperidin-1-yl)prop-2-en-1-one (80 mg, 0.17) was added THF (2 ml). The reaction mixture was cooled to 0° C. and t-BuOK (0.348 mL, 0.3 mmol) was added. The ice bath was removed after 1 hr. After 1.5 hr, 0.5 mL (0.5 mmol) of additional t-BuOK was added and the reaction stirred at rt. After 2 hrs, the reaction was quenched with NH$_4$Cl (aq) and the mixture extracted with DCM. The DCM layer was dried and the solvent removed to give the crude product, which was purified by chromatography (silica, MeOH/DCM) to give rac-1-(5-((7H-pyrrolo[2,3-d]pyrimidin-4-yl)amino)-2,2-dimethylpiperidin-1-yl)prop-2-en-1-one. The racemate was separated by chiral HPLC to give two peaks. Example 61a: Enantiomer 1, 3.2 mg, RT 3.27, m/z 299.9 (M+H). Example 61b: Enantiomer 2, 4.4 mg, RT 3.92, m/z 299.8 (M+H).

Example 62: 3-(4-{[(3R)-1-Acryloylpiperidin-3-yl]amino}-7H-pyrrolo[2,3-d]pyrimidin-5-yl)propanenitrile Step 1. (R)-tert-Butyl 3-((5-(2-cyanoethyl)-7H-pyrrolo[2,3-d]pyrimidin-4-yl)amino)piperidine-1-carboxylate (a) To a flask containing (R)-tert-butyl 3-((5-(2-hydroxyethyl)-7H-pyrrolo[2,3-d]pyrimidin-4-yl)amino)piperidine-1-carboxylate (400 mg, 1.11 mmol) in DCM (6.0 mL) at 0° C. was added CH$_3$SO$_2$Cl (0.10 mL, 1.33 mmol) and DIPEA (0.6 mL, 3.32 mmol). The mixture was stirred at 0° C. for 30 min and then poured into water/DCM. The layers were separated and the organic extracts collected and dried (Na$_2$SO$_4$). The solvent was removed to give crude (R)-tert-butyl 3-((5-(2-((methylsulfonyl)oxy)ethyl)-7H-pyrrolo[2,3-d]pyrimidin-4-yl)amino)piperidine-1-carboxylate (540 mg), which was used in the next step without purification. (b) To the crude (R)-tert-butyl 3-((5-(2-((methylsulfonyl)oxy)ethyl)-7H-pyrrolo[2,3-d]pyrimidin-4-yl)amino)piperidine-1-carboxylate (540 mg, 1.23 mmol) was added DMF (5 mL) and NaCN (303 mg, 6.1 mmol). The reaction was stirred at 50° C. for 30 mins and then poured into water/ethyl acetate. The layers were separated and the organic extract collected and dried (Na$_2$SO$_4$). The solvent was removed to give the crude, which after chromatography (silica, MeOH/DCM 0 to 5%) gave (R)-tert-butyl 3-((5-(2-cyanoethyl)-7H-pyrrolo[2,3-d]pyrimidin-4-yl)amino)piperidine-1-carboxylate (302 mg, 66%).

LC/MS (M+H) 371.4.

Step 2. (R)-3-(4-(Piperidin-3-ylamino)-7H-pyrrolo[2,3-d]pyrimidin-5-yl)propanenitrile (c) To a flask containing (R)-tert-butyl 3-((5-(2-cyanoethyl)-7H-pyrrolo[2,3-d]pyrimidin-4-yl)amino)piperidine-1-carboxylate (302 mg, 0.82 mmol) was added DCM (2 mL) and TFA (0.32 mL). The mixture was stirred at rt for 4 hrs and the solvent removed to give crude (R)-3-(4-(piperidin-3-ylamino)-7H-pyrrolo[2,3-d]pyrimidin-5-yl)propanenitrile, which was used without further purification. LC/MS (M+H) 271.3.

Step 3. 3-(4-{[(3R)-1-Acryloylpiperidin-3-yl]amino}-7H-pyrrolo[2,3-d]pyrimidin-5-yl)propanenitrile To a flask containing (R)-3-(4-(piperidin-3-ylamino)-7H-pyrrolo[2,3-d]pyrimidin-5-yl)propanenitrile (53 mg, 0.20 mmol) in DCM (1.5 mL) at 0° C. was added DIPEA (0.10 mL, 0.58 mmol). After 30 min, acryloyl chloride (14.2 mg, 0.157 mmol) was added and the reaction stirred for 1 hr. The reaction was diluted with saturated NaHCO$_3$/DCM and the layers separated. The organic layer was collected, dried (Na$_2$SO$_4$) and the solvent removed. The crude material was purified by chromatography (silica, MeOH/DCM, 5-8%) to give (R)-3-(4-(piperidin-3-ylamino)-7H-pyrrolo[2,3-d]pyrimidin-5-yl)propanenitrile (32 mg, 50%). LC/MS (M+H) 325.4. $^1$H NMR (400 MHz, DMSO-d$_6$) δ 1.29-1.52 (m, 1H) 1.60-2.05 (m, 3H) 2.59-2.76 (m, 2H) 2.82-2.95 (m, 1H) 2.99-3.24 (m, 3H) 3.60-3.86 (m, 1H) 3.95-4.22 (m, 2H) 5.38-5.73 (m, 1H) 5.86-6.21 (m, 2H) 6.55-6.87 (m, 1H) 6.97 (s, 1H) 7.94-8.18 (m, 1H) 11.42 (br s, 1H).

Example 63: 1-[(3R)-3-{[2-(Pyridin-3-ylamino)-7H-pyrrolo[2,3-d]pyrimidin-4-yl]amino}piperidin-1-yl]prop-2-en-1-one Step 1. 2,4-Dichloro-7-((2-(trimethylsilyl)ethoxy)methyl)-7H-pyrrolo[2,3-d]pyrimidine To a suspension of sodium hydride (60 wt %, 510 mg, 12.76 mmol) in DMF (15 mL) at 0° C. was added dropwise a solution of 2,4-Dichloro-7H-pyrrolo[2,3-d]pyrimidine (2 g, 10.63 mmol) in anhydrous DMF (5 mL). When addition was complete, 2-(trimethylsilyl)ethoxymethyl chloride (2.45 mL, 13.83 mmol) was added dropwise and the reaction mixture stirred at 0° C. After 1.5 hours, the reaction mixture was diluted with water and ethyl acetate. The layers were separated and the organic extract washed with brine and dried (Na$_2$SO$_4$). The solvent was removed in vacuo to give the crude material, which after chromatography (silica, EtOAc/Hex, 0-5%) to provide 3.1 g (92%) of 2,4-dichloro-7-((2-(trimethylsilyl)ethoxy)methyl)-7H-pyrrolo[2,3-d]pyrimidine as a light yellow liquid. LC/MS 318.0.

Step 2. (R)-tert-Butyl 3-((2-chloro-7-((2-(trimethylsilyl)ethoxy)methyl)-7H-pyrrolo[2,3-d]pyrimidin-4-yl)amino)piperidine-1-carboxylate To a stirred solution of 2,4-dichloro-7-((2-(trimethylsilyl)ethoxy)methyl)-7H-pyrrolo[2,3-d]pyrimidine (2.85 g, 8.95 mmol) in n-butanol (100 mL) was added (R)-tert-butyl 3-aminopiperidine-1-carboxylate (1.79 g, 8.95 mmol) and DIPEA (7.80 mL, 44.77 mL). The reaction mixture was heated at 80° C. for 16 hours. After TLC indicated completion of the reaction with traces of unreacted SM, the crude mixture was concentrated in vacuo and purified by CombiFlash® chromatography (using 0-30% Ethyl acetate/Hexane) to provide 2.5 g (58%) of (R)-tert-butyl 3-((2-chloro-7-((2-(trimethylsilyl)ethoxy)methyl)-7H-pyrrolo[2,3-d]pyrimidin-4-yl)amino)piperidine-1-carboxylate as colorless sticky solid. LC/MS (M+H) 482.4.

Step 3. (R)-tert-Butyl 3-((2-(pyridin-3-ylamino)-7-((2-(trimethylsilyl)ethoxy)methyl)-7H-pyrrolo[2,3-d]pyrimidin-4-yl)amino)piperidine-1-carboxylate To a stirred solution of (R)-tert-butyl 3-((2-chloro-7-((2-(trimethylsilyl)ethoxy)methyl)-7H-pyrrolo[2,3-d]pyrimidin-4-yl)amino)piperidine-1-carboxylate (1.4 g, 2.90 mmol) in dioxane (30 mL) was added pyridin-3-amine (314 mg, 3.34 mmol), Cs$_2$CO$_3$ (2.36 g, 7.26 mmol) and Xantphos (67 mg, 0.116 mmol). The reaction mixture was degassed by the subsurface flow of argon for 30 minutes. Pd$_2$(dba)3 (53 mg, 0.058 mmol) was added to the reaction mixture which was then heated to 150° C. in a sealed tube for 16 hours. After TLC (40% EtOAc in hexane) indicated completion of the reaction, the reaction mixture was filtered through Celite® and washed with ethyl acetate. The filtrate was concentrated in vacuo and purified by CombiFlash® chromatography (using 0-80% Ethyl acetate/Hexane) to obtain 1.3 g (83%) of (R)-tert-butyl 3-((2-(pyridin-3-ylamino)-7-((2-(trimethylsilyl) ethoxy)methyl)-7H-pyrrolo[2,3-d]pyrimidin-4-yl) amino)piperidine-1-carboxylate as an off-white solid. LC/MS (M+H) 540.2.

Step 4. (R)—N4-(Piperidin-3-yl)-N2-(pyridin-3-yl)-7H-pyrrolo[2,3-d]pyrimidine-2,4-diamine To a stirred solution of (R)-tert-butyl 3-((2-(pyridin-3-ylamino)-7-((2-(trimethylsilyl)ethoxy)methyl)-7H-pyrrolo[2,3-d]pyrimidin-4-yl)amino)piperidine-1-carboxylate (300 mg, 0.556 mmol) in DCM (5 mL) was added TFA (5 mL) dropwise at 0° C. The reaction mixture was stirred at room temperature for 3 hours. After TLC (50% EtOAc in hexane) indicated completion of the reaction, the reaction was concentrated under reduced pressure. The crude material was dissolved in methanol (6 mL) and ethylene diamine (0.5 mL) was added dropwise at 0° C. The mixture was stirred at room temperature for 2 hours. The reaction was concentrated and partitioned between DCM and water. The organic layer was separated and washed with water, brine, dried over Na$_2$SO$_4$ and concentrated to give 210 mg (~100%) of (R)—N4-(piperidin-3-yl)-N2-(pyridin-3-yl)-7H-pyrrolo[2,3-d]pyrimidine-2,4-diamine as brown sticky solid. LC/MS (M+H) 310.4.

Step 5. (R)-1-(3-((2-(Pyridin-3-ylamino)-7H-pyrrolo[2,3-d]pyrimidin-4-yl)amino)piperidin-1-yl)prop-2-en-1-one To a stirred solution of (R)—N4-(piperidin-3-yl)-N2-(pyridin-3-yl)-7H-pyrrolo[2,3-d]pyrimidine-2,4-diamine (210 mg, 0.679 mmol) in DCM (5 mL) was added DIPEA (0.356 mL, 2.04 mmol) and acryloyl chloride (0.06 mL, 0.747 mmol) at 0° C. The reaction mixture was stirred for 30 minutes at 0° C. After TLC (5% MeOH in DCM) indicated completion of the reaction, the organic mixture was diluted with DCM/water. The organic extracts were separated and washed with water, brine, dried over Na$_2$SO$_4$ and concentrated in vacuo. The crude material was purified by CombiFlash® chromatography (using 0-3% MeOH/DCM) followed by trituration with ether-pentane to obtain 38 mg (16%) of (R)-1-(3-((2-(pyridin-3-ylamino)-7H-pyrrolo[2,3-d]pyrimidin-4-yl)amino)piperidin-1-yl)prop-2-en-1-one as an off-white solid. $^1$H NMR (400 MHz, DMSO-d$_6$) δ 11.07 (br, 1H), 8.89-8.86 (m, 2H), 8.32-8.23 (m, 1H), 8.00-8.01 (m, 1H), 7.19-7.17 (m, 1H), 6.83-6.81 (m, 1H), 6.90-6.60 (m, 1H), 6.47 (br, 1H), 6.15-5.99 (m, 1H), 5.72-5.47 (m, 1H), 4.55-4.15 (m, 2H), 4.10-3.90 (1H), 3.21-2.60 (m, 2H), 2.20-1.92 (m 1H), 1.90-1.82 (m, 1H), 1.75-1.32 (m, 2H); m/z 364.2 (M+H).

Example 64: 1-[(3S,4R)-4-Hydroxy-3-(7H-pyrrolo[2,3-d]pyrimidin-4-ylamino)piperidin-1-yl]prop-2-en-1-one) (rac-cis)

Step 1. tert-Butyl 5,6-dihydropyridine-1(2H)-carboxylate

Boc-anhydride (61.4 mL, 267.7 mmol) was added to a stirred solution of 1,2,3,6-tetrahydropyridine (22 g, 265 mmol) in 10% Na2CO3 (74.8 mL) at 0° C. The reaction mixture was stirred for 1 h at 0° C. and then at room temperature for 3 h. Saturated NaCl solution was added to the reaction mixture and the aqueous mixture extracted with diethyl ether. The organic layer was dried (Na$_2$SO$_4$), and concentrated to give tert-butyl 5,6-dihydropyridine-1(2H)-carboxylate (39.6 g, 81.8%) as pale yellow liquid. TLC system: Rf=0.5 (20% ethyl acetate in petroleum ether). $^1$H NMR (400 MHz, DMSO-d$_6$) δ 5.75-5.85 (m, 1H), 5.6-5.72 (m, 1H), 3.8 (d, 2H), 3.6 (dt, 2H), 2.15 (d, 2H), 1.4 (s, 9H). GCMS: (m/z)=82.2 (M+−Boc)+; (Purity: 87.95%).

Step 2. tert-Butyl 7-oxa-3-azabicyclo[4.1.0]heptane-3-carboxylate

Sodium bicarbonate (29 g, 346.2 mmol) was added in portions to a solution of tert-butyl 5,6-dihydropyridine-1(2H)-carboxylate (39.6 g, 216.3 mmol) in DCM (871 mL) at 0° C. m-Chloroperbenzoic acid (78 g, 454.4 mmol) was then added portionwise at 0° C. and stirred for 2 h at the same temperature, and then at room temperature for another 2 h. The insoluble material was filtered away and the filtrate was washed with water, dried (Na$_2$SO$_4$) and concentrated. The residue was purified by column chromatography on silica (100-200 mesh), eluting with 10% ethyl acetate in petroleum ether to give tert-butyl 7-oxa-3-azabicyclo[4.1.0]hep-tane-3-carboxylate (29.25 g, 69%) as a pale yellow liquid. TLC system: Rf=0.3 (30% Ethyl acetate in petroleum ether). $^1$H NMR (300 MHz, DMSO-d$_6$) δ 3.7 (t, 2H), 3.05-3.45 (overlapping signals, 4H), 1.7-2.0 (m, 2H), 1.4 (s, 9H). GCMS: (m/z) 199.2 (M+); (Purity: 98%).

Step 3. tert-Butyl 4-azido-3-hydroxypiperidine-1-carboxylate and tert-butyl 3-azido-4-hydroxypiperidine-1-carboxylate To a solution of tert-butyl 7-oxa-3-azabicyclo[4.1.0]heptane-3-carboxylate (29 g, 145.7 mmol) in 1,4-Dioxane (406 mL), was added water (81 mL) and sodium azide (13.8 g, 212.7 mmol) at room temperature and the resulting mixture was heated at 110° C. for 12 h. After cooling to rt, water was added to the reaction mixture and the resulting aqueous mixture extracted with ethyl acetate. The organic extracts were dried (Na$_2$SO$_4$), filtered and concentrated. The crude product was purified by column chromatography on silica (100-200 mesh) by gradient elution with 10% to 20% ethyl acetate in petroleum ether to give tert-butyl 4-azido-3- hydroxypiperidine-1-carboxylate (16.9 g) as pale yellow liquid and tert-butyl 3-azido-4-hydroxypiperidine-1-carboxylate (4 g) as yellow liquid. (Combined yield: 59%). TLC system: Rf=0.3 (40% Ethyl acetate in petroleum ether). tert-butyl 4-azido-3-hydroxypiperidine-1-carboxylate: $^1$H NMR (300 MHz, DMSO-$d_6$) δ 5.55 (d, 1H), 3.9 (dd, 1H), 3.8 (dd, 1H), 3.35-3.45 (m, 1H), 3.2-3.35 (m, 1H), 2.65-2.85 (br, 1H), 2.5-2.65 (br, 1H), 1.8 (dd, 1H), 1.4 (s, 9H). LCMS: (m/z) 143.1 (M+H-Boc)+; (Purity: 98.5%).

tert-butyl 3-azido-4-hydroxypiperidine-1-carboxylate: $^1$H NMR (300 MHz, DMSO-$d_6$) δ 5.35 (d, 1H), 3.7-3.85 (broad, 1H), 3.6-3.7 (broad, 1H), 3.4-3.55 (m, 1H), 3.2-3.35 (broad, 1H), 2.6-3.0 (overlapping, 2H), 1.70-1.85 (m, 1H), 1.40 (s, 9H). LCMS: (m/z)=143.1 (M+H-Boc)+; (Purity: 98.7%).

Step 4. rac-(3S,4S)-tert-Butyl 4-amino-3-hydroxypiperidine-1-carboxylate

10% Pd—C (5 g) was added portionwise to a solution of tert-butyl 4-azido-3-hydroxypiperidine-1-carboxylate (23 g, 181 mmol) in methanol (200 mL over 45 min under nitrogen. The resulting mixture was stirred for 12 h under hydrogen balloon pressure. The mixture was filtered through Celite® and the pad washed with methanol. The filtrate was concentrated and the crude dissolved in DCM, and filtered again through Celite® to remove the residual Pd. The filtrate was concentrated to give rac-(3S,4S)-tert-butyl 4-amino-3-hydroxypiperidine-1-carboxylate (11.5 g, 76%) as yellow syrup. TLC system: Rf=0.3 (10% MeOH in DCM). $^1$H NMR (400 MHz, DMSO-$d_6$) δ 4.9-5.1 (br s, 1H), 3.60-4.0 (2H), 2.85-2.95 (m, 2H), 2.60-2.80 (br, 1H), 2.35-2.45 (m, 1H), 1.50-1.80 (overlapping, 3H), 1.40 (s, 9H). LCMS: (m/z)=217.15 (M+H)+; (Purity: 96.5%).

Step 5. Rac-(3S,4S)-tert-Butyl 3-((2-chloro-7H-pyrrolo[2,3-d]pyrimidin-4-yl)amino)-4-hydroxypiperidine-1-carboxylate To a flask containing rac-(3S,4S)-tert-butyl 4-amino-3-hydroxypiperidine-1-carboxylate (460 mg, 2.13 mmol) was added n-butanol (4 mL), 2,4-dichloro-7H-pyrrolo[2,3-d]pyrimidine (400 mg, 2.13 mmol) and DIPEA (2 mL, 10 mmol). The mixture was heated to 95° C. overnight. The reaction was poured into EtOAc/Brine and the layers separated. The organic extract was washed with brine, dried ($Na_2SO_4$) and the solvent removed to give the crude, which after chromatography (silica, EtOAc/Heptane) gave rac-(3S,4S)-tert-butyl 3-((2-chloro-7H-pyrrolo[2,3-d]pyrimidin-4-yl)amino)-4-hydroxypiperidine-1-carboxylate (549 mg, 70%). LC/MS (M+H) 368.1. $^1$H NMR (400 MHz, CHCl$_3$) δ 1.10-1.72 (m, 10H) 1.96-2.11 (m, 1H) 2.74-3.19 (m, 2H) 3.59-4.37 (m, 4H) 5.69 (br s, 1H) 6.29 (br s, 1H) 6.82-7.07 (m, 1H) 10.82 (br. s, 1H).

Step 6. Rac-(3S,4R)-tert-Butyl 3-((2-chloro-7H-pyrrolo[2,3-d]pyrimidin-4-yl)amino)-4-((4-nitrobenzoyl)oxy) piperidine-1-carboxylate To a mixture of rac-(3S,4S)-tert-butyl 3-((2-chloro-7H-pyrrolo[2,3-d]pyrimidin-4-yl)amino)-4-hydroxypiperidine-1-carboxylate (0.4 g, 1.09 mmol) in toluene (6 mL) was added 4-nitrobenzoic acid (0.254 g, 1.52 mmol) and triphenylphosphine (0.461 g, 1.74 mmol)). The mixture was degassed with nitrogen and sealed in a vial with a septa top. DEAD (0.316 mL, 1.74 mmol) was added dropwise to the slurry. All solids dissolved and the mixture was stirred at room temperature for 4 h. The mixture was partitioned between brine and ethyl acetate. The layers were separated and the organic phase washed with 1N HCl, saturated sodium bicarbonate and then brine. The organic phase was dried over anhydrous magnesium sulfate and concentrated under reduced pressure. The residue was purified via chromatography (silica, EtOAc/Heptane) to give rac-(3S,4R)-tert-butyl 3-((2-chloro-7H-pyrrolo[2,3-d]pyrimidin-4-yl)amino)-4-((4-nitrobenzoyl)oxy)piperidine-1-carboxylate (499.5 mg, 88%). LC/MS (M+H) 517.2.

Step 7. Rac-(3S,4R)-tert-Butyl 3-((2-chloro-7H-pyrrolo[2,3-d]pyrimidin-4-yl)amino)-4-hydroxypiperidine-1-carboxylate To a flask containing (3S,4R)-tert-butyl 3-((2-chloro-7H-pyrrolo[2,3-d]pyrimidin-4-yl)amino)-4-((4-nitrobenzoyl)oxy)piperidine-1-carboxylate (499 mg, 0.96 mmol) was added dioxane (8 mL) and NaOH (5 mL, 1M solution). The mixture was heated to 50° C. for 1 h and the poured into brine/EtOac. The layers were separated and the aqueous phase extracted twice with 25 mL ethyl acetate. The combined ethyl acetate extracts were washed with brine, dried over anhydrous magnesium sulfate and concentrated under reduced pressure to give crude, which was purified by chromatography (silica, EtOAc/Hep, 0 to 100%) to give rac-(3S,4R)-tert-butyl 3-((2-chloro-7H-pyrrolo[2,3-d]pyrimidin-4-yl)amino)-4-hydroxypiperidine-1-carboxylate (183 mg, 51%). LC/MS (M+H) 368.2. $^1$H NMR (400 MHz, CHCl$_3$) δ 1.37-1.49 (m, 10H) 1.60-1.88 (m, 3H) 3.08-3.90 (m, 4H) 4.34-4.48 (m, 1H) 6.35 (br s, 1H) 6.47 (br s, 1H) 7.03 (s, 1H) 10.42 (br s, 1H).

Step 8. Rac-(3S,4R)-3-((7H-Pyrrolo[2,3-d]pyrimidin-4-yl)amino)piperidin-4-ol To a mixture of rac-(3S,4R)-tert-butyl 3-((2-chloro-7H-pyrrolo[2,3-d]pyrimidin-4-yl)amino)-4-hydroxypiperidine-1-carboxylate (0.1826 g) in ethanol (2 mL) was added cyclohexene (2 mL) and 1.25 M HCl in methanol (1 mL). The mixture was placed under nitrogen and 10% Pd/C was added and refluxed overnight. After cooling to rt, the mixture was filtered through Celite® and the filtrate concentrated to give rac-(3S,4R)-3-((7H-pyrrolo[2,3-d]pyrimidin-4-yl)amino)piperidin-4-ol (150 mg, 98%). LC/MS (M+H) 234.2. $^1$H NMR (400 MHz, MeOH-$d_4$) δ 1.89-2.20 (m, 3H) 3.03-3.22 (m, 1H) 3.36-3.53 (m, 2H) 4.12-4.28 (m, 1H) 4.51-4.73 (m, 1H) 7.02 (br s, 1H) 7.36 (br s, 1H) 8.38 (br s, 1H).

Step 9. Rac-1-((3S,4R)-3-((7H-Pyrrolo[2,3-d]pyrimidin-4-yl)amino)-4-hydroxypiperidin-1-yl)prop-2-en-1-one To a mixture of rac-(3S,4R)-3-((7H-pyrrolo[2,3-d]pyrimidin-4-yl)amino)piperidin-4-ol (75 mg, 0.24 mmol) in DCM (2 mL) and acetonitrile (2 mL) was added NMM (0.083 mL, 0.73 mmol). The mixture was stirred in an ice bath for 10 minutes at which time a solution of acryloyl chloride (0.02 mL, 0.24 mmol)) in DCM (0.5 mL) was added dropwise over 10 minutes. The mixture was stirred at 0° C. for 1.5 h. DMF (3 mL) was added and the reaction stirred at room temperature for 1 h. The mixture was concentrated under reduced pressure and the residue purified by RP-HPLC to give rac-1-((3S,4R)-3-((7H-pyrrolo[2,3-d]pyrimidin-4-yl)amino)-4-hydroxypiperidin-1-yl)prop-2-en-1-one (7.1 mg). LC/MS (M+H) 288.18.

Example 65: Rac-1-((3R,5R)-3-((7H-Pyrrolo[2,3-d]pyrimidin-4-yl)amino)-5-methylpiperidin-1-yl)prop-2-en-1-one

Step 1. Rac-N-((3R,5R)-5-Methylpiperidin-3-yl)-7H-pyrrolo[2,3-d]pyrimidin-4-amine To a dry Parr bottle was added Pd/C (200 mg) under $N_2$ atmosphere. Then, a solution of rac-(3R,5R)-benzyl 3-((2-chloro-7H-pyrrolo[2,3-d]pyrimidin-4-yl)amino)-5-methylpiperidine-1-carboxylate (see Example 14, Step 5, rac-trans, 559 mg, 1.398 mmol) in MeOH/THF (30 mL/10 mL) was added and the resulting mixture was heated to 40° C. under 50 psi of $H_2$ for 3 days. LCMS indicated the reaction was completed. The reaction mixture was filtered and the filter cake was washed with MeOH. The combined filtrate was evaporated to give rac-N-((3R,5R)-5-methylpiperidin-3-yl)-7H-pyrrolo[2,3-d]pyrimidin-4-amine (rac-trans, 413 mg, 100%) as a pink solid.

Step 2. Rac-1-((3R,5R)-3-((7H-Pyrrolo[2,3-d]pyrimidin-4-yl)amino)-5-methylpiperidin-1-yl)prop-2-en-1-one To a solution of rac-N-((3R,5R)-5-methylpiperidin-3-yl)-7H-pyrrolo[2,3-d]pyrimidin-4-amine ((413 mg, 1.542 mmol) in THF (20 mL) was added saturated aq.NaHCO3 (15 mL) and acryloyl chloride (154 mg, 1.70 mmol, 1.1 eq.) at 0° C. After 2 hrs at 0° C., TLC (EtOAc:MeOH=10:1) indicated the reaction was complete. The reaction mixture was diluted with water (50 mL), and extracted with EtOAc (50 mL×2). The combined organic layers were washed with brine, dried over $Na_2SO_4$ and concentrated. The residue was purified by flash column chromatography (EtOAc:MeOH=10:1) to give rac-1-((3R,5R)-3-((7H-pyrrolo[2,3-d]pyrimidin-4-yl)amino)-5-methylpiperidin-1-yl)prop-2-en-1-one (221 mg, 50%) as a white solid. $^1$H NMR (400 MHz, DMSO-$d_6$) δ 11.48 (br s, 1H), 8.30-8.04 (m, 1H), 7.13-6.96 (m, 2H), 6.83 (dd, J=10.3, 16.8 Hz, 1H), 6.69-6.54 (m, 1H), 6.36 (dd, J=10.5, 16.6 Hz, 1H), 6.08 (d, J=17.8 Hz, 1H), 5.89 (d, J=17.1 Hz, 1H), 5.66 (d, J=8.8 Hz, 1H), 5.35 (d, J=10.5 Hz, 1H), 4.47-4.20 (m, 1H), 4.04-3.84 (m, 2H), 3.61-3.37 (m, 2H), 2.88-2.75 (m, 1H), 2.15 (br s, 1H), 1.93-1.76 (m, 1H), 1.71-1.53 (m, 1H), 0.98-0.88 (m, 3H). LC/MS (M+H) 285.9.

Example 66. (R)-1-(3-((5-(6-Methylpyridin-3-yl)-7H-pyrrolo[2,3-d]pyrimidin-4-yl)amino)piperidin-1-yl)prop-2-en-1-one Prepared as the derivatives in Examples 23-40. LC/MS (M+H) 363.2.

Example 67. 1-(5-((7H-Pyrrolo[2,3-d]pyrimidin-4-yl)amino)-2,2-dimethylpiperidin-1-yl)prop-2-en-1-one Prepared as described in Example 61, except no chiral separation.

Example 68. 1-((2R,5S)-5-((7H-Pyrrolo[2,3-d]pyrimidin-4-yl)amino)-2-methylpiperidin-1-yl)prop-2-en-1-one Prepared as described in Example 5, Step 9; pk1: $^1$H NMR (400 MHz, DMSO-$d_6$) δ 11.53 (br s, 1H), 8.12 (d, J=12.8 Hz, 1H), 7.30 (dd, J=6.8, 18.8 Hz, 1H), 7.10 (br s, 1H), 6.89-6.71 (m, 1H), 6.56 (d, J=1.8 Hz, 1H), 6.10 (dd, J=2.1, 16.7 Hz, 1H), 5.72-5.61 (m, 1H), 4.81 (br s, 0.5H), 4.56 (d, J=10.3 Hz, 0.5H), 4.37 (br s, 0.5H), 4.20-3.95 (m, 1.5H), 2.96 (t, J=11.9, 10 Hz, 0.5H), 2.60 (t, J=12.0 Hz, 0.5H), 1.92-1.59 (m, 4H), 1.30-1.07 (m, 3H). 19 H's obs; 19 exp. LC/MS (M+H) 286.2. OR=[a]$_D^{20}$=+0.34 (c=0.6, MeOH).

Example 69: 1-(5-((7H-Pyrrolo[2,3-d]pyrimidin-4-yl)amino)-2-(hydroxymethyl)piperidin-1-yl)prop-2-en-1-one Prepared as in Example 7, except no separation of diastereomers or enantiomers.
LC/MS (M+H) 302.2. See Example 52.

Examples 70, 71 and 72

Example 70: (S)-1-(3-((7H-Pyrrolo[2,3-d]pyrimidin-4-yl)amino)-3-methylpiperidin-1-yl)prop-2-en-1-one

Example 71: 1-(3-((7H-Pyrrolo[2,3-d]pyrimidin-4-yl)amino)-3-methylpiperidin-1-yl)prop-2-en-1-one

Example 72: (R)-1-(3-((7H-pyrrolo[2,3-d]pyrimidin-4-yl)amino)-3-methylpiperidin-1-yl)prop-2-en-1-one

Step 1. 1-tert-Butyl 3-methyl 3-methylpiperidine-1,3-dicarboxylate

To a solution of 1-tert-butyl 3-methyl piperidine-1,3-dicarboxylate (15 g, 0.062 mol) in THF (250 ml) was added LHMDS (74.4 ml, 0.074 mol) dropwise at −65° C. under $N_2$ protection. The reaction mixture was stirred at −65° C. for 1 h. MeI (10.5 g, 0.074 mol) was added dropwise. The resulting solution was stirred at −65° C. for 2 h and at room temperature for 1 h. The resulting solution was quenched with sat.NH$_4$Cl (aq) (200 ml). The organic layer was separated and the aqueous layer was extracted with MTBE (200 ml×2). The combined organic layers were washed with brine, dried over $Na_2SO_4$ and concentrated to dryness to give 1-tert-butyl 3-methyl 3-methylpiperidine-1,3-dicarboxylate (15.86 g, 100%) as yellow oil. $^1$H NMR (400 MHz, DMSO-$d_6$) δ 1.08 (s, 3H) 1.32-1.47 (m, 12H) 1.94 (br s, 1H) 3.05 (d, J=12.30 Hz, 2H) 3.42 (br s, 1H) 3.61 (br s, 3H) 3.82 (br s, 1H).

Step 2. 1-tert-Butyl 3-methyl 3-methylpiperidine-1,3-dicarboxylate

To a solution of 1-tert-butyl 3-methyl 3-methylpiperidine-1,3-dicarboxylate (15.86 g, 0.062 mol) in THF (100 ml) and $H_2O$ (10 ml) was added LiOH.$H_2O$ (7.76 g, 0.186 mol) at room temperature. The mixture was refluxed at 70° C. for 6 h. After TLC (Petroleum ether/EtOAc, 4:1, stained by iodine) showed the starting material to be consumed, the mixture was concentrated to dryness. The residue was diluted with $H_2O$ (300 mL) and then extracted with MTBE (100 mL×2). The organic layers were discarded. The resulting aqueous layer was acidified to pH 1 with 1M HCl (aq.) and then extracted with MTBE twice. The combined organic layers were washed with brine, dried over $Na_2SO_4$ and concentrated to dryness to give 1-tert-butyl 3-methyl 3-methylpiperidine-1,3-dicarboxylate (13.97 g, 93%) as a white solid.

Step 3. tert-Butyl 3-isocyanato-3-methylpiperidine-1-carboxylate

To a solution of 1-tert-butyl 3-methyl 3-methylpiperidine-1,3-dicarboxylate (5.97 g, 24.5 mmol) in anhydrous toluene (65 mL) was TEA (3.5 mL, 24.5 mmol) and DPPA (6 mL, 27 mmol) dropwise at room temperature. The reaction mixture was stirred at rt for 30 min and then refluxed at 90° C. for 2 h. The reaction was poured into ice water (100 mL) and extracted with MTBE (100 mL×3). The combined organic layers were washed with brine, dried ($Na_2SO_4$) and concentrated to dryness to give tert-butyl 3-isocyanato-3-methylpiperidine-1-carboxylate (5.9 g, 100%) as a yellow oil, which was used without purification in the next step.

Step 4. tert-Butyl 3-amino-3-methylpiperidine-1-carboxylate

To a solution of tert-butyl 3-isocyanato-3-methylpiperidine-1-carboxylate (5.89 g, 24.54 mmol) in THF (140 ml) was added 2M NaOH (aq) (140 ml). The resulting solution was stirred vigorously at room temperature overnight. TLC showed the desired product was formed. The reaction mixture was acidified to pH 1 with 1M HCl (aq) and then extracted with MTBE (200 ml×3). The organic layers were discarded. The resulting aqueous layer was basified to pH 10 with 1M NaOH (aq.) and then extracted with MTBE (250 ml×3). The combined organic layers were washed with brine to neutral pH, dried over $Na_2SO_4$ and concentrated to dryness to give tert-butyl 3-amino-3-methylpiperidine-1-carboxylate (3.7 g, 36%) as colorless oil which was directly used to the next step without further purification. $^1H$ NMR (400 MHz, $CHCl_3$) δ d 1.09 (s, 3H) 1.27-1.40 (m, 2H) 1.46 (s, 10H) 1.53-1.65 (m, 2H) 3.04-3.56 (m, 4H).

Step 5. tert-Butyl 3-methyl-3-((7-tosyl-7H-pyrrolo[2,3-d]pyrimidin-4-yl)amino)piperidine-1-carboxylate tert-Butyl 3-amino-3-methylpiperidine-1-carboxylate (3.3 g, 15.398 mmol) and tert-butyl 3-amino-3-methylpiperidine-1-carboxylate (3.9 g, 12.7 mmol) was stirred at 140° C. overnight. After TLC showed tert-butyl 3-amino-3-methylpiperidine-1-carboxylate to be consumed, the mixture was diluted with DCM (80 ml). The DCM layer was washed with sat $NaHCO_3$ (aq) and brine and concentrated to dryness to give crude product which was purified by chromatography (silica, EtOAc/Petroleum ether, 0-40%) to give tert-butyl 3-methyl-3-((7-tosyl-7H-pyrrolo[2,3-d]pyrimidin-4-yl)amino)piperidine-1-carboxylate (2.4 g, 40%) as a white solid.

Step 6. N-(3-Methylpiperidin-3-yl)-7-tosyl-7H-pyrrolo[2,3-d]pyrimidin-4-amine To a solution of tert-butyl 3-methyl-3-((7-tosyl-7H-pyrrolo[2,3-d]pyrimidin-4-yl)amino)piperidine-1-carboxylate (3 g, 6.2 mmol) in dioxane (30 ml) was added 4 M HCl/dioxane (30 ml) dropwise at 0° C. Then the reaction mixture was warmed to room temperature and stirred for 2 h. After LC-MS showed the starting material to be consumed, the reaction mixture was concentrated to dryness to give crude product (2.6 g, 100%) as a white solid which was directly used to the next step without further purification.

Step 7. 1-(3-Methyl-3-((7-tosyl-7H-pyrrolo[2,3-d]pyrimidin-4-yl)amino)piperidin-1-yl)prop-2-en-1-one To a solution of N-(3-methylpiperidin-3-yl)-7-tosyl-7H-pyrrolo[2,3-d]pyrimidin-4-amine (2.5 g, 5.93 mmol) in THF (100 ml)/sat.$NaHCO_3$ (aq) (100 ml) was added acryloyl chloride (0.64 g, 7.115 mmol) dropwise at 0° C. The reaction mixture was stirred at 0° C. for 1 h. After TLC showed the starting material to be consumed, the reaction mixture was diluted with water (50 ml) and extracted with EtOAc (100 ml×3). The combined organic layers were concentrated to dryness to give crude product which was purified by chromatography (silica, EtOAc/petroleum ether=0-66%) to give 1-(3-methyl-3-((7-tosyl-7H-pyrrolo[2,3-d]pyrimidin-4-yl)amino)piperidin-1-yl)prop-2-en-1-one (1.618 g, 62%) as a white solid. LC/MS (M+H) 440.2.

Step 8. 1-(3-((7H-Pyrrolo[2,3-d]pyrimidin-4-yl)amino)-3-methylpiperidin-1-yl)prop-2-en-1-one To a solution of 1-(3-methyl-3-((7-tosyl-7H-pyrrolo[2,3-d]pyrimidin-4-yl)amino)piperidin-1-yl)prop-2-en-1-one (1 g, 2.277 mmol) in THF (10 ml) and $H_2O$ (2 ml) was added LiOH.$H_2O$ (0.2 g, 4.554 mmol) and t-BuOK (0.5 g, 4.554 mmol). The reaction mixture was refluxed at 65° C. for 7 h. After TLC showed the starting material to be consumed mostly, the mixture was neutralized with AcOH and concentrated to dryness to give crude product, which was purified by chromatography (silica, MeOH/EtOAc, 0-6%, 6-8%) to give 1-(3-((7H-pyrrolo[2,3-d]pyrimidin-4-yl)amino)-3-methylpiperidin-1-yl)prop-2-en-1-one (180 mg) (97% purity by LC-MS). The crude product was further purified by SP1 (MeOH/EtOAc, 0-2%) to give 70 mg (12%) of a white solid. $^1H$ NMR (400 MHz, DMSO-$d_6$) δ 1.51 (s, 3H) 1.58 (br s, 1H) 1.75 (d, J=8.53 Hz, 2H) 3.12-3.26 (m, 3H) 3.59 (d, J=11.80 Hz, 1H) 3.81 (br s, 1H) 5.44 (br s, 1H) 5.93 (br s, 1H) 6.23 (br s, 1H) 6.60 (br s, 2H) 7.03 (d, J=3.26 Hz, 1H) 8.13 (s, 1H) 11.00-11.57 (m, 1H).

Step 9. (R)-1-(3-((7H-Pyrrolo[2,3-d]pyrimidin-4-yl)amino)-3-methylpiperidin-1-yl)prop-2-en-1-one and (S)-1-(3-((7H-Pyrrolo[2,3-d]pyrimidin-4-yl)amino)-3-methylpiperidin-1-yl)prop-2-en-1-one Seventy milligrams of 1-(3-((7H-pyrrolo[2,3-d]pyrimidin-4-yl)amino)-3-methylpiperidin-1-yl)prop-2-en-1-one were separated by chiral SFC to give two peaks, arbitrarily assigned: pk1, (R)-1-(3-((7H-pyrrolo[2,3-d]pyrimidin-4-yl)amino)-3-methylpiperidin-1-yl)prop-2-en-1-one (17 mg) and pk 2, (S)-1-(3-((7H-pyrrolo[2,3-d]pyrimidin-4-yl)amino)-3-methylpiperidin-1-yl)prop-2-en-1-one (21.3 mg).

Pk1: (R)-1-(3-((7H-pyrrolo[2,3-d]pyrimidin-4-yl)amino)-3-methylpiperidin-1-yl)prop-2-en-1-one: $^1H$ NMR (400 MHz, DMSO-$d_6$) δ 1.51 (d, J=1.25 Hz, 3H) 1.58 (br s, 1H) 1.68-1.83 (m, 2H) 1.76 (d, J=8.78 Hz, 2H) 3.07 (br s, 2H) 3.30 (br s, 1H) 3.60 (d, J=13.55 Hz, 1H) 3.78 (br s, 1H) 5.50 (br s, 1H) 5.96 (br s, 1H) 6.20 (br s, 1H) 6.57 (br s, 2H) 7.03 (br s, 1H) 8.13 (s, 1H) 11.24 (br s, 1H).

Pk2: (S)-1-(3-((7H-Pyrrolo[2,3-d]pyrimidin-4-yl)amino)-3-methylpiperidin-1-yl)prop-2-en-1-one. $^1H$ NMR (400 MHz, DMSO-$d_6$) δ 1.51 (s, 3H) 1.59 (br s, 2H) 1.75 (d, J=8.28 Hz, 2H) 3.06 (br s, 2H) 3.31 (br s, 1H) 3.60 (d, J=13.30 Hz, 1H) 3.78 (br s, 1H) 5.48 (br s, 1H) 5.96 (br s, 1H) 6.19 (br s, 1H) 6.57 (br s, 2H) 7.03 (d, J=2.51 Hz, 1H) 8.13 (s, 1H) 11.25 (br s, 1H).

Example 73: 1-[(3aS,7aS)-1-(2-Amino-7H-pyrrolo[2,3-d]pyrimidin-4-yl)octahydro-6H-pyrrolo[2,3-c]pyridin-6-yl]prop-2-en-1-one

Step 1. (3aS,7aS)-Benzyl 1-(2-amino-7H-pyrrolo[2,3-d]pyrimidin-4-yl)hexahydro-1H-pyrrolo[2,3-c]pyridine-6(2H)-carboxylate A mixture of (3aS,7aS)-benzyl hexahydro-1H-pyrrolo[2,3-c]pyridine-6(2H)-carboxylate (Example 8, Step 7, pk2) (464 mg, 1.786 mmol), DIPEA (1.15 g, 8.928 mmol) and 4-chloro-7H-pyrrolo[2,3-d]pyrimidin-2-amine (300 mg, 1.786 mol) in n-BuOH (6 mL) was heated to 130° C. for 8 hours. After TLC (DCM/MeOH, 10:1) indicated the reaction be complete, the reaction mixture was cooled to room temperature and evaporated to dryness and the residue was purified by chromatography (silica, DCM/MeOH, 1%-12%) to give (3aS,7aS)-benzyl 1-(2-amino-7H-pyrrolo[2,3-d]pyrimidin-4-yl)hexahydro-1H-pyrrolo[2,3-c]pyridine-6(2H)-carboxylate (350 mg, 50%) as a brown solid. LC/MS (M+H) 393.4. $^1$H NMR (400 MHz, CHCl$_3$) δ 1.73-1.76 (m, 1H), 2.17-2.04 (m, 3H), 2.51 (br. s, 1H), 3.05-2.41 (m, 2H), 4.11-3.81 (m, 3H), 4.81-4.47 (m, 3H), 5.29-5.07 (m, 3H), 6.79-6.35.

Step 2. 4-((3aR,7aS)-Octahydro-1H-pyrrolo[2,3-c]pyridin-1-yl)-7H-pyrrolo[2,3-d]pyrimidin-2-amine To a dry Parr bottle, Pd/C (50 mg) was added under Ar atmosphere. Then a solution of (3aS,7aS)-benzyl 1-(2-amino-7H-pyrrolo[2,3-d]pyrimidin-4-yl)hexahydro-1H-pyrrolo[2,3-c]pyridine-6(2H)-carboxylate (200 mg, 0.510 mol) in EtOH (15 mL) was added and the resulting mixture was hydrogenated under 45 psi of H$_2$ at 25° C. for 18 hours. After TLC (DCM/MeOH, 10:1) indicated starting material to be consumed, the reaction mixture was filtered and the filter cake was washed with EtOH. The combined filtrate was evaporated to give 4-((3aR,7aS)-octahydro-1H-pyrrolo[2,3-c]pyridin-1-yl)-7H-pyrrolo[2,3-d]pyrimidin-2-amine (120 mg, 91.6%) as a white solid. LC/MS (M+H) 259.2.

Step 3. 1-[(3aS,7aS)-1-(2-Amino-7H-pyrrolo[2,3-d]pyrimidin-4-yl)octahydro-6H-pyrrolo[2,3-c]pyridin-6-yl]prop-2-en-1-one To a stirred solution of 4-((3aR,7aS)-octahydro-1H-pyrrolo[2,3-c]pyridin-1-yl)-7H-pyrrolo[2,3-d]pyrimidin-2-amine (150 mg, 0.58 mol) and NaHCO3 (150 mg, 1.74 mmol) in H$_2$O (8 mL) was added acryloyl chloride (63 mg, 0.70 mmol) dropwise at 0° C. carefully. After addition, the resulting mixture was stirred at room temperature for 6 hours. After LC-MS showed 4-((3aR,7aS)-octahydro-1H-pyrrolo[2,3-c]pyridin-1-yl)-7H-pyrrolo[2,3-d]pyrimidin-2-amine to be consumed, the reaction mixture was diluted with H$_2$O (20 mL) and extracted with EtOAc (20 mL×4), the combined organic layer was concentrated to give crude product, which was purified by column chromatography to give 1-[(3aS,7aS)-1-(2-amino-7H-pyrrolo[2,3-d]pyrimidin-4-yl)octahydro-6H-pyrrolo[2,3-c]pyridin-6-yl]prop-2-en-1-one (56 mg, 30.9%) as a white solid. $^1$H NMR (400 MHz, DMSO-d$_6$) δ 10.655 (s, 1H) 6.72-6.71 (m, 2H) 6.41 (s, 1H), 6.09-6.05 (m, 1H), 5.64-5.61 (m, 1H), 5.33 (s, 2H), 4.28-3.69 (m, 5H), 3.34-3.29 (d, 1H), 3.20 (s, 1H), 2.09-1.72 (m, 5H).

Examples 74 and 75

Example 74: 1-[(3R,5R)-3-Methyl-5-(7H-pyrrolo[2,3-d]pyrimidin-4-ylamino)piperidin-1-yl]prop-2-en-1-one

Example 75: 1-((3S,5S)-3-((7H-Pyrrolo[2,3-d]pyrimidin-4-yl)amino)-5-methylpiperidin-1-yl)prop-2-en-1-one See Example 14 (Step 5) and Example 65 (Step 2).

Step 1. 1-[(3R,5R)-3-Methyl-5-(7H-pyrrolo[2,3-d]pyrimidin-4-ylamino)piperidin-1-yl]prop-2-en-1-one and 1-((3S,5S)-3-((7H-Pyrrolo[2,3-d]pyrimidin-4-yl)amino)-5-methylpiperidin-1-yl)prop-2-en-1-one rac-trans: 1-((3R,5R)-3-((7H-Pyrrolo[2,3-d]pyrimidin-4-yl)amino)-5-methylpiperidin-1-yl)prop-2-en-1-one (see Example 14, Step 5; Example 65, Step 2) (150 mg) was separated by chiral SFC to give two peaks arbitrarily assigned: 1-((3R,5R)-3-((7H-pyrrolo[2,3-d]pyrimidin-4-yl)amino)-5-methylpiperidin-1-yl)prop-2-en-1-one (pk 1, 60 mg, 80%) as a white solid and 1-((3S,5S)-3-((7H-pyrrolo[2,3-d]pyrimidin-4-yl)amino)-5-methylpiperidin-1-yl)prop-2-en-1-one (pk 2, 60 mg, 80%) as a white solid. SFC conditions: ChiralPak AD (250 mm×30 mm, 5 μm); 20% EtOH, NH$_3$H$_2$O; 60 mL/min. Pk1: 1-((3R,5R)-3-((7H-pyrrolo[2,3-d]pyrimidin-4-yl)amino)-5-methylpiperidin-1-yl)prop-2-en-1-one: $^1$H NMR (400 MHz, DMSO-d$_6$) δ 11.51 (br s, 1H), 8.19-8.07 (m, 1H), 7.06 (d, J=6.0 Hz, 2H), 6.84 (dd, J=10.2, 16.4 Hz, 1H), 6.70-6.55 (m, 1H), 6.35 (dd, J=10.4, 16.7 Hz, 1H), 6.08 (d, J=18.6 Hz, 1H), 5.88 (dd, J=2.3, 16.8 Hz, 1H), 5.66 (d, J=10.3 Hz, 1H), 5.35 (dd, J=2.3, 10.5 Hz, 1H), 4.41-4.21 (m, 1H), 4.06-3.84 (m, 2H), 3.61-3.42 (m, 1H), 2.85-2.75 (m, 1H), 2.15 (br s, 1H), 1.99-1.78 (m, 1H), 1.73-1.50 (m, 1H), 1.23 (s, 1H), 1.00-0.86 (m, 3H). LCMS (M+H) 286.1.

Pk 2: 1-((3S,5S)-3-((7H-pyrrolo[2,3-d]pyrimidin-4-yl)amino)-5-methylpiperidin-1-yl)prop-2-en-1-one:

$^1$H NMR (400 MHz, DMSO-d$_6$) δ 11.51 (br s, 1H), 8.19-8.05 (m, 1H), 7.06 (br s, 1H), 6.84 (dd, J=10.3, 16.8 Hz, 1H), 6.69-6.55 (m, 1H), 6.35 (dd, J=10.5, 16.6 Hz, 1H), 6.08 (d, J=16.6 Hz, 1H), 5.88 (d, J=15.1 Hz, 1H), 5.66 (d, J=9.3 Hz, 1H), 5.35 (d, J=10.0 Hz, 1H), 4.42-4.19 (m, 1H), 4.06-3.82 (m, 1H), 3.62-3.44 (m, 1H), 2.86-2.73 (m, 1H), 2.15 (br s, 1H), 1.96-1.77 (m, 1H), 1.72-1.53 (m, 1H), 1.23 (br s, 1H), 1.01-0.64 (m, 3H). LCMS (M+H) 286.1.

Example 76: 1-[(3aR,7aR)-1-(7H-Pyrrolo[2,3-d]pyrimidin-4-yl)octahydro-6H-pyrrolo[2,3-c]pyridin-6-yl]prop-2-en-1-one Prepared as in Example 8, except using rac-(3aS,7aS)-benzyl hexahydro-1H-pyrrolo[2,3-c]pyridine-6(2H)-carboxylate in step 7. LC/MS (M+H) 298.0. $^1$H NMR (400 MHz, DMSO-d$_6$) δ 11.58 (s, 1H) 8.09-8.07 (d, J=9.2 Hz, 1H) 7.11 (s, 1H), 6.82-6.78 (m, 1H), 6.51 (m, 1H), 6.05-6.01 (m, 1H), 5.69-5.85 (m, 1H), 4.69-4.68 (m, 0.5H), 4.27 (s, 1H), 3.90-3.74 (m, 3H), 3.13-3.24 (m, 2H), 2.74-2.71 (m, 0.5H), 2.19-1.74 (m, 4.5H).

Examples 77 and 78

Example 77: 1-[(3R,5R)-3-Methoxy-5-(7H-pyrrolo[2,3-d]pyrimidin-4-ylamino)piperidin-1-yl]prop-2-en-1-one

Example 78: 1-{(3R,5R)-3-Methoxy-5-[methyl(7H-pyrrolo[2,3-d]pyrimidin-4-yl)amino]piperidin-1-yl}prop-2-en-1-one

Step 1. N-((3R,5R)-1-Benzyl-5-((tert-butyldimethylsilyl)oxy)piperidin-3-yl)-7-trityl-7H-pyrrolo[2,3-d]pyrimidin-4-amine To a mixture of 4-chloro-7-trityl-7H-pyrrolo[2,3-d]pyrimidine (16.3 g, 41.18 mmol) and (3R,5R)-1-benzyl-5-((tert-butyldimethylsilyl)oxy)piperidin-3-amine (12 g, 37.44 mmol) in n-BuOH (250 mL) was added DIPEA (14.5 g, 112.32 mmol). The mixture was heated to 110° C. for 3 days. After TLC (DCM/MeOH, 10:1) indicated the reaction to be complete, the reaction mixture was cooled to room temperature and evaporated to dryness. The residue was diluted into EtOAc (800 mL) and water (500 mL). The organic layer was washed with brine, dried over $Na_2SO_4$ and concentrated to give crude product, which was purified by chromatography (silica, EtOAc/PE, 0% to 30%) to give N-((3R,5R)-1-benzyl-5-((tert-butyldimethylsilyl)oxy)piperidin-3-yl)-7-trityl-7H-pyrrolo[2,3-d]pyrimidin-4-amine (15 g, 65%) as a yellow solid. $^1$H NMR (400 MHz, $CHCl_3$) δ −0.02 (s, 6H), 0.82 (s, 9H), 1.50-1.45 (m, 1H), 2.31-2.29 (m, 2H), 2.75-2.73 (m, 1H), 2.97 (br. S, 1H), 3.69-3.49 (m, 2H), 4.00-3.98 (m, 1H), 4.49 (br. s, 1H), 5.57 (br s, 1H), 6.32 (s, 1H), 6.90 (s, 1H), 7.17-7.15 (m, 5H), 7.33-7.26 (m, 15H), 7.99 (s, 1H).

Step 2. (3R,5R)-tert-Butyl 3-((tert-butyldimethylsilyl)oxy)-5-((7-trityl-7H-pyrrolo[2,3-d]pyrimidin-4-yl)amino)piperidine-1-carboxylate To a Parr bottle, 10% dry Pd/C (1.5 g) was added under Ar atmosphere. Then a solution of N-((3R,5R)-1-benzyl-5-((tertbutyldimethylsilyl)oxy)piperidin-3-yl)-7-trityl-7H-pyrrolo[2,3-d]pyrimidin-4-amine (14.8 g, 21.76 mmol) and $(Boc)_2O$ (5.22 g, 23.94 mmol) in MeOH (300 mL) was added. The resulting mixture was hydrogenated under 50 psi of $H_2$ at 40° C. for 12 hours. After TLC (PE/EtOAc, 4:1) indicated the reaction to be complete, the reaction solution was filtered through a pad of Celite® and the filter cake was washed three times with MeOH. The combined filtrate was concentrated to give (3R,5R)-tert-butyl 3-((tert-butyldimethylsilyl)oxy)-5-((7-trityl-7H-pyrrolo[2, 3-d]pyrimidin-4-yl)amino)piperidine-1-carboxylate (14.8 g, ~100%) as a yellow solid, which was used directly to next step without further purification. $^1$H NMR (400 MHz, $CHCl_3$) δ 0.06 (s, 6H), 0.86 (s, 9H), 1.53 (s, 9H), 1.83 (br. s, 1H), 2.28-2.04 (m, 1H), 3.09 (br s 1H), 3.49 (br s, 2H), 3.93-3.71 (m, 4H), 4.44 (br. s, 1H), 6.30 (s, 1H), 6.80 (s, 1H) 7.26-7.14 (m, 15H), 8.00 (s, 1H).

Step 3. (3R,5R)-tert-Butyl 3-hydroxy-5-((7-trityl-7H-pyrrolo[2,3-d]pyrimidin-4-yl)amino)piperidine-1-carboxylate To a solution of (3R,5R)-tert-butyl 3-((tertbutyldimethylsilyl)oxy)-5-((7-trityl-7H-pyrrolo[2,3-d]pyrimidin-4-yl)amino)piperidine-1-carboxylate (15 g, 21.74 mmol) in anhydrous THF (300 mL) was added n-$Bu_4NF$ (11.38 g, 43.47 mmol) and then heated to 40° C. overnight. After TLC (PE/EtOAc, 4:1) showed the reaction to be complete, the reaction solution was diluted with water (300 mL) and then extracted with EtOAc (200 mL×2). The combined organic layers were washed with water and brine in turns, dried over $Na_2SO_4$ and concentrated to give (3R,5R)-tert-butyl 3-hydroxy-5-((7-trityl-7H-pyrrolo[2,3-d]pyrimidin-4-yl)amino)piperidine-1-carboxylate (14.6 g, ~100%), which was used directly in the next step without further purification. $^1$H NMR (400 MHz, $CHCl_3$) δ 8.01 (s, 1H), 7.37-7.08 (m, 17H), 6.91 (d, J=3.5 Hz, 1H), 6.30 (br s, 1H), 4.48 (d, J=3.5 Hz, 1H), 4.05 (br s, 1H), 3.83-3.51 (m, 4H), 3.23 (br s, 1H), 1.58-1.29 (m, 10H).

Step 4. (3R,5R)-tert-Butyl 3-methoxy-5-((7-trityl-7H-pyrrolo[2,3-d]pyrimidin-4-yl)amino)piperidine-1-carboxylate and (3R,5R)-tert-butyl 3-methoxy-5-(methyl(7-trityl-7H-pyrrolo[2,3-d]pyrimidin-4-yl)amino)piperidine-1-carboxylate To a solution of (3R,5R)-tert-butyl 3-hydroxy-5-((7-trityl-7H-pyrrolo[2,3-d]pyrimidin-4-yl)amino)piperidine-1-carboxylate (0.6 g, 1.043 mmol) in DMF (1 mL) was added $Ag_2O$ (0.48 g, 2.086 mmol), followed by MeI (0.6 g, 4.22 mmol). The reaction mixture was sealed and heated to 30° C. for 48 hours. After LC-MS showed the starting material to be consumed, and ~20% of dimethylation product was formed, the mixture was filtrated through a pad of Celite® and the cake was washed with EtOAc. The combined filtrates were washed with water, brine, dried ($Na_2SO_4$) and the solvent removed to give crude product, which was purified by chromatography (silica, EtOAc/PE, 0% to 50%) to give (3R,5R)-tert-butyl 3-methoxy-5-((7-trityl-7H-pyrrolo[2,3-d]pyrimidin-4-yl)amino)piperidine-1-carboxylate and (3R,5R)-tert-butyl 3-methoxy-5-(methyl(7-trityl-7H-pyrrolo[2,3-d]pyrimidin-4-yl)amino)piperidine-1-carboxylate (250 mg, 50%) as a white solid. LC-MS showed the ratio monomethylation and di-methylation was ~1:1. LC/MS (M+H) 590 and 604.

Step 5. N-((3R,5R)-5-Methoxypiperidin-3-yl)-7-trityl-7H-pyrrolo[2,3-d]pyrimidin-4-amine and N-((3R,5R)-5-methoxypiperidin-3-yl)-N-methyl-7-trityl-7H-pyrrolo[2,3-d]pyrimidin-4-amine To a solution of mono and dimethylated compound (250 mg, 0.36 mmol) in DCM (2 mL) was added 4M HCl (g)/dioxane (2 mL) at 10-15° C. After stirring for 2 h, LC-MS showed the reaction was completed. The reaction solution was concentrated to give N-((3R,5R)-5-methoxypiperidin-3-yl)-7-trityl-7H-pyrrolo[2,3-d]pyrimidin-4-amine and N-((3R,5R)-5-methoxypiperidin-3-yl)-N-methyl-7-trityl-7H-pyrrolo[2,3-d]pyrimidin-4-amine (208 mg, 100%), which was used directly to next step without further purification. LC/MS (M+H) 490.1 and 504.1.

Step 6. 1-((3R,5R)-3-Methoxy-5-((7-trityl-7H-pyrrolo[2,3-d]pyrimidin-4-yl)amino)piperidin-1-yl)prop-2-en-1-one and 1-((3R,5R)-3-Methoxy-5-(methyl(7-trityl-7H-pyrrolo[2,3-d]pyrimidin-4-yl)amino)piperidin-1-yl)prop-2-en-1-one To a stirred solution of mono/dimethylated compound (208 mg, 0.36 mmol) in THF (5 mL) and saturated aqueous $NaHCO_3$ solution (5 mL) was added acryloyl chloride (40 mg, 0.43 mmol) dropwise at 0-5° C. After the resulting mixture was stirred at 0-10° C. for 2 hours, TLC (DCM/MeOH/$NH_4OH$, 10:1:1) indicated amine consumed completely. The reaction mixture was diluted with H$_2$O (10 mL) and extracted with EtOAc (30 mL×3), the combined organic layer was washed with brine, dried over Na$_2$SO$_4$ and concentrated to afford crude 1-((3R,5R)-3-methoxy-5-((7-trityl-7H-pyrrolo[2,3-d]pyrimidin-4-yl)amino)piperidin-1-yl)prop-2-en-1-one and 1-((3R,5R)-3-methoxy-5-(methyl(7-trityl-7H-pyrrolo[2,3-d]pyrimidin-4-yl)amino)piperidin-1-yl)prop-2-en-1-one (240 mg, ~100%), which was used directly to next step without further purification.

Step 7. 1-((3R,5R)-3-((7H-Pyrrolo[2,3-d]pyrimidin-4-yl)amino)-5-methoxypiperidin-1-yl)prop-2-en-1-one and 1-((3R,5R)-3-Methoxy-5-(methyl(7H-pyrrolo[2,3-d]pyrimidin-4-yl)amino)piperidin-1-yl)prop-2-en-1-one A solution of mono/dimethylated compound (240 mg, 0.44 mmol) in TFA (3 mL) was stirred at ambient temperature (10-20° C.) overnight. After TLC (DCM/MeOH/NH4OH, 10:1:1) showed ~30% of starting material to remain, the reaction was heated to 40° C. for another 6 h, whereupon LC-MS showed the starting material was consumed. The reaction solution was diluted with THF and concentrated to give crude product, which was purified by prep-HPLC directly to give 1-((3R,5R)-3-((7H-pyrrolo[2,3-d]pyrim-idin-4-yl)amino)-5-methoxypiperidin-1-yl)prop-2-en-1-one (32 mg, 24% for 3 steps) and 1-((3R,5R)-3-methoxy-5-(methyl(7H-pyrrolo[2,3-d]pyrimidin-4-yl)amino)piperidin-1-yl)prop-2-en-1-one (25 mg) as a white solid. Pk1(mono-Me): $^1$H NMR (400 MHz, DMSO-d$_6$) δ 11.32 (br s, 1H), 8.14 (s, 1H), 7.13-6.94 (m, 2H), 6.69 (d, J=16.1 Hz, 1H), 6.59 (br s, 1H), 6.07 (d, J=15.6 Hz, 1H), 5.62 (d, J=9.0 Hz, 1H), 4.40 (br s, 1H), 4.14 (br s, 1H), 3.65 (br s, 1H), 3.32 (s, 3H), 3.20 (d, J=14.1 Hz, 2H), 2.15 (br s, 1H), 1.85 (br s, 1H). Pk2 (di-Me): $^1$H NMR (400 MHz, DMSO-d$_6$) δ 11.81 (br s, 1H), 8.19-8.04 (m, 1H), 7.18 (d, J=8.6 Hz, 1H), 6.85-6.69 (m, 1H), 6.68-6.53 (m, 1H), 6.10 (dd, J=7.2, 16.6 Hz, 1H), 5.73-5.58 (m, 1H), 5.03-4.80 (m, 1H), 4.72 (d, J=13.7 Hz, 1H), 4.45 (d, J=11.7 Hz, 1H), 4.19 (d, J=14.1 Hz, 1H), 4.03 (d, J=12.1 Hz, 1H), 3.69-3.55 (m, 2H), 3.28-3.10 (m, 6H), 2.96 (t, J=11.5 Hz, 1H), 2.78-2.68 (m, 1H), 2.18-1.90 (m, 2H).

Example 79: 1-[(1S,2S,5S)-2-(7H-Pyrrolo[2,3-d]pyrimidin-4-ylamino)-8-azabicyclo[3.2.1]oct-8-yl]prop-2-en-1-one Prepared as described in Example 16, except pk2 after chiral separation was carried through Steps 3 and 4.

Example 80-87

The following compounds were prepared as in Example 41, using the appropriate acid or acid chloride.

| Example | LC/MS | Name |
|---|---|---|
| 80 | 348.2 | (2E)-4,4-difluoro-1-[(3aS,7aS)-1-(7H-pyrrolo[2,3-d]pyrimidin-4-yl)octahydro-6H-pyrrolo[2,3-c]pyridin-6-yl]but-2-en-1-one |
| 81 | 366.2 | (2E)-4,4,4-trifluoro-1-[(3aS,7aS)-1-(7H-pyrrolo[2,3-d]pyrimidin-4-yl)octahydro-6H-pyrrolo[2,3-c]pyridin-6-yl]but-2-en-1-one |
| 82 | 355.2 | (2E)-4-(dimethylamino)-1-[(3aS,7aS)-1-(7H-pyrrolo[2,3-d]pyrimidin-4-yl)octahydro-6H-pyrrolo[2,3-c]pyridin-6-yl]but-2-en-1-one |
| 83 | 355.2 | (2E)-4-(dimethylamino)-1-[(3aS,7aS)-1-(7H-pyrrolo[2,3-d]pyrimidin-4-yl)octahydro-6H-pyrrolo[2,3-c]pyridin-6-yl]but-2-en-1-one |
| 84 | 312.2 | (2E)-1-[(3aS,7aS)-1-(7H-pyrrolo[2,3-d]pyrimidin-4-yl)octahydro-6H-pyrrolo[2,3-c]pyridin-6-yl]but-2-en-1-one |
| 85 | 312.2 | 2-methyl-1-[(3aS,7aS)-1-(7H-pyrrolo[2,3-d]pyrimidin-4-yl)octahydro-6H-pyrrolo[2,3-c]pyridin-6-yl]prop-2-en-1-one |
| 86 | 324.2 | cyclobut-1-en-1-yl[(3aS,7aS)-1-(7H-pyrrolo[2,3-d]pyrimidin-4-yl)octahydro-6H-pyrrolo[2,3-c]pyridin-6-yl]methanone |
| 87 | 330.2 | (2E)-4-fluoro-1-[(3aS,7aS)-1-(7H-pyrrolo[2,3-d]pyrimidin-4-yl)octahydro-6H-pyrrolo[2,3-c]pyridin-6-yl]but-2-en-1-one |

Example 88: 1-[(3R,5R)-3-(Dimethylamino)-5-(7H-pyrrolo[2,3-d]pyrimidin-4-ylamino)piperidin-1-yl]prop-2-en-1-one Prepared as in Example 57, except using the trans-isomer.

Step 1. (3R,5R)—N3,N3-Dimethyl-N5-(7-trityl-7H-pyrrolo[2,3-d]pyrimidin-4-yl)piperidine-3,5-diamine To a solution of (3R,5R)-tert-butyl 3-(dimethylamino)-5-((7-trityl-7H-pyrrolo[2,3-d]pyrimidin-4-yl)amino)piperidine-1-carboxylate (300 mg, 0.498 mmol) in dioxane (15 mL) was added 4N HCl/Dioxane (10 mL) dropwise at 0° C. and stirred at rt for 4 h. TLC (CH2Cl2/MeOH=10:1) indicated the reaction was complete. The reaction solution was concentrated to provide crude (3R,5R)—N3,N3-dimethyl-N5-(7-trityl-7H-pyrrolo[2,3-d]pyrimidin-4-yl)piperidine-3,5-diamine (300 mg, 100%) as a yellow solid.

Step 2. 1-((3R,5R)-3-(Dimethylamino)-5-((7-trityl-7H-pyrrolo[2,3-d]pyrimidin-4-yl)amino)piperidin-1-yl)prop-2-en-1-one To a stirred solution of (3R,5R)—N3,N3-dimethyl-N5-(7-trityl-7H-pyrrolo[2,3-d]pyrimidin-4-yl)piperidine-3,5-diamine (300 mg, 0.597 mmol) in THF (18 mL) and aq. NaHCO$_3$ solution (18 mL) at 0° C. was added acryloyl chloride (59.4 mg, 0.657 mmol) dropwise. After the resulting mixture was stirred at 0° C. for 2 hours, TLC (DCM/

MeOH, 10:1) indicated the reaction was complete. The reaction mixture was diluted with H₂O (10 mL) and extracted with EtOAc (30 mL×2), the combined organic layer was washed with brine, dried over Na₂SO₄ and concentrated to give crude product, which was used to next step directly without further purification.

Step 3. 1-((3R,5R)-3-((7H-Pyrrolo[2,3-d]pyrimidin-4-yl)amino)-5-(dimethylamino)piperidin-1-yl)prop-2-en-1-one 1-((3R,5R)-3-(Dimethylamino)-5-((7-trityl-7H-pyrrolo[2,3-d]pyrimidin-4-yl)amino)piperidin-1-yl)prop-2-en-1-one (170 mg, 0.305 mmol) in TFA (5 mL) was stirred at 30° C. overnight. TLC (DCM/MeOH/NH₄OH, 10:1:1) indicated starting material was consumed completely. The reaction mixture was concentrated in vacuo to give crude product, which was purified by chromatography (silica, MeOH/NH3/DCM=0-10%) and further purified via pre-HPLC to give 1-((3R,5R)-3-((7H-pyrrolo[2,3-d]pyrimidin-4-yl)amino)-5-(dimethylamino)piperidin-1-yl)prop-2-en-1-one (59 mg, 61.4%) as a white solid. LC/MS (M+H) 315.2. ¹H NMR (400 MHz, DMSO-d₆) δ 11.26 (br s, 1H), 8.13 (s, 1H), 7.04 (br s, 1H), 6.81 (br s, 1H), 6.60 (br s, 2H), 5.98 (d, J=15.8 Hz, 1H), 5.49 (br s, 1H), 4.47 (br s, 1H), 3.59 (br s, 4H), 2.66-2.53 (m, 1H), 2.29 (s, 6H), 2.08 (br s, 1H), 1.87 (br s, 1H).

Example 89: 1-{(3aS,7aS)-1-[5-(2-Methoxyethyl)-7H-pyrrolo[2,3-d]pyrimidin-4-yl]octahydro-6H-pyrrolo[2,3-c]pyridin-6-yl}prop-2-en-1-one Prepared as in Example 8, except using rac-(3aS,7aS)-benzyl hexahydro-1H-pyrrolo[2,3-c]pyridine-6(2H)-carboxylate and 4-chloro-5-(2-methoxyethyl)-7-tosyl-7H-pyrrolo[2,3-d]pyrimidine in step 7. LC/MS (M+H) 356.2. ¹H NMR (400 MHz, CHCl₃) δ 1.44-1.99 (m, 5H) 2.42-2.58 (m, 1H) 2.83-2.77 (m, 1H) 2.89-3.06 (m, 2H) 3.24-3.38 (m, 4H) 3.59-3.42 (m, 3H) 3.98-3.91 (m, 1H) 4.25-4.41 (m, 1H) 4.45-4.65 (m, 2H) 5.21 (dd, J=9.37, 3.32 Hz, 1H) 5.89-6.15 (m, 2H) 6.95 (s, 1H) 8.33 (br s, 1H) 10.25 (br s, 1H).

Example 90: 1-[(4aR,8aS)-4-(7H-Pyrrolo[2,3-d]pyrimidin-4-yl)hexahydro-2H-pyrido[4,3-b][1,4]oxazin-6(5H)-yl]prop-2-en-1-one

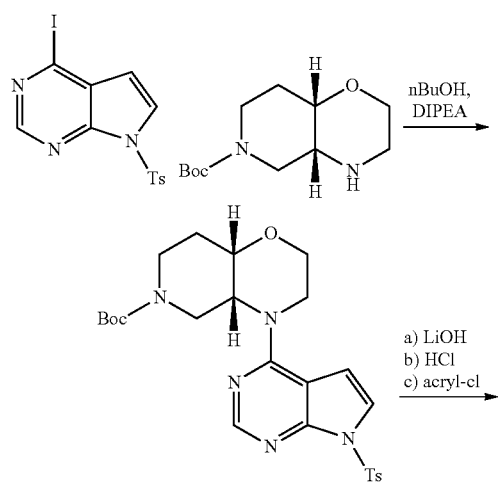

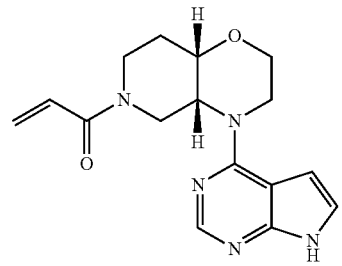

Step 1. (4aR,8aS)-tert-Butyl 4-(7-tosyl-7H-pyrrolo[2,3-d]pyrimidin-4-yl)hexahydro-2H-pyrido[4,3-b][1,4]oxazine-6(7H)-carboxylate To a flask containing (4aR,8aS)-tert-butyl hexahydro-2H-pyrido[4,3-b][1,4]oxazine-6(7H)-carboxylate (500 mg, 2.06 mmol) and 4-iodo-7-tosyl-7H-pyrrolo[2,3-d]pyrimidine (800 mg, 2.0 mmol) in n-butanol (2 mL) was added DIPEA (0.9 mL, 5 mmol). The reaction was heated to 85° C. overnight and then poured into brine/ethyl acetate. The layers were separated and the aqueous phase extracted with ethyl acetate. The combined ethyl acetate extracts were washed twice with brine, dried over anhydrous magnesium sulfate and concentrated under reduced pressure. The residue was purified via flash chromatography (silica, 12 g, EtOAc/Hep) to give (4aR,8aS)-tert-butyl 4-(7-tosyl-7H-pyrrolo[2,3-d]pyrimidin-4-yl)hexahydro-2H-pyrido[4,3-b][1,4]oxazine-6(7H)-carboxylate (877 mg, 85%).

Step 2. 1-((4aR,8aS)-4-(7H-Pyrrolo[2,3-d]pyrimidin-4-yl)hexahydro-2H-pyrido[4,3-b][1,4]oxazin-6(7H)-yl)prop-2-en-1-one Similar to Example 12 (Steps 2-4). LC/MS (M+H) 314.2. ¹H NMR (400 MHz, CHCl₃) δ 1.70-2.07 (m, 2H) 2.90 (t, J=12.59 Hz, 1H) 3.16-3.65 (m, 3H) 3.70-3.99 (m, 3H) 4.15 (d, J=8.98 Hz, 1H) 4.36 (d, J=11.13 Hz, 1H) 4.48-4.87 (m, 2H) 5.52-5.77 (m, 1H) 6.32 (d, J=16.79 Hz, 1H) 6.44-6.70 (m, 2H) 7.13 (d, J=3.71 Hz, 1H) 8.18-8.42 (m, 1H) 10.95 (br s, 1H).

Example 91-107

Prepared as in Example 12, except for final step the corresponding acid or acid chloride was used.

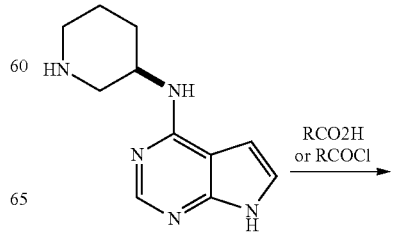

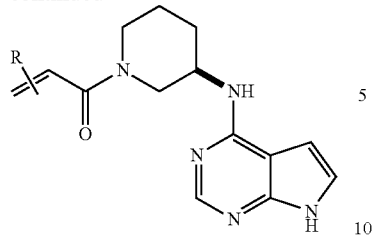

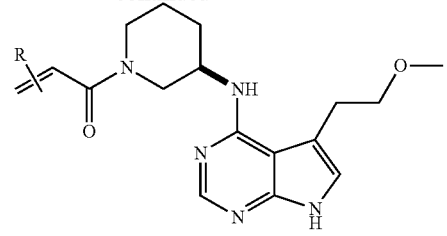

| Example | LC/MS | Name |
|---|---|---|
| 91 | 290 | 2-fluoro-1-[(3R)-3-(7H-pyrrolo[2,3-d]pyrimidin-4-ylamino)piperidin-1-yl]prop-2-en-1-one |
| 92 | 329 | 2-[(dimethylamino)methyl]-1-[(3R)-3-(7H-pyrrolo[2,3-d]pyrimidin-4-ylamino)piperidin-1-yl]prop-2-en-1-one |
| 93 | 302 | 2-(hydroxymethyl)-1-[(3R)-3-(7H-pyrrolo[2,3-d]pyrimidin-4-ylamino)piperidin-1-yl]prop-2-en-1-one |
| 94 | 316 | 2-(methoxymethyl)-1-[(3R)-3-(7H-pyrrolo[2,3-d]pyrimidin-4-ylamino)piperidin-1-yl]prop-2-en-1-one |
| 95 | 286 | (2E)-1-[(3R)-3-(7H-pyrrolo[2,3-d]pyrimidin-4-ylamino)piperidin-1-yl]but-2-en-1-one |
| 96* | 325 | 3-methyl-2-{[3-(7H-pyrrolo[2,3-d]pyrimidin-4-ylamino)piperidin-1-yl]carbonyl}but-2-enenitrile |
| 97 | 344 | methyl (3E)-5-oxo-5-[(3R)-3-(7H-pyrrolo[2,3-d]pyrimidin-4-ylamino)piperidin-1-yl]pent-3-enoate |
| 98 | 318 | (2E)-3-(methylsulfanyl)-1-[(3R)-3-(7H-pyrrolo[2,3-d]pyrimidin-4-ylamino)piperidin-1-yl]prop-2-en-1-one |
| 99 | 325 | (2E)-2-{[(3R)-3-(7H-pyrrolo[2,3-d]pyrimidin-4-ylamino)piperidin-1-yl]carbonyl}pent-2-enenitrile |
| 100 | 302 | (2Z)-4-hydroxy-1-[(3R)-3-(7H-pyrrolo[2,3-d]pyrimidin-4-ylamino)piperidin-1-yl]but-2-en-1-one |
| 101 | 367 | 3-oxo-3-[(3R)-3-(7H-pyrrolo[2,3-d]pyrimidin-4-ylamino)piperidin-1-yl]-2-(tetrahydro-4H-pyran-4-ylidene)propanenitrile |
| 102 | 286 | (2Z)-1-[(3R)-3-(7H-pyrrolo[2,3-d]pyrimidin-4-ylamino)piperidin-1-yl]but-2-en-1-one |
| 103 | 272 | 1-[3-(7H-pyrrolo[2,3-d]pyrimidin-4-ylamino)piperidin-1-yl]prop-2-en-1-one |
| 104 | 272 | 1-[(3S)-3-(7H-pyrrolo[2,3-d]pyrimidin-4-ylamino)piperidin-1-yl]prop-2-en-1-one |
| 105 | 286 | (2E)-1-[(3R)-3-(7H-pyrrolo[2,3-d]pyrimidin-4-ylamino)piperidin-1-yl]but-2-en-1-one |
| 106 | 329 | (2E)-4-(dimethylamino)-1-[(3S)-3-(7H-pyrrolo[2,3-d]pyrimidin-4-ylamino)piperidin-1-yl]but-2-en-1-one |
| 107 | 338 | (2E)-3-(1H-imidazol-4-yl)-1-[(3R)-3-(7H-pyrrolo[2,3-d]pyrimidin-4-ylamino)piperidin-1-yl]prop-2-en-1-one |

Example 108-111

Prepared as in Example 12, except in the final step, the corresponding acid or acid chloride was used.

| Example | LC/MS | Name |
|---|---|---|
| 108 | 387 | (2E)-4-(dimethylamino)-1-[(3R)-3-{[5-(2-methoxyethyl)-7H-pyrrolo[2,3-d]pyrimidin-4-yl]amino}pipendin-1-yl]but-2-en-1-one |
| 109 | 344 | (2E)-1-[(3R)-3-{[5-(2-methoxyethyl)-7H-pyrrolo[2,3-d]pyrimidin-4-yl]amino}pipendin-1-yl]but-2-en-1-one |
| 110 | 344 | 1-[(3R)-3-{[5-(2-methoxyethyl)-7H-pyrrolo[2,3-d]pyrimidin-4-yl]amino}piperidin-1-yl]-2-methylprop-2-en-1-one |

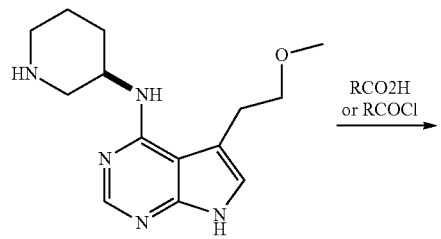

Example 111: 1-[(3aR,7aR)-1-(5-Acetyl-7H-pyrrolo[2,3-d]pyrimidin-4-yl)octahydro-6H-pyrrolo[2,3-c]pyridin-6-yl]prop-2-en-1-one Step 1. 1-[(3aR,7aR)-1-(5-Acetyl-7H-pyrrolo[2,3-d]pyrimidin-4-yl)octahydro-6H-pyrrolo[2,3-c]pyridin-6-yl]prop-2-en-1-one To a flask containing 1-((3aR,7aR)-1-(5-ethynyl-7H-pyrrolo[2,3-d]pyrimidin-4-yl)hexahydro-1H-pyrrolo[2,3-c]

pyridin-6(2H)-yl)prop-2-en-1-one (30 mg, 0.1 mmol) was added acetonitrile/water 0.1% TFA (5 mL). The mixture was stirred at rt for 2 hrs and then the solvent removed in vacuo to give the crude product, which was purified by RP-HPLC to give 1-[(3aR,7aR)-1-(5-acetyl-7H-pyrrolo[2,3-d]pyrimidin-4-yl)octahydro-6H-pyrrolo[2,3-c]pyridin-6-yl]prop-2-en-1-one (9.4 mg). LC/MS (M+H) 340.2.

Example 112: 1-[(3S,4R)-4-Methyl-3-(7H-pyrrolo[2,3-d]pyrimidin-4-ylamino)piperidin-1-yl]prop-2-en-1-one Prepared as in Example 11, Step 5. 1-((3R,4S)-3-((7H-Pyrrolo[2,3-d]pyrimidin-4-yl)amino)-4-methylpiperidin-1-yl)prop-2-en-1-one (pk 1) and 1-((3S,4R)-3-((7H-pyrrolo[2,3-d]pyrimidin-4-yl)amino)-4-methylpiperidin-1-yl)prop-2-en-1-one (pk 2). rac-1-((3R,4S)-3-((7H-Pyrrolo[2,3-d]pyrimidin-4-yl)amino)-4-methylpiperidin-1-yl)prop-2-en-1-one (120 mg) was separated by chiral chromatography to give 1-((3R,4S)-3-((7H-pyrrolo[2,3-d]pyrimidin-4-yl)amino)-4-methylpiperidin-1-yl)prop-2-en-1-one (peak 1, 47.8 mg, 80%) as a white solid and 1-((3S,4R)-3-((7H-pyrrolo[2,3-d]pyrimidin-4-yl)amino)-4-methylpiperidin-1-yl)prop-2-en-1-one (peak 2, 48.2 mg, 80%) as a white solid. Chiral SFC: ChiralPak AD (250×30 mm, 5 μm); 30% EtOH/NH$_4$OH; 30% EtOH (0.05% NH$_3$ in H$_2$O) in CO$_2$), 60 mL/min. Peak 1 data (Example 11): $^1$H NMR (400 MHz, DMSO-d$_6$) δ 11.50 (br s, 1H), 8.08 (d, J=14.3 Hz, 1H), 7.33-7.16 (m, 1H), 7.08 (br s, 1H), 6.88-6.72 (m, 1H), 6.59 (br s, 1H), 6.12 (d, J=16.1 Hz, 1H), 5.68 (d, J=10.5 Hz, 1H), 4.60 (d, J=9.5 Hz, 1H), 4.43 (d, J=12.5 Hz, 1H), 4.21 (d, J=10.5 Hz, 1H), 4.06 (d, J=14.6 Hz, 1H), 3.93-3.71 (m, 1H), 3.09-2.97 (m, 1H), 2.83 (t, J=11.8 Hz, 1H), 2.66 (t, J=12.8 Hz, 1H), 2.46-2.35 (m, 1H), 1.82 (d, J=11.5 Hz, 2H), 1.28-1.13 (m, 1H), 0.94 (dd, J=6.1, 11.7 Hz, 3H). LCMS (M+H)=285.9. Peak 2 data (Example 112): $^1$H NMR (400 MHz, DMSO-d$_6$) δ 11.50 (br s, 1H), 8.09 (d, J=14.1 Hz, 1H), 7.33-7.16 (m, 1H), 7.08 (br s, 1H), 6.89-6.72 (m, 1H), 6.59 (br s, 1H), 6.12 (d, J=16.6 Hz, 1H), 5.68 (d, J=10.3 Hz, 1H), 4.60 (d, J=8.8 Hz, 1H), 4.43 (d, J=13.1 Hz, 1H), 4.21 (d, J=10.5 Hz, 1H), 4.06 (d, J=13.3 Hz, 1H), 3.93-3.70 (m, 1H), 3.02 (t, J=13.3 Hz, 1H), 2.83 (t, J=11.7 Hz, 1H), 2.66 (t, J=12.0 Hz, 1H), 2.42 (t, J=11.5 Hz, 1H), 1.82 (d, J=11.3 Hz, 2H), 1.30-1.12 (m, 1H), 0.94 (dd, J=6.0, 11.5 Hz, 3H). LCMS (M+H) 285.9.

Example 113: rac-1-[(3S,4S)-4-Hydroxy-3-(7H-pyrrolo[2,3-d]pyrimidin-4-ylamino)piperidin-1-yl]prop-2-en-1-one Prepared as in Example 5, except using the amine(rac-(3R,4R)-tert-butyl 3-amino-4-hydroxypiperidine-1-carboxylate). 1-[(3S,4S)-4-Hydroxy-3-(7H-pyrrolo[2,3-d]pyrimidin-4-ylamino) piperidin-1-yl]prop-2-en-1-one. To a solution of rac-(3R,4R)-3-((7H-pyrrolo[2,3-d]pyrimidin-4-yl)amino)piperidin-4-ol (100 mg, 0.33 mmol) in DCM (5 mL) at 0° C. was added DBU (0.20 mL, 1.3 mmol), followed by acryloyl chloride (29.6 mg, 0.33 mmol). The reaction mixture was stirred at 60° C. for 4 hrs. The reaction mixture was concentrated and a portion of the crude material (50 mg) purified by RP-HPLC to give rac-1-[(3S,4S)-4-hydroxy-3-(7H-pyrrolo[2,3-d]pyrimidin-4-ylamino)piperidin-1-yl] prop-2-en-1-one (5.0 mg). LC/MS (M+H) 288.2.

Examples 114 and 115

Example 114: 1-[(2S,5S)-2-Methyl-5-(7H-pyrrolo[2,3-d]pyrimidin-4-ylamino)piperidin-1-yl]prop-2-en-1-one

Example 115: 1-[(2R,5R)-2-Methyl-5-(7H-pyrrolo[2,3-d]pyrimidin-4-ylamino)piperidin-1-yl]prop-2-en-1-one Prepared as in Example 5, except using the rac-trans-(2S,5S)-tert-butyl 5-amino-2-methylpiperidine-1-carboxylate.

Step 1. (2R,5R)-Benzyl 5-((2-chloro-7H-pyrrolo[2,3-d]pyrimidin-4-yl)amino)-2-methylpiperidine-1-carboxylate A mixture of 2,4-dichloro-7H-pyrrolo[2,3-d]pyrimidine (266.5 mg, 1.425 mmol), DIPEA (613 mg, 4.75 mmol) and rac-(2R,5R)-benzyl 5-amino-2-methylpiperidine-1-carboxylate (270 mg, 0.950 mmol) in n-BuOH (10 mL) was heated to 130° C. overnight. LC-MS indicated rac-(2R,5R)-benzyl 5-amino-2-methylpiperidine-1-carboxylate was consumed completely. The reaction mixture was cooled to room temperature and evaporated to dryness in vacuo and the residue purified by chromatography (silica, PE/EA, 12%-100%) to give (2R,5R)-benzyl 5-((2-chloro-7H-pyrrolo[2,3-d]pyrimidin-4-yl)amino)-2-methylpiperidine-1-carboxylate (290 mg, 76.5%) as a white solid. $^1$H NMR (400 MHz, DMSO-d$_6$) δ 11.70 (br s, 1H), 7.57 (d, J=5.8 Hz, 1H), 7.21-6.98 (m, 6H), 6.78 (br s, 1H), 5.04-4.92 (m, 1H), 4.92-4.79 (m, 1H), 4.34 (br s, 1H), 4.29-4.14 (m, 2H), 3.19 (d, J=12.3 Hz, 1H), 2.27-2.12 (m, 1H), 2.08-1.95 (m, 1H), 1.66 (d, J=11.5 Hz, 1H), 1.44-1.30 (m, 1H), 1.22-1.10 (m, 3H).

Step 2. N-((3R,6R)-6-Methylpiperidin-3-yl)-7H-pyrrolo[2,3-d]pyrimidin-4-amine To a Parr bottle, 10% Pd/C (100 mg) was added under Ar atmosphere. Then a solution of (2R,5R)-benzyl 5-((2-chloro-7H-pyrrolo[2,3-d]pyrimidin-4-yl)amino)-2-methylpiperidine-1-carboxylate (290 mg, 0.727 mmol) in MeOH (20 mL) was added and the resulting mixture was hydrogenated under 45 psi of H$_2$ at 25° C. for 18 hours. After TLC (DCM/MeOH, 10:1) indicated the starting material to be consumed, the reaction mixture was filtered and the filter cake was washed with MeOH. The combined filtrate was evaporated to give rac-N-((3R,6R)-6-methylpiperidin-3-yl)-7H-pyrrolo[2,3-d]pyrimidin-4-amine (180 mg, 100%) as a white solid.

Step 3. rac-1-((2R,5R)-5-((7H-Pyrrolo[2,3-d]pyrimidin-4-yl)amino)-2-methylpiperidin-1-yl)prop-2-en-1-one To a stirred solution of rac-N-((3R,6R)-6-methylpiperidin-3-yl)-7H-pyrrolo[2,3-d]pyrimidin-4-amine (130 mg, 0.563 mmol) in aq. NaHCO$_3$ solution (1 mL) and THF (1 mL) at 0° C. was added acryloyl chloride (55.7 mg, 0.619 mmol) dropwise. After the addition, the resulting mixture was stirred at 0° C. for 3 hours. TLC (CH2Cl2/MeOH/NH4OH=10:1:1) indicated rac-N-((3R,6R)-6-methylpiperidin-3-yl)-7H-pyrrolo[2,3-d]pyrimidin-4-amine was consumed completely. The reaction mixture was diluted with H$_2$O (5 mL) and extracted with EtOAc (5 mL*4), the combined organic layer was washed with brine, dried over Na2SO4 and concentrated to give crude product, which was purified by prep TLC to give rac-1-((2R,5R)-5-((7H-pyrrolo [2,3-d]pyrimidin-4-yl)amino)-2-methylpiperidin-1-yl)prop-2-en-1-one (30 mg, 18.75%).

Step 4. 1-[(2S,5S)-2-Methyl-5-(7H-pyrrolo[2,3-d] pyrimidin-4-ylamino)piperidin-1-yl]prop-2-en-1-one and 1-[(2R,5R)-2-methyl-5-(7H-pyrrolo[2,3-d]pyrimidin-4-ylamino)piperidin-1-yl]prop-2-en-1-one rac-1-((2R,5R)-5-((7H-Pyrrolo[2,3-d]pyrimidin-4-yl) amino)-2-methylpiperidin-1-yl)prop-2-en-1-one was purified by chiral SFC to give two peaks, stereochemistry arbitrarily assigned: Pk1, 1-[(2S,5S)-2-methyl-5-(7H-pyrrolo[2,3-d]pyrimidin-4-ylamino)piperidin-1-yl]prop-2-en-1-one (5.1 mg) and Pk2, 1-[(2R,5R)-2-methyl-5-(7H-pyrrolo[2,3-d]pyrimidin-4-ylamino)piperidin-1-yl]prop-2-en-1-one (5.2 mg).

SFC Conditions: Column: ChiralPak IC 250×4.6 mm I.D., 5 μm; Mobile phase: ethanol (0.05% DEA) in $CO_2$ from 5% to 40%; Flow rate: 2.35 mL/min; Wavelength: 215 nm Pk1: $^1$H NMR (400 MHz, MeOH-$d_4$) δ 8.15 (s, 1H), 7.06 (d, J=3.5 Hz, 1H), 6.64 (d, J=3.3 Hz, 1H), 6.28 (br s, 1H), 5.95 (br s, 1H), 5.34 (br s, 1H), 4.59 (br s, 1H), 4.38 (br s, 2H), 3.53-3.34 (m, 1H), 2.25-2.09 (m, 2H), 1.80 (br s, 1H), 1.57-1.45 (m, 1H), 1.29 (d, J=6.8 Hz, 3H). Pk2: $^1$H NMR (400 MHz, MeOH-$d_4$) δ 8.16 (s, 1H), 7.07 (d, J=3.5 Hz, 1H), 6.65 (d, J=3.3 Hz, 1H), 6.30 (br s, 1H), 5.96 (br s, 1H), 5.35 (br s, 1H), 4.59 (s, 1H), 4.50-4.22 (m, 2H), 3.52-3.34 (m, 1H), 2.23-2.17 (m, 2H), 1.89-1.76 (m, 1H), 1.57-1.48 (m, 1H), 1.29 (s, 3H).

Example 116: Rac-1-((1R,4R,5S)-4-(7H-pyrrolo[2, 3-d]pyrimidin-4-ylamino)-2-azabicyclo[3.2.1]octan-2-yl)prop-2-en-1-one For preparation of similar ring system see (Tetrahedron, 2012, 68, 7848). Step 1. Rac-(1R,3S,4S)-Methyl 2-benzyl-2-azabicyclo[2.2.1]heptane-3-carboxylate. To a Parr bottle was added rac-(1S,3S,4R)-methyl 2-benzyl-2-azabicyclo [2.2.1]hept-5-ene-3-carboxylate (1.0 g, 4.11 mmol), EtOAc/HOAc (10:1, 20 mL) and 10% Pd/C (50 mg). The reaction was shaken for 4 hrs @ 40 psi $H_2$. The reaction was filtered through a pad of Celite® and the solvent removed to give rac-(1R,3S,4S)-methyl 2-benzyl-2-azabicyclo[2.2.1]heptane-3-carboxylate (990 mg). GC/MS 245. $^1$H NMR (400 MHz, CHCl$_3$) δ 1.16-1.51 (m, 3H) 1.53-1.75 (m, 2H) 1.89-2.08 (m, 2H) 2.56 (d, J=3.90 Hz, 1H) 2.72 (s, 1H) 3.36 (s, 1H) 3.68-3.87 (m, 4H) 7.12-7.45 (m, 5H).

Step 2. Rac-((1R,3S,4S)-2-Benzyl-2-azabicyclo [2.2.1]heptan-3-yl)methanol

To a solution of rac-(1R,3S,4S)-methyl 2-benzyl-2-azabicyclo[2.2.1]heptane-3-carboxylate (2.2 g, 9.0 mmol) in THF (20 mL) at 0° C. was added LAH (9.05 mL, 1M in THF). After the addition the reaction was allowed to warm to rt and stirred for 12 hrs. The reaction mixture was poured into 1N NaOH/Et$_2$O and the layers separated. The organic layer was collected and the aqueous layer extracted (2×) with ethyl acetate. The organic extracts were combined, washed with brine and dried (Na$_2$SO$_4$). The solvent was remove to give an oil (1.52 g, 78%), which was used without further purification. GC/MS 217. $^1$H NMR (400 MHz, CHCl$_3$) δ 1.11-1.43 (m, 3H) 1.51-1.72 (m, 2H) 1.81 (d, J=9.76 Hz, 1H) 1.95-2.12 (m, 1H) 2.17-2.28 (m, 2H) 3.17-3.38 (m, 2H) 3.60-3.81 (m, 2H) 4.16 (q, J=7.15 Hz, 1H) 7.18-7.41 (m, 5H).

Step 3. Rac-(1R,4R,5S)-4-azido-2-benzyl-2-azabicyclo[3.2.1]octane

To a flask containing rac-((1R,3S,4S)-2-benzyl-2-azabicyclo[2.2.1]heptan-3-yl)methanol (2.0 g, 9.20 mmol) in DCM (150 mL) at rt was added Bu$_4$N$_3$ (2.97 g, 10.1 mmol). The reaction was cooled to −78° C. and Xtal-FluorE (2.37 g, 4.25 mmol) was added. The reaction mixture was allowed to warm to rt over 2 hrs. After 2 hrs, the reaction was quenched with 3.75 N NaOH (100 mL). The layers were separated and the organic layer collected, dried (Na$_2$SO$_4$) and solvent removed to give the crude product, which was purified by chromatography (silica, EtOAc/Hep, 5 to 45%) to give rac-(1R,4R,5S)-4-azido-2-benzyl-2-azabicyclo[3.2.1]octane (1.0 g, 45%). GC/MS 242. $^1$H NMR (400 MHz, CHCl$_3$) δ 1.08-1.51 (m, 3H) 1.69-1.99 (m, 2H) 2.15 (d, J=11.32 Hz, 1H) 2.33-2.48 (m, 2H) 2.73 (d, J=13.27 Hz, 1H) 3.19 (br s, 1H) 3.34-3.60 (m, 3H) 7.14-7.44 (m, 5H).

Step 4. Rac-(1R,4R,5S)-2-benzyl-2-azabicyclo [3.2.1]octan-4-amine

To a flask containing rac-(1R,4R,5S)-4-azido-2-benzyl-2-azabicyclo[3.2.1]octane (1.9 g, 7.84 mmol) was added THF:H$_2$O (10:1, 20 mL) and PPh$_3$ (2.3 g, 8.62 mmol). The reaction was heated to 50° C. overnight and then cooled to rt. The solvent was removed in vacuo to give a white solid. The crude material was purified by chromatography (silica, MeOH/DCM/NH$_4$OH (10:1 MeOH/NH$_4$OH), 5 to 20%) to give rac-(1R,4R,5S)-2-benzyl-2-azabicyclo[3.2.1]octan-4-amine (1.25 g, 73%) as an oil. GC/MS 216. $^1$H NMR (400 MHz, CHCl$_3$) δ 1.12-1.47 (m, 3H) 1.68-1.94 (m, 2H) 2.06 (d, J=12.10 Hz, 1H) 2.17-2.30 (m, 1H) 2.36-2.52 (m, 2H) 2.74 (br s, 1H) 3.13 (t, J=4.68 Hz, 1H) 3.35-3.55 (m, 3H) 7.15-7.45 (m, 5H).

Step 5. Rac-N-((1R,4R,5S)-2-Benzyl-2-azabicyclo [3.2.1]octan-4-yl)-2-chloro-7H-pyrrolo[2,3-d]pyrimidin-4-amine To a flask containing rac-(1R,4R,5S)-2-benzyl-2-azabicyclo[3.2.1]octan-4-amine (1.23 g, 5.68 mmol) was added n-BuOH (10 mL), DIPEA (2.2 mL, 12.5 mmol) and 2,4-dichloro-7H-pyrrolo[2,3-d]pyrimidine (1.07 g, 5.69 mmol). The mixture was heated to 80° C. overnight. The reaction mixture was concentrated and the residue diluted with DCM/H$_2$O. The layers were separated and the aqueous layer extracted (2×EtOAc). The organic extracts were combined, washed with brine, dried (Na$_2$SO$_4$) and the solvent removed to give an oil, which after chromatography (silica, EtOAc/Hep, 80 to 100%) gave rac-N-((1R,4R,5S)-2-benzyl-2-azabicyclo[3.2.1]octan-4-yl)-2-chloro-7H-pyrrolo[2,3-d] pyrimidin-4-amine (1.44 g, 68%). LC/MS (M+H) 368.1. $^1$H NMR (400 MHz, CHCl$_3$) δ 1.24-1.34 (m, 2H) 1.37-1.61 (m, 3H) 1.71 (s, 2H) 1.76-2.04 (m, 4H) 2.65 (br s, 3H) 3.21 (br s, 1H) 3.38-3.57 (m, 2H) 4.16 (q, J=7.41 Hz, 1H) 6.42 (br s, 1H) 7.09 (br s, 1H).

Step 6. Rac-N-((1R,4R,5S)-2-Azabicyclo[3.2.1] octan-4-yl)-7H-pyrrolo[2,3-d]pyrimidin-4-amine To a round bottom flask containing rac-N-((1R,4R,5S)-2-benzyl-2-azabicyclo[3.2.1]octan-4-yl)-2-chloro-7H-pyrrolo[2,3-d]pyrimidin-4-amine (1.22 g, 3.3 mmol) was added EtOH (40 mL), 10% Pd/C (400 mg) and ammonium formate (1.08 g, 16.6 mmol). The reaction mixture was heated to reflux for 24 hrs. The reaction was filtered through a pad of Celite® and the solvent removed to give the crude rac-N-((1R,4R,5S)-2-azabicyclo[3.2.1]octan-4-yl)-7H-pyrrolo[2,3-d]pyrimidin-4-amine, which was used without further purification. LC/MS (M+H) 244.1. $^1$H NMR (400 MHz, MeOH-$d_4$) δ 1.29-1.63 (m, 4H) 1.80 (d, J=9.76 Hz, 1H) 2.09 (d, J=12.10 Hz, 1H) 2.69 (d, J=3.90 Hz, 1H) 2.84 (d, J=14.05 Hz, 1H) 3.29 (d, J=4.68 Hz, 1H) 3.49 (br s, 1H) 4.04 (t, J=4.10 Hz, 1H) 6.65 (d, J=3.51 Hz, 1H) 7.12 (d, J=3.51 Hz, 1H) 8.12 (s, 1H).

Step 7. Rac-1-((1R,4R,5S)-4-((7H-Pyrrolo[2,3-d]pyrimidin-4-yl)amino)-2-azabicyclo[3.2.1]octan-2-yl)prop-2-en-1-one To a flask containing rac-N-((1R,4R,5S)-2-azabicyclo[3.2.1]octan-4-yl)-7H-pyrrolo[2,3-d]pyrimidin-4-amine (129 mg, 0.53 mmol) in DCM at 0° C. was added DIPEA (0.31 mL, 1.75 mL). After 30 min, acryloyl chloride (59.3 mg, 0.64 mmol in 5 mL DCM) was added. The reaction was stirred at rt for 1 hr and then poured into water/DCM. The layers were separated and aqueous layer extracted (2×DCM). The organic extracts were combine, dried ($Na_2SO_4$) and the solvent removed to give crude rac-1-((1R,4R,5S)-4-((7H-pyrrolo[2,3-d]pyrimidin-4-yl)amino)-2-azabicyclo[3.2.1]octan-2-yl)prop-2-en-1-one (110 mg), a portion (50 mg) was purified by RP-HPLC to give (6.5 mg) of pure material. LC/MS (M+H) 298.2.

Example 117: 1-[(2S,5S)-2-(Hydroxymethyl)-5-(7H-pyrrolo[2,3-d]pyrimidin-4-ylamino)piperidin-1-yl]prop-2-en-1-one Example 118: 1-[2-(Hydroxymethyl)-5-(7H-pyrrolo[2,3-d]pyrimidin-4-ylamino)piperidin-1-yl]prop-2-en-1-one Example 118: Prepared as described in Example 7, except (2S,5S)-benzyl 5-((2-chloro-7-tosyl-7H-pyrrolo[2,3-d]pyrimidin-4-yl)amino)-2-(hydroxymethyl)piperidine-1-carboxylate (other cis isomer, pk 2) was carried through Steps 7-10. LC/MS (M+H) 302.2. $^1$H NMR (400 MHz, MeOH-$d_4$) δ 1.72-2.22 (m, 4H) 2.81-2.99 (m, 1H) 3.65-3.85 (m, 2H) 3.88-4.17 (m, 2H) 4.25-4.45 (m, 1H) 5.80 (d, J=12.10 Hz, 1H) 6.26 (d, J=16.78 Hz, 1H) 6.80-6.99 (m, 2H) 7.39 (br s, 1H) 8.21-8.40 (m, 1H).

Example 119: 1-[(4aS,8aS)-4-(7H-Pyrrolo[2,3-d]pyrimidin-4-yl)hexahydro-2H-pyrido[4,3-b][1,4]oxazin-6(5H)-yl]prop-2-en-1-one Prepared as in Example 1, except using (4aS,8aS)-tert-butyl hexahydro-2H-pyrido[4,3-b][1,4]oxazine-6(7H)-carboxylate instead of (R)-tert-butyl 3-aminopiperidine-1-carboxylate. LC/MS (M+H) 314.2. $^1$H NMR (400 MHz, $CHCl_3$) δ 1.32-1.58 (m, 2H) 2.45-2.76 (m, 2H) 3.46-3.95 (m, 3H) 3.98-4.14 (m, 2H) 4.80 (d, J=12.49 Hz, 1H) 5.10 (d, J=12.88 Hz, 1H) 5.74 (d, J=11.52 Hz, 1H) 6.22-6.57 (m, 2H) 6.90 (dd, J=16.88, 10.44 Hz, 1H) 7.08-7.29 (m, 2H) 8.50 (s, 1H) 9.98 (br s, 1H).

Example 120: 1-(4-{[(3S,4R)-1-Acryloyl-4-fluoropiperidin-3-yl]amino}-7H-pyrrolo[2,3-d]pyrimidin-5-yl)prop-2-en-1-one Example 121: rac-1-((2R,3S)-3-((7H-Pyrrolo[2,3-d]pyrimidin-4-yl)amino)-2-methylpiperidin-1-yl)prop-2-en-1-one Prepared as in Example 12, except rac-(2R,3S)-benzyl 3-amino-2-methylpiperidine-1-carboxylate was used instead of (R)-tert-butyl 3-am inopiperidine-1-carboxylate. LC/MS (M+H) 286.4.

Example 122: 1-((3aR,7aR)-3a-Methyl-1-(7H-pyrrolo[2,3-d]pyrimidin-4-yl)hexahydro-1H-pyrrolo[2,3-c]pyridin-6(2H)-yl)prop-2-en-1-one 1-((3aR,7aR)-3a-methyl-1-(7H-pyrrolo[2,3-d]pyrimidin-4-yl)hexahydro-1H-pyrrolo[2,3-c]pyridin-6(2H)-yl)prop-2-en-1-one was prepared as in Example 59, except using (4-((3aS,7aR)-6-benzyl-3a-methyloctahydro-1H-pyrrolo[2,3-c]pyridin-1-yl)-7H-pyrrolo[2,3-d]pyrimidine in step 5. LC/MS (M+H) 312.2.

Example 123: 1-[(5S)-2,2-Dimethyl-5-(7H-pyrrolo[2,3-d]pyrimidin-4-ylamino)piperidin-1-yl]prop-2-en-1-one For preparation, see Example 61 and Example 67.

Examples 124 and 125

Example 124: 1-[(2R,5R)-2-Ethyl-5-(7H-pyrrolo[2,3-d]pyrimidin-4-ylamino)piperidin-1-yl]prop-2-en-1-one Example 125: 1-[(2S,5S)-2-Ethyl-5-(7H-pyrrolo[2,3-d]pyrimidin-4-ylamino)piperidin-1-yl]prop-2-en-1-one Prepared as Example 9 for cis-derivative, starting from optically pure trans-amines isolated by chiral SFC (Peaks 1 and 2). Pk1: 1-[(2R,5R)-2-ethyl-5-(7H-pyrrolo[2,3-d]pyrimidin-4-ylamino)piperidin-1-yl]prop-2-en-1-one. LC/MS (M+H) 300.3. $^1$HNMR appeared to show two sets of signals possibly derived from rotamers at RT. $^1$HNMR at 345 K: (500 MHz, DMSO-$d_6$) δ 11.22 (br s, 1H), 8.05 (br s, 1H), 6.96-6.94 (m, 1H), 6.69-6.63 (m, 1H), 6.58-6.55 (m, 1H), 6.35 (s, 1H), 5.82-5.78 (m, 1H), 5.30-5.28 (m, 1H), 4.30-4.24 (m, 3H), 3.07 (apparent br s, water+1H), 2.05 (m, 1H), 1.95 (m, 1H), 1.62 (m, 2H), 1.55-1.35 (m, 2H), 0.75 (t, J=10 Hz, 3H). Pk2: 1-[(2S,5S)-2-ethyl-5-(7H-pyrrolo[2,3-d]pyrimidin-4-ylamino)piperidin-1-yl]prop-2-en-1-one. LC/MS (M+H) 300.3. $^1$H NMR at 345 K: (500 MHz, DMSO-$d_6$) δ 11.22 (br s, 1H), 8.05 (br s, 1H), 6.96-6.94 (m, 1H), 6.69-6.63 (m, 1H), 6.58-6.55 (m, 1H), 6.35 (s, 1H), 5.82-5.78 (m, 1H), 5.30-5.28 (m, 1H), 4.30-4.24 (m, 3H), 3.07 (apparent br s, water+1H), 2.05 (m, 1H), 1.95 (m, 1H), 1.62 (m, 2H), 1.55-1.35 (m, 2H), 0.75 (t, J=10 Hz, 3).

Examples 126 and 127

Example 126: 1-((1S,4S,5R)-4-(7H-pyrrolo[2,3-d]pyrimidin-4-ylamino)-2-azabicyclo[3.2.1]octan-2-yl)prop-2-en-1-one Example 127:1-((1R,4R,5S)-4-(7H-Pyrrolo[2,3-d]pyrimidin-4-ylamino)-2-azabicyclo[3.2.1]octan-2-yl)prop-2-en-1-one Examples 126 and 127 were prepared by purifying the racemic product of Example 116 by chiral RP-HPLC (IA, 21×250 mm, 5 um, CO2/0.1% NH4OH in EtOH, 80:20 A/B hold for 10 min, 40° C., 75 mL/min), absolute stereochemistry arbitrarily assigned.

Pk1: Rt=5.67 min (IA, 4.6×100 mm, 5 um, CO2/0.1% NH4OH in EtOH, 800:20 hold for 10 min), Example 126: LC/MS (M+H) 297.9. Pk2: Rt=5.72 min (same as above), Example 127: LC/MS (M+H) 297.9.

Example 128: 1-[(3R,5S)-3-Methyl-5-(7H-pyrrolo[2,3-d]pyrimidin-4-ylamino)piperidin-1-yl]prop-2-en-1-one For preparation of 1-[(3R,5S)-3-methyl-5-(7H-pyrrolo[2,3-d]pyrimidin-4-ylamino)piperidin-1-yl]prop-2-en-1-one, see Example 14, Step 8. Peak 2: $^1$H NMR (400 MHz, DMSO-$d_6$) δ 11.53 (br s, 1H), 8.10 (d, J=14.6 Hz, 1H), 7.38-7.23 (m, 1H), 7.08 (br s, 1H), 6.94-6.79 (m, 1H), 6.56 (br s, 1H), 6.12 (dd, J=7.8, 16.8 Hz, 1H), 5.75-5.64 (m, 1H), 4.71 (d, J=11.8 Hz, 1H), 4.49-4.30 (m, 1H), 4.03 (d, J=11.5 Hz, 1H), 2.81-2.54 (m, 1H), 2.42-2.15 (m, 1H), 2.06 (d, J=12.3 Hz, 1H), 1.62 (brs, 1H), 1.38-1.18 (m, 1H), 0.99-0.88 (m, 3H). LCMS (M+H) 285.9.

Example 129: rac-1-[(2S,5R)-2-Methyl-5-(7H-pyrrolo[2,3-d]pyrimidin-4-ylamino)piperidin-1-yl]prop-2-en-1-one For preparation of rac-1-[(2S,5R)-2-methyl-5-(7H-pyrrolo[2,3-d]pyrimidin-4-ylamino)piperidin-1-yl]prop-2-en-1-one, see Example 5, Step 8. $^1$H NMR (400 MHz, DMSO-$d_6$) δ 11.53 (brs, 1H), 8.12 (d, J=12.8 Hz, 1H), 7.30 (dd, J=6.8, 18.8 Hz, 1H), 7.10 (brs, 1H), 6.89-6.71 (m, 1H), 6.56 (d, J=1.8 Hz, 1H), 6.10 (dd, J=2.1, 16.7 Hz, 1H), 5.72-5.61 (m, 1H), 4.81 (br s, 0.5H), 4.56 (d, J=10.3 Hz, 0.5H), 4.37 (br s, 0.5H), 4.20-3.95 (m, 1.5H), 2.96 (t, J=11.9 Hz, 0.5H), 2.60 (t, J=12.0 Hz, 0.5H), 1.92-1.59 (m, 4H), 1.30-1.07 (m, 3H).

Example 130: 1-{(3R,4R)-4-Methyl-3-[methyl(7H-pyrrolo[2,3-d]pyrimidin-4-yl)amino]piperidin-1-yl}prop-2-en-1-one Prepared as in Example 12, Step 4, except using N-methyl-N-((3R,4R)-4-methylpiperidin-3-yl)-7H-pyrrolo[2,3-d]pyrimidin-4-amine as the amine partner. LC/MS (M+H) 300.1. $^1$H NMR (400 MHz, DMSO-$d_6$) δ 0.82-1.19 (m, 3H) 1.49-1.85 (m, 2H) 2.41 (brs, 1H) 3.34 (s, 3H) 3.39-4.08 (m, 4H) 4.86 (br s, 1H) 5.48-5.78 (m, 1H) 6.12 (d, J=16.39 Hz, 1H) 6.56 (br s, 1H) 6.74-6.93 (m, 1H) 7.14 (br s, 1H) 8.10 (s, 1H) 11.66 (brs, 1H).

Example 131: 1-[(1S,6R)-8-(7H-Pyrrolo[2,3-d]pyrimidin-4-yl)-3,8-diazabicyclo[4.2.0]oct-3-yl]prop-2-en-1-one Prepared as in Example 12, except using (1S,6R)-tert-butyl 3,8-diazabicyclo[4.2.0]oc-tane-3-carboxylate in step 1. LC/MS (M+H) 284.1.

Example 132: rac-1-[(3S,4S)-4-Methyl-3-(7H-pyrrolo[2,3-d]pyrimidin-4-ylamino)piperidin-1-yl]prop-2-en-1-one Prepared as in Example 12 except using rac-(3R,4R)-tert-butyl 3-amino-4-methylpiperidine-1-carboxylate in Step 1. LC/MS (M+H) 286.2. $^1$H NMR (400 MHz, DMSO-$d_6$) δ 0.97 (d, J=6.87 Hz, 3H) 1.39-1.63 (m, 1H) 1.84 (d, J=10.44 Hz, 1H) 2.00-2.22 (m, 1H) 2.89 (t, J=10.30 Hz, 1H) 3.98-4.19 (m, 1H) 4.26-4.52 (m, 1H) 5.33 (d, J=9.34 Hz, 1H) 5.66 (d, J=8.79 Hz, 1H) 5.89 (d, J=16.21 Hz, 1H) 6.06 (d, J=15.66 Hz, 1H) 6.33 (dd, J=16.76, 10.44 Hz, 1H) 6.60-6.87 (m, 2H) 7.07 (br s, 1H) 7.97-8.21 (m, 1H) 11.46 (br s, 1H).

Example 133: 1-{(3R)-3-[Methyl(7H-pyrrolo[2,3-d]pyrimidin-4-yl)amino]piperidin-1-yl}prop-2-en-1-one Prepared as in Example 12, except using (R)-tert-butyl 3-(methylamino)piperidine-1-carboxylate, in step 1. LC/MS (M+H) 285.2. $^1$H NMR (500 MHz, DMSO-$d_6$) δ ppm 1.49-1.53 (m, 1H), 1.80-1.82 (d, J=9.28 Hz, 2H), 1.90-1.95 (m, 1H), 2.55-2.63 (m, 1H), 2.85-2.90 (t, J=11.48 Hz, 0.5H), 2.99-3.04 (t, J=12.7 Hz, 0.5H), 3.22-3.24 (d, J=11.72 Hz, 3H), 4.03 (m, 1H), 4.44 (m, 1H), 4.67 (m, 1H), 5.64-5.69 (t, J=13.2 Hz, 1H), 6.09-6.12 (dd, J=2.0, 16.7 Hz, 1H), 6.55-6.57 (d, J=9.28 Hz, 1H), 6.75-6.84 (m, 1H), 7.13 (t, 1H), 8.06-8.11 (m, 1H), 11.65 (br s, 1H).

Example 134: 1-[(1R,6S)-8-(7H-Pyrrolo[2,3-d]pyrimidin-4-yl)-3,8-diazabicyclo[4.2.0]oct-3-yl]prop-2-en-1-one Prepared as in Example 12, except using (1R,6S)-tert-butyl 3,8-diazabicyclo[4.2.0]octane-3-carboxylate in step 1. LC/MS (M+H) 284.1.

Examples 135 and 136

Example 135: (2E)-1-[(3R)-3-{[5-(2-Methoxyethyl)-7H-pyrrolo[2,3-d]pyrimidin-4-yl](methyl)amino}-piperidin-1-yl]but-2-en-1-one

Example 136: 1-[(3R)-3-{[5-(2-Methoxyethyl)-7H-pyrrolo[2,3-d]pyrimidin-4-yl](methyl)amino}piperidin-1-yl]prop-2-en-1-one Prepared as in Example 12, except using (R)-tert-butyl 3-(methylamino)piper-idine-1-carboxylate and 4-chloro-5-(2-methoxyethyl)-7-tosyl-7H-pyrrolo[2,3-d]pyrimidine in step 1 and for step 4, (E)-but-2-enoic acid and acrylic acid was used in combination with EDCl/DIEA/DCM. Ex 135: LC/MS (M+H) 358.1. Ex 136: LC/MS (M+H) 344.1.

Example 137: 1-[(3R)-3-{[5-(4-Hydroxybenzyl)-7H-pyrrolo[2,3-d]pyrimidin-4-yl]amino}piperidin-1-yl]prop-2-en-1-one Prepared as in Example 12, except using 5-(4-(benzyloxy)benzyl)-4-chloro-7H-pyrrolo[2,3-d]pyrimidine in Step 1 and the additional step of removing benzyl protecting group after chloro displacement. For Step 4, acrylic acid was used in combination with EDC/DIPEA/DMAP/DMF. LC/MS (M+H) 378.1.

Example 138: (2E)-1-[(3R)-3-{[5-(4-Hydroxybenzyl)-7H-pyrrolo[2,3-d]pyrimidin-4-yl]amino}piperidin-1-yl]but-2-en-1-one Prepared as in Example 12, except using 5-(4-(benzyloxy)benzyl)-4-chloro-7H-pyrrolo[2,3-d]pyrimidine in Step 1 and the additional step of removing benzyl protecting group after chloro displacement. For step 4, (E)-but-2-enoic acid was used in combination with EDC/DIPEA/DMAP/DMF. Ex 138: LC/MS (M+H)=392.0.

Example 139: 1-[(3R)-3-{[5-(4-hydroxybenzyl)-7H-pyrrolo[2,3-d]pyrimidin-4-yl]amino}piperidin-1-yl]-2-methylprop-2-en-1-one Prepared as in Example 12, except using 5-(4-(benzyloxy)benzyl)-4-chloro-7H-pyrrolo[2,3-d]pyrimidine in Step 1 and the additional step of removing benzyl protecting group after chloro displacement. For Step 4, (E)-but-2-enoic acid was used in combination with EDC/DIPEA/DMAP/DMF was used in combination with EDC/DIPEA/DMAP/DMF. Ex 139: LC/MS (M+H) 392.3.

Examples 140-148

Examples 140-148 were prepared according to the scheme below

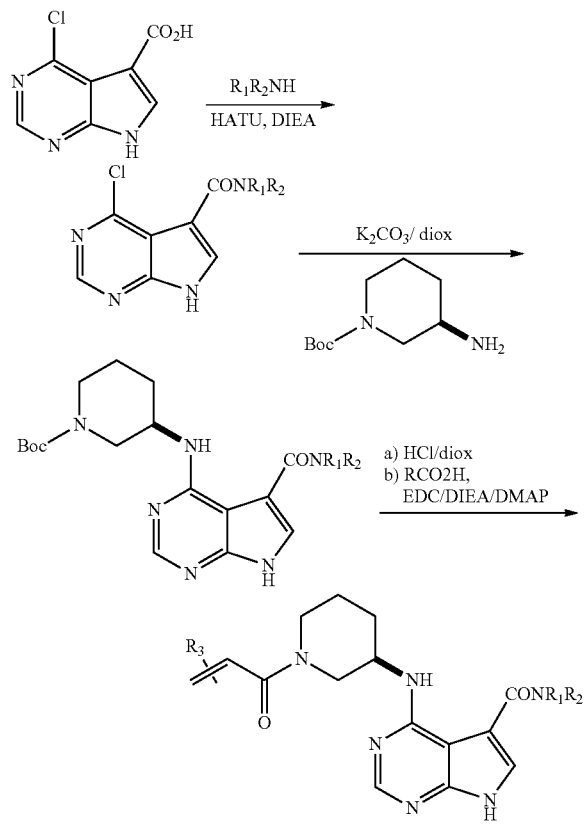

Example 140

Step 1. 4-Chloro-N,N-dimethyl-7H-pyrrolo[2,3-d]pyrimidine-5-carboxamide

To a flask was added 4-chloro-7H-pyrrolo[2,3-d]pyrimidine-5-carboxylic acid (200 mg, 1.01 mmol), dimethyl amine (82.5 mg, 1.01 mmol) and CH3CN (2 mL). After 10 min, HATU (476 mg, 1.21 mmol) and DIEA (0.44 mL, 2.43 mmol) was added. The reaction mixture was stirred at rt for 2 hrs and then poured into water/DCM. The layers were separated and the organic extract washed with water, brine and dried (Na$_2$SO$_4$). The solvent was removed to give the crude, which was purified by chromatography (silica, MeOH/DCM, 0 to 10%) to give 4-chloro-N,N-dimethyl-7H-pyrrolo[2,3-d]pyrimidine-5-carboxamide (100 mg, 44%). LC/MS (M+H) 225.1.

Step 2. (R)-tert-Butyl 3-((5-(dimethylcarbamoyl)-7H-pyrrolo[2,3-d]pyrimidin-4-yl)amino)piperidine-1-carboxylate To a microwave tube containing 4-chloro-N,N-dimethyl-7H-pyrrolo[2,3-d]pyrimidine-5-carboxamide (100 mg, 0.44 mmol) in dioxane/water (2 mL/0.5 mL) was added (R)-tert-butyl 3-am inopiperidine-1-carboxylate (267 mg, 1.34 mmol) and K$_2$CO$_3$ (123 mg, 0.89 mmol). The reaction mixture was heated to 120° C. overnight and then allowed to cool. The mixture was poured into EtOAc/water and the layers were separated and the organic extract washed with water, brine and dried (Na$_2$SO$_4$). The solvent was removed to give the crude, which was purified by chromatography (silica, EtOAc/Hep, 90 to 100%) to give (R)-tert-butyl 3-((5-(dimethylcarbamoyl)-7H-pyrrolo[2,3-d]pyrimidin-4-yl)amino)piperidine-1-carboxylate (75 mg, 43%). LC/MS (M+H) 389.3.

Step 3. (R)—N,N-Dimethyl-4-(piperidin-3-ylamino)-7H-pyrrolo[2,3-d]pyrimidine-5-carboxamide A flask containing (R)-tert-butyl 3-((5-(dimethylcarbamoyl)-7H-pyrrolo[2,3-d]pyrimidin-4-yl)amino)-piperidine-1-carboxylate (70 mg, 0.18 mmol) in DCM (2 mL) was treated with 4N HCl in dioxane (0.360 mL, 1.44 mmol). The reaction was stirred at rt for 2 hrs and then the solvent was removed to give (R)—N,N-dimethyl-4-(piperidin-3-ylamino)-7H-pyrrolo[2,3-d]pyrimidine-5-carboxamide (50 mg, 70%).

Step 4. (R)-4-((1-acryloylpiperidin-3-yl)amino)-N,N-dimethyl-7H-pyrrolo[2,3-d]pyrimidine-5-carboxamide To a flask containing (R)—N,N-dimethyl-4-(piperidin-3-ylamino)-7H-pyrrolo[2,3-d]pyrimidine-5-carboxamide (40 mg, 0.14 mmol) in DMF (2 mL) was added acrylic acid (0.01 mL, 0.12 mmol), EDCl (47 mg, 0.23 mmol) and DIEA (0.06 mL, 0.35 mmol). The reaction was stirred at rt for 2 hrs and then poured into water/ethyl acetate. The layers were separated and the organic extract washed with water, dried (Na$_2$SO$_4$) and the solvent removed to give crude (R)-4-((1-acryloylpiperidin-3-yl)amino)-N,N-dimethyl-7H-pyrrolo[2,3-d]pyrimidine-5-carboxamide, which was purified by RP-HPLC to give pure product (48 mg, 63%). LC/MS (M+H) 343.3.

| Ex | LC/MS | Name |
|---|---|---|
| 142 | 343 | 4-{[(3R)-1-acryloylpiperidin-3-yl]amino}-N,N-dimethyl-7H-pyrrolo[2,3-d]pyrimidine-5-carboxamide |
| 143 | 359 | 4-{[(3R)-1-acryloylpiperidin-3-yl]amino}-N-(2-hydroxyethyl)-7H-pyrrolo[2,3-d]pyrimidine-5-carboxamide |
| 144 | 343 | 4-{[(3R)-1-acryloylpiperidin-3-yl]amino}-N-ethyl-7H-pyrrolo[2,3-d]pyrimidine-5-carboxamide |

| Ex | LC/MS | Name |
|---|---|---|
| 145 | 329 | 4-{[(3R)-1-acryloylpiperidin-3-yl]amino}-N-methyl-7H-pyrrolo[2,3-d]pyrimidine-5-carboxamide |
| 146 | 369 | 1-[(3R)-3-{[5-(pyrrolidin-1-ylcarbonyl)-7H-pyrrolo[2,3-d]pyrimidin-4-yl]amino}piperidin-1-yl]prop-2-en-1-one |
| 147 | 383 | (2E)-1-[(3R)-3-{[5-(pyrrolidin-1-ylcarbonyl)-7H-pyrrolo[2,3-d]pyrimidin-4-yl]amino}piperidin-1-yl]but-2-en-1-one |
| 148 | 373 | 4-({(3R)-1-[(2E)-but-2-enoyl]piperidin-3-yl}amino)-N-(2-hydroxyethyl)-7H-pyrrolo[2,3-d]pyrimidine-5-carboxamide |
| 149 | 387 | 4-({(3R)-1-[(2E)-but-2-enoyl]piperidin-3-yl}amino)-N-(2-methoxyethyl)-7H-pyrrolo[2,3-d]pyrimidine-5-carboxamide |
| 150 | 373 | 4-{[(3R)-1-acryloylpiperidin-3-yl]amino}-N-(2-methoxyethyl)-7H-pyrrolo[2,3-d]pyrimidine-5-carboxamide |

Example 151: (2E)-1-[(3R)-3-{[5-(2-hydroxyethyl)-7H-pyrrolo[2,3-d]pyrimidin-4-yl]amino}piperidin-1-yl]but-2-en-1-one Step 1. (R)-tert-Butyl 3-((5-(2-((tert-butyldimethylsilyl)oxy)ethyl)-7H-pyrrolo[2,3-d]pyrimidin-4-yl)amino)piperidine-1-carboxylate To a flask containing 5-(2-((tertbutyldimethylsilyl)oxy)ethyl)-4-chloro-7H-pyrrolo[2,3-d]pyrimidine (1.0 g, 3.2 mmol) in dioxane/water (10 mL/6 mL) was added (R)-tert-butyl 3-aminopiperidine-1-carboxylate and $K_2CO_3$ (1.33 g, 9.6 mmol). The mixture was heated to 100° C. for 30 hrs and the cooled to rt. The reaction was poured into ethyl acetate/brine and the layers separated. The organic extract was collected, dried ($Na_2SO_4$) and the solvent removed to give an oil, which after chromatography (silica, MeOH/DCM, 0 to 10%) gave (R)-tert-butyl 3-((5-(2-((tert-butyldimethylsilyl)-oxy)ethyl)-7H-pyrrolo[2,3-d]pyrimidin-4-yl)amino)piperidine-1-carboxylate (914 mg, 60%). LC/MS (M+H) 476.5.

Step 2. (R)-2-(4-(Piperidin-3-ylamino)-7H-pyrrolo[2,3-d]pyrimidin-5-yl)ethanol

To a flask containing (R)-tert-butyl 3-((5-(2-((tert-butyldimethylsilyl)oxy)ethyl)-7H-pyrrolo[2,3-d]pyrimidin-4-yl)amino)piperidine-1-carboxylate (914 mg, 1.92 mmol) was added dioxane (8 mL) followed by 4M HCl/dioxane (3 mL). The reaction mixture was stirred for 4 h. Ether was added, and the solid filtered to give (R)-2-(4-(piperidin-3-ylamino)-7H-pyrrolo[2,3-d]pyrimidin-5-yl)ethanol (750 mg) as the HCl salt. LC/MS (M+H) 262.3.

Step 3. (2E)-1-[(3R)-3-{[5-(2-Hydroxyethyl)-7H-pyrrolo[2,3-d]pyrimidin-4-yl]amino}piperidin-1-yl]but-2-en-1-one To a flask containing (R)-2-(4-(piperidin-3-ylamino)-7H-pyrrolo[2,3-d]pyrimidin-5-yl)ethanol (100 mg, 0.38 mmol) in DCM (3 mL) was added trans-crotonic acid (27 mg, 0.30 mmol), EDCl (81.5 mg, 0.42 mmol), DIEA (0.67 mL, 3.83 mmol) and DMAP (2.30 mg, 0.02 mmol). The reaction mixture was stirred for 3 hrs, and then poured into water/DCM. The layers were separated and the organic extract dried ($Na_2SO_4$) and the solvent removed to give 114 mg of crude material, which was purified by chromatography (silica, MeOH/DCM, 0 to 10%) and then RP-HPLC to give (2E)-1-[(3R)-3-{[5-(2-hydroxyethyl)-7H-pyrrolo[2,3-d]pyrimidin-4-yl]amino}piperidin-1-yl]but-2-en-1-one (26 mg, 21%). LC/MS (M+H) 330.3. $^1$H NMR (400 MHz, DMSO-$d_6$) δ 1.33-1.86 (m, 5H) 2.77 (m, 2H) 2.86-3.20 (m, 2H) 3.54-3.79 (m, 3H) 3.84-4.21 (m, 2H) 5.05-5.46 (m, 1H) 6.21-6.63 (m, 2H) 6.84 (s, 1H) 6.96-7.31 (m, 1H) 8.04 (br s, 1H) 11.25 (br s, 1H).

Example 152: 1-[(3R)-3-{[5-(2-Hydroxyethyl)-7H-pyrrolo[2,3-d]pyrimidin-4-yl]amino}piperidin-1-yl]-2-methylprop-2-en-1-one Prepared as in Example 151, except using methacrylic acid in step 3. LC/MS (M+H) 330.3.

Example 153: 2-Methyl-1-[(3R)-3-(3-methyl-3,4-dihydro-1,5,6,8-tetraazaacenaphthylen-5(1H)-yl)piperidin-1-yl]prop-2-en-1-one Step 1. (R)-tert-Butyl 3-((5-bromo-7-((2-(trimethylsilyl)ethoxy)methyl)-7H-pyrrolo[2,3-d]pyrimidin-4-yl)amino)piperidine-1-carboxylate To a solution of 5-bromo-4-chloro-7-((2-(trimethylsilyl)ethoxy)methyl)-7H-pyrrolo[2,3-d]pyrimidine (2.0 g, 5.5 mmol) in dioxane/water (10 mL:5 mL) was added (R)-tert-butyl 3-aminopiperidine-1-carboxylate (2.21 g, 11.0 mmol) and $K_2CO_3$ (1.52 g, 11.0 mmol). The reaction mixture was heated to 100° C. for 72 hrs and then cooled to rt. The reaction mixture was diluted with water (10 mL) and the aqueous mixture extracted with ethyl acetate (3×). The combined organic extracts were washed with water, brine and dried ($Na_2SO_4$). The solvent was removed to give an oil, which after chromatography (silica, EtOAc/Hep, 0 to 50%) gave (R)-tert-butyl 3-((5-bromo-7-((2-(trimethylsilyl)ethoxy)methyl)-7H-pyrrolo[2,3-d]pyrimidin-4-yl)amino)piperidine-1-carboxylate (600 mg, 41%). LC/MS (M+H) 528.3. $^1$H NMR (400 MHz, CDCl$_3$) δ −0.26−−0.01 (m, 9H) 0.69-0.91 (m, 2H) 1.29 (s, 9H) 1.51-1.93 (m, 4H) 3.12-3.31 (m, 1H) 3.38-3.51 (m, 2H) 3.53 (d, J=14.05 Hz, 3H) 4.29 (br s, 1H) 5.36-5.54 (m, 2H) 6.11 (d, J=7.61 Hz, 1H) 6.87-7.03 (m, 1H) 8.17-8.30 (m, 1H).

Step 2. (R)-tert-Butyl 3-(allyl(5-bromo-7-((2-(trimethylsilyl)ethoxy)methyl)-7H-pyrrolo[2,3-d]pyrimidin-4-yl)amino)piperidine-1-carboxylate To a flask containing (R)-tert-butyl 3-((5-bromo-7-((2-(trimethylsilyl) ethoxy)methyl)-7H-pyrrolo[2,3-d]pyrimidin-4-yl)amino)piperidine-1-carboxylate (100 mg, 0.19 mmol) in THF (4 mL) was added NaH (8.4 mg, 0.21 mmol). After 15 min, allyl iodide (64 mg, 0.38 mmol) was added and the reaction stirred at 40° C. for 2 hrs. The mixture was poured into water/EtOAc and the layers separated. The organic layer was collected, dried ($Na_2SO_4$) and the solvent removed to give (R)-tert-butyl 3-(allyl(5-bromo-7-((2-(trimethylsilyl)ethoxy)methyl)-7H-pyrrolo[2,3-d]pyrimidin-4-yl)amino)piperidine-1-carboxylate. LC/MS (M+H) 568.3. $^1$H NMR (400 MHz, $CDCl_3$) δ −0.22−−0.01 (m, 9H) 0.72-0.96 (m, 3H) 1.15-1.46 (m, 11H) 2.65 (t, J=11.81 Hz, 1H) 2.92-3.07 (m, 1H) 3.30-3.60 (m, 2H) 3.93-4.35 (m, 6H) 5.04 (d, J=10.15 Hz, 1H) 5.21 (d, J=17.18 Hz, 1H) 5.44-5.59 (m, 2H) 5.79-5.99 (m, 1H) 7.13-7.23 (m, 1H) 8.36 (s, 1H).

Step 3. (R)-tert-Butyl 3-(3-methylene-1-((2-(trimethylsilyl)ethoxy)methyl)-3,4-dihydro-1,5,6,8-tetraazaacenaphthylen-5(1H)-yl)piperidine-1-carboxylate To a flask containing (R)-tert-butyl 3-(allyl(5-bromo-7-((2-(trimethylsilyl)ethoxy)methyl)-7H-pyrrolo[2,3-d]pyrimidin-4-yl)amino)piperidine-1-carboxylate (400 mg, 0.71 mmol) was added DMF (5 mL), KOAc (173 mg, 1.76 mmol) and $Pd(PPh_3)_4$ (83.7 mg, 0.07 mmol). The flask was heated to 85° C. for 5 hrs and then cooled to rt. The reaction mixture was diluted with water (10 mL) and the aqueous mixture extracted with ethyl acetate. The organic extracts were combined, washed with brine, dried ($Na_2SO_4$) and the solvent removed to give the crude product, which after chromatography (silica, EtOAc/Hep, 0 to 25%) gave two main fractions, F1: (R)-tert-butyl 3-(3-methylene-3,4-dihydro-1,5,6,8-tetraazaacenaphthylen-5(1H)-yl)piperidine-1-carboxylate and F2: (R)-tert-butyl 3-(3-methyl-1,5,6,8-tetraazaacenaphthylen-5(1H)-yl)piperidine-1-carboxylate. F1: LC/MS (M+H) 486.3. F2: LC/MS (M+H) 486.3.

Step 4. (3R)-tert-Butyl 3-(3-methyl-1-((2-(trimethylsilyl)ethoxy)methyl)-3,4-dihydro-1,5,6,8-tetraazaacenaphthylen-5(1H)-yl)piperidine-1-carboxylate To a Parr bottle containing (R)-tert-butyl 3-(3-methylene-3,4-dihydro-1,5,6,8-tetraazaacenaphthylen-5(1H)-yl)piperidine-1-carboxylate (420 mg, 0.86 mmol) was added ethanol (10 mL) and 10% Pd/C (104.8 mg). The reaction was shaken at rt at 40 psi $H_2$ for 3 hrs and then filtered through a pad of Celite®. The pad was washed with methanol and the solvent removed to give (3R)-tert-butyl 3-(3-methyl-3,4-dihydro-1,5,6,8-tetraazaacenaphthylen-5(1H)-yl)piper-idine-1-carboxylate (422 mg, 100%), which was used without further purification. LC/MS (M+H) 488.5.

Step 5. 3-Methyl-5-((R)-piperidin-3-yl)-1,3,4,5-tetrahydro-1,5,6,8-tetraazaacenaphthylene To a flask containing (3R)-tert-butyl 3-(3-methyl-1-((2-(trimethylsilyl)ethoxy)methyl)-3,4-dihydro-1,5,6,8-tetraaza-acenaphthylen-5(1H)-yl)piperidine-1-carboxylate (422 mg, 0.86 mmol) was added DCM (10 mL) and TFA (5 mL). The reaction mixture was stirred at rt for 3 hrs and then concentrated in vacuo. The residue was dissolved in methanol and then $NH_4OH$ (10 mL) was added. The mixture was stirred for 3 hrs at rt and the solvent removed in vacuo and the residue purified by chromatography (silica, MeOH/DCM, 0 to 10%) to give 3-methyl-5-((R)-piperidin-3-yl)-1,3,4,5-tetrahydro-1,5,6,8-tetraazaacenaphthylene (300 mg, 135% salt contaminant). LC/MS (M+H) 258.3.

Step 6. 2-Methyl-1-((3R)-3-(3-methyl-3,4-dihydro-1,5,6,8-tetraazaacenaphthylen-5(1H)-yl)piperidin-1-yl)prop-2-en-1-one To a flask containing 3-methyl-5-((R)-piperidin-3-yl)-1,3,4,5-tetrahydro-1,5,6,8-tetraazaacenaphthylene (75 mg, 0.29 mmol) was added THF (5 mL) and TEA (0.1 mL, 0.58 mmol). The mixture was cooled to 0° C. and then methacryloyl chloride (30.4 mg, 0.29 mmol) was added. After stirring at rt for 5 hrs, the reaction was diluted with ethyl acetate/water. The layers were separated and the organic layer collected, dried ($Na_2SO_4$) and the solvent removed to give crude material, which after chromatography (silica, MeOH/DCM, 0 to 15%) gave 2-methyl-1-((3R)-3-(3-methyl-3,4-dihydro-1,5,6,8-tetraazaacenaphthylen-5(1H)-yl)piperidin-1-yl)prop-2-en-1-one (5.0 mg, 5%). LC/MS (M+H)=326.4. $^1$H NMR (400 MHz, CDCl3) δ 1.11-1.34 (m, 3H) 1.54-2.11 (m, 8H) 2.82-3.28 (m, 3H) 3.41-3.65 (m, 1H) 3.88-4.25 (m, 1H) 4.54 (br s, 2H) 4.94-5.19 (m, 2H) 6.66 (s, 1H) 8.33 (br s, 1H) 9.47 (br s, 1H).

Example 154: (2E)-1-[(3R)-3-(3-methyl-3,4-dihydro-1,5,6,8-tetraazaacenaphthylen-5(1H)-yl)piperidin-1-yl]but-2-en-1-one Prepared as in Example 153, except for Step 6 in which trans-crotonyl chloride was used instead of methacryloyl chloride. LC/MS (M+H) 326.4.

Example 155: 1-[(3R)-3-(3-Methyl-3,4-dihydro-1,5,6,8-tetraazaacenaphthylen-5(1H)-yl)piperidin-1-yl]prop-2-en-1-one Prepared as in Example 153, except for Step 6 in which acryloyl chloride was used instead of methacryloyl chloride. LC/MS (M+H) 312.2.

Example 156: 4-{[(3R)-1-Acryloylpiperidin-3-yl]amino}-1H-pyrrolo[2,3-b]pyridine-5-carbonitrile Step 1. (R)-4-((1-Benzylpiperidin-3-yl)amino)-1H-pyrrolo[2,3-b]pyridine-5-carbonitrile To a microwave tube was added 4-chloro-1H-pyrrolo[2,3-b]pyridine-5-carbonitrile (172 mg, 0.97 mmol), (R)-1-benzyl-piperidin-3-amine (553 mg, 2.91 mmol) and NMP (0.5 mL). The mixture was heated to 130° C. for 2 h and then cooled to rt. The mixture was diluted with water/ethyl acetate and the layers separated. The organic extract was washed with water, dried ($Na_2SO_4$) and the solvent removed to give the crude, which after chromatography (silica, EtOAc/Hep, 0 to 100%) gave (R)-4-((1-benzylpiperidin-3-yl)amino)-1H-pyrrolo[2,3-b]pyridine-5-carbonitrile (249 mg, 77%). LC/MS (M+H) 332.3. $^1$H NMR (400 MHz, DMSO-$d_6$) δ 1.39-1.80 (m, 5H) 2.38 (br s, 2H) 2.56-2.73 (m, 1H) 3.50 (s, 2H) 4.23 (br s, 1H) 6.44 (d, J=8.59 Hz, 1H) 6.55 (dd, J=3.71, 1.95 Hz, 1H) 7.10-7.40 (m, 6H) 8.04 (s, 1H) 11.77 (br s, 1H).

Step 2. (R)-4-(Piperidin-3-ylamino)-1H-pyrrolo[2,3-b]pyridine-5-carbonitrile

To a flask containing (R)-4-((1-benzylpiperidin-3-yl)amino)-1H-pyrrolo[2,3-b]pyridine-5-carbonitrile (155 mg, 0.47 mmol) was added ethanol (3 mL), ammonium formate (296 mg, 4.68 mmol) and $Pd(OH)_2$ (32.3 mg, 0.02 mmol). The mixture was heated to 100° C. for 2 hrs and then cooled to rt. The mixture was filtered through Celite® and the solvent removed to give the crude, which after chromatography (silica, MeOH/DCM 0 to 40%) gave (R)-4-(piperidin-3-ylamino)-1H-pyrrolo[2,3-b]pyridine-5-carbonitrile (71 mg, 63%). LC/MS (M+H) 242.3.

Step 3. 4-{[(3R)-1-Acryloylpiperidin-3-yl]amino}-1H-pyrrolo[2,3-b]pyridine-5-carbonitrile To a flask containing (R)-4-(piperidin-3-ylamino)-1H-pyrrolo[2,3-b]pyridine-5-carbonitrile (25 mg, 0.1 mmol) was added THF (1 mL) and TEA (30 μL, 0.2 mmol). The mixture was cooled to 0° C. and then acryloyl chloride (7.5 μL, 0.10 mmol) was added and the reaction stirred for 1 hr. The mixture was diluted with water/ethyl acetate and the layers separated. The organic extract was washed with water, brine and dried (Na$_2$SO$_4$). The solvent was removed in vacuo to give the crude, which after chromatography (silica, MeOH/DCM, 0 to 15%) gave 4-{[(3R)-1-acryloylpiperidin-3-yl]amino}-1H-pyrrolo[2,3-b]pyridine-5-carbonitrile (17 mg, 55%). LC/MS (M+H) 296.2. $^1$H NMR (400 MHz, DMSO-d$_6$) δ 1.47 (br s, 1H) 1.61-1.79 (m, 2H) 1.92-2.14 (m, 1H) 2.64-3.21 (m, 2H) 3.76-4.26 (m, 2H) 4.43 (d, J=11.13 Hz, 1H) 5.45-5.70 (m, 1H) 5.92-6.19 (m, 1H) 6.44-6.89 (m, 3H) 7.23 (br s, 1H) 7.90-8.10 (m, 1H) 11.81 (br s, 1H).

Example 157: 3-[4-({(3R)-1-[(2E)-4-(Dimethylamino)but-2-enoyl]piperidin-3-yl}amino)-7H-pyrrolo[2,3-d]pyrimidin-5-yl]propanenitrile

Step 1. (R)-tert-Butyl 3-((5-(2-cyanoethyl)-7H-pyrrolo[2,3-d]pyrimidin-4-yl)amino)piperidine-1-carboxylate To a flask containing (R)-tert-butyl 3-((5-(2-hydroxyethyl)-7H-pyrrolo[2,3-d]pyrimidin-4-yl)amino)piperidine-1-carboxylate (400 mg, 1.11 mmol) in DCM (6.0 mL) at 0° C. was added CH$_3$SO$_2$Cl (0.10 mL, 1.33 mmol) and DIPEA (0.6 mL, 3.32 mmol). The mixture was stirred at 0° C. for 30 min and then poured into water/DCM. The layers were separated and the organic extracts collected and dried (Na$_2$SO$_4$). The solvent was removed to give crude (R)-tert-butyl 3-((5-(2-((methylsulfonyl)oxy)ethyl)-7H-pyrrolo[2,3-d]pyrimidin-4-yl)amino)piperidine-1-carboxylate (540 mg), which was used in the next step without purification. To the crude (R)-tert-butyl 3-((5-(2-((methylsulfonyl)oxy)ethyl)-7H-pyrrolo[2,3-d]pyrimidin-4-yl)amino)piperidine-1-carboxylate (540 mg, 1.23 mmol) was added DMF (5 mL) and NaCN (303 mg, 6.1 mmol). The reaction was stirred at 50° C. for 30 mins and then poured into water/ethyl acetate. The layers were separated and the organic extract collected and dried (Na$_2$SO$_4$). The solvent was removed to give the crude, which after chromatography (silica, MeOH/DCM 0 to 5%) gave (R)-tert-butyl 3-((5-(2-cyanoethyl)-7H-pyrrolo[2,3-d]pyrimidin-4-yl)amino)piperidine-1-carboxylate (302 mg, 66%). LC/MS (M+H) 371.4.

Step 2. (R)-3-(4-(Piperidin-3-ylamino)-7H-pyrrolo[2,3-d]pyrimidin-5-yl)propanenitrile To a flask containing (R)-tert-butyl 3-((5-(2-cyanoethyl)-7H-pyrrolo[2,3-d]pyrimidin-4-yl)amino)piperidine-1-carboxylate (302 mg, 0.82 mmol) was added DCM (2 mL) and TFA (0.32 mL). The mixture was stirred at rt for 4 hrs and the solvent removed to give crude (R)-3-(4-(piperidin-3-ylamino)-7H-pyrrolo[2,3-d]pyrimidin-5-yl)propanenitrile, which was used without further purification. LC/MS (M+H) 271.3.

Step 3. 3-[4-({(3R)-1-[(2E)-4-(Dimethylamino)but-2-enoyl]piperidin-3-yl}amino)-7H-pyrrolo[2,3-d]pyrimidin-5-yl]propanenitrile To a flask containing (R)-3-(4-(piperidin-3-ylamino)-7H-pyrrolo[2,3-d]pyrimidin-5-yl)propanenitrile (100 mg, 0.37 mmol) was added DCM (2 mL), EDCl (78 mg, 0.41 mmol), (E)-4-(dimethylamino)but-2-enoic acid (61 mg, 0.37 mmol), DIPEA (0.6 mL, 3.7 mmol) and DMAP (2.2 mg, 0.018 mmol). The mixture was stirred overnight at rt. The reaction was diluted with saturated Na—HCO$_3$ and DCM. The layers were separated and organic extract collected and dried (Na$_2$SO$_4$). The solvent was removed to give crude 3-[4-({(3R)-1-[(2E)-4-(dimethylamino)but-2-enoyl]piperidin-3-yl}amino)-7H-pyrrolo[2,3-d]pyrimidin-5-yl]propanenitrile, which was purified by RP-HPLC to give pure material (32.8 mg). LC/MS (M+H) 382.1.

Example 158: 3-[4-({(3R)-1-[(2E)-4-Hydroxybut-2-enoyl]piperidin-3-yl}amino)-7H-pyrrolo[2,3-d]pyrimidin-5-yl]propanenitrile Prepared as in Example 157, except in Step 3 the acid used was (E)-4-hydroxybut-2-enoic acid. LC/MS (M+H) 355.3.

Example 159: (2E)-1-[(3R)-3-{[5-(2-Hydroxy-2-methylpropyl)-7H-pyrrolo[2,3-d]pyrimidin-4-yl]amino}piperidin-1-yl]but-2-en-1-one Prepared as in Example 53, except (E)-but-2-enoyl chloride used instead of acryloyl chloride in final step.

Example 160: rac-(2E)-1-[(3S,4R)-4-Hydroxy-3-(7H-pyrrolo[2,3-d]pyrimidin-4-ylamino)piperidin-1-yl]but-2-en-1-one Prepared as in Example 64, except in the last step (E)-but-2-enoyl chloride was used instead of acryloyl chloride. LC/MS (M+H) 302.1.

Example 161: 1-[(2R,5R)-2-(Hydroxymethyl)-5-(7H-pyrrolo[2,3-d]pyrimidin-4-ylamino)piperidin-1-yl]prop-2-en-1-one For preparation, see Example 7.

Example 162: 1-{(3R,5S)-3-[(5-Chloro-7H-pyrrolo[2,3-d]pyrimidin-4-yl)amino]-5-hydroxypiperidin-1-yl}prop-2-en-1-one

Step 1. (3S,5R)-tert-Butyl 3-((tert-butyldimethylsilyl)oxy)-5-((5-chloro-7H-pyrrolo[2,3-d]pyrimidin-4-yl)amino)piperidine-1-carboxylate A mixture of (3R,5S)-tert-butyl 3-amino-5-((tert-butyldimethylsilyl)-oxy)piperidine-1-carboxylate (200 mg, 0.61 mmol), 4,5-dichloro-7H-pyrrolo[2,3-d]pyrimidine (136 mg, 0.73 mmol) and DIPEA (156 mg, 1.21 mmol) in n-BuOH (5 mL) was heated to 80° C. for 20 hours. LC-MS showed about 60% 4,5-dichloro-7H-pyrrolo[2,3-d]pyrimidine was remaining. 200 mg of (3R,5S)-tert-butyl 3-amino-5-((tert-butyldimethylsilyl)oxy)piperidine-1-carboxylate was added, and the reaction mixture was heated to 90° C. for 20 hours. The reaction mixture was evaporated to dryness to give crude material, which after chromatography (silica, DCM/MeOH, 100:0-90:10) gave (3S,5R)-tert-butyl 3-((tert-butyldimethylsilyl)oxy)-5-((5-chloro-7H-pyrrolo[2,3-d]pyrimidin-4-yl)amino)piperidine-1-carboxylate (290 mg, 83%) as a yellow solid. LC/MS (M+H) 482.1.

Step 2. N-((3R,5S)-5-((tert-Butyldimethylsilyl)oxy) piperidin-3-yl)-5-chloro-7H-pyrrolo[2,3-d]pyrimidin-4-amine To a 0oC stirred solution of (3S,5R)-tert-butyl 3-((tert-butyldimethylsilyl)oxy)-5-((5-chloro-7H-pyrrolo[2, 3-d]pyrimidin-4-yl)amino)piperidine-1-carboxylate (290 mg, 0.60 mmol) in CH2Cl2 (10 mL) was added TFA (3 mL). After the resulting mixture was stirred at room temperature for 2 hours, TLC (DCM/MeOH, 10:1) showed starting material was consumed completely. The reaction mixture was evaporated to dryness and then purified by chromatography (silica, EtOAc/MeOH, 100:0-80:20) to give N-((3R,5S)-5-((tert-butyldimethylsilyl)oxy)piperidin-3-yl)-5-chloro-7H-pyrrolo[2,3-d]pyrimidin-4-amine (120 mg, 52.4%) as a yellow solid.

Step 3. 1-((3S,5R)-3-((tert-Butyldimethylsilyl)oxy)-5-((5-chloro-7H-pyrrolo[2,3-d]pyrimidin-4-yl)amino)piperidin-1-yl)prop-2-en-1-one To a 0° C. stirred solution of N-((3R,5S)-5-((tert-butyldimethylsilyl)oxy)piperidin-3-yl)-5-chloro-7H-pyrrolo[2,3-d] pyrimidin-4-amine (100 mg, 0.26 mmol) and DIPEA (68 mg, 0.52 mmol) in THF-H2O (5 mL, v/v=1:1) was added acryloyl chloride (28.5 mg, 0.31 mmol). After the addition, the resulting mixture was stirred at room temperature for 20 min. TLC (DCM/MeOH, 10:1) showed starting material was consumed completely. The reaction mixture was evaporated to dryness and the crude material used in the next step without purification.

Step 4. 1-((3R,5S)-3-((5-Chloro-7H-pyrrolo[2,3-d]pyrimidin-4-yl)amino)-5-hydroxypiperidin-1-yl)prop-2-en-1-one To a flask containing crude 1-((3S,5R)-3-((tert-butyldimethylsilyl)oxy)-5-((5-chloro-7H-pyrrolo[2,3-d]pyrimidin-4-yl)amino)piperidin-1-yl)prop-2-en-1-one was dissolved in THF (5 mL) at 0° C. was added TBAF (0.3 mL, 1 M in THF). After the addition, the resulting mixture was stirred at room for 18 hours. LC-MS showed starting material was consumed completely. The reaction mixture was evaporated to dryness and the crude material was purified by RP-HPLC (base modifier) to give 1-((3R,5S)-3-((5-chloro-7H-pyrrolo [2,3-d]pyrimidin-4-yl)amino)-5-hydroxypiperidin-1-yl) prop-2-en-1-one (31 mg) as a white solid. HNMR showed some TBAF present, thus further purification by RP-HPLC (TFA modifier) gave 1-((3R,5S)-3-((5-chloro-7H-pyrrolo[2, 3-d]pyrimidin-4-yl)amino)-5-hydroxypiperidin-1-yl)prop-2-en-1-one (13 mg, 16.7) as a white solid. $^1$H NMR (400 MHz, DMSO-$d_6$) δ 11.82 (br s, 1H), 8.20 (br s, 1H), 8.13 (d, J=12.3 Hz, 1H), 7.36 (dd, J=7.9, 18.2 Hz, 1H), 7.23 (d, J=13.3 Hz, 1H), 6.79 (dd, J=10.7, 16.7 Hz, 1H), 6.35 (dd, J=10.4, 16.7 Hz, 1H), 6.01-5.83 (m, 1H), 5.61 (d, J=12.5 Hz, 1H), 5.51-5.29 (m, 1H), 4.45 (br s, 1H), 4.39-4.27 (m, 1H), 4.04-3.74 (m, 3H), 3.51 (d, J=14.3 Hz, 1H), 3.11 (d, J=11.8 Hz, 1H), 2.08-1.97 (m, 1H), 1.83 (d, J=13.1 Hz, 1H).

Example 163: 4-{[(3R,6S)-1-Acryloyl-6-methylpiperidin-3-yl]amino}-7H-pyrrolo[2,3-d]pyrimidine-5-carbonitrile Prepared as in Example 18, except using 4-chloro-7H-pyrrolo[2,3-d]pyrimidine-5-carbo-nitrile in Step 1. LC/MS (M+H) 311.4. $^1$H NMR (400 MHz, CDCl$_3$) δ 1.04-1.27 (m, 3H) 1.59-2.08 (m, 5H) 2.76 (br s, 1H) 4.04-4.24 (m, 1H) 4.44-4.82 (m, 2H) 5.45 (d, J=7.02 Hz, 1H) 5.56-5.70 (m, 1H) 6.24 (dd, J=16.78, 1.95 Hz, 1H) 6.60 (dd, J=16.59, 10.73 Hz, 1H) 7.19 (s, 1H) 7.60 (s, 1H) 8.36 (s, 1H).

Example 164: 4-{[(3R,6S)-1-Acryloyl-6-methylpiperidin-3-yl]amino}-7H-pyrrolo[2,3-d]pyrimidine-5-carboxamide Prepared as in Example 18, except using 4-chloro-7H-pyrrolo[2,3-d]pyrimidine-5-carbonitrile in Step 1. Amide is by-product of Z-isomer removal with HBr/AcOH. LC/MS (M+H) 328.4. $^1$H NMR (400 MHz, CD$_3$OD) δ 1.02-1.29 (m, 3H) 1.54-2.06 (m, 5H) 2.51-2.73 (m, 1H) 2.91 (br s, 1H) 3.96 (br s, 2H) 5.66 (d, J=1.56 Hz, 1H) 5.96-6.20 (m, 1H) 6.72 (dd, J=16.78, 10.54 Hz, 1H) 8.06 (s, 1H) 9.65 (d, J=7.02 Hz, 1H).

Example 165: 4-{[(3R,6S)-1-Acryloyl-6-methylpiperidin-3-yl]amino}-1H-pyrrolo[2,3-b]pyridine-3-carbonitrile Prepared as in Example 2, except using (2S,5R)-tert-butyl 5-amino-2-methylpiperidine-1-carboxylate instead of (R)-tert-butyl 3-aminopiperidine-1-carboxylate. LC/MS (M+H) 310.3. $^1$H NMR (400 MHz, CDCl$_3$) δ 1.15-1.36 (m, 3H) 1.60-1.86 (m, 3H) 1.98-2.12 (m, 1H) 2.54-2.78 (m, 1H) 3.42-3.52 (m, 2H) 5.12-5.29 (m, 1H) 5.59-5.63 (m, 1H) 5.64-5.73 (m, 1H) 6.19-6.31 (m, 1H) 6.44 (br s 1H) 6.45-6.62 (m, 1H) 7.24 (br s, 1H) 7.52-7.69 (m, 1H) 7.96-8.10 (m, 1H).

Example 166: 1-[1-Methyl-7-(7H-pyrrolo[2,3-d]pyrimidin-4-ylamino)-1,4,6,7-tetrahydro-5H-imidazo[4,5-c]pyridin-5-yl]prop-2-en-1-one

Step 1. 3-Bromo-N-methyl-5-nitropyridin-4-amine

To a solution of 3-bromo-4-chloro-5-nitropyridine (10 g, 42 mmol) in THF (100 mL) was added slowly 30% MeNH$_2$/H$_2$O (20 mL, 210 mmol) at room temperature. After the addition, the reaction mixture was stirred at room temperature for 3 hours. TLC (Petroleum ether/EtOAc, 4:1) showed starting material was consumed completely. The reaction mixture was partitioned between EtOAc (300 mL) and water (200 mL) and the organic layer was dried over Na$_2$SO$_4$ and concentrated to dryness to give 3-bromo-N-methyl-5-nitropyridin-4-amine (8 g, 80%) as a yellow solid, which was used directly to next step without further purification. $^1$H NMR (400 MHz, CDCl$_3$) δ 3.22 (d, J=5.52 Hz, 3H) 7.15 (br s, 1H) 8.47 (s, 1H) 8.90 (s, 1H).

Step 2. 5-Bromo-N4-methylpyridine-3,4-diamine

To a solution of crude 3-bromo-N-methyl-5-nitropyridin-4-amine (8 g, 34.56 mmol) in AcOH (200 ml) was added Fe (11.6 g, 207.34 mmol) at room temperature. The resulting mixture was heated to 80° C. for 3 hours. TLC (EtOAc) showed starting material was consumed completely. The reaction mixture was filtered and the filtrate was concentrated to dryness and then purified by chromatography (silica, MeOH/DCM, 0% to 10%) to give 8 g of 5-bromo-N4-methyl-pyridine-3,4-diamine (yield 100%).

Step 3. 7-Bromo-1-methyl-1H-imidazo[4,5-c]pyridine

To a stirred solution of 5-bromo-N4-methylpyridine-3,4-diamine (8 g, 40 mmol) in trimethyl ortho-formate (200 mL)

was added TsOH.H2O (344 mg, 1.8 mmol). The reaction was then stirred at 80° C. for 4 hours. TLC (EtOAc) showed starting material was consumed completely. The reaction mixture was concentrated to dryness and then purified by chromatography (silica, MeOH/EtOAc, 0% to 10%) to give 6.5 g of 7-bromo-1-methyl-1H-imidazo[4,5-c]pyridine (yield 77%). $^1$H NMR (400 MHz, DMSO-d$_6$) δ 4.09 (s, 3H) 8.43 (d, J=6.27 Hz, 2H) 8.92 (s, 1H).

Step 4. N-(Diphenylmethylene)-1-methyl-1H-imidazo[4,5-c]pyridin-7-amine

To a stirred solution of 7-bromo-1-methyl-1H-imidazo[4,5-c]pyridine (5.5 g, 26.2 mmol) and NHCPh$_2$ (7.07 g, 39.3 mmol) in anhydrous toluene (200 mL) was added BINAP (1.7 g, 2.62 mmol) and Cs$_2$CO$_3$ (34 g, 104.8 mmol). After the addition, the reaction was degassed under vacuum and purged with N$_2$ several times. Then Pd(OAc)$_2$ (588 mg, 2.62 mmol) was added into the reaction mixture under N$_2$. The suspension was degassed under vacuum and purged with N$_2$ several times. The reaction mixture was stirred at 130° C. for 12 hours. LCMS showed starting material was consumed completely. The reaction mixture was filtrated and the filtrate was concentrated to dryness and then purified by chromatography (silica, MeOH/EtOAc, 0% to 10%) to give N-(diphenylmethylene)-1-methyl-1H-imidazo[4,5-c]pyridin-7-amine (6.2 g, 76%) as a yellow solid. LC/MS (M+H) 312.9.

Step 5. 1-Methyl-1H-imidazo[4,5-c]pyridin-7-amine

To a stirred solution of N-(diphenylmethylene)-1-methyl-1H-imidazo[4,5-c]pyridin-7-amine (6.2 g, 20 mmol) in MeOH (150 mL) was added NaOAc (4.24 g, 52 mmol) and NH$_2$OH.HCl (2.78 g, 40 mmol). After the mixture with stirred at 80° C. for 12 hours, TLC (DCM/MeOH, 10:1) showed starting material was consumed completely. The reaction mixture was filtered and the filtrate was concentrated to dryness and then purified by chromatography (silica, MeOH/DCM, 0% to 30%) to give 1-methyl-1H-imidazo[4,5-c]pyridin-7-amine (5 g, 100% including some inorganic salt) as a white solid.

Step 6. N-(1-Methyl-1H-imidazo[4,5-c]pyridin-7-yl)acetamide

A solution of 1-methyl-1H-imidazo[4,5-c]pyridin-7-amine (3.3 g, 22.3 mmol) in acetic anhydride (20 mL) was stirred at 60° C. for 4 hours. TLC (DCM/MeOH, 10:1) showed starting material was consumed completely. The reaction mixture was quenched with saturated sodium carbonate (20 ml). The solution was concentrated to dryness and the crude product was purified by chromatography (silica, MeOH/DCM, 0% to 30%) to give N-(1-methyl-1H-imidazo[4,5-c]pyridin-7-yl)acetamide (2 g, 47% for 2 steps) as a yellow oil.

Step 7. 7-Aacetamido-5-benzyl-1-methyl-1H-imidazo[4,5-c]pyridin-5-ium

To a stirred solution of N-(1-methyl-1H-imidazo[4,5-c]pyridin-7-yl)acetamide (2 g, 10.5 mmol) in toluene (20 mL) was added BnBr (1.8 g, 10.5 mmol). After the mixture with stirred at 110° C. for 12 hours, TLC (DCM/MeOH, 10:1) showed starting material was consumed completely. The reaction mixture was filtered to give 7-acetamido-5-benzyl-1-methyl-1H-imidazo[4,5-c]pyridin-5-ium (2.6 g, 88%) as a white solid. $^1$H NMR (400 MHz, DMSO-d$_6$) δ 3.91-4.18 (m, 3H) 5.84 (s, 2H) 7.32-7.65 (m, 5H) 8.69-9.01 (m, 2H) 9.77 (s, 1H).

Step 8. N-(5-Benzyl-1-methyl-4,5,6,7-tetrahydro-1H-imidazo[4,5-c]pyridin-7-yl)acetamide To a stirred solution of 7-acetamido-5-benzyl-1-methyl-1H-imidazo[4,5-c]pyridin-5-ium (500 mg, 1.8 mmol) in MeOH (10 mL) was added NaBH$_4$ (140 mg, 3.6 mmol) in portions at −10° C. After the mixture with stirred at the same temperature for 30 mins. TLC (DCM/MeOH, 10:1) showed starting material was consumed completely. The reaction mixture was concentrated to dryness and the crude product was purified by chromatography (silica, MeOH/DCM, 0% to 10%) to give N-(5-benzyl-1-methyl-4,5,6,7-tetrahydro-1H-imidazo[4,5-c]pyridin-7-yl)acetamide (180 mg, 36%) as a yellow oil.

Step 9. 5-Benzyl-1-methyl-4,5,6,7-tetrahydro-1H-imidazo[4,5-c]pyridin-7-amine

A solution of N-(5-benzyl-1-methyl-4,5,6,7-tetrahydro-1H-imidazo[4,5-c]pyridin-7-yl)acetamide (100 mg, 0.36 mmol) in 6M HCl solution (5 mL) was stirred at 70° C. for 12 hours. TLC (DCM/MeOH, 10:1) showed starting material was consumed completely. The reaction mixture was azeotroped with EtOH three times to give compound 5-benzyl-1-methyl-4,5,6,7-tetrahydro-1H-imidazo[4,5-c]pyridin-7-amine (100 mg, 95%) as a yellow solid. $^1$H NMR (400 MHz, CHCl$_3$) δ 1.86 (br s, 2H) 2.62-2.76 (m, 1H) 3.23-3.33 (m, 1H) 3.62-3.73 (m, 2H) 3.67-3.72 (m, 1H) 3.83 (s, 1H) 3.74-3.81 (m, 1H) 3.84-3.93 (m, 1H) 7.17-7.55 (m, 5H).

Step 10. 5-Benzyl-N-(2-chloro-7H-pyrrolo[2,3-d]pyrimidin-4-yl)-1-methyl-4,5,6,7-tetrahydro-1H-imidazo[4,5-c]pyridin-7-amine A mixture of 5-benzyl-1-methyl-4,5,6,7-tetrahydro-1H-imidazo[4,5-c]pyridin-7-amine (300 mg, 1.08 mmol), DIPEA (697 mg, 5.4 mmol) and 2,4-dichloro-7H-pyrrolo[2,3-d]pyrimidine (244 mg, 1.3 mmol) in n-BuOH (10 mL) was heated to 135° C. overnight. LC-MS showed the reaction was complete. The reaction mixture was cooled to room temperature and evaporated to dryness. The residue was diluted with EtOAc (30 mL) and washed with water (20 mL). The aqueous layer was extracted with EtOAc (30 mL). The combined organic layers were washed with water and brine, dried over Na$_2$SO$_4$ and concentrated to give crude product, which was purified via chromatography (silica, EtOAc/petroleum ether, 10% to 80%) to give 5-benzyl-N-(2-chloro-7H-pyrrolo[2,3-d]pyrimidin-4-yl)-1-methyl-4,5,6,7-tetrahydro-1H-imidazo[4,5-c]pyridin-7-amine (250 mg, 60%) as a yellow solid. LC/MS (M+H) 393.9.

Step 11. 1-Methyl-N-(7H-pyrrolo[2,3-d]pyrimidin-4-yl)-4,5,6,7-tetrahydro-1H-imidazo[4,5-c]pyridin-7-amine To a Parr hydrogenation bottle, 10% dry Pd/C (10 mg) was added under Ar atmosphere. Then a solution of 5-benzyl-N-(2-chloro-7H-pyrrolo[2,3-d]pyrimidin-4-yl)-1-methyl-4,5,6,7-tetrahydro-1H-imidazo[4,5-c]pyridin-7-amine (100 mg, 0.25 mmol) in MeOH (10 mL) was added and the resulting mixture was hydrogenated under 50 psi of H$_2$ at 30° C. for 72 hours. The reaction solution was filtered through a pad of Celite® and the cake was washed with MeOH for three times. The combined filtrate was concentrated to give 1-methyl-N-(7H-pyrrolo[2,3-d]pyrimidin-4-yl)-4,5,6,7-tetrahydro-1H-imidazo[4,5-c]pyridin-7-amine (60 mg, 89.5%) as a yellow oil, which was used for the next step directly without further work up.

Step 12. 1-(7-((7H-Pyrrolo[2,3-d]pyrimidin-4-yl)amino)-1-methyl-6,7-dihydro-1H-imidazo[4,5-c]pyridin-5(4H)-yl)prop-2-en-1-one To a stirred solution of 1-methyl-N-(7H-pyrrolo[2,3-d]pyrimidin-4-yl)-4,5,6,7-tetrahydro-1H-imidazo[4,5-c]pyridin-7-amine (60 mg, 0.22 mmol) in THF (2 mL) and water (2 mL) at 0° C. was added DIPEA (86 mg, 0.67 mmol) and acryloyl chloride (24 mg, 0.27 mmol). After the resulting mixture was stirred at 0° C. for 2 hours, LCMS showed starting material was consumed completely. The reaction mixture was diluted with H$_2$O (20 mL) and extracted with EtOAc (30 mL×2). The combined organic extracts were washed with brine, dried over Na$_2$SO$_4$ and concentrated to give crude product, which was further purified by HPLC to give 1-(7-((7H-pyrrolo[2,3-d]pyrimidin-4-yl)amino)-1-methyl-6,7-dihydro-1H-imidazo[4,5-c]pyridin-5(4H)-yl)prop-2-en-1-one (1.5 mg, 2.5%) as a white solid. LC/MS (M+H) 324.2. $^1$H NMR (400 MHz, DMSO-d$_6$) δ 2.02-2.14 (m, 1H) 2.26-2.38 (m, 1H) 2.61-2.73 (m, 1H) 3.44-3.52 (m, 3H) 3.59 (dd, J=14.43, 2.64 Hz, 1H) 3.91-4.21 (m, 2H) 4.36-4.52 (m, 1H) 5.04-5.63 (m, 1H) 5.88-6.39 (m, 1H) 6.52-6.64 (m, 1H) 6.99-7.10 (m, 1H) 7.59-7.85 (m, 1H) 8.17-8.27 (m, 1H) 11.56 (br s, 1H).

Examples 167-196

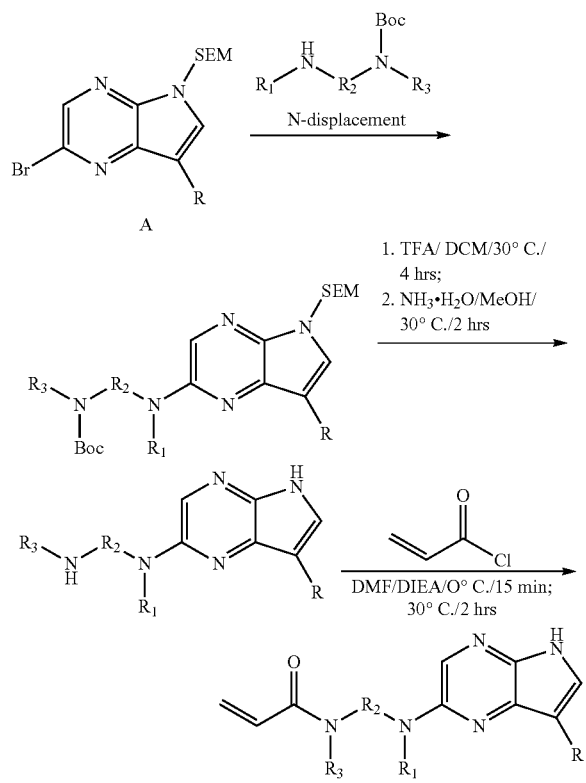

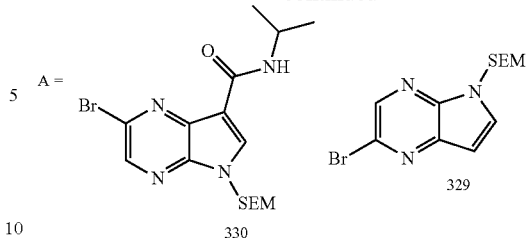

Starting templates A (2-bromo-N-isopropyl-5-((2-(trimethylsilyl)ethoxy)methyl)-5H-pyrrolo[2,3-b]pyrazine-7-carboxamide and 2-bromo-5-((2-(trimethylsilyl)ethoxy)methyl)-5H-pyrrolo[2,3-b]pyrazine) were prepared as described in WO2010/063634 and *Journal of Medicinal Chemistry*, 56(4), 1677-1692 (2013). Examples 165-196 were prepared according to the synthetic procedure below.

Step 1: (a) Precursor 330 (CONHiPr). A 0.1 M solution of 2-bromo-N-isopropyl-5-((2-(trimethylsilyl)eth-oxy)methyl)-5H-pyrrolo[2,3-b]pyrazine-7-carboxamide (330) was prepared in toluene. Amine partners (150 μmol, 2.0 eq.) were dispensed to 8 ml reaction vials. Cs$_2$CO$_3$ (48.9 mg, 150 μmol, 2.0 eq.) was dispensed to each vial. 750 μl (75 μmol, 1.0 eq.) of 2-bromo-N-isopropyl-5-((2-(trimethylsilyl)eth-oxy)methyl)-5H-pyrrolo[2,3-b]pyrazine-7-carboxamide solution was added to each vial, followed by Pd$_2$(dba)$_3$ (6.9 mg, 7.5 μmol, 0.1 eq.) and then dppf (2.5 mg, 10 μmol, 0.13 eq.) under N$_2$ atmosphere. Vials were capped and shaken at 100° C. for 16 hrs. After reactions were deemed complete by LC-MS, solvents were evaporated under reduced pressure. The crude product was washed with H$_2$O (1 mL) and exact with EtOAc (1 mL×3). The organic layer was collected and concentrated to obtain the intermediates of step 1.

(b) Precursor 329 (H). A 0.1 M solution of 2-bromo-5-((2-(trimethylsilyl)ethoxy)methyl)-5H-pyrrolo[2,3-b]pyrazine (329) was prepared in dioxane. Amine partners (150 μmol, 2.0 eq.) were dispensed to 8 ml reaction vials. t-BuONa (14.4 mg, 150 μmol, 2.0 eq.) was added to each vial, followed by 750 μl (75 μmol, 1.0 eq.) of 2-bromo-5-((2-(trimethylsilyl)ethoxy)methyl)-5H-pyrrolo[2,3-b]pyrazine solution, Pd$_2$(dba)$_3$ (6.9 mg, 7.5 μmol, 0.1 eq.) and Ruphos (4.2 mg, 9 μmol, 0.12 eq.) under N$_2$ atmosphere. Vials were capped and shaken at 110° C. for 16 hrs. After reactions were deemed complete by LC-MS, solvents were evaporated under reduced pressure. The crude product was washed with H$_2$O (1 mL) and exact with EtOAc (1 mL×3). The organic layer was collected and concentrated to obtain the intermediates of step 1.

Step 2: De-protection (De-Boc & De-SEM). One mL of TFA/DCM (v/v=1/7) was dispensed to vials containing intermediates of step 1. Vials were capped and shaken at 30° C. for 4 hrs. Solvents were evaporated under reduced pressure. One and two tenths mL of NH$_3$.H$_2$O/MeOH (v/v=1/3) were added to each vial. Vials were capped and shaken at 30° C. for 2 hrs. After reactions were deemed complete by LC-MS, solvents were evaporated under reduced pressure to obtain the intermediate of Step 2.

Step 3: Acylation. Five hundred μl of anhydrous DMF were dispensed to vials containing the intermediate of Step 2. DIEA (29 mg, 225 μmol, 3.0 eq.) was added to each vial, followed by acryloyl chloride (8.1 mg, 90 μmol, 1.2 eq.) at temperatures under 0° C. Vials were kept at 0° C. for 15 mins, and then shaken at 30° C. for 2 hrs. After reactions were deemed complete by LC-MS, solvents were evaporated under reduced pressure, and the residue was purified by prep. HPLC to give final product.

| Example | MW | MW (obs) | Name |
|---|---|---|---|
| 167 | 257.3 | 258 | N-[1-(5H-pyrrolo[2,3-b]pyrazin-2-yl)pyrrolidin-3-yl]prop-2-enamide |
| 168 | 356.43 | 257 | 2-[(1-acryloylpiperidin-4-yl)amino]-N-(propan-2-yl)-5H-pyrrolo[2,3-b]pyrazine-7-carboxamide |
| 169 | 370.46 | 371 | 2-{4-[acryloyl(methyl)amino]piperidin-1-yl}-N-(propan-2-yl)-5H-pyrrolo[2,3-b]pyrazine-7-carboxamide |
| 170 | 368.44 | 369 | 2-[(3aR,6aR)-1-acryloylhexahydropyrrolo[3,4-b]pyrrol-5(1H)-yl]-N-(propan-2-yl)-5H-pyrrolo[2,3-b]pyrazine-7-carboxamide |
| 171 | 342.4 | 343 | 2-{[(3S)-1-acryloylpyrrolidin-3-yl]amino}-N-(propan-2-yl)-5H-pyrrolo[2,3-b]pyrazine-7-carboxamide |
| 172 | 257.3 | 258 | 1-[4-(5H-pyrrolo[2,3-b]pyrazin-2-yl)piperazin-1-yl]prop-2-en-1-one |
| 173 | 328.38 | 329 | 2-[3-(acryloylamino)azetidin-1-yl]-N-(propan-2-yl)-5H-pyrrolo[2,3-b]pyrazine-7-carboxamide |
| 174 | 342.4 | 343 | 2-(4-acryloylpiperazin-1-yl)-N-(propan-2-yl)-5H-pyrrolo[2,3-b]pyrazine-7-carboxamide |
| 175 | 269.31 | 270 | 1-[6-(5H-pyrrolo[2,3-b]pyrazin-2-yl)-2,6-diazaspiro[3.3]hept-2-yl]prop-2-en-1-one |
| 176 | 271.32 | 272 | 1-[4-(5H-pyrrolo[2,3-b]pyrazin-2-ylamino)piperidin-1-yl]prop-2-en-1-one |
| 177 | 356.43 | 357 | 2-({[(2S)-1-acryloylpyrrolidin-2-yl]methyl}amino)-N-(propan-2-yl)-5H-pyrrolo[2,3-b]pyrazine-7-carboxamide |
| 178 | 368.44 | 369 | 2-(5-acryloylhexahydropyrrolo[3,4-b]pyrrol-1(2H)-yl)-N-(propan-2-yl)-5H-pyrrolo[2,3-b]pyrazine-7-carboxamide |
| 179 | 358.4 | 359 | 2-[(1-acryloyl-4-hydroxypyrrolidin-3-yl)amino]-N-(propan-2-yl)-5H-pyrrolo[2,3-b]pyrazine-7-carboxamide |
| 180 | 356.43 | 357 | 2-({[(2R)-1-acryloylpyrrolidin-2-yl]methyl}amino)-N-(propan-2-yl)-5H-pyrrolo[2,3-b]pyrazine-7-carboxamide |
| 181 | 342.4 | 343 | 2-[(3R)-3-(acryloylamino)pyrrolidin-1-yl]-N-(propan-2-yl)-5H-pyrrolo[2,3-b]pyrazine-7-carboxamide |
| 182 | 370.46 | 371 | 2-{[cis-4-(acryloylamino)cyclohexyl]amino}-N-(propan-2-yl)-5H-pyrrolo[2,3-b]pyrazine-7-carboxamide |
| 183 | 368.44 | 369 | 2-{(1R,5S)-1-[(acryloylamino)methyl]-3-azabicyclo[3.1.0]hex-3-yl}-N-(propan-2-yl)-5H-pyrrolo[2,3-b]pyrazine-7-carboxamide |
| 184 | 342.4 | 343 | 2-{[cis-3-(acryloylamino)cyclobutyl]amino}-N-(propan-2-yl)-5H-pyrrolo[2,3-b]pyrazine-7-carboxamide |
| 185 | 356.43 | 357 | 2-(4-acryloyl-1,4-diazepan-1-yl)-N-(propan-2-yl)-5H-pyrrolo[2,3-b]pyrazine-7-carboxamide |
| 186 | 257.3 | 258 | N-[(3S)-1-(5H-pyrrolo[2,3-b]pyrazin-2-yl)pyrrolidin-3-yl]prop-2-enamide |
| 187 | 342.4 | 343 | 2-{3-[acryloyl(methyl)amino]azetidin-1-yl}-N-(propan-2-yl)-5H-pyrrolo[2,3-b]pyrazine-7-carboxamide |
| 188 | 328.38 | 329 | 2-[(1-acryloylazetidin-3-yl)amino]-N-(propan-2-yl)-5H-pyrrolo[2,3-b]pyrazine-7-carboxamide |
| 189 | 354.41 | 355 | 2-{[(1R,5S,6s)-3-acryloyl-3-azabicyclo[3.1.0]hex-6-yl]amino}-N-(propan-2-yl)-5H-pyrrolo[2,3-b]pyrazine-7-carboxamide |
| 190 | 356.43 | 357 | 2-{(3R)-3-[acryloyl(methyl)amino]pyrrolidin-1-yl}-N-(propan-2-yl)-5H-pyrrolo[2,3-b]pyrazine-7-carboxamide |
| 191 | 356.43 | 357 | 2-({[(3S)-1-acryloylpyrrolidin-3-yl]methyl}amino)-N-(propan-2-yl)-5H-pyrrolo[2,3-b]pyrazine-7-carboxamide |
| 192 | 243.27 | 244 | N-[1-(5H-pyrrolo[2,3-b]pyrazin-2-yl)azetidin-3-yl]prop-2-enamide |
| 193 | 370.46 | 371 | 2-{[(1-acryloylpiperidin-4-yl)methyl]amino}-N-(propan-2-yl)-5H-pyrrolo[2,3-b]pyrazine-7-carboxamide |
| 194 | 342.4 | 343 | 2-[(3S)-3-(acryloylamino)pyrrolidin-1-yl]-N-(propan-2-yl)-5H-pyrrolo[2,3-b]pyrazine-7-carboxamide |
| 195 | 342.4 | 343 | 2-[3-(acryloylamino)pyrrolidin-1-yl]-N-(propan-2-yl)-5H-pyrrolo[2,3-b]pyrazine-7-carboxamide |
| 196 | 372.43 | 373 | 2-{[(3R,4R)-1-acryloyl-3-hydroxypiperidin-4-yl]amino}-N-(propan-2-yl)-5H-pyrrolo[2,3-b]pyrazine-7-carboxamide |

| Example | MW | MW (obs) | Name |
|---|---|---|---|
| 197 | 283.34 | 284 | N-{[(1R,5S)-3-(5H-pyrrolo[2,3-b]pyrazin-2-yl)-3-azabicyclo[3.1.0]hex-1-yl]methyl}prop-2-enamide |
| 198 | 342.4 | 343 | 2-{[trans-3-(acryloylamino)cyclobutyl]amino}-N-(propan-2-yl)-5H-pyrrolo[2,3-b]pyrazine-7-carboxamide |

Examples 199-212 were prepared as described in the Scheme below.

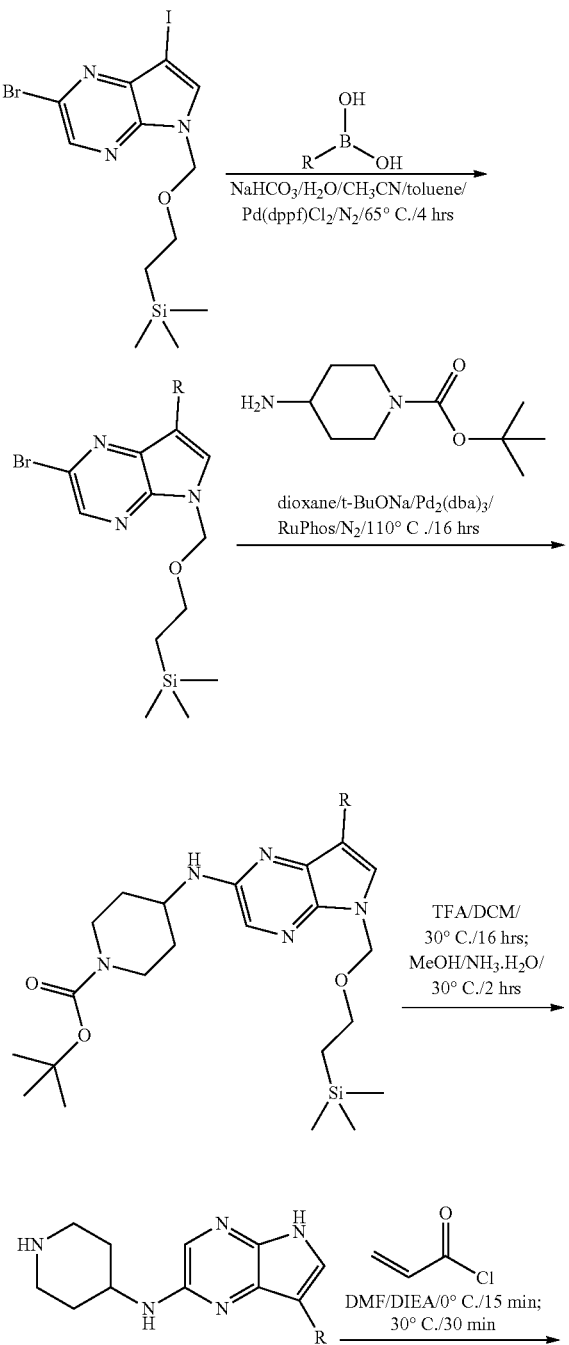

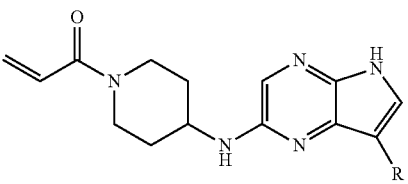

Step 1: Suzuki Coupling. Boronic acids/boronates (200 µmol, 2.0 eq.) were dispensed to 8 mL reaction vials, followed by 600 µl (100 µmol, 1.0 eq.) of 2-bromo-7-iodo-5-((2-(trimethylsilyl)ethoxy)methyl)-5H-pyrrolo[2,3-b]pyrazine solution (0.167 M) in $CH_3CN$, 200 µl of toluene, 400 µl (400 µmol, 4.0 eq.) of $NaHCO_3$ solution (1.0 M in $H_2O$), and then $Pd(dppf)Cl_2$ (7.3 mg, 10 µmol, 0.1 eq.) under $N_2$ atmosphere. Vials were capped and shaken at 65° C. for 4 hrs. After reactions were deemed complete by LC-MS, solvents were evaporated under reduced pressure, and the residue was washed with $H_2O$ (1 mL) and extracted with EtOAc (1 mL×3). Organic layers were concentrated under reduced pressure to obtain intermediates of step 1.

Step 2: N-Displacement. A solution of t-BuONa (19.2 mg, 200 µmol, 2.0 eq.) to the vials containing intermediates from step 1, followed by 800 µl (200 µmol, 2.0 eq.) of tert-butyl 4-aminopiperidine-1-carboxylate solution (0.25 M in dioxane), $Pd_2(dba)_3$ (9.2 mg, 10 µmol, 0.1 eq.), and RuPhos (5.6 mg, 12 µmol, 0.12 eq.) under $N_2$ atmosphere. Vials were capped and shaken at 110° C. for 16 hrs. After reactions were deemed complete by LC-MS, solvents were evaporated under reduced pressure, and the residue was washed with $H_2O$ (1 mL) and extracted with EtOAc (1 mL×3). Organic layers were concentrated under reduced pressure to obtain intermediates of step 2.

Step 3 & 4: De-protection (De-Boc & De-SEM). One mL of TFA/DCM (1:7, v/v) was dispensed to vials containing step 2 intermediates. Vials were capped and shaken at 30° C. for 16 hrs. Solvents were evaporated under reduced pressure. One and two tenths mL of $NH_3 \cdot H_2O$/MeOH (1:3, v/v) solution were added to each vial. Vials were capped and shaken at 30° C. for 2 hrs. After reactions were deemed complete by LC-MS, solvents were evaporated under reduced pressure to afford the intermediates of step 3/4.

Step 5: Acylation. Eight hundred (800) µl of DMF were dispensed to vials containing intermediates of Steps 3 and 4, followed by DIEA (38.7 mg, 300 µmol, 3.0 eq.) and acryloyl chloride (18 mg, 200 µmol, 2.0 eq.) at 0° C. Vials were kept at 0° C. for 15 min, and then shaken at 30° C. for 30 min. After reactions were deemed complete by LC-MS, solvents were evaporated under reduced pressure. The residue was purified by prep. HPLC to give final product.

| Ex | MW | MW (obs) | Name |
|---|---|---|---|
| 199 | 362.44 | 362 | 1-(4-{[7-(6-methylpyridin-3-yl)-5H-pyrrolo[2,3-b]pyrazin-2-yl]amino}piperidin-1-yl)prop-2-en-1-one |
| 200 | 366.4 | 366 | 1-(4-{[7-(3-fluoropyridin-4-yl)-5H-pyrrolo[2,3-b]pyrazin-2-yl]amino}piperidin-1-yl)prop-2-en-1-one |
| 201 | 362.44 | 362 | 1-(4-{[7-(2-methylpyridin-4-yl)-5H-pyrrolo[2,3-b]pyrazin-2-yl]amino}piperidin-1-yl)prop-2-en-1-one |
| 202 | 349.4 | 349 | 1-(4-{[7-(pyrimidin-5-yl)-5H-pyrrolo[2,3-b]pyrazin-2-yl]amino}piperidin-1-yl)prop-2-en-1-one |
| 203 | 425.51 | 426 | 1-[4-({7-[4-(methylsulfonyl)phenyl]-5H-pyrrolo[2,3-b]pyrazin-2-yl}amino)piperidin-1-yl]prop-2-en-1-one |
| 204 | 404.47 | 404 | 3-{2-[(1-acryloylpiperidin-4-yl)amino]-5H-pyrrolo[2,3-b]pyrazin-7-yl}-N-methylbenzamide |
| 205 | 362.44 | 348 | 1-(4-{[7-(pyridin-3-yl)-5H-pyrrolo[2,3-b]pyrazin-2-yl]amino}piperidin-1-yl)prop-2-en-1-one |
| 206 | 373.42 | 373 | 5-{2-[(1-acryloylpiperidin-4-yl)amino]-5H-pyrrolo[2,3-b]pyrazin-7-yl}pyridine-3-carbonitrile |
| 207 | 366.4 | 366 | 1-(4-{[7-(6-fluoropyridin-3-yl)-5H-pyrrolo[2,3-b]pyrazin-2-yl]amino}piperidin-1-yl)prop-2-en-1-one |
| 208 | 434.5 | 434 | 1-[4-({7-[2-(morpholin-4-yl)pyrimidin-5-yl]-5H-pyrrolo[2,3-b]pyrazin-2-yl}amino)piperidin-1-yl]prop-2-en-1-one |
| 209 | 347.42 | 347 | 1-{4-[(7-phenyl-5H-pyrrolo[2,3-b]pyrazin-2-yl)amino]piperidin-1-yl}prop-2-en-1-one |
| 210 | 379.42 | 379 | 1-(4-{[7-(2-methoxypyrimidin-5-yl)-5H-pyrrolo[2,3-b]pyrazin-2-yl]amino}piperidin-1-yl)prop-2-en-1-one |
| 211 | 366.4 | 366 | 1-(4-{[7-(2-fluoropyridin-4-yl)-5H-pyrrolo[2,3-b]pyrazin-2-yl]amino}piperidin-1-yl)prop-2-en-1-one |
| 212 | 366.4 | 366 | 1-(4-{[7-(5-fluoropyridin-3-yl)-5H-pyrrolo[2,3-b]pyrazin-2-yl]amino}piperidin-1-yl)prop-2-en-1-one |

Examples 213-229 were prepared as detailed in the Scheme below.

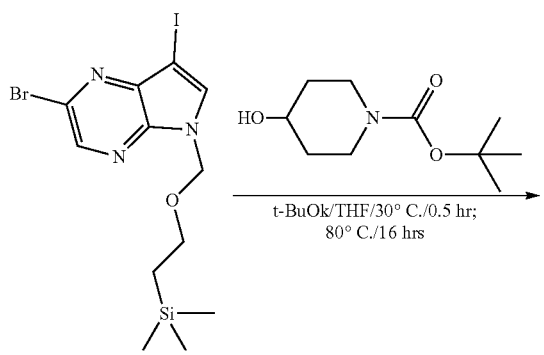

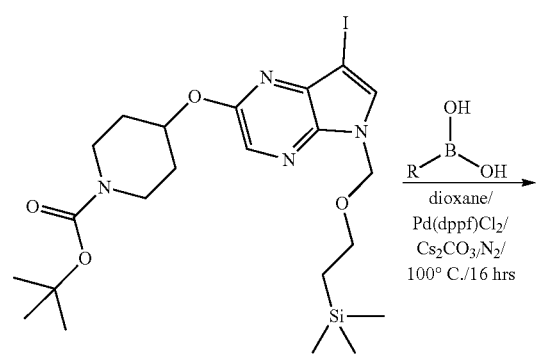

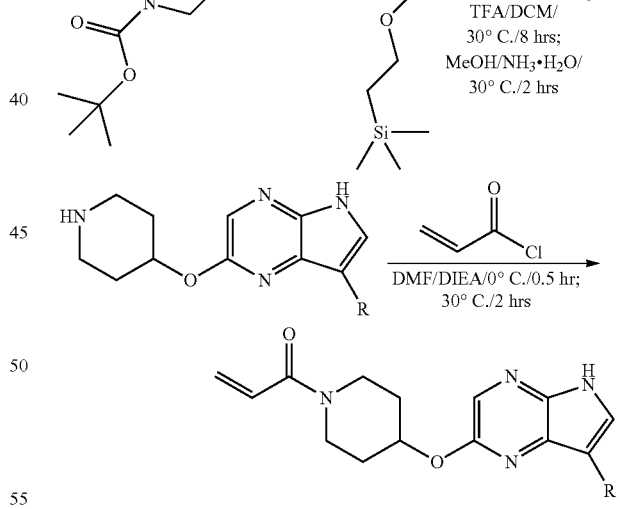

Step 1: O-Displacement. t-BuOK (33.6 mg, 300 μmol, 2.0 eq.) was dispensed to 8 mL reaction vials, followed by 600 μl (150 μmol, 1.0 eq.) of 2-bromo-7-iodo-5-((2-(trimethylsilyl)ethoxy)methyl)-5H-pyrrolo[2,3-b]pyrazine solution (0.25 M in THF), 600 μl (600 μmol, 4.0 eq.) of tert-butyl 4-hydroxy piperidine-1-solution (1.0 M in THF). Vials were capped and shaken at 30° C. for 0.5 hr and then shaken at 80° C. for 16 hrs. After reactions were deemed complete by LC-MS, solvents were evaporated under reduced pressure, and the residue was washed using H₂O (1 mL) and extracted using EtOAc (1 mL×3). The organic layer was concentrated under reduced pressure to obtain intermediates of step 1.

Step 2: Suzuki Coupling. The step 1 intermediates (0.15 M in dioxane) were dispensed to 8 mL reaction vials, followed by $Cs_2CO_3$ (97.7 mg, 300 μmol, 3.0 eq.), 1 mL (150 μmol, 1.0 eq.) of boronic acids/boronate solution, and $Pd(dppf)Cl_2$ (11 mg, 15 μmol, 0.1 eq.) under $N_2$ atmosphere. Vials were capped and shaken at 100° C. for 16 hrs. After reactions were deemed complete by LC-MS, solvents were evaporated under reduced pressure, and the residue was washed using $H_2O$ (1 mL) and extracted using EtOAc (1 mL×3). The organic layer was concentrated under reduced pressure to obtain intermediates of step 2.

Step 3 & 4: De-protection (De-Boc & De-SEM). One and one-half mL of TFA/DCM (1:4, v/v) solution was dispensed to vials containing intermediates of step 2. Vials were capped and shaken at 30° C. for 8 hrs. Solvents were evaporated under reduced pressure. Two mL of $NH_3 \cdot H_2O$/MeOH (1:3, v/v) solution were dispensed to each vial. Vials were capped and shaken at 30° C. for 2 hrs. After reactions were deemed complete by LC-MS, solvents were evaporated under reduced pressure. Solvents were evaporated to obtain intermediates of step 3.

Step 5: Acylation. 750 μl of DMF were dispensed to vials containing intermediates of step 3, followed by DIEA (58 mg, 450 μmol, 3.0 eq.) and acyloyl chloride (27 mg, 300 μmol, 2.0 eq.) at 0° C. Vials were kept at 0° C. for 0.5 hr, and then shaken at 30° C. for 2 hrs. After reactions were deemed complete by LC-MS, solvents were evaporated under reduced pressure. The residue was purified by prep. HPLC to give final product.

| Ex | MW | MW (obs) | Name |
|---|---|---|---|
| 213 | 367.38 | 367 | 1-(4-{[7-(5-fluoropyridin-3-yl)-5H-pyrrolo[2,3-b]pyrazin-2-yl]oxy}piperidin-1-yl)prop-2-en-1-one |
| 214 | 363.42 | 363 | 1-(4-{[7-(6-methylpyridin-3-yl)-5H-pyrrolo[2,3-b]pyrazin-2-yl]oxy}piperidin-1-yl)prop-2-en-1-one |
| 215 | 350.38 | 350 | 1-(4-{[7-(pyrimidin-5-yl)-5H-pyrrolo[2,3-b]pyrazin-2-yl]oxy}piperidin-1-yl)prop-2-en-1-one |
| 216 | 374.4 | 374 | 5-{2-[(1-acryloylpiperidin-4-yl)oxy]-5H-pyrrolo[2,3-b]pyrazin-7-yl}pyridine-2-carbonitrile |
| 217 | 367.38 | 367 | 1-(4-{[7-(2-fluoropyridin-3-yl)-5H-pyrrolo[2,3-b]pyrazin-2-yl]oxy}piperidin-1-yl)prop-2-en-1-one |
| 218 | 352.4 | 352 | 1-(4-{[7-(1-methyl-1H-pyrazol-4-yl)-5H-pyrrolo[2,3-b]pyrazin-2-yl]oxy}piperidin-1-yl)prop-2-en-1-one |
| 219 | 380.41 | 380 | 1-(4-{[7-(2-methoxypyrimidin-5-yl)-5H-pyrrolo[2,3-b]pyrazin-2-yl]oxy}piperidin-1-yl)prop-2-en-1-one |
| 220 | 363.42 | 363 | 1-(4-{[7-(2-methylpyridin-4-yl)-5H-pyrrolo[2,3-b]pyrazin-2-yl]oxy}piperidin-1-yl)prop-2-en-1-one |
| 221 | 380.45 | 380 | 1-(4-{[7-(1,3,5-trimethyl-1H-pyrazol-4-yl)-5H-pyrrolo[2,3-b]pyrazin-2-yl]oxy}piperidin-1-yl)prop-2-en-1-one |
| 222 | 367.38 | 367 | 1-(4-{[7-(2-fluoropyridin-4-yl)-5H-pyrrolo[2,3-b]pyrazin-2-yl]oxy}piperidin-1-yl)prop-2-en-1-one |
| 223 | 435.49 | 435 | 1-[4-({7-[2-(morpholin-4-yl)pyrimidin-5-yl]-5H-pyrrolo[2,3-b]pyrazin-2-yl}oxy)piperidin-1-yl]prop-2-en-1-one |
| 224 | 367.41 | 367 | 1-(4-{[7-(3,5-dimethyl-1,2-oxazol-4-yl)-5H-pyrrolo[2,3-b]pyrazin-2-yl]oxy}piperidin-1-yl)prop-2-en-1-one |
| 225 | 374.4 | 374 | 5-{2-[(1-acryloylpiperidin-4-yl)oxy]-5H-pyrrolo[2,3-b]pyrazin-7-yl}pyridine-3-carbonitrile |
| 226 | 367.38 | 367 | 1-(4-{[7-(6-fluoropyridin-3-yl)-5H-pyrrolo[2,3-b]pyrazin-2-yl]oxy}piperidin-1-yl)prop-2-en-1-one |
| 227 | 405.46 | 405 | 3-{2-[(1-acryloylpiperidin-4-yl)oxy]-5H-pyrrolo[2,3-b]pyrazin-7-yl}-N-methylbenzamide |
| 228 | 367.38 | 367 | 1-(4-{[7-(3-fluoropyridin-4-yl)-5H-pyrrolo[2,3-b]pyrazin-2-yl]oxy}piperidin-1-yl)prop-2-en-1-one |
| 229 | 426.5 | 426 | 1-[4-({7-[4-(methylsulfonyl)phenyl]-5H-pyrrolo[2,3-b]pyrazin-2-yl}oxy)piperidin-1-yl]prop-2-en-1-one |

Examples 230-291 were prepared as detailed in the Scheme below.

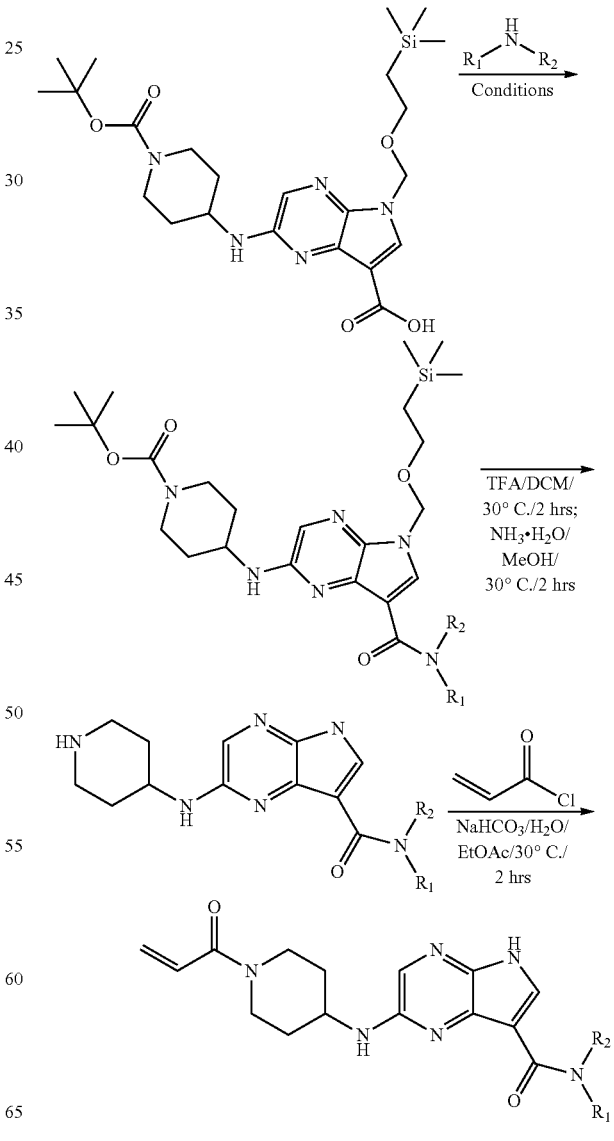

For general primary amines (Group 1), step 1 conditions are DMF/DIEA/HBTU/30° C./16 hrs.

For primary amines with an cyano group (Group 2, step 1 conditions are DMF/DIEA/HATU/60° C./16 hrs.

Step 1: Amide formation.

Group 1: Amines (150 µmol, 1.5 eq.) were placed in 8 mL reaction vials, followed by 300 µl of DMF, 500 µl of 2-((1-(tert-butoxycarbonyl)piperidin-4-yl)amino)-5-((2-(trimethylsilyl) ethoxy)methyl)-5H-pyrrolo[2,3-b]pyrazine-7-carboxylic acid (0.2 M in DMF; 100 µmol, 1.0 eq.), DIEA (70 µl, 400 µmol, 4.0 eq.), and HBTU (170 µmol, 1.7 eq.) to each vial. Vials were capped and shaken at 30° C. for 16 hrs. After reactions were deemed complete by LC-MS, solvents were evaporated under reduced pressure. One mL of saturated NaHCO$_3$ solution to each vial. The resulting mixture was extracted with EtOAc (2 mL×3). Organic layers were combined and dried with anhydrous Na$_2$SO$_4$. Filtration and evaporation under reduced pressure afforded crude intermediates which were used directly in the next step.

Group 2: Amines (150 µmol, 1.5 eq.) were placed in 8 mL reaction vials, followed by 500 µl of 2-((1-(tert-butoxycarbonyl)piperidin-4-yl)amino)-5-((2-(trimethylsilyl)ethoxy) methyl)-5H-pyrrolo[2,3-b]pyrazine-7-carboxylic acid (0.2 M in DMF; 100 µmol, 1.0 eq.), DIEA (70 µl, 400 µmol, 4.0 eq.) and 300 µl of HATU solution (0.67 M in DMF; 200 µmol, 2.0 eq.). Vials were capped and shaken at 30° C. for 16 hrs. After reactions were deemed complete by LC-MS, solvents were evaporated under reduced pressure. One mL of saturated NaHCO$_3$ solution to each vial. The resulting mixture was extracted with EtOAc (2 mL×3). Organic layers were combined and dried with anhydrous Na$_2$SO$_4$. Filtration and evaporation under reduced pressure afforded crude intermediates which were used directly in the next step.

Step 2 & 3: De-Boc & De-SEM. One and one-half mL of TFA/DCM (1:4, v/v) were dispensed to vials containing intermediates of step 1. Vials were capped and shaken at 30° C. for 2 hrs. Solvents were evaporated under reduced pressure. One and two-tenths mL of NH$_3$.H$_2$O/MeOH (1:2, v/v) were then dispensed to each vial. Vials were capped and shaken at 30° C. for 2 hrs. After reactions were deemed complete by LC-MS, solvents were evaporated under reduced pressure to obtain intermediates of step 2/3, which were used directly for next step.

Step 4: Acylation: One mL of saturated NaHCO$_3$ solution was dispensed to the vials containing intermediates of step 2/3, followed by 1 mL of EtOAc and acryloyl chloride (200 µmol, 2.0 eq.) to each vial. Vials were capped and shaken at 30° C. for 2 hrs. After reactions were deemed complete by LC-MS, solvents were evaporated under reduced pressure to obtain residues which were purified by prep. HPLC to give final product.

| Ex | MW | MW (obs) | Name |
|---|---|---|---|
| 230 | 356.43 | 357 | 2-[(1-acryloylpiperidin-4-yl)amino]-N-(propan-2-yl)-5H-pyrrolo[2,3-b]pyrazine-7-carboxamide |
| 231 | 398.47 | 399 | 2-[(1-acryloylpiperidin-4-yl)amino]-N-[(1-hydroxycyclobutyl)methyl]-5H-pyrrolo[2,3-b]pyrazine-7-carboxamide |
| 232 | 412.49 | 413 | 2-[(1-acryloylpiperidin-4-yl)amino]-N-[(1-hydroxycyclopentyl)methyl]-5H-pyrrolo[2,3-b]pyrazine-7-carboxamide |
| 233 | 422.41 | 423 | 2-[(1-acryloylpiperidin-4-yl)amino]-N-[(1R,2R)-2-(trifluoromethyl)cyclopropyl]-5H-pyrrolo[2,3-b]pyrazine-7-carboxamide |
| 234 | 418.45 | 419 | 2-[(1-acryloylpiperidin-4-yl)amino]-N-(2,2-difluorocyclopentyl)-5H-pyrrolo[2,3-b]pyrazine-7-carboxamide |
| 235 | 426.52 | 428 | 2-[(1-acryloylpiperidin-4-yl)amino]-N-[(1-hydroxy-3-methylcyclopentyl)methyl]-5H-pyrrolo[2,3-b]pyrazine-7-carboxamide |
| 236 | 432.48 | 433 | 2-[(1-acryloylpiperidin-4-yl)amino]-N-(3,3-difluorocyclohexyl)-5H-pyrrolo[2,3-b]pyrazine-7-carboxamide |
| 237 | 400.46 | 401 | 2-[(1-acryloylpiperidin-4-yl)amino]-N-[(1R,2R)-2-fluorocyclopentyl]-5H-pyrrolo[2,3-b]pyrazine-7-carboxamide |
| 238 | 418.45 | 419 | 2-[(1-acryloylpiperidin-4-yl)amino]-N-[(3,3-difluorocyclobutyl)methyl]-5H-pyrrolo[2,3-b]pyrazine-7-carboxamide |
| 239 | 426.52 | 428 | 2-[(1-acryloylpiperidin-4-yl)amino]-N-{[(3R)-1-hydroxy-3-methylcyclopentyl]methyl}-5H-pyrrolo[2,3-b]pyrazine-7-carboxamide |
| 240 | 424.43 | 425 | 2-[(1-acryloylpiperidin-4-yl)amino]-N-(4,4,4-trifluorobutyl)-5H-pyrrolo[2,3-b]pyrazine-7-carboxamide |
| 241 | 438.45 | 439 | 2-[(1-acryloylpiperidin-4-yl)amino]-N-[(2R)-4,4,4-trifluoro-2-methylbutyl]-5H-pyrrolo[2,3-b]pyrazine-7-carboxamide |
| 242 | 381.44 | 382 | 2-[(1-acryloylpiperidin-4-yl)amino]-N-(3-cyanopropyl)-5H-pyrrolo[2,3-b]pyrazine-7-carboxamide |
| 243 | 386.43 | 387 | 2-[(1-acryloylpiperidin-4-yl)amino]-N-(3-fluorocyclobutyl)-5H-pyrrolo[2,3-b]pyrazine-7-carboxamide |
| 244 | 400.46 | 401 | 2-[(1-acryloylpiperidin-4-yl)amino]-N-[(1S,3R)-3-fluorocyclopentyl]-5H-pyrrolo[2,3-b]pyrazine-7-carboxamide |
| 245 | 404.42 | 405 | 2-[(1-acryloylpiperidin-4-yl)amino]-N-(3,3-difluorocyclobutyl)-5H-pyrrolo[2,3-b]pyrazine-7-carboxamide |

-continued

| Ex | MW | MW (obs) | Name |
|---|---|---|---|
| 246 | 410.4 | 411 | 2-[(1-acryloylpiperidin-4-yl)amino]-N-(3,3,3-trifluoropropyl)-5H-pyrrolo[2,3-b]pyrazine-7-carboxamide |
| 247 | 400.46 | 401 | 2-[(1-acryloylpiperidin-4-yl)amino]-N-[(1S,3S)-3-fluorocyclopentyl]-5H-pyrrolo[2,3-b]pyrazine-7-carboxamide |
| 248 | 468.48 | 469 | 2-[(1-acryloylpiperidin-4-yl)amino]-N-[(2R,3R)-1,1,1-trifluoro-2-hydroxy-4-methylpentan-3-yl]-5H-pyrrolo[2,3-b]pyrazine-7-carboxamide |
| 249 | 462.5 | 463 | 2-[(1-acryloylpiperidin-4-yl)amino]-N-[(3,3-difluoro-1-hydroxycyclohexyl)methyl]-5H-pyrrolo[2,3-b]pyrazine-7-carboxamide |
| 250 | 444.51 | 446 | 2-[(1-acryloylpiperidin-4-yl)amino]-N-{[(2R)-2-fluoro-1-hydroxycyclohexyl]methyl}-5H-pyrrolo[2,3-b]pyrazine-7-carboxamide |
| 251 | 400.46 | 401 | 2-[(1-acryloylpiperidin-4-yl)amino]-N-[(1R,2S)-2-fluorocyclopentyl]-5H-pyrrolo[2,3-b]pyrazine-7-carboxamide |
| 252 | 468.48 | 469 | 2-[(1-acryloylpiperidin-4-yl)amino]-N-[(2S,3S)-1,1,1-trifluoro-2-hydroxy-4-methylpentan-3-yl]-5H-pyrrolo[2,3-b]pyrazine-7-carboxamide |
| 251b | 426.52 | 428 | 2-[(1-acryloylpiperidin-4-yl)amino]-N-[1-(1-hydroxycyclobutyl)propyl]-5H-pyrrolo[2,3-b]pyrazine-7-carboxamide |
| 252b | 462.5 | 463 | 2-[(1-acryloylpiperidin-4-yl)amino]-N-[(4,4-difluoro-1-hydroxycyclohexyl)methyl]-5H-pyrrolo[2,3-b]pyrazine-7-carboxamide |
| 253 | 438.45 | 439 | 2-[(1-acryloylpiperidin-4-yl)amino]-N-(4,4,4-trifluoro-2-methylbutyl)-5H-pyrrolo[2,3-b]pyrazine-7-carboxamide |
| 254 | 444.51 | 446 | 2-[(1-acryloylpiperidin-4-yl)amino]-N-{[(2S)-2-fluoro-1-hydroxycyclohexyl]methyl}-5H-pyrrolo[2,3-b]pyrazine-7-carboxamide |
| 255 | 400.46 | 401 | 2-[(1-acryloylpiperidin-4-yl)amino]-N-[(1R,3S)-3-fluorocyclopentyl]-5H-pyrrolo[2,3-b]pyrazine-7-carboxamide |
| 256 | 432.48 | 433 | 2-[(1-acryloylpiperidin-4-yl)amino]-N-(2,2-difluorocyclohexyl)-5H-pyrrolo[2,3-b]pyrazine-7-carboxamide |
| 257 | 506.61 | 508 | 2-[(1-acryloylpiperidin-4-yl)amino]-N-{(2S)-1-[(2S)-2-cyanopyrrolidin-1-yl]-3,3-dimethyl-1-oxobutan-2-yl}-5H-pyrrolo[2,3-b]pyrazine-7-carboxamide |
| 258 | 492.58 | 494 | 2-[(1-acryloylpiperidin-4-yl)amino]-N-{(2S)-1-[(2S)-2-cyanopyrrolidin-1-yl]-3-methyl-1-oxobutan-2-yl}-5H-pyrrolo[2,3-b]pyrazine-7-carboxamide |
| 259 | 418.45 | 419 | 2-[(1-acryloylpiperidin-4-yl)amino]-N-(3,3-difluorocyclopentyl)-5H-pyrrolo[2,3-b]pyrazine-7-carboxamide |
| 260 | 451.58 | 453 | 2-[(1-acryloylpiperidin-4-yl)amino]-N-(8-cyanooctyl)-5H-pyrrolo[2,3-b]pyrazine-7-carboxamide |
| 261 | 367.41 | 368 | 2-[(1-acryloylpiperidin-4-yl)amino]-N-(2-cyanoethyl)-5H-pyrrolo[2,3-b]pyrazine-7-carboxamide |
| 262 | 435.53 | 437 | 2-[(1-acryloylpiperidin-4-yl)amino]-N-[(1S,3S)-3-(cyanomethyl)cyclohexyl]-5H-pyrrolo[2,3-b]pyrazine-7-carboxamide |
| 263 | 395.47 | 396 | 2-[(1-acryloylpiperidin-4-yl)amino]-N-[(2R)-1-cyanobutan-2-yl]-5H-pyrrolo[2,3-b]pyrazine-7-carboxamide |
| 264 | 438.49 | 439 | 2-[(1-acryloylpiperidin-4-yl)amino]-N-{(2S)-1-[(2-cyanoethyl)aminop]-oxopropan-2-yl}-5H-pyrrolo[2,3-b]pyrazine-7-carboxamide |

Examples 265-289 were prepared according to the scheme and procedure for Examples 230-291. (Group 1 amines)

| Ex | Mw | Mwobs | Name |
|---|---|---|---|
| 265 | 356.43 | 357 | 2-[(1-acryloylpiperidin-4-yl)amino]-N-(propan-2-yl)-5H-pyrrolo[2,3-b]pyrazine-7-carboxamide |
| 266 | 370.46 | 371 | 2-[(1-acryloylpiperidin-4-yl)amino]-N-tert-butyl-5H-pyrrolo[2,3-b]pyrazine-7-carboxamide |
| 267 | 384.48 | 385 | 2-[(1-acryloylpiperidin-4-yl)amino]-N-[(2S)-pentan-2-yl]-5H-pyrrolo[2,3-b]pyrazine-7-carboxamide |
| 268 | 386.46 | 387 | 2-[(1-acryloylpiperidin-4-yl)amino]-N-[(2R)-1-methoxypropan-2-yl]-5H-pyrrolo[2,3-b]pyrazine-7-carboxamide |
| 269 | 370.46 | 371 | 2-[(1-acryloylpiperidin-4-yl)amino]-N-butyl-5H-pyrrolo[2,3-b]pyrazine-7-carboxamide |

| Ex | Mw | Mwobs | Name |
|---|---|---|---|
| 270 | 396.5 | 397 | 2-[(1-acryloylpiperidin-4-yl)amino]-N-(cyclopentylmethyl)-5H-pyrrolo[2,3-b]pyrazine-7-carboxamide |
| 271 | 384.48 | 385 | 2-[(1-acryloylpiperidin-4-yl)amino]-N-(2,2-dimethylpropyl)-5H-pyrrolo[2,3-b]pyrazine-7-carboxamide |
| 272 | 370.46 | 371 | 2-[(1-acryloylpiperidin-4-yl)amino]-N-(2-methylpropyl)-5H-pyrrolo[2,3-b]pyrazine-7-carboxamide |
| 273 | 396.37 | 397 | 2-[(1-acryloylpiperidin-4-yl)amino]-N-(2,2,2-trifluoroethyl)-5H-pyrrolo[2,3-b]pyrazine-7-carboxamide |
| 274 | 384.48 | 385 | 2-[(1-acryloylpiperidin-4-yl)amino]-N-[(2R)-pentan-2-yl]-5H-pyrrolo[2,3-b]pyrazine-7-carboxamide |
| 275 | 372.43 | 373 | 2-[(1-acryloylpiperidin-4-yl)amino]-N-(2-methoxyethyl)-5H-pyrrolo[2,3-b]pyrazine-7-carboxamide |
| 276 | 384.48 | 385 | 2-[(1-acryloylpiperidin-4-yl)amino]-N-(2-methylbutan-2-yl)-5H-pyrrolo[2,3-b]pyrazine-7-carboxamide |
| 277 | 386.46 | 387 | 2-[(1-acryloylpiperidin-4-yl)amino]-N-[(2S)-1-methoxypropan-2-yl]-5H-pyrrolo[2,3-b]pyrazine-7-carboxamide |
| 278 | 396.5 | 397 | 2-[(1-acryloylpiperidin-4-yl)amino]-N-cyclohexyl-5H-pyrrolo[2,3-b]pyrazine-7-carboxamide |
| 279 | 370.46 | 371 | 2-[(1-acryloylpiperidin-4-yl)amino]-N-methyl-N-(propan-2-yl)-5H-pyrrolo[2,3-b]pyrazine-7-carboxamide |
| 280 | 368.44 | 369 | 2-[(1-acryloylpiperidin-4-yl)amino]-N-cyclobutyl-5H-pyrrolo[2,3-b]pyrazine-7-carboxamide |
| 281 | 380.45 | 381 | 2-[(1-acryloylpiperidin-4-yl)amino]-N-(bicyclo[1.1.1]pent-1-yl)-5H-pyrrolo[2,3-b]pyrazine-7-carboxamide |
| 282 | 392.41 | 393 | 2-[(1-acryloylpiperidin-4-yl)amino]-N-(2,2-difluoropropyl)-5H-pyrrolo[2,3-b]pyrazine-7-carboxamide |
| 283 | 382.47 | 383 | 2-[(1-acryloylpiperidin-4-yl)amino]-N-cyclopentyl-5H-pyrrolo[2,3-b]pyrazine-7-carboxamide |
| 284 | 354.41 | 355 | 1-(4-{[7-(azetidin-1-ylcarbonyl)-5H-pyrrolo[2,3-b]pyrazin-2-yl]amino}piperidin-1-yl)prop-2-en-1-one |
| 285 | 370.46 | 371 | 2-[(1-acryloylpiperidin-4-yl)amino]-N-[(2S)-butan-2-yl]-5H-pyrrolo[2,3-b]pyrazine-7-carboxamide |
| 286 | 368.44 | 369 | 2-[(1-acryloylpiperidin-4-yl)amino]-N-cyclopropyl-N-methyl-5H-pyrrolo[2,3-b]pyrazine-7-carboxamide |
| 287 | 368.44 | 369 | 1-(4-{[7-(pyrrolidin-1-ylcarbonyl)-5H-pyrrolo[2,3-b]pyrazin-2-yl]amino}piperidin-1-yl)prop-2-en-1-one |
| 288 | 382.47 | 383 | 2-[(1-acryloylpiperidin-4-yl)amino]-N-(1-cyclopropylethyl)-5H-pyrrolo[2,3-b]pyrazine-7-carboxamide |
| 289 | 370.46 | 371 | 2-[(1-acryloylpiperidin-4-yl)amino]-N-[(2R)-butan-2-yl]-5H-pyrrolo[2,3-b]pyrazine-7-carboxamide |

Examples 290-328 were prepared as detailed in the Scheme below.

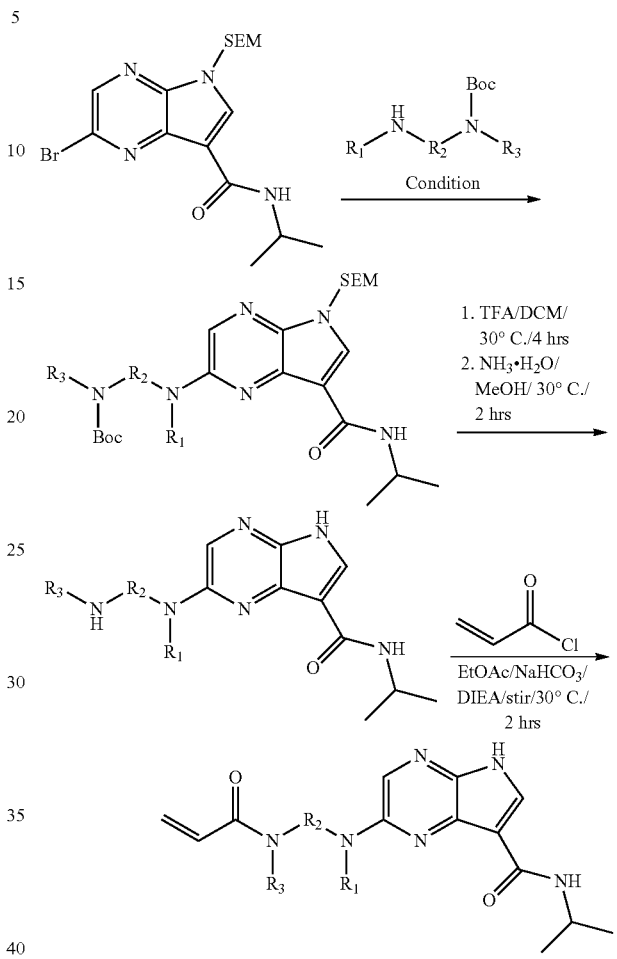

Group 1: For general amines, conditions for Step 1 are dioxane/Pd$_2$(dba)$_3$/Xphos/Cs$_2$CO$_3$/N$_2$/120° C./16 hrs. Group 2: For secondary amines with a sterically demanding group conditions for Step 1 are toluene/Pd$_2$(dba)$_3$/Ruphos/t-BuONa/N$_2$/65° C./2 days.

Step 1: N-displacement. Group 1: Amines (195 μmol, 1.5 eq.) were placed in 8 ml reaction vials. One thousand μl of 2-bromo-N-isopropyl-5-((2-(trimethylsilyl)ethoxy)methyl)-5H-pyrrolo[2,3-b]pyrazine-7-carboxamide (0.13 M in dioxane; 130 μmol, 1.0 eq.) solution was dispensed to each vial, followed by Cs$_2$CO$_3$ (81.9 mg, 260 μmol, 2.0 eq.), Pd$_2$(dba)$_3$ (11.9 mg, 13 μmol, 0.1 eq.) and Xphos (6.2 mg, 13 μmol, 0.1 eq.) under N$_2$. Vials were capped and shaken at 120° C. for 16 hrs.

After reactions were deemed complete by LC-MS, solvents were evaporated under reduced pressure to obtain residues. The crude product was washed with H$_2$O (1 mL) and extracted with EtOAc (1 mL×3). The organic layers were combined and dried over Na$_2$SO$_4$. The filtrate was concentrated to give crude intermediates from step 1, which were used directly for the next step.

Group 2: Amines (195 μmol, 1.5 eq.) were placed in 8 ml reaction vials. One thousand μl of 2-bromo-N-isopropyl-5-((2-(trimethylsilyl)ethoxy)methyl)-5H-pyrrolo[2,3-b]pyrazine-7-carboxamide (0.1 M in toluene; 130 μmol, 1.0 eq.)

solution to each vial, followed by t-BuONa (24.9 mg, 260 µmol, 2.0 eq.) and Pd$_2$(dba)$_3$ (11.9 mg, 13 µmol, 0.1 eq.) and Ruphos (6.0 mg, 13 µmol, 0.1 eq.) under N$_2$. Vials were capped and shaken at 65° C. for 2 days. After reactions were deemed complete by LC-MS, solvents were evaporated under reduced pressure to obtain residues. The crude product was washed with H$_2$O (1 mL) and extracted with EtOAc (1 mL×3). The organic layers were combined and dried over Na$_2$SO$_4$. The filtrate was concentrated to give crude intermediates from step 1, which were used directly for the next step.

Step 2&3: De-protection (De-Boc & De-SEM). One mL of TFA/DCM (1:7, v/v) solution was dispensed to vials containing intermediates of step 1. Vials were capped and shaken at 30° C. for 4 hrs. Solvents were evaporated under reduced pressure. One and two-tenths mL of NH$_3$.H$_2$O/MeOH (1:3, v/v) solution were dispensed to each vial. Vials were capped and shaken at 30° C. for 2 hrs. After reactions were deemed complete by LC-MS, solvents were evaporated under reduced pressure to obtain the intermediates of step 2.

Step 4: Acylation. Five hundred (500) µl of EtOAc were dispensed to each vial containing intermediates of Step 2 (130 µmol, 1.0 eq.), followed by 500 µl of saturated NaHCO$_3$ solution, acryloyl chloride (195 µmol, 1.5 eq.), and DIEA (390 µmol, 3.0 eq.). Vials were capped and stirred at 30° C. for 2 hrs. After reactions were deemed complete by LC-MS, solvents were evaporated under reduced pressure to obtain residues which were purified by prep. HPLC to obtain final products.

| Ex | MW | MW (obs) | Name |
|---|---|---|---|
| 290 | 342.4 | 343 | 2-(4-acryloylpiperazin-1-yl)-N-(propan-2-yl)-5H-pyrrolo[2,3-b]pyrazine-7-carboxamide |
| 291 | 374.42 | 375 | 2-{[(3R,4R)-1-acryloyl-3-fluoropiperidin-4-yl]amino}-N-(propan-2-yl)-5H-pyrrolo[2,3-b]pyrazine-7-carboxamide |
| 292 | 368.44 | 369 | 2-[(1R,4R)-5-acryloyl-2,5-diazabicyclo[2.2.2]oct-2-yl]-N-(propan-2-yl)-5H-pyrrolo[2,3-b]pyrazine-7-carboxamide |
| 293 | 370.46 | 371 | 2-(4-acryloyl-3,3-dimethylpiperazin-1-yl)-N-(propan-2-yl)-5H-pyrrolo[2,3-b]pyrazine-7-carboxamide |
| 294 | 384.48 | 385 | 2-[(3R)-4-acryloyl-3-(propan-2-yl)piperazin-1-yl]-N-(propan-2-yl)-5H-pyrrolo[2,3-b]pyrazine-7-carboxamide |
| 295 | 356.43 | 357 | 2-[(3S)-4-acryloyl-3-methylpiperazin-1-yl]-N-(propan-2-yl)-5H-pyrrolo[2,3-b]pyrazine-7-carboxamide |
| 296 | 368.44 | 369 | 2-(2-acryloyl-2,6-diazaspiro[3.4]oct-6-yl)-N-(propan-2-yl)-5H-pyrrolo[2,3-b]pyrazine-7-carboxamide |
| 297 | 356.43 | 357 | 2-[(2S)-4-acryloyl-2-methylpiperazin-1-yl]-N-(propan-2-yl)-5H-pyrrolo[2,3-b]pyrazine-7-carboxamide |
| 298 | 370.46 | 371 | 2-[(2S,5R)-4-acryloyl-2,5-dimethylpiperazin-1-yl]-N-(propan-2-yl)-5H-pyrrolo[2,3-b]pyrazine-7-carboxamide |
| 299 | 370.46 | 371 | 2-[(3S)-4-acryloyl-3-ethylpiperazin-1-yl]-N-(propan-2-yl)-5H-pyrrolo[2,3-b]pyrazine-7-carboxamide |
| 300 | 354.41 | 355 | 2-[(1S,4S)-5-acryloyl-2,5-diazabicyclo[2.2.1]hept-2-yl]-N-(propan-2-yl)-5H-pyrrolo[2,3-b]pyrazine-7-carboxamide |
| 301 | 368.44 | 369 | 2-[(1R,5S)-8-acryloyl-3,8-diazabicyclo[3.2.1]oct-3-yl]-N-(propan-2-yl)-5H-pyrrolo[2,3-b]pyrazine-7-carboxamide |
| 302 | 386.46 | 387 | 2-{[(3S,4R)-1-acryloyl-3-methoxypiperidin-4-yl]amino}-N-(propan-2-yl)-5H-pyrrolo[2,3-b]pyrazine-7-carboxamide |
| 303 | 398.51 | 400 | 2-[(3S)-4-acryloyl-3-(2-methylpropyl)piperazin-1-yl]-N-(propan-2-yl)-5H-pyrrolo[2,3-b]pyrazine-7-carboxamide |
| 304 | 368.44 | 369 | 2-[(1S,4S)-5-acryloyl-2,5-diazabicyclo[2.2.2]oct-2-yl]-N-(propan-2-yl)-5H-pyrrolo[2,3-b]pyrazine-7-carboxamide |
| 305 | 386.46 | 387 | 2-{[(3R,4R)-1-acryloyl-3-methoxypiperidin-4-yl]amino}-N-(propan-2-yl)-5H-pyrrolo[2,3-b]pyrazine-7-carboxamide |
| 306 | 370.46 | 371 | 2-[(3R,5S)-4-acryloyl-3,5-dimethylpiperazin-1-yl]-N-(propan-2-yl)-5H-pyrrolo[2,3-b]pyrazine-7-carboxamide |
| 307 | 356.43 | 357 | 2-[(2R)-4-acryloyl-2-methylpiperazin-1-yl]-N-(propan-2-yl)-5H-pyrrolo[2,3-b]pyrazine-7-carboxamide |
| 308 | 368.44 | 369 | 2-(5-acryloyl-2,5-diazabicyclo[2.2.2]oct-2-yl)-N-(propan-2-yl)-5H-pyrrolo[2,3-b]pyrazine-7-carboxamide |
| 309 | 382.47 | 383 | 2-[(2R)-4-acryloyl-2-cyclopropylpiperazin-1-yl]-N-(propan-2-yl)-5H-pyrrolo[2,3-b]pyrazine-7-carboxamide |
| 310 | 354.41 | 355 | 2-(6-acryloyl-2,6-diazaspiro[3.3]hept-2-yl)-N-(propan-2-yl)-5H-pyrrolo[2,3-b]pyrazine-7-carboxamide |
| 311 | 370.46 | 371 | 2-[(3R)-4-acryloyl-3-ethylpiperazin-1-yl]-N-(propan-2-yl)-5H-pyrrolo[2,3-b]pyrazine-7-carboxamide |
| 312 | 370.46 | 371 | 2-(4-acryloyl-2,2-dimethylpiperazin-1-yl)-N-(propan-2-yl)-5H-pyrrolo[2,3-b]pyrazine-7-carboxamide |
| 313 | 368.44 | 369 | 2-(7-acryloyl-4,7-diazaspiro[2.5]oct-4-yl)-N-(propan-2-yl)-5H-pyrrolo[2,3-b]pyrazine-7-carboxamide |
| 314 | 382.47 | 383 | 2-[(2S)-4-acryloyl-2-cyclopropylpiperazin-1-yl]-N-(propan-2-yl)-5H-pyrrolo[2,3-b]pyrazine-7-carboxamide |
| 315 | 382.47 | 383 | 2-{[(3-endo)-8-acryloyl-8-azabicyclo[3.2.1]oct-3-yl]amino}-N-(propan-2-yl)-5H-pyrrolo[2,3-b]pyrazine-7-carboxamide |
| 316 | 370.46 | 371 | 2-[(2S,5S)-4-acryloyl-2,5-dimethylpiperazin-1-yl]-N-(propan-2-yl)-5H-pyrrolo[2,3-b]pyrazine-7-carboxamide |

-continued

| Ex | MW | MW (obs) | Name |
|---|---|---|---|
| 317 | 386.46 | 387 | 2-{[(3R,4S)-1-acryloyl-3-methoxypiperidin-4-yl]amino}-N-(propan-2-yl)-5H-pyrrolo[2,3-b]pyrazine-7-carboxamide |
| 318 | 370.46 | 371 | 2-[(1-acryloyl-4-methylpiperidin-4-yl)amino]-N-(propan-2-yl)-5H-pyrrolo[2,3-b]pyrazine-7-carboxamide |
| 319 | 382.47 | 383 | 2-{[(3-exo)-8-acryloyl-8-azabicyclo[3.2.1]oct-3-yl]amino}-N-(propan-2-yl)-5H-pyrrolo[2,3-b]pyrazine-7-carboxamide |
| 320 | 374.42 | 375 | 2-{[(3S,4R)-1-acryloyl-3-fluoropiperidin-4-yl]amino}-N-(propan-2-yl)-5H-pyrrolo[2,3-b]pyrazine-7-carboxamide |
| 321 | 370.46 | 371 | 2-[(2R)-4-acryloyl-2-ethylpiperazin-1-yl]-N-(propan-2-yl)-5H-pyrrolo[2,3-b]pyrazine-7-carboxamide |
| 322 | 368.44 | 369 | 2-(6-acryloyl-1-methyl-2,6-diazaspiro[3.3]hept-2-yl)-N-(propan-2-yl)-5H-pyrrolo[2,3-b]pyrazine-7-carboxamide |
| 323 | 384.48 | 385 | 2-[(2S)-4-acryloyl-2-(propan-2-yl)piperazin-1-yl]-N-(propan-2-yl)-5H-pyrrolo[2,3-b]pyrazine-7-carboxamide |
| 324 | 384.44 | 385 | 2-(7-acryloyl-3-oxa-7,9-diazabicyclo[3.3.1]non-9-yl)-N-(propan-2-yl)-5H-pyrrolo[2,3-b]pyrazine-7-carboxamide |
| 325 | 370.46 | 371 | 2-[(2S)-4-acryloyl-2-ethylpiperazin-1-yl]-N-(propan-2-yl)-5H-pyrrolo[2,3-b]pyrazine-7-carboxamide |
| 326 | 370.46 | 371 | 2-[(2R,5R)-4-acryloyl-2,5-dimethylpiperazin-1-yl]-N-(propan-2-yl)-5H-pyrrolo[2,3-b]pyrazine-7-carboxamide |
| 327 | 370.46 | 371 | 2-[(2R,5S)-4-acryloyl-2,5-dimethylpiperazin-1-yl]-N-(propan-2-yl)-5H-pyrrolo[2,3-b]pyrazine-7-carboxamide |
| 328 | 370.46 | 371 | 2-[(2R,6S)-4-acryloyl-2,6-dimethylpiperazin-1-yl]-N-(propan-2-yl)-5H-pyrrolo[2,3-b]pyrazine-7-carboxamide |

Preparation 329: 2-Bromo-5-((2-(trimethylsilyl)ethoxy)methyl)-5H-pyrrolo[2,3-b]pyrazine Prepared as described in WO2010/063634.

Preparation 330: 2-Bromo-N-isopropyl-5-((2-(trimethylsilyl)ethoxy)methyl)-5H-pyrrolo[2,3-b]pyrazine-7-carboxamide Prepared as described in *Journal of Medicinal Chemistry*, 56(4), 1677-1692 (2013). Preparation 331: 2-Bromo-N-(tert-butyl)-5-((2-(trimethylsilyl)ethoxy)methyl)-5H-pyrrolo[2,3-b]pyrazine-7-carboxamide.

Prepared as described in *Journal of Medicinal Chemistry*, 56(4), 1677-1692 (2013).

Preparation 332: 2-Bromo-5-((2-(trimethylsilyl)ethoxy)methyl)-5H-pyrrolo[2,3-b]pyrazine-7-carboxylic acid Prepared as described in *Journal of Medicinal Chemistry*, 56(4), 1677-1692 (2013).

Preparation 333: 2-Bromo-7-iodo-5-((2-(trimethylsilyl)ethoxy)methyl)-5H-pyrrolo[2,3-b]pyrazine Step 1. 2-Bromo-7-iodo-5H-pyrrolo[2,3-b]pyrazine To a solution of 2-bromo-5H-pyrrolo[2,3-b]pyrazine (8 g, 40.4 mmol) in DMF (160 mL) was added N-iodosuccinimide (11.8 g, 3.6 mmol) at room temperature, and stirred for 1 h. TLC (Petroleum ether: EtOAc, 2:1) indicated the reaction was completed. reaction mixture was diluted with water (500 mL), and extracted with EtOAc (300 mL×3). The combined organic layers were washed with brine, and dried over $Na_2SO_4$. After filtration, the solvent was removed under reduced pressure to give 2-bromo-7-iodo-5H-pyrrolo[2,3-b]pyrazine (26.1 g, 100%) as brown solid (containing some DMF).

Step 2. 2-Bromo-7-iodo-5-((2-(trimethylsilyl)ethoxy)methyl)-5H-pyrrolo[2,3-b]pyrazine To a suspension of NaH (4.83 g, 120.83 mmol) in DMF (100 mL) was added a solution of compound 2 (26.1 g, 80.56 mmol) in DMF (200 mL) at 0° C. dropwise, and stirred at this temperature for 20 min. Then, sem-Cl (16.14 g, 96.67 mmol) was added dropwise at 0° C., and warmed to room temperature for 1 hour. TLC (petroleum ether/EtOAc, 2:1) indicated the reaction was complete. The reaction mixture was poured into ice-water (300 mL) slowly. The mixture was extracted with EtOAc (200 mL×4), and the combined organic layers were washed with brine, and dried over $Na_2SO_4$. After filtration, the solvent was removed under reduced pressure, and purified with flash column chromatography (petroleum ether/ethyl acetate, 4:1) to give product (13 g, 36%) as a yellow solid. $^1H$ NMR (400 MHz, $CDCl_3$) δ: 8.33 (s, 1H), 7.76 (s, 1H), 5.62 (s, 2H), 3.55-3.48 (m, 2H), 0.94-0.88 (m, 2H), −0.05 (s, 9H). LCMS (M+H) 455.7.

Preparation 334: Methyl 2-bromo-5-((2-(trimethylsilyl)ethoxy)methyl)-5H-pyrrolo[2,3-b]pyrazine-7-carboxylate

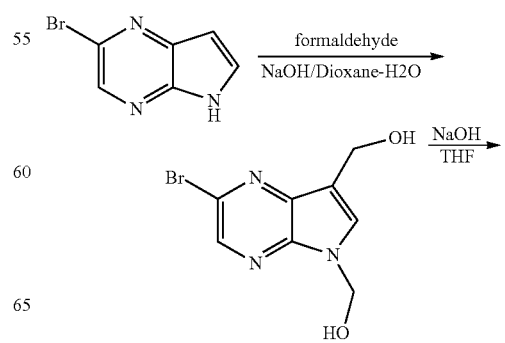

147

-continued

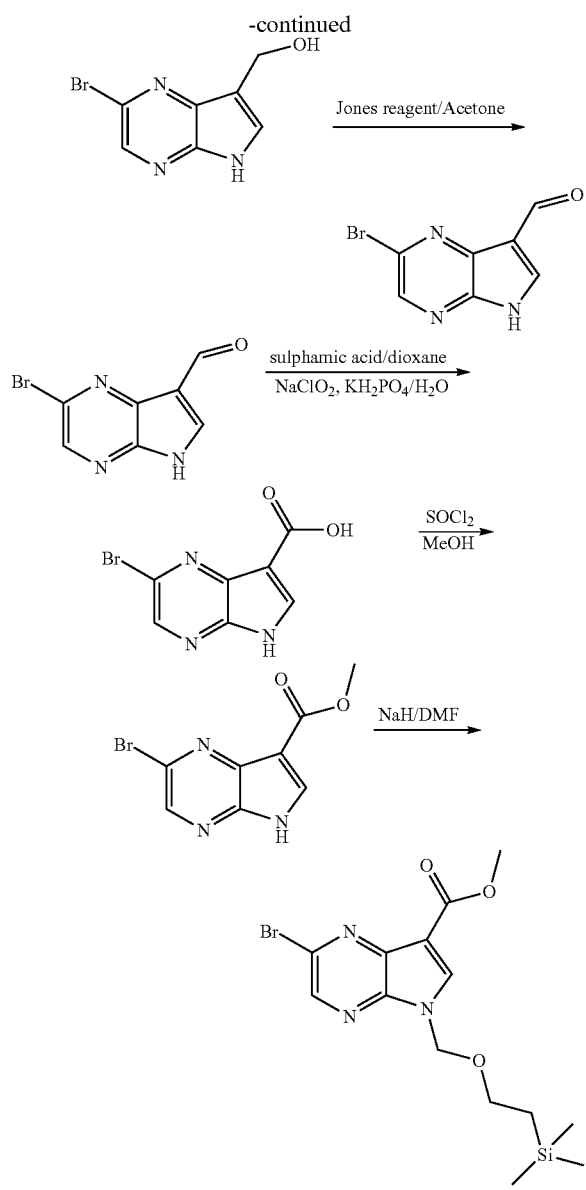

Step 1. (2-Bromo-5H-pyrrolo[2,3-b]pyrazine-5,7-diyl)dimethanol

To a stirred solution of 2-bromo-5H-pyrrolo[2,3-b]pyrazine (116.5 g, 589 mmol) in dioxane (1.75 L) was added dropwise aqueous NaOH (590 mL, 1175 mmol, 2 M) at room temperature, then formaldehyde (481 mL, 5884 mmol, 37% aqueous solution) was added to the mixture at room temperature. After that, the resulting mixture was stirred at room temperature for 18 hours. TLC (petroleum ether/EtOAc, 2:1) showed starting material was consumed completely. The three batches were combined for workup together. The reaction mixture was evaporated to remove most of solvent. The residue was neutralized with 2 M HCl and extracted with EtOAc (1 L×3), the combined organic layers were washed water (1 mL) and brine (1 mL), dried over Na2SO4 and concentrated to dryness, which was triturated with MTBE to give (2-bromo-5H-pyrrolo[2,3-b]pyrazine-5,7-diyl)dimethanol (450 g, 95.5%) as a yellow solid.

148

Step 2. (2-Bromo-5H-pyrrolo[2,3-b]pyrazin-7-yl)methanol

To a suspension of (2-bromo-5H-pyrrolo[2,3-b]pyrazine-5,7-diyl)dimethanol (150 g, 586 mmol) in THF (1.5 L) was added dropwise a solution of NaOH (70.3 g, 1758 mmol) in H₂O (880 mL) at room temperature. After the addition, the resulting mixture was stirred at room temperature for 18 hours. HNMR showed about 18% starting material was remained. The reaction mixture was stirred at room temperature for 48 hours. HNMR showed staring material was consumed completely. The three batches were combined for workup together. The reaction mixture was evaporated to remove most of THF. The aqueous residue was acidified to pH=3-4 with 2M HCl and extracted with EtOAc (3 mL×3), the combined organic layers were washed with water (3 L) and brine (3 L), dried over Na₂SO₄ and concentrated to give (2-bromo-5H-pyrrolo[2,3-b]pyrazin-7-yl)methanol (381 g, 96%) as s yellow solid, which was used for next step without purification Step 3. 2-Bromo-5H-pyrrolo[2,3-b]pyrazine-7-carbaldehyde To a suspension of (2-bromo-5H-pyrrolo[2,3-b]pyrazin-7-yl)methanol (127 g, 562 mmol) in acetone (2.5 L) was added dropwise Jones reagent (253 mL, 674 mol?2.67 M) below 10° C. After the addition, the resulting mixture was stirred at room temperature for 50 min, which time suspension became clean and then brown solid was precipitated. The three batches were combined for workup together. The reaction mixture was quenched with i-PrOH (60 mL) and filtered, the filter cake was washed with acetone (1 L×2), the combined filtrate was evaporated to give 2-bromo-5H-pyrrolo[2,3-b]pyrazine-7-carbaldehyde (320 g, 84.4%) as a yellow solid. (A stock of Jones reagent (2.67 M) was prepared by carefully adding concentrated H₂SO₄ (184 mL) to CrO₃ (213.6 g) then diluting to 800 mL with H₂O.)

Step 4. 2-Bromo-5H-pyrrolo[2,3-b]pyrazine-7-carboxylic acid

To a stirred solution of 2-bromo-5H-pyrrolo[2,3-b]pyrazine-7-carbaldehyde (75 g, 333 mmol) and sulphamic acid (163 g, 1667 mmol) in dioxane-H₂O (1.5 L, 4:1, v/v) was added dropwise a solution of NaClO₂ (36.4 g, 400 mmol) and KH₂PO₄ (227 g, 1667 mmol) in H₂O (0.5 L) over a period of 40 min below 0° C. After the addition, the resulting mixture was stirred at room temperature for 18 hours. TLC (petroleum ether/EtOAc, 1:1) showed the starting material was consumed completely. The two batches were combined for workup together. The reaction mixture was partitioned between EtOAc (2 L) and water (1 L), further extracted with EtOAc (1.5 L). The combined organic layers were washed with water (1 L) and brine (1 L), dried over Na2SO4 and concentrated to give 2-bromo-5H-pyrrolo[2,3-b]pyrazine-7-carboxylic acid (120 g, 75%) as a yellow solid.

Step 5. Methyl 2-bromo-5H-pyrrolo[2,3-b]pyrazine-7-carboxylate

To a 0° C. suspension of 2-bromo-5H-pyrrolo[2,3-b]pyrazine-7-carboxylic acid (145 g, 602 mmol) in MeOH (1.5 L) was added dropwise SOCl₂ (93 g, 781 mmol) over a period of 40 min. after the addition, the resulting mixture was heated to reflux for 4 hours, which time suspended solution became clear and then yellow solid was precipitated. TLC (petroleum ether/EtOAc, 1:1) showed starting material was consumed completely. The reaction mixture was evaporated to dryness, which was triturated with MTBE to give methyl 2-bromo-5H-pyrrolo[2,3-b]pyrazine-7-carboxylate (109 g, 71%) as a yellow solid.

Step 6. Methyl 2-bromo-5-((2-(trimethylsilyl)ethoxy)methyl)-5H-pyrrolo[2,3-b]pyrazine-7-carboxylate To a 0° C. suspension of NaH (11.9 g, 297 mmol, 60% in oil) in DMF (500 mL) was added methyl 2-bromo-5H-pyrrolo[2,3-b]pyrazine-7-carboxylate (55 g, 228 mmol) in portions. After the addition, the reaction mixture was stirred at 0° C. for 10 min. Then SEMCl (49.3 g, 251 mmol) was added dropwise to the mixture below 0° C. After that, the resulting mixture was stirred at room temperature for 3 hours. TLC (petroleum ether/EtOAc, 1:1) showed starting material was consumed completely. The two batches were combined for workup together. The reaction mixture was poured into ice-water (1.5 L), then extracted with EtOAc (1.5 L×3). The combined organic layers were washed with water (2 L) and brine (1.5 L3), dried over $Na_2SO_4$ and concentrated to dryness. The residue was triturated with MTBE to give methyl 2-bromo-5-((2-(trimethylsilyl)ethoxy)methyl)-5H-pyrrolo[2,3-b]pyrazine-7-carboxylate (105 g, 59.7%) as a white solid. $^1$H NMR (400 MHz, DMSO-$d_6$) δ 8.90-8.85 (m, 1H), 8.61 (s, 1H), 5.70 (s, 2H), 3.87 (s, 3H), 3.57 (t, J=8.0 Hz, 2H), 0.83 (t, J=7.8 Hz, 2H), −0.05-0.14 (m, 9H).

Example 335: (R)-1-(3-((5H-Pyrrolo[2,3-b]pyrazin-2-yl)amino)pyrrolidin-1-yl)prop-2-en-1-one

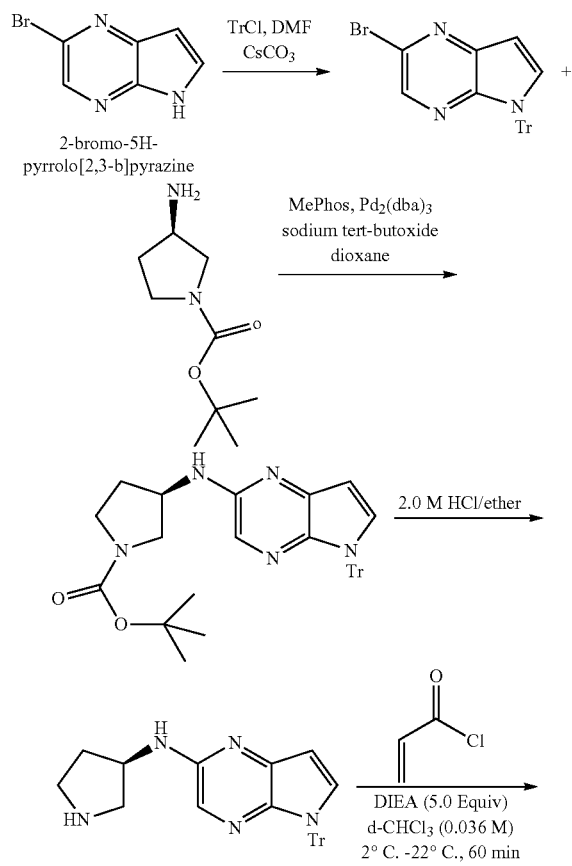

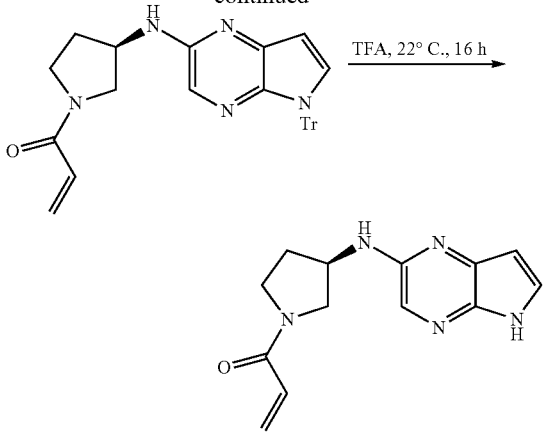

Step 1. 2-Bromo-5-trityl-5H-pyrrolo[2,3-b]pyrazine

At 40° C., a solution of 2-bromo-5H-pyrrolo[2,3-b]pyrazine (725 mg, 3.66 mmol) and cesium carbonate (3250 mg, 9.95 mmol) in DMF (20.0 mL) was treated with trityl chloride (925 mg, 3.32 mmol). After 2 hours, the reaction mixture was cooled to ambient temperature and poured onto water (150 mL). The mixture was filtered and the filter cake was triturated with water (250 mL) for 1 hour. The solid was isolated and recrystallized from hot ethanol to afford 2-bromo-5-trityl-5H-pyrrolo[2,3-b]pyrazine (750 mg, 52%) as a colorless crystalline solid. LC/MS (M+H) 440.16.

Step 2. (R)-tert-Butyl 3-((5-trityl-5H-pyrrolo[2,3-b]pyrazin-2-yl)amino)pyrrolidine-1-carboxylate Under nitrogen, a solution of (R)-tert-butyl 3-aminopyrrolidine-1-carboxylate (850 mg, 4.5 mmol), 2-bromo-5-trityl-5H-pyrrolo[2,3-b]pyrazine (1000 mg, 2.3 mmol), degassed dioxane (9.0 mL), sodium tert-butoxide (500 mg, 5.2 mmol), $Pd_2(dba)_3$ (35 mg, 0.23 mmol), and MePhos (85 mg, 0.23 mmol) was heated to 125° C. After 90 minutes, the reaction mixture was filtered through a thin pad of Celite™ and the solvent was removed in vacuo. The resulting crude oil was dissolved in 100 mL of 1:1 EtOAc:water and the organic layer was extracted. The aqueous layer was back extracted with EtOAc (2×50 mL). Organic layers were combined, dried over sodium sulfate, filtered, concentrated in vacuo, and purified via column chromatography to afford (R)-tert-butyl 3-((5-trityl-5H-pyrrolo[2,3-b]pyrazin-2-yl)amino)pyrrolidine-1-carboxylate (520 mg, 42%) as a colorless solid. LC/MS (M+H) 546.39.

Step 3. (R)—N-(Pyrrolidin-3-yl)-5-trityl-5H-pyrrolo[2,3-b]pyrazin-2-amine

A solution of (R)-tert-butyl 3-((5-trityl-5H-pyrrolo[2,3-b]pyrazin-2-yl)amino)pyrrolidine-1-carboxylate (250 mg, 0.46 mmol) was treated with 2.0 M HCl/ether (10 mL) and sonicated for 15 minutes. The reaction mixture was then stirred for 3 hours at ambient temperature and the solvent was removed in vacuo to afford (R)—N-(pyrrolidin-3-yl)-5-trityl-5H-pyrrolo[2,3-b]pyrazin-2-amine (221 mg, 100%) as the HCl salt. LC/MS (M–H) 446.33.

Step 4. (R)-1-(3-((5-Trityl-5H-pyrrolo[2,3-b]pyrazin-2-yl)amino)pyrrolidin-1-yl)prop-2-en-1-one A solution of (R)—N-(pyrrolidin-3-yl)-5-trityl-5H-pyrrolo[2,3-b]pyrazin-2-amine (220 mg, 0.47 mmol) in anhydrous chloroform (10.0 mL) was treated with Hunig's base (0.4 mL, 3.0 mmol), cooled to 2° C., and treated, dropwise, with a solution of acrylic chloride (0.38 mL, 0.47 mmol) in anhydrous chloroform (2.0 mL). After 30 minutes, the reaction mixture was warmed to ambient temperature and allowed to stir for 1 hour before being cooled to 2° C. and quenched with 10% sodium bicarbonate (15 mL). The organic layer was extracted and the aqueous layer was back extracted with chloroform (2×10 mL). Organic layers were combined, dried over magnesium sulfate, filtered, concentrated in vacuo and purified via column chromatography to afford (R)-1-(3-((5-trityl-5H-pyrrolo[2,3-b]pyrazin-2-yl) amino)pyrrolidin-1-yl)prop-2-en-1-one (221 mg, 97%) as a colorless solid. LC/MS (M+H) 500.35.

Step 5. (R)-1-(3-((5H-Pyrrolo[2,3-b]pyrazin-2-yl) amino)pyrrolidin-1-yl)prop-2-en-1-one A solution of (R)-1-(3-((5-trityl-5H-pyrrolo[2,3-b] pyrazin-2-yl)amino)pyrrolidin-1-yl)prop-2-en-1-one (221 mg, 0.5 mmol) in TFA (4.9 mL) was allowed to stir at ambient temperature for 22 hours. Concentrated in vacuo and purified via column chromatography to afford (R)-1-(3-((5H-pyrrolo[2,3-b]pyrazin-2-yl)amino)pyrrolidin-1-yl) prop-2-en-1-one (107 mg, 84%) as a colorless solid. LC/MS (M+H) 258.3. $^1$H NMR (400 MHz, DMSO-$d_6$) δ 11.41 (s, 1H), 7.62 (s, 1H), 7.43 (s, 1H), 6.77-6.71 (m, 1H), 6.59-5.54 (m, 1H), 6.26 (s, 1H), 6.15-6.09 (m, 1H), 5.65-5.59 (m, 1H), 4.45-4.01 (m, 1H), 3.99-3.88 (m, 1H), 3.70-3.44 (m, 3H), 2.22-1.86 (m, 1H), 1.19-1.14 (m, 1H).

Example 336: (S)-1-(3-((5H-Pyrrolo[2,3-b]pyrazin-2-yl)amino)pyrrolidin-1-yl)prop-2-en-1-one Prepared as in Example 173, except using (S)-tert-butyl 3-aminopyrrolidine-1-carboxylate in step 2.
LC/MS (M+H) 258.3. $^1$H NMR (400 MHz, DMSO-$d_6$) δ 11.41 (s, 1H), 7.62 (s, 1H), 7.43 (s, 1H), 6.77-6.71 (m, 1H), 6.59-5.54 (m, 1H), 6.26 (s, 1H), 6.15-6.09 (m, 1H), 5.65-5.59 (m, 1H), 4.45-4.01 (m, 1H), 3.99-3.88 (m, 1H), 3.70-3.44 (m, 3H), 2.22-1.86 (m, 1H), 1.19-1.14 (m, 1H).

Example 337: 1-(3-((5H-Pyrrolo[2,3-b]pyrazin-2-yl) amino)azetidin-1-yl)prop-2-en-1-one Prepared as in Example 173, except using tert-butyl 3-aminoazetidine-1-carboxylate in step 2. LC/MS (M+H) 244.3. $^1$H NMR (400 MHz, DMSO-$d_6$) δ 11.47 (s, 1H), 7.62 (s, 1H), 7.46 (s, 1H), 7.17 (bs, 1H), 6.36-6.29 (m, 1H), 6.24 (s, 1H), 6.11-6.06 (m, 1H), 5.65-5.62 (m, 1H), 4.56-4.54 (m, 2H), 4.68-3.75 (m, 3H).

Example 338: 2-((1-Acryloylpiperidin-4-yl)oxy)-N-(tert-butyl)-5H-pyrrolo[2,3-b]pyrazine-7-carboxamide

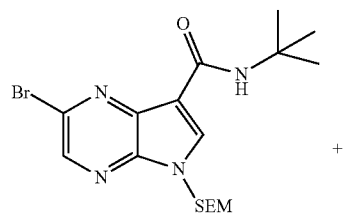

+

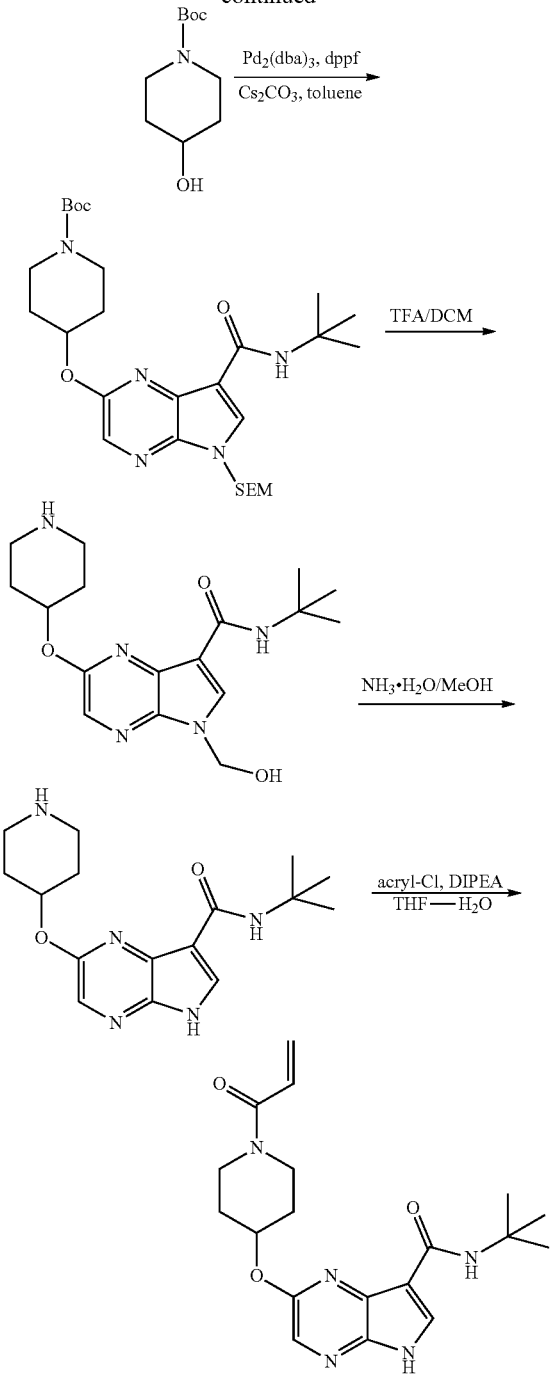

Step 1. tert-Butyl 4-((7-(tert-butylcarbamoyl)-5-((2-(trimethylsilyl)ethoxy)methyl)-5H-pyrrolo[2,3-b] pyrazin-2-yl)oxy)piperidine-1-carboxylate To a solution of 2-bromo-N-(tert-butyl)-5-((2-(trimethylsilyl)ethoxy)methyl)-5H-pyrrolo[2,3-b]pyrazine-7-carboxamide (200 mg, 0.468 mmol) in 10 mL of toluene was added tert-butyl 4-hydroxypiperidine-1-carboxylate (188 mg, 0.935 mmol) and Cs2CO3 (305 mg, 0.935 mmol) at room temperature. The mixture was degassed and purged with N2 several times. Pd2(dba)3 (43 mg, 0.0468 mmol) and dppf (34 mg, 0.06 mmol) was added quickly and the flaks degassed and purged N₂ several times as before. After addition, the mixture was heated to 100° C. overnight. TLC (petroleum ether: EtOAc, 4:1) showed 2-bromo-N-(tert-butyl)-5-((2-(trimethylsilyl) ethoxy)methyl)-5H-pyrrolo[2,3-b]pyrazine-7-carboxamide (was consumed completely. The resulting mixture was cooled to ambient temperature and the mixture was diluted with H₂O (30 mL). The aqueous mixture was extracted with ethyl acetate (30 mL×2). The combined organic layers were washed with brine, dried over anhydrous Na₂SO₄, concentrated and purified by chromatography (silica, petroleum ether: EtOAc from 10:1 to 1:2) to give tert-butyl 4-((7-(tert-butylcarbamoyl)-5-((2-(trimethylsilyl)ethoxy)methyl)-5H-pyrrolo[2,3-b]pyrazin-2-yl)oxy)piperidine-1-carboxylate (160 mg, 62.7%) as an oil.

Step 2. N-(tert-Butyl)-5-(hydroxymethyl)-2-(piperidin-4-yloxy)-5H-pyrrolo[2,3-b]pyrazine-7-carboxamide tert-Butyl 4-((7-(tert-butylcarbamoyl)-5-((2-(trimethylsilyl)ethoxy)methyl)-5H-pyrrolo[2,3-b]pyrazin-2-yl)oxy)piperidine-1-carboxylate (160 mg, 0.29 mmol) was dissolved in a mixed solution of TFA/DCM (1 mL/7 mL, 1:7, v/v) at room temperature. The mixture was stirred at room temperature overnight. LC-MS showed most of tert-butyl 4-((7-(tert-butylcarbamoyl)-5-((2-(trimethylsilyl)ethoxy)methyl)-5H-pyrrolo[2,3-b]pyrazin-2-yl)oxy)piperidine-1-carboxylate was consumed. The resulting mixture was concentrated in vacuo, and chased with DCM several times to give the crude TFA salt of N-(tert-butyl)-5-(hydroxymethyl)-2-(piperidin-4-yloxy)-5H-pyrrolo[2,3-b]pyrazine-7-carboxamide (200 mg, ~0.29 mmol) as oil which was used to next step without further workup. LC/MS (M+H) 348.2.

Step 3. N-(tert-Butyl)-2-(piperidin-4-yloxy)-5H-pyrrolo[2,3-b]pyrazine-7-carboxamide The TFA salt of N-(tert-butyl)-5-(hydroxymethyl)-2-(piperidin-4-yloxy)-5H-pyrrolo[2,3-b]pyrazine-7-carboxamide (200 mg, ~0.29 mmol) was dissolved in a mixed solution of NH₃—H₂O/MeOH (1.8 mL/5.4 mL, 1:3, v/v) at room temperature. The mixture was stirred at room temperature for 2 h. TLC (DCM/MeOH, 10:1) showed starting material was consumed. The resulting mixture was evaporated in vacuo, and chased with DCM several times to give a crude N-(tert-butyl)-2-(piperidin-4-yloxy)-5H-pyrrolo[2,3-b]pyrazine-7-carboxamide (160 mg, ~0.29 mmol) as an oil which was used to next step without further workup. LC/MS (M+H) 318.2.

Step 4. 2-((1-Acryloylpiperidin-4-yl)oxy)-N-(tert-butyl)-5H-pyrrolo[2,3-b]pyrazine-7-carboxamide To a solution of N-(tert-butyl)-2-(piperidin-4-yloxy)-5H-pyrrolo[2,3-b]pyrazine-7-carboxamide (80 mg, ~0.145 mmol) in a mixed solution of THF/H₂O (2 mL/2 mL, 1:1, v/v) at room temperature was added DIPEA (56 mg, 0.435 mmol) dropwise. The mixture was then cooled to 0° C. and acryloyl chloride (26 mg, 0.29 mmol) was added dropwise. After addition, the mixture was stirred at 0° C. for 2 h. TLC (DCM/MeOH, 10:1) showed the reaction was complete. To the mixture was added 10 mL of H₂O, and the aqueous mixture extracted with ethyl acetate (10 mL×2). The combined organic fractions were washed with brine, dried over anhydrous Na₂SO₄ and concentrated in vacuo. The resulting residue was purified via prep-HPLC to give 2-((1-acryloylpiperidin-4-yl)oxy)-N-(tert-butyl)-5H-pyrrolo[2,3-b]pyrazine-7-carboxamide (overall 30 mg, 30% of 3 steps) as a white solid. LC/MS (M+H) 372.2. ¹H NMR (400 MHz, DMSO-d₆) δ 8.114 (s, 1H), 7.981 (s, 1H), 7.790 (s, 1H), 6.870-6.802 (m, 1H), 6.126-6.078 (m, 1H), 5.688-5.656 (m, 1H), 5.236-5.217 (m, 1H), 3.946 (s, 2H), 3.461 (m, 3H), 2.080 (m, 2H), 1.838-1.722 (m, 2H), 1.428 (s, 9H).

Example 339: 2-((1-Acryloylpiperidin-4-yl)oxy)-N-isopropyl-5H-pyrrolo[2,3-b]pyrazine-7-carboxamide Prepared as in Example 176: ((1-acryloylpiperidin-4-yl)oxy)-N-(tert-butyl)-5H-pyrrolo[2,3-b]pyrazine-7-carboxamide, except using 2-bromo-N-isopropyl-5-((2-(trimethylsilyl)ethoxy)methyl)-5H-pyrrolo[2,3-b]pyrazine-7-carboxamide in the first step. LC/MS (M+H) 358.2. ¹H NMR (400 MHz, DMSO-d₆) δ 1.15-1.38 (m, 6H) 1.74 (br. s., 2H) 2.13 (br. s., 2H) 3.41-3.60 (m, 2H) 3.84-4.28 (m, 3H) 5.25 (dt, J=8.09, 4.11 Hz, 1H) 5.59-5.80 (m, 1H) 6.13 (dd, J=16.69, 2.38 Hz, 1H) 6.87 (dd, J=16.69, 10.42 Hz, 1H) 7.78 (d, J=7.53 Hz, 1H) 7.95-8.07 (m, 1H) 8.13-8.32 (m, 1H) 11.76-12.61 (m, 1H).

Example 341: 2-(((2S,4S)-1-Acryloyl-2-methylpiperidin-4-yl)amino)-N-(tert-butyl)-5H-pyrrolo[2,3-b]pyrazine-7-carboxamide Example 342: 2-(((2R,4R)-1-Acryloyl-2-methylpiperidin-4-yl)amino)-N-(tert-butyl)-5H-pyrrolo[2,3-b]pyrazine-7-carboxamide Step 1. (2S,4S)-tert-Butyl 4-((7-(tert-butylcarbamoyl)-5-((2-(trimethylsilyl)ethoxy)methyl)-5H-pyrrolo[2,3-b]pyrazin-2-yl)amino)-2-methylpiperidine-1-carboxylate To a solution of 2-bromo-N-(tert-butyl)-5-((2-(trimethylsilyl)ethoxy)methyl)-5H-pyrrolo[2,3-b]pyrazine-7-carboxamide (250 mg, 0.58 mmol) in 15 mL of toluene was added (2S,4S)-tert-butyl 4-amino-2-methylpiperidine-1-carboxylate (250 mg, 1.17 mmol) and Cs₂CO₃ (381 mg, 1.17 mmol) at room temperature. The mixture was degassed and purged with N₂ several times. Pd₂(dba)₃ (55 mg, 0.058 mmol) and dppf (40 mg, 0.075 mmol) was added and the flask degassed and purged N₂ several times as before. The mixture was heated to 100° C. overnight. TLC (petroleum ether/EtOAc, 2:1) showed starting material was consumed completely. The resulting mixture was cooled to ambient temperature and the mixture was diluted with H₂O (30 mL). The aqueous mixture was extracted with ethyl acetate (30 mL×2). The combined organic phase were washed with brine, dried over anhydrous Na₂SO₄, concentrated and purified by chromatography (silica, petroleum ether/EtOAc from 10:1 to 1:2) to give (2S,4S)-tert-butyl 4-((7-(tert-butylcarbamoyl)-5-((2-(trimethylsilyl)ethoxy)methyl)-5H-pyrrolo[2,3-b]pyrazin-2-yl)amino)-2-methylpiperidine-1-carboxylate (308 mg, 95%) as an oil.

Step 2. N-(tert-Butyl)-2-(((2S,4S)-2-Methylpiperidin-4-yl)amino)-5H-pyrrolo[2,3-b]pyrazine-7-carboxamide (2S,4S)-tert-Butyl 4-((7-(tert-butylcarbamoyl)-5-((2-(trimethylsilyl)ethoxy)methyl)-5H-pyrrolo[2,3-b]pyrazin-2-yl)amino)-2-methylpiperidine-1-carboxylate (345 mg, 0.616 mmol) was dissolved in a mixed solution of TFA/DCM (1 mL/7 mL, 1:7, v/v) at room temperature. The mixture was stirred at room temperature overnight. LC-MS indicated starting material consumed. The resulting mixture was evaporated in vacuo, and chased with DCM several times to give the crude TFA salt of N-(tert-butyl)-5-(hydroxymethyl)-2-(((2S,4S)-2-methylpiperidin-4-yl)amino)-5H-pyrrolo[2,3-b]pyrazine-7-carboxamide (500 mg, ~0.616 mmol) as an oil which was used to next step without further workup. LC/MS (M+H) 361.2.

The TFA salt of N-(tert-butyl)-5-(hydroxymethyl)-2-(((2S,4S)-2-methylpiperidin-4-yl)amino)-5H-pyrrolo[2,3-b]pyrazine-7-carboxamide (500 mg, ~0.616 mmol) was dissolved in a mixed solution of NH3.H$_2$O/MeOH (3 mL/9 mL, 1:3, v/v) at room temperature. The mixture was stirred at room temperature for 2 h. LC-MS showed starting material was consumed. The resulting mixture was evaporated in vacuo, and chased with DCM several times to give a crude N-(tert-butyl)-2-(((2S,4S)-2-methylpiperidin-4-yl)amino)-5H-pyrrolo[2,3-b]pyrazine-7-carboxamide (500 mg, ~0.616 mmol) as an oil, which was used to next step without further workup. LC/MS (M+H) 331.2.

Step 3. rac-2-(((2S,4S)-1-Acryloyl-2-methylpiperidin-4-yl)amino)-N-(tert-butyl)-5H-pyrrolo[2,3-b]pyrazine-7-carboxamide To a solution of N-(tert-butyl)-2-(((2S,4S)-2-methylpiperidin-4-yl)amino)-5H-pyrrolo[2,3-b]pyrazine-7-carboxamide (500 mg, ~0.616 mmol) in a mixed solution of THF/H$_2$O (8 mL, 1:1, v/v) at room temperature was added DIPEA (232 mg, 1.8 mmol) dropwise. The mixture was then cooled to 0° C. and acryloyl chloride (108.6 mg, 1.2 mmol) was added dropwise at 0° C. After addition, the mixture was warmed to ambient temperature and stirred for 2 h. TLC (DCM/MeOH, 10:1) showed the reaction was complete. The mixture was diluted with 10 mL of H$_2$O, and extracted with ethyl acetate (10 mL×2). The combined organic extracts were washed with brine, dried over anhydrous Na$_2$SO$_4$ and concentrated in vacuo. The resulting residue was purified via prep-HPLC to give rac-2-(((2S,4S)-1-acryloyl-2-methyl-piperidin-4-yl)amino)-N-(tert-butyl)-5H-pyrrolo[2,3-b]pyrazine-7-carboxamide (overall 32 mg, 14% of 3 steps) as a white solid. LC/MS (M+H) 385.2. $^1$H NMR (400 MHz, DMSO-d$_6$) δ 8.776 (s, 1H), 8.107 (s, 1H), 7.999-7.991 (d, 1H), 7.673 (s, 1H), 6.622-6.554 (m, 1H), 6.352-6.306 (m, 1H), 5.729-5.698 (m, 1H), 4.596-4.582 (d, 2H), 4.240-4.191 (m, 2H), 3.333-3.273 (m, 1H), 2.176-2.090 (m, 2H), 1.970-1.925 (m, 2H), 1.503 (s, 9H) 1.407-1.390 (d, 3H).

Step 4. 2-(((2S,4S)-1-Acryloyl-2-methylpiperidin-4-yl)amino)-N-(tert-butyl)-5H-pyrrolo[2,3-b]pyrazine-7-carboxamide and 2-(((2R,4R)-1-acryloyl-2-methylpiperidin-4-yl)amino)-N-(tert-butyl)-5H-pyrrolo[2,3-b]pyrazine-7-carboxamide rac-2-(((2S,4S)-1-Acryloyl-2-methylpiperidin-4-yl)amino)-N-(tert-butyl)-5H-pyrrolo[2,3-b]pyrazine-7-carboxamide was purified by chiral SFC (21×250 ChiralPak IA, CO$_2$/EtOH) to give two peaks, arbitrarily assigned absolute stereochemistry.

Peak 1: 2-(((2S,4S)-1-Acryloyl-2-methylpiperidin-4-yl)amino)-N-(tert-butyl)-5H-pyrrolo[2,3-b]pyrazine-7-carboxamide. LC/MS (M+H) 385.2.

Peak 2: 2-(((2R,4R)-1-Acryloyl-2-methylpiperidin-4-yl)amino)-N-(tert-butyl)-5H-pyrrolo[2,3-b]pyrazine-7-carboxamide. LC/MS (M+H) 385.2.

Example 343: 2-((1-Acryloylpiperidin-4-yl)amino)-N-(prop-2-yn-1-yl)-5H-pyrrolo[2,3-b]pyrazine-7-carboxamide Step 1. tert-Butyl 4-((7-(prop-2-yn-1-ylcarbamoyl)-5-((2-(trimethylsilyl)ethoxy)methyl)-5H-pyrrolo[2,3-b]pyrazin-2-yl)amino)piperidine-1-carboxylate To a stirred solution of compound 2-((1-(tert-butoxycarbonyl)piperidin-4-yl)amino)-5-((2-(trimethylsilyl)ethoxy)methyl)-5H-pyrrolo[2, 3-b]pyrazine-7-carboxylic acid (3 g, 6.1 mmol) in 50 mL of DMF was added HATU (2.78 g, 7.32 mmol) at 0° C. After addition, the mixture was stirred at room temperature for 20 min. Then compound prop-2-yn-1-amine (0.67 g, 12.2 mmol) and Et$_3$N (1.23 g, 12.2 mmol) was added separately. After addition, the mixture was stirred at room temperature for 3 hrs. LC-MS indicated acid was consumed completely. To the mixture was added H$_2$O (70 mL) and the aqueous mixture extracted with ethyl acetate (50 mL×4). The organic extracts were dried over anhydrous Na$_2$SO$_4$ and solvent removed in vacuo. The crude product was purified by column chromatography (silica, EtOAc/Hep) to give tert-butyl 4-((7-(prop-2-yn-1-ylcarbamoyl)-5-((2-(trimethylsilyl)ethoxy)methyl)-5H-pyrrolo[2,3-b]pyrazin-2-yl)amino)piperidine-1-carboxylate (2.7 g, 83%) as a yellow solid.

1H NMR (400 MHz, CHCl$_3$-d) δ −0.07-−0.05 (m, 7H) 0.85-0.95 (m, 2H) 1.48 (s, 9H) 1.66 (br s, 6H) 2.16 (d, J=9.54 Hz, 2H) 2.29 (t, J=2.51 Hz, 1H) 2.94-3.06 (m, 2H) 3.47-3.56 (m, 3H) 4.01 (br s, 1H) 4.12 (d, J=7.28 Hz, 2H) 4.32 (d, J=2.01 Hz, 2H) 4.50-4.62 (m, 1H) 5.55 (s, 2H) 7.66 (s, 1H) 8.04 (s, 1H) 8.39 (t, J=4.89 Hz, 1H).

Step 2. 5-(Hydroxymethyl)-2-(piperidin-4-ylamino)-N-(prop-2-yn-1-yl)-5H-pyrrolo[2,3-b]pyrazine-7-carboxamide To a solution of tert-butyl 4-((7-(prop-2-yn-1-ylcarbamoyl)-5-((2-(trimethylsilyl)ethox-y)methyl)-5H-pyrrolo[2,3-b]pyrazin-2-yl)amino)piperidine-1-carboxylate (2.2 g, 4.16 mmol) in anhydrous DCM (10 mL) was cooled to −5° C. in ice-methanol bath. Then TFA (20 mL) was added dropwise. After addition, the cooled bath was removed and the resulting solution was stirred at room temperature for 2 hrs. LC-MS indicated the reaction was complete. The reaction solution was concentrated to remove most of the DCM and TFA. Then MeOH (10 mL) was added and the resulting solution was concentrated again and dried under high vacuum to give the TFA salt of 5-(hydroxymethyl)-2-(piperidin-4-ylamino)-N-(prop-2-yn-1-yl)-5H-pyrrolo[2,3-b]pyrazine-7-carboxamide (3.57 g, >100%) as a yellow solid/oil. LC/MS (M+H)=329.0.

Step 3. 2-(piperidin-4-ylamino)-N-(prop-2-yn-1-yl)-5H-pyrrolo[2,3-b]pyrazine-7-carboxamide To a stirred solution of TFA salt of 5-(hydroxymethyl)-2-(piperidin-4-ylamino)-N-(prop-2-yn-1-yl)-5H-pyrrolo[2, 3-b]pyrazine-7-carboxamide (3.57 g, crude) in anhydrous MeOH (20 mL) was added K$_2$CO$_3$ (5.7 g, 41.6 mmol) in portions at room temperature. After addition, the resulting mixture was stirred at room temperature for 2 hrs. LC-MS indicated the reaction was complete. The reaction suspension was filtered, and the filtrate was concentrated to give crude 2-(piperidin-4-ylamino)-N-(prop-2-yn-1-yl)-5H-pyrrolo[2,3-b]pyrazine-7-carboxamide (4.47 g, >100%). LC/MS (M+H)=299.2

Step 4. 2-((1-acryloylpiperidin-4-yl)amino)-N-(prop-2-yn-1-yl)-5H-pyrrolo[2,3-b]pyrazine-7-carboxamide To a solution of 2-(piperidin-4-ylamino)-N-(prop-2-yn-1-yl)-5H-pyrrolo[2,3-b]pyrazine-7-carboxamide (4.49 g, crude, 4.16 mmol) in THF/H$_2$O (20 mL/20 mL, V/V=1:1) was added DIPEA (2.7 mL, 20.8 mmol) dropwise. The resulting mixture was cooled to 0° C. and acryloyl chloride (376 mg, 4.16 mmol) was added dropwise at 0° C. After addition, the mixture was stirred at 0° C. for 1 h. LC-MS indicated ~20% of starting material was remaining. Additional acryloyl chloride (376 mg) was added at 0-5° C. and then stirred at the temperature for 0.5 h. LC-MS indicated most of starting material was consumed. The reaction mixture was extracted with ethyl acetate (20 mL×3). The organic phases were combined and washed with brine, dried over anhydrous Na$_2$SO$_4$ and concentrated. The resulting residue was purified via prep-HPLC to give 2-((1-acryloylpiperidin-4-yl)amino)-N-(prop-2-yn-1-yl)-5H-pyrrolo[2,3-b]pyrazine-7-carboxamide (9 mg) as an off-white solid. LC/MS (M+H)=353.0

1H NMR (400 MHz, MeOH-d4) δ 1.48-1.62 (m, 2H) 2.24 (t, J=14.18 Hz, 2H) 2.87 (t, J=2.51 Hz, 1H) 3.07-3.22 (m, 1H) 3.45 (br. s., 1H) 4.08-4.23 (m, 2H) 4.30 (d, J=2.26 Hz, 2H) 4.50 (d, J=13.55 Hz, 1H) 5.77 (dd, J=10.54, 2.01 Hz, 1H) 6.23 (dd, J=16.81, 2.01 Hz, 1H) 6.84 (dd, J=16.81, 10.79 Hz, 1H) 7.72 (s, 1H) 7.94 (s, 1H).

Preparation 344: 2-((1-(tert-Butoxycarbonyl)piperidin-4-yl)amino)-5-((2-(trimethylsilyl)ethoxy)methyl)-5H-pyrrolo[2,3-b]pyrazine-7-carboxylic acid

Step 1. methyl 2-bromo-5-((2-(trimethylsilyl)ethoxy)methyl)-5H-pyrrolo[2,3-b]pyrazine-7-carboxylate A mixture of 2-bromo-5-((2-(trimethylsilyl)ethoxy)methyl)-5H-pyrrolo[2,3-b]pyrazine-7-carboxylic acid (50 g, 134.8 mmol), K$_2$CO$_3$ (28 g, 202.2 mmol) and iodomethane (34.5 g, 242.9 mmol) in DMF (1200 mL) was heated at 35° C. for 2 h. The mixture was cooled to room temperature, diluted with water (500 mL) and the mixture extracted with ethyl acetate (800 mL×3). The combined organic phases were washed with water (2000 mL×1) and brine (1000 mL×1), dried over anhydrous Na$_2$SO$_4$ and concentrated to give methyl 2-bromo-5-((2-(trimethylsilyl)ethoxy)methyl)-5H-pyrrolo[2,3-b]pyrazine-7-carboxylate (49 g, 94.4%) as a yellow solid. LC/MS (M+H)=387.9.

Step 2. Methyl 2-((1-(tert-butoxycarbonyl)piperidin-4-yl)amino)-5-((2-(trimethylsilyl)ethoxy)methyl)-5H-pyrrolo[2,3-b]pyrazine-7-carboxylate To a solution of methyl 2-bromo-5-((2-(trimethylsilyl)ethoxy)methyl)-5H-pyrrolo[2,3-b]pyrazine-7-carboxylate (39 g, 101.3 mmol) in 780 mL of toluene was added tert-butyl 4-aminopiperidine-1-carboxylate (30.4 g, 151.9 mmol) and Cs$_2$CO$_3$ (66 g, 202.6 mmol) at room temperature. The mixture was degassed and purged with N$_2$ several times, followed by addition of Pd$_2$(dba)$_3$ (9.3 g, 10.13 mmol) and dppf (7.3 g, 13.17 mmol). The mixture was subsequently degassed and purged with N$_2$ several times as before. The resulting mixture was heated to 80° C. and stirred at this temperature overnight under N$_2$. TLC (Petroleum ether: EtOAc=4:1) indicated methyl 2-bromo-5-((2-(trimethylsilyl)ethoxy)methyl)-5H-pyrrolo[2,3-b]pyrazine-7-carboxylate was consumed completely. The resulting mixture was cooled to ambient temperature and H$_2$O (400 mL) added. The aqueous mixture was extracted with EtOAc (300 mL×3). The combined organic phase was washed with brine, dried over anhydrous Na$_2$SO$_4$, concentrated and purified by chromatography column (silica, petroleum ether: EtOAc from 10:0 to 10:3) to give methyl 2-((1-(tert-butoxycarbonyl)piperidin-4-yl)amino)-5-((2-(trimethylsilyl)ethoxy)methyl)-5H-pyrrolo[2,3-b]pyrazine-7-carboxylate (50 g, 78%) as a yellow solid.

1H NMR (400 MHz, DMSO-d$_6$) δ ppm −0.09 (s, 9H) 0.81 (t, J=7.91 Hz, 2H) 1.42 (s, 9H) 1.94-2.01 (m, 3H) 2.96 (br. s., 2H) 3.52 (t, J=8.03 Hz, 2H) 3.77 (s, 3H) 3.84-3.96 (m, 3H) 5.54 (s, 2H) 6.86 (d, J=7.28 Hz, 1H) 7.73 (s, 1H) 8.29 (s, 1H)

Step 3. 2-((1-(tert-butoxycarbonyl)piperidin-4-yl)amino)-5-((2-(trimethylsilyl)ethoxy)methyl)-5H-pyrrolo[2,3-b]pyrazine-7-carboxylic acid To a solution of methyl 2-((1-(tert-butoxycarbonyl)piperidin-4-yl)amino)-5-((2-(trimethylsilyl)ethoxy)methyl)-5H-pyrrolo[2,3-b]pyrazine-7-carboxylate (50 g, 99 mmol) in THF (1000 mL) was added aqueous 1M NaOH (396 mL). The reaction mixture was stirred at room temperature overnight. TLC (PE/EA=2:1) showed most of the methyl 2-((1-(tert-butoxycarbonyl)piperidin-4-yl)amino)-5-((2-(trimethylsilyl)ethoxy)methyl)-5H-pyrrolo[2,3-b]pyrazine-7-carboxylate remained. The reaction mixture was heated to 45° C. for 3 h. TLC (PE/EA=2:1) still showed ester remained. The reaction mixture was heated to 60° C. overnight. LC-MS indicated about 15% of ester remained. A solution of NaOH (7.9 g, 198 mmol) in H$_2$O (200 mL) was added to the reaction mixture. The reaction mixture was heated to reflux. LC-MS indicated about 8% of ester remained. After cooling to rt, a majority of the THF was removed and during this time a green solid formed. The mixture was filtered and 45 g of light green solid was obtained. This solid was acidified to pH=4-5 with HCl (2M in H$_2$O) and extracted with ethyl acetate (400 mL×3). The combined organics were washed with brine, dried over anhydrous Na$_2$SO$_4$ and concentrated under reduced pressure to give 2-((1-(tert-butoxycarbonyl)piperidin-4-yl)amino)-5-((2-(trimethylsilyl)ethoxy)methyl)-5H-pyrrolo[2,3-b]pyrazine-7-carboxylic acid (overall 29.1 g, 44% of 3 steps) as a yellow solid.

1H NMR (400 MHz, CDCl$_3$) δ ppm −0.04 (s, 8H) 0.89-0.95 (m, 2H) 1.48 (s, 9H) 2.11 (d, J=11.29 Hz, 2H) 2.94-3.05 (m, 3H) 3.53-3.60 (m, 2H) 3.97 (br. s., 1H) 4.08 (br. s., 2H) 4.71 (br. s., 1H) 5.58 (s, 2H) 7.72 (s, 1H) 8.05 (s, 1H)

Biological Evaluation

JAK Caliper Enzyme Assay at 4 μM or 1 mM ATP

Test article was solubilized in dimethyl sulfoxide (DMSO) to a stock concentration of 30 mM. An 11-point half log dilution series was created in DMSO with a top concentration of 600 μM. The test compound plate also contained positive control wells containing a known inhibitor to define 100% inhibition and negative control wells containing DMSO to define no inhibition. The compound plates were diluted 1 to 60 resulting in a top final assay compound concentration of 10 μM and a 2% DMSO concentration.

Test article and assay controls were added to a 384-well plate. Reaction mixtures contained 20 mM HEPES, pH 7.4, 10 mM magnesium chloride, 0.01% bovine serum albumin (BSA), 0.0005% Tween 20, 4 µM or 1 mM ATP and 1 µM peptide substrate. The JAK3 assays contained 1 µM of the JAKtide peptide (FITC-KGGEEEEYFELVKK). The assays were initiated by the addition 1 nM JAK3 enzyme and were incubated at room temperature 75 minutes for JAK3. Enzyme concentrations and incubation times were optimized for each new enzyme preps and were modified slightly over time to ensure 20%-30% phosphorylation. The assays were stopped with a final concentration of 10 mM EDTA, 0.1% Coating Reagent and 100 mM HEPES, pH=7.4. The assay plates were placed on a Caliper Life Science Lab Chip 3000 (LC3000) instrument, and each well was sampled using appropriate separation conditions to measure the unphosphorylated and phosphorylated peptide.

Stability of JAK3 Covalent Inhibitors in Rat and Human Whole Blood

Rat blood was collected from 3 male Sprague-Dawley rats (200-250 g, Charles River Laboratories) and pooled for each study. Human blood was collected from one male and one female healthy subjects at the Occupational Health & Wellness Center at Pfizer, Groton, Conn. and pooled for each study. Both rat and human blood was collected freshly into $K_2$-EDTA tubes and kept on ice. An aliquot of the blood was transferred to microtubes and pre-warmed for 10 min at 37° C. using a heat block. The test compound was then added (1 µM final concentration) and the incubation was continued for 180 min at 37° C. in duplicates. An aliquot of the incubation mixture was removed at designated time points during the course of the incubation, mixed with an aliquot of acetonitrile containing an internal standard, vortexed and centrifuged. The resulting supernatants were removed and subjected to LC-MS/MS analyses to determine parent compound concentrations. Peak area ratios of the parent compound vs the internal standard were used to determine the % of parent compound remaining vs incubation time.

HWB IL-15 Induced STAT5 Phosphorylation Assay

After serial dilution of the test compounds 1:2 in DMSO at desired concentration (500× of final), the compounds were further diluted in PBS (by adding 4 µL compound/DMSO in 96 µL PBS, [DMSO]=4%, 20× final). To 96-well polypropylene plates were added 90 µl HWB (heparin treated Human Whole Blood)/well, followed by 5 µl/well 4% DMSO in D-PBS or various concentrations of 20× inhibitor in 4% DMSO in D-PBS (w/o $Ca^{+2}$ or $Mg^{+2}$) to give 1× in 0.2% DMSO. After mixing and incubating for 45 minutes at 37° C., 5 µl D-PBS (unstimulated control) or 20× stocks of 5 µl human IL-15 (final concentration is 50 ng/ml) were added, and mixed three times. After incubating 15 minutes at 37° C., 1× Lyse/Fix Buffer (BD Phosflow 5× Lyse/Fix Buffer) was added to all wells at 1000 µl/well, then incubated for 20 minutes at 37° C. and spun 5 mins at 1200 rpm. After washing in 1000 µl FACS buffer 1× and spinning for 5 mins at 1200 rpm, 400 µl ice cold Perm Buffer III were added to each well. After mixing gently (1-2×) and incubating on ice for 30 minutes, spinning for 5 mins at 1200 rpm without interruption, and washing 1× in cold 1000 ml FACS buffer (D-PBS containing 0.1% BSA and 0.1% sodium azide) 250 µl/well of the desired AlexaFluor647-conjugated anti-phospho STAT5 antibody at 1:125 dilution in FACS buffer was added. Following incubating at 4° C. over night, all the samples were transferred to 96-well polypropylene U-bottom plate, and checked by flow cytometry gated on total lymphocytes. $IC_{50}$ values obtained are listed in the Table.

PBMC IL-15 Induced P-STAT5

Test compounds were serially diluted in DMSO, with further dilution of the compounds in RPMI 1640 medium (Invitrogen #72400) supplemented with 10 mM HEPES, pH 7.4, 1 mM sodium pyruvate, and Penicillin/Streptomycin (by adding 5 µL compound/DMSO in 120 µL Dulbecco's Phosphate-Buffered Saline (D-PBS, 1×), [DMSO]=4%, and mixing the solution by repeated pipetting, 6×). IL-15 was diluted to the concentration at 820 ng/mL in RPMI 1640 medium.

Frozen human PBMC (200-250 million cells/vial) was thawed at 37° C. The cells were transferred to 10 mL warm medium in a 50-mL conical tube, and centrifuged at 1,200 RPM at room temperature for 5 min. The supernatant was aspirated. Cells were suspended in 3 mL warm human plasma and incubated at 37° C. in a tissue culture incubator for 1.5 to 2 h. After adding 47 ml D-PBS (37° C.) to PBMC/FBS suspension, centrifuging at 1,200 RPM at room temperature for 5 min, and aspirating the supernatant, the cells were resuspended in 20 mL warm RPMI medium. Ninety µL of cell suspension were pipetted per well in a 96-well, deep-well, V-bottom plate, and the plate was incubated at 37° C. for 30 min. Five µL of compound were transferred to each well (final 0.2% DMSO), vortex gently and incubate at 37° C. for 15 min; 5 µL 4% DMSO/PBS were added to the control wells. After adding 5 µL 820 ng/mL of human IL-15 (final 41 ng/mL) to each well (5 µL PBS to the control wells), vortexing gently and incubating at 37° C. for 15 min, followed by 0.3 mL 1% paraformaldehyde/PBS (37° C.) to each well, and incubating the plate at room temperature for 15 min, the plates were centrifuged at 1,200 RPM (Beckman GS-6R or Sorvall Legend) at room temperature for 5 min, and the supernatant was aspirated using a 8-channel or 12-channel manifold. After adding 0.8 mL staining buffer per well, the plates were centrifuged at 1,200 RPM (Beckman GS-6R or Sorvall Legend) at room temperature for 5 min, and again the supernatant was aspirated using a 8-channel or 12-channel manifold. The plate was vortexed, and 0.35 mL 90% methanol/10% $H_2O$ (−20° C.) was added per well, and the plate incubated on ice for 20 min. After again adding 0.8 mL staining buffer per well, the plates were centrifuged at 1,200 RPM (Beckman GS-6R or Sorvall Legend) at room temperature for 5 min, and again the supernatant was aspirated using a 8-channel or 12-channel manifold, and then 0.8 mL Staining buffer was added per well. After once again adding 0.8 mL staining buffer per well, the plates were centrifuged at 1,200 RPM (Beckman GS-6R or Sorvall Legend) at room temperature for 5 min, and again the supernatant was aspirated using a 8-channel or 12-channel manifold. Then the plate was vortexed, and 250 µL/well of Alexa Fluor® 647 conjugated anti-STAT5 antibody (1 to 125 dilution; 1 µL antibody per 250 µL staining buffer) was added, and the plate was incubated at 4° C. overnight in the dark. Samples of 250 µL/well were transferred to a 96-well U-bottom plate, and the FACS analysis was performed gating on total lymphocytes. Samples were analyzed using a BD Calibur™ or BD FACSCanto™ flow cytometer equipped with the BD High Throughput Sampler.

TABLE 1
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 1 | 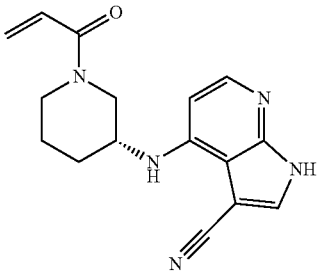 [SMILES: C=CC(=O)N1CCC[C@@H](Nc2ccnc3[nH]cc(C#N)c23)C1] | 0.2 | 16.8 | 50.8 | 494.1 | 209.9 |
| 2 | 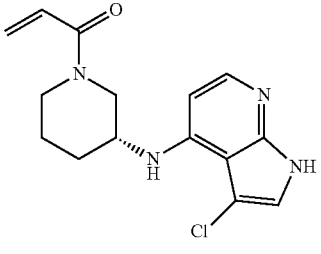 [SMILES: C=CC(=O)N1CCC[C@@H](Nc2ccnc3[nH]cc(Cl)c23)C1] | 0.2 | 18.9 | 30.4 | 220.2 | >360.0 |
| 3 | 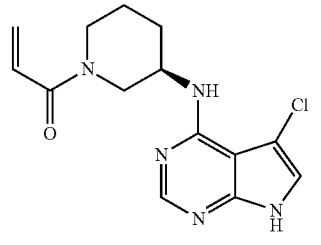 [SMILES: C=CC(=O)N1CCC[C@@H](Nc2ncnc3[nH]cc(Cl)c23)C1] | <0.1 | 22 | 35.2 | 152.7 | 191.8 |
| 4 | 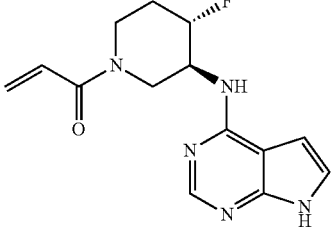 | 0.5 | 32.1 | 19.7 | 115.1 | 139.7 |
| 5 | 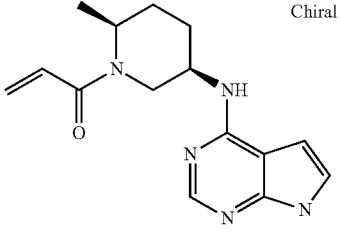 [SMILES: C=CC(=O)N1C[C@H](Nc2ncnc3[nH]ccc23)CC[C@@H]1C] Chiral | 0.3 | 33.1 | 51.7 | 197.2 | >331.0 |

TABLE 1-continued

Enzyme Assay and Blood Stability Data.

| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 6 | 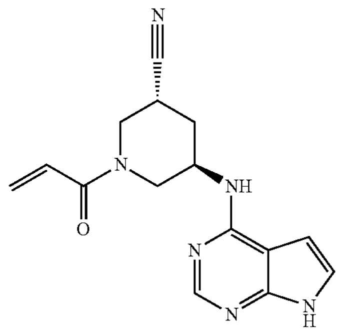 [SMILES: C=CC(=O)N1C[C@H](C#N)C[C@@H](Nc2ncnc3[nH]ccc23)C1] | 0.3 | 40 | 45.8 | 870.5 | 253 |
| 7 | 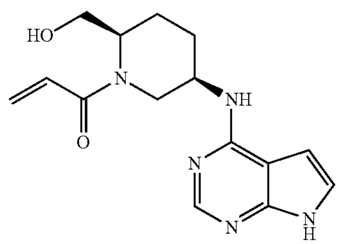 [SMILES: C=CC(=O)N1C[C@H](Nc2ncnc3[nH]ccc23)CC[C@@H]1CO] | 0.3 | 45.3 | 76.9 | 455.3 | >333.5 |
| 8 | 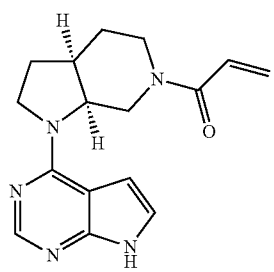 [SMILES: C=CC(=O)N1CC[C@@H]2CCN(c3ncnc4[nH]ccc34)[C@@H]2C1] | <0.4 | 47.7 | 115.9 | 399.2 | 192 |
| 9 | 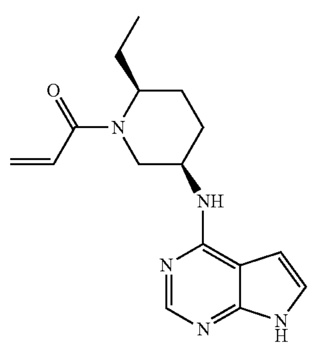 [SMILES: C=CC(=O)N1C[C@H](Nc2ncnc3[nH]ccc23)CC[C@@H]1CC] | 0.4 | 53.9 | 35.5 | 578 | >360.0 |
| 10 | 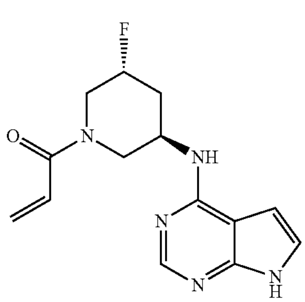 [SMILES: C=CC(=O)N1C[C@H](F)C[C@@H](Nc2ncnc3[nH]ccc23)C1] | 0.6 | 54.8 | 133.1 | 461.1 | 163 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 11 | 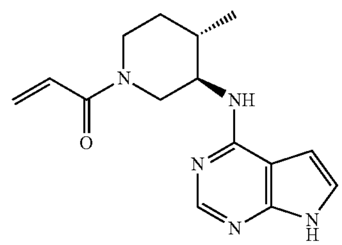 [SMILES: C=CC(=O)N1CC[C@H](C)[C@@H](Nc2ncnc3[nH]ccc23)C1] | 0.4 | 55.9 | 97.9 | 362.6 | >295.8 |
| 12 | 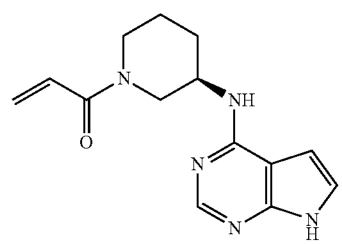 [SMILES: C=CC(=O)N1CCC[C@@H](Nc2ncnc3[nH]ccc23)C1] | 0.7 | 56.8 | 107.1 | 392.1 | >331.5 |
| 13 | 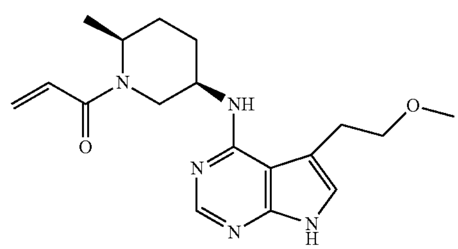 [SMILES: C=CC(=O)N1C[C@H](Nc2ncnc3[nH]cc(CCOC)c23)CC[C@@H]1C] | 0.4 | 60.6 | 113.5 | 548.8 | 305 |
| 14 | Chiral | 0.5 | 60.5 | 114.4 | 538.3 | >250.7 |
| 15 | 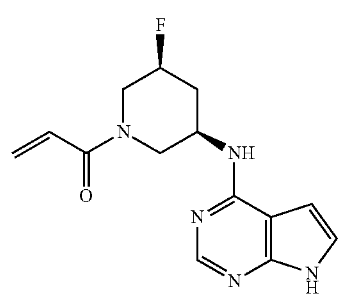 [SMILES: C=CC(=O)N1C[C@@H](F)C[C@@H](Nc2ncnc3[nH]ccc23)C1] | 0.9 | 82.7 | 128.1 | 399.7 | 232 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 16 | 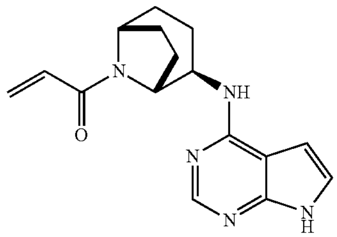 [SMILES: C=CC(=O)N1[C@H]2CC[C@@H]1[C@H](Nc1ncnc3[nH]ccc13)CC2] | 0.8 | 89.2 | 61.5 | 498.9 | >358.5 |
| 17 | 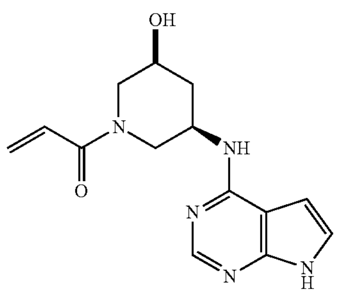 [SMILES: C=CC(=O)N1C[C@@H](O)C[C@@H](Nc2ncnc3[nH]ccc23)C1] | 1.7 | 92.2 | 71.8 | 209.9 | >310.0 |
| 18 | 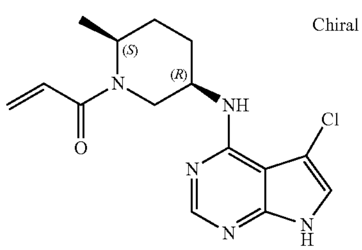 | 0.2 | 16.1 | 31.5 | 555.4 | >318.5 |
| 19 | 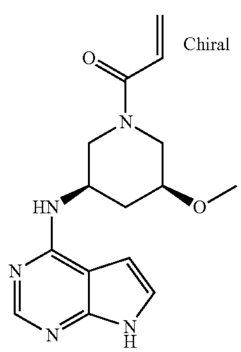 [SMILES: C=CC(=O)N1C[C@H](Nc2ncnc3[nH]ccc23)C[C@H](OC)C1] | 0.6 | 67.6 | 139.3 | 505.2 | 210.5 |
| 20 | 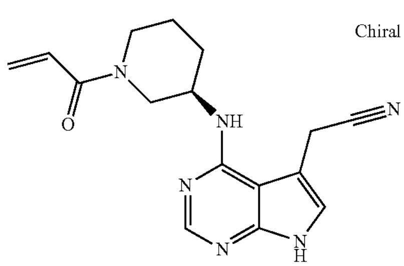 [SMILES: C=CC(=O)N1CCC[C@@H](Nc2ncnc3[nH]cc(CC#N)c23)C1] | 1 | 76.5 | 361.6 | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15- pSTAT5 IC$_{50}$ (nM) | HWB- IL15- pSTAT5 IC$_{50}$ (nM) | Human blood stability t$_{1/2}$ (min) |
|---|---|---|---|---|---|---|
| 21 | 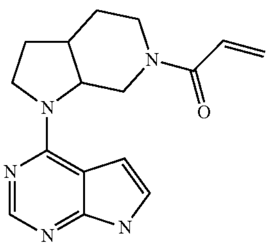 [SMILES: C=CC(=O)N1CCC2CCN(c3ncnc4[nH]ccc34)C2C1] | 1.4 | 106 | 235.7 | | |
| 22 | 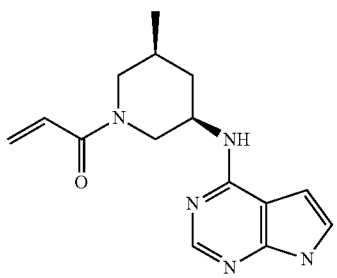 [SMILES: C=CC(=O)N1C[C@@H](C)C[C@@H](Nc2ncnc3[nH]ccc23)C1] | 1.2 | 81.6 | 216 | 712 | 347 |
| 23 | 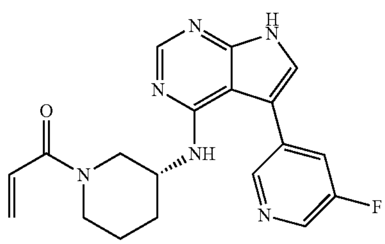 [SMILES: C=CC(=O)N1CCC[C@@H](Nc2ncnc3[nH]cc(-c4cncc(F)c4)c23)C1] | 1.3 | 86.6 | 187.8 | | >360.0 |
| 24 | 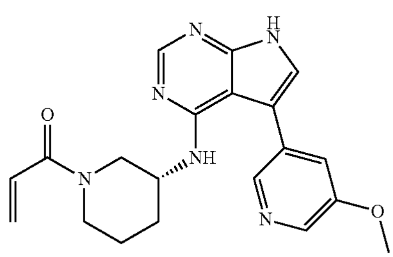 [SMILES: C=CC(=O)N1CCC[C@@H](Nc2ncnc3[nH]cc(-c4cncc(OC)c4)c23)C1] | 1.2 | 98.1 | 319.9 | | >360.0 |
| 25 | 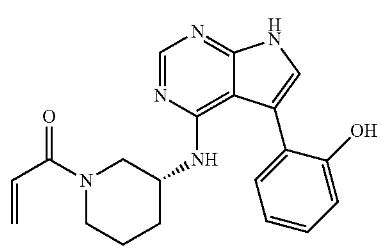 [SMILES: C=CC(=O)N1CCC[C@@H](Nc2ncnc3[nH]cc(-c4ccccc4O)c23)C1] | 2.9 | 149.1 | 84 | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 26 | 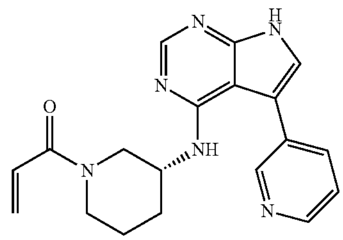 [SMILES: C=CC(=O)N1CCC[C@@H](Nc2ncnc3[nH]cc(-c4cccnc4)c23)C1] | 1.6 | 153 | 254.4 | | >360.0 |
| 27 | 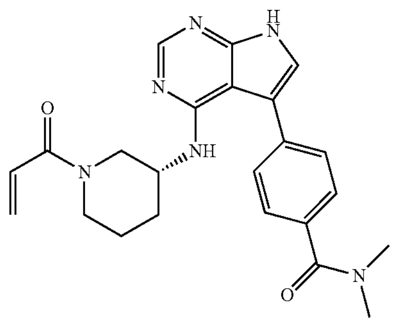 [SMILES: C=CC(=O)N1CCC[C@@H](Nc2ncnc3[nH]cc(-c4ccc(C(=O)N(C)C)cc4)c23)C1] | 2.8 | 293.6 | 1866.4 | | 46 |
| 28 | 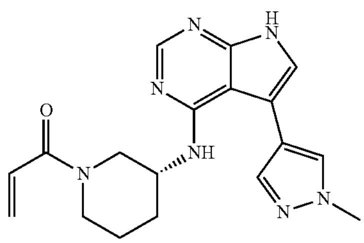 [SMILES: C=CC(=O)N1CCC[C@@H](Nc2ncnc3[nH]cc(-c4cnn(C)c4)c23)C1] | 48.2 | 358.5 | >10000.0 | | >360.0 |
| 29 | 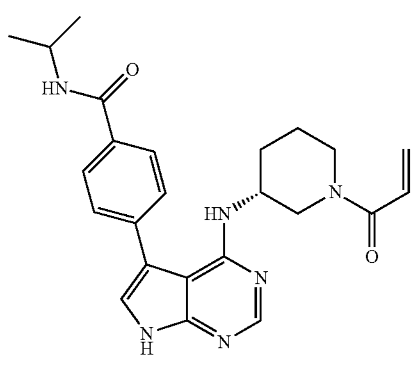 [SMILES: C=CC(=O)N1CCC[C@@H](Nc2ncnc3[nH]cc(-c4ccc(C(=O)NC(C)C)cc4)c23)C1] | 6.6 | 664.9 | 463.7 | | |
| 30 | 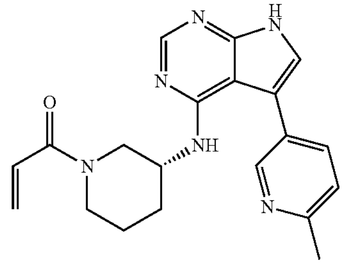 [SMILES: C=CC(=O)N1CCC[C@@H](Nc2ncnc3[nH]cc(-c4ccc(C)nc4)c23)C1] | 14.6 | 1536.1 | | | >360.0 |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 31 | 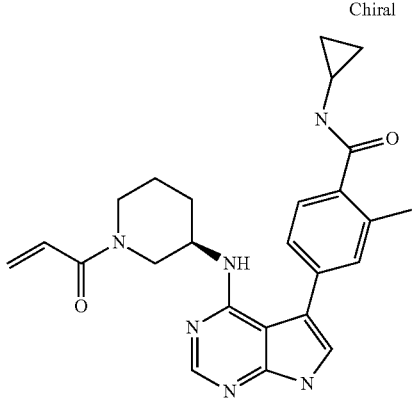 [SMILES: C=CC(=O)N1CCC[C@@H](Nc2ncnc3[nH]cc(-c4ccc(C(=O)NC5CC5)c(C)c4)c23)C1] Chiral | 24.1 | 1859 | | | >360.0 |
| 32 | 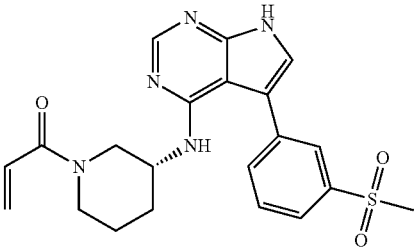 [SMILES: C=CC(=O)N1CCC[C@@H](Nc2ncnc3[nH]cc(-c4cccc(S(C)(=O)=O)c4)c23)C1] | 26.2 | 2114.8 | | | |
| 33 | 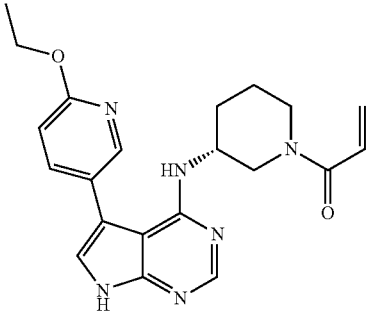 [SMILES: C=CC(=O)N1CCC[C@@H](Nc2ncnc3[nH]cc(-c4ccc(OCC)nc4)c23)C1] | 49.5 | 3809.1 | | | >360.0 |
| 34 | 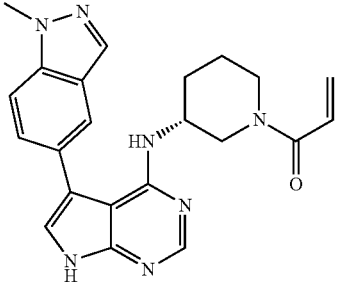 [SMILES: C=CC(=O)N1CCC[C@@H](Nc2ncnc3[nH]cc(-c4ccc5c(cnn5C)c4)c23)C1] | 54.4 | 4822 | | | >360.0 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 35 | 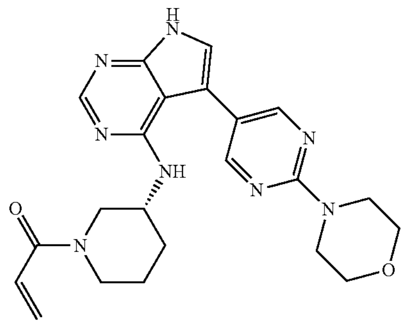 [SMILES: C=CC(=O)N1CCC[C@@H](Nc2ncnc3[nH]cc(-c4cnc(N5CCOCC5)nc4)c23)C1] | 83.4 | | | | |
| 36 | 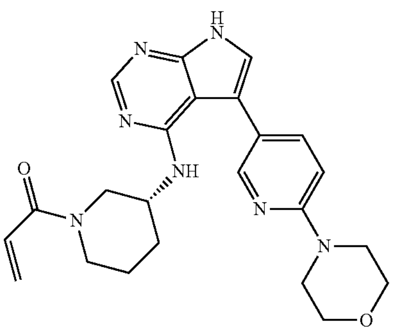 [SMILES: C=CC(=O)N1CCC[C@@H](Nc2ncnc3[nH]cc(-c4ccc(N5CCOCC5)nc4)c23)C1] | 64.4 | | | | >360.0 |
| 37 | 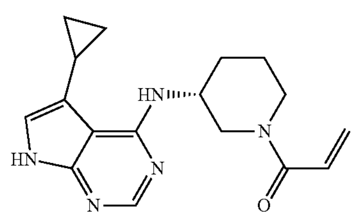 [SMILES: C=CC(=O)N1CCC[C@@H](Nc2ncnc3[nH]cc(C4CC4)c23)C1] | 295.1 | | | | |
| 38 | 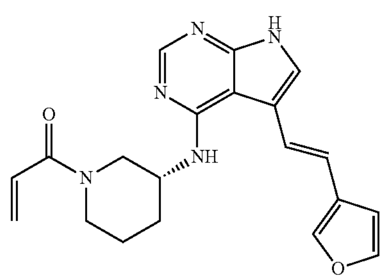 [SMILES: C=CC(=O)N1CCC[C@@H](Nc2ncnc3[nH]cc(/C=C/c4ccoc4)c23)C1] | 3254 | | | | |
| 39 | 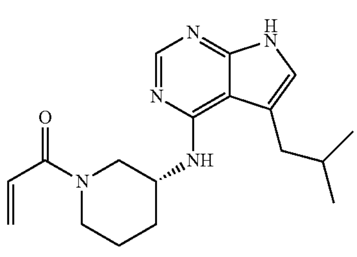 [SMILES: C=CC(=O)N1CCC[C@@H](Nc2ncnc3[nH]cc(CC(C)C)c23)C1] | >10000.0 | | | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 40 | 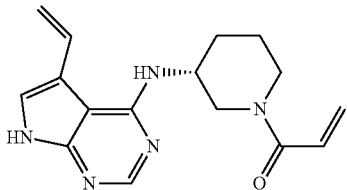 [SMILES: C=CC(=O)N1CCC[C@@H](Nc2ncnc3[nH]cc(C=C)c23)C1] | >10000.0 | | | | |
| 41 | Chiral 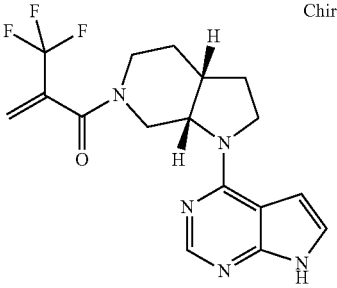 | 1 | 92.5 | 446.4 | | 2.8 |
| 42 | Chiral 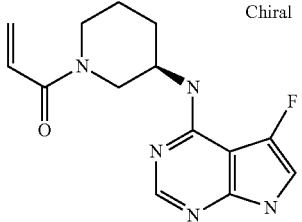 [SMILES: C=CC(=O)N1CCC[C@@H](Nc2ncnc3[nH]cc(F)c23)C1] | 0.9 | 94.4 | 292.8 | 818.6 | >360.0 |
| 43 | Chiral 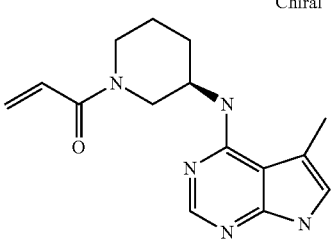 | 1.2 | 99.5 | 116.3 | 463 | 274.1 |
| 44 | 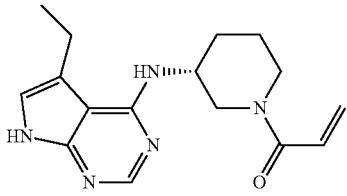 [SMILES: C=CC(=O)N1CCC[C@@H](Nc2ncnc3[nH]cc(CC)c23)C1] | 0.3 | 167.8 | 320.2 | 1181.1 | 165.9 |
| 45 | Chiral 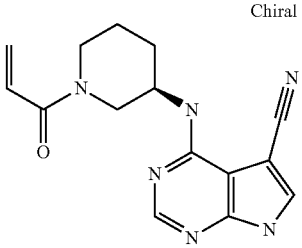 [SMILES: C=CC(=O)N1CCC[C@@H](Nc2ncnc3[nH]cc(C#N)c23)C1] | 1 | 168.5 | 347.7 | 1010.6 | >360.0 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 46 | 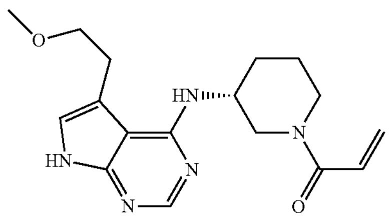 [SMILES: C=CC(=O)N1CCC[C@@H](Nc2ncnc3[nH]cc(CCOC)c23)C1] | 2.8 | 305.4 | 278.8 | 359 | >344.3 |
| 47 | Chiral | 4 | 608.1 | 1076 | | 315.8 |
| 48 | Abs | 0.8 | 101.1 | 65.2 | | 149.8 |
| 49 | 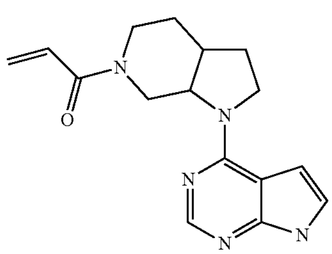 [SMILES: C=CC(=O)N1CCC2CCN(c3ncnc4[nH]ccc34)C2C1] | 1 | 111 | 354.9 | | |
| 50 | Rac | 2 | 115.7 | 202.4 | 925.6 | >360.0 |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 52 | 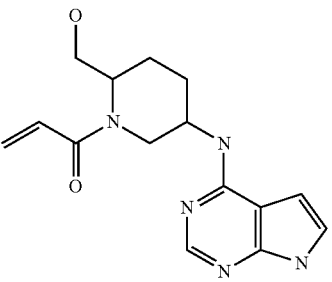 [SMILES: C=CC(=O)N1CC(Nc2ncnc3[nH]ccc23)CCC1CO] | 10.6 | >180.1 | >354.3 | 234.7 | >358.0 |
| 53 | 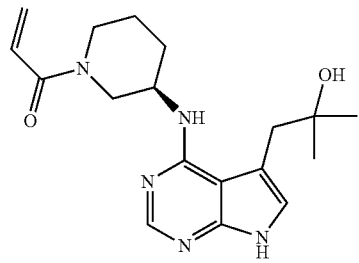 Chiral | 4 | 191.5 | | | |
| 54 | 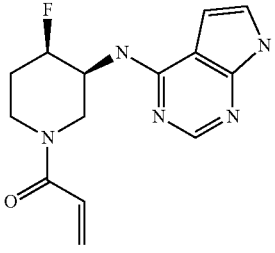 Chiral | 1.7 | 192.2 | 222 | 366.4 | 210 |
| 55 | 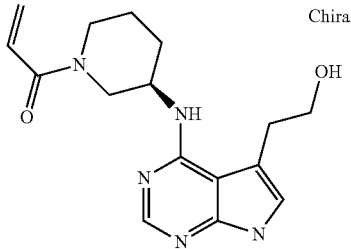 [SMILES: C=CC(=O)N1CCC[C@@H](Nc2ncnc3[nH]cc(CCO)c23)C1] Chiral | 2 | 203 | 430.5 | | |
| 56 | 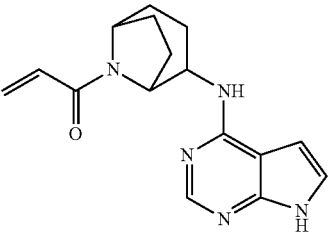 [SMILES: C=CC(=O)N1C2CCC(Nc3ncnc4[nH]ccc34)C1CC2] | 2.5 | 242.3 | 158.4 | 2099.5 | >360.0 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 57 | Chiral | 1.4 | 360.6 | 1227.7 | 2610.3 | 81.2 |
| 58 | Chiral | 2.5 | 360.7 | 2785.4 | 7837.9 | 35 |
| 59 | 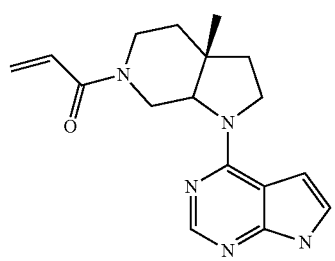 [SMILES: C=CC(=O)N1CC[C@]2(C)CCN(c3ncnc4[nH]ccc34)C2C1] | 3.2 | 402.9 | >2553.1 |  | 184.2 |
| 60 | Chiral | 4.2 | 603 | 2472.7 | 2784.1 | >360.0 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 61 | Chiral | 7.5 | 608.7 | 1029.5 | 1873.4 | |
| 62 | Chiral | 9 | 649.8 | | | |
| 63 | 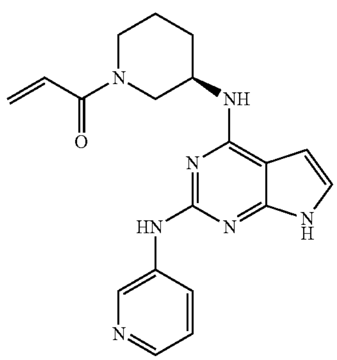 [SMILES: C=CC(=O)N1CCC[C@@H](Nc2nc(Nc3cccnc3)nc3[nH]ccc23)C1] | 9.1 | 671.7 | 1376 | >360.0 | |
| 64 | 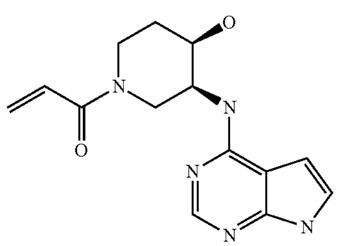 [SMILES: C=CC(=O)N1CC[C@@H](O)[C@@H](Nc2ncnc3[nH]ccc23)C1] | 5.3 | 996.1 | 4638.6 | | |
| 65 | 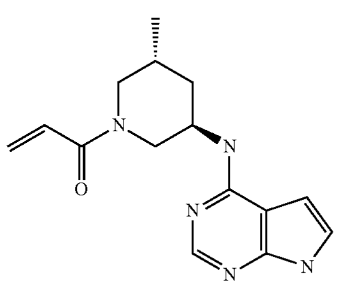 [SMILES: C=CC(=O)N1C[C@H](C)C[C@@H](Nc2ncnc3[nH]ccc23)C1] | 17.9 | 1495.5 | 3742.1 | >10000.0 | 267 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 66 | 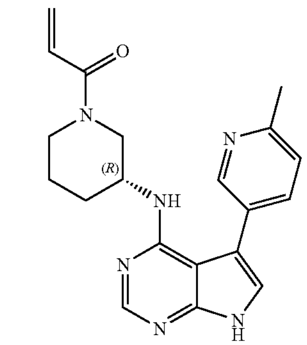 | 14.6 | 1536.1 | | | >360.0 |
| 67 | 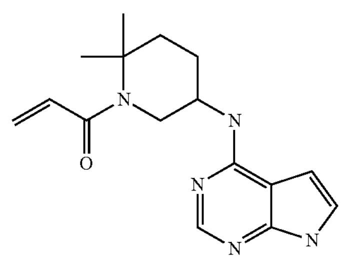 [SMILES: C=CC(=O)N1CC(Nc2ncnc3[nH]ccc23)CCC1(C)C] | 30 | 1682.6 | 6895.2 | | >360.0 |
| 68 | 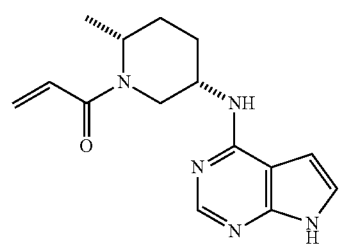 | 144.8 | >2477.8 | | | >360.0 |
| 69 | 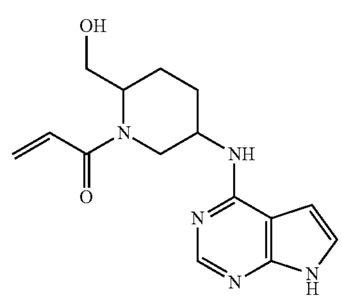 [SMILES: C=CC(=O)N1CC(Nc2ncnc3[nH]ccc23)CCC1CO] | 33.7 | 1852.4 | | | |
| 70 | 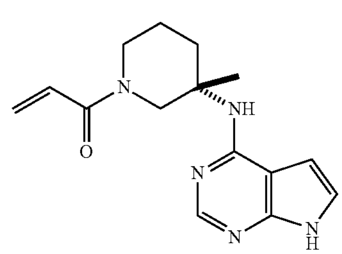 | 19.5 | 1868.3 | 5527.1 | | 343.2 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 71 | 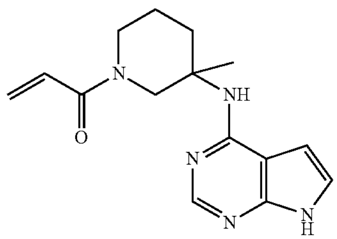 [SMILES: C=CC(=O)N1CCCC(C)(Nc2ncnc3[nH]ccc23)C1] | 57.9 | 3423.4 | >10000.0 | | 229.2 |
| 72 | 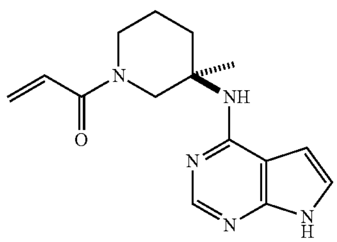 | 828.2 | >10000.0 | >10000.0 | | |
| 73 | Chiral | 48.4 | 1959.2 | | | 195 |
| 74 | Chiral | 22.8 | 2021.2 | | | 103 |
| 75 | Chiral | 715.6 | >10000.0 | | | >360.0 |

TABLE 1-continued
Enzyme Assay and Blood Stability Data.
| Ex | Structure | JAK3 (4 µM ATP) IC$_{50}$ (nM) | JAK3 (1 mM ATP) IC$_{50}$ (nM) | PBMC IL15- pSTAT5 IC$_{50}$ (nM) | HWB- IL15- pSTAT5 IC$_{50}$ (nM) | Human blood stability t$_{1/2}$ (min) |
|---|---|---|---|---|---|---|
| 76 | 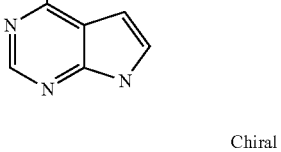 | 42.4 | 2038.2 | >6077.4 | | |
| 77 | Chiral 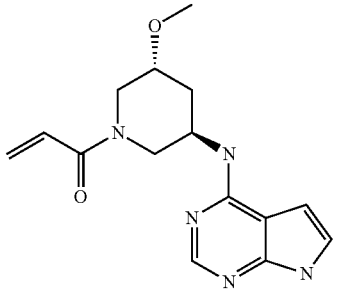 | 15.5 | 2065.3 | 3972.7 | | 252 |
| 78 | Chiral 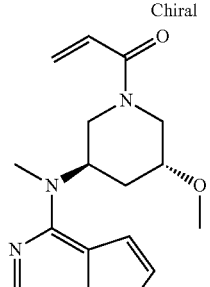 | 386.6 | >10000.0 | >10000.0 | | |
| 79 | Chiral 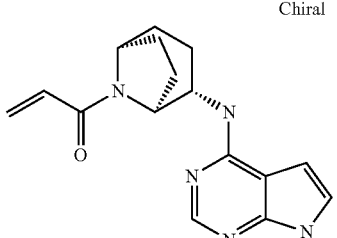 | 26.6 | 2379.3 | 2365.5 | | 230 |
| 80 | 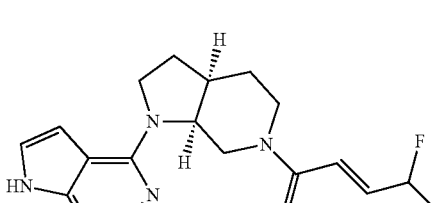 | 22.7 | 2944.1 | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 81 | 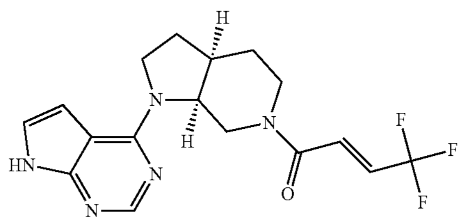 [SMILES: O=C(/C=C/C(F)(F)F)N1CC[C@@H]2CCN(c3ncnc4[nH]ccc34)[C@@H]2C1] | 35.3 | 3753.6 | >4000.0 | | 16.9 |
| 82 | 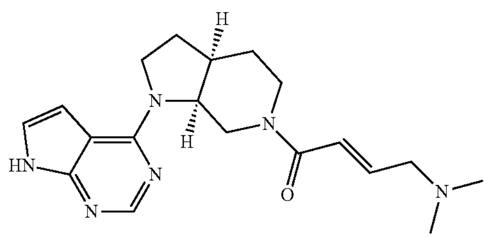 [SMILES: CN(C)C/C=C/C(=O)N1CC[C@@H]2CCN(c3ncnc4[nH]ccc34)[C@@H]2C1] | 57.2 | 5292.6 | >7295.1 | | >360.0 |
| 84 | Chiral | 727 | >10000.0 | | | |
| 85 | Chiral | 2181.8 | >10000.0 | | | >360.0 |
| 86 | Chiral | 149.1 | >10000.0 | | | >360.0 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 87 | 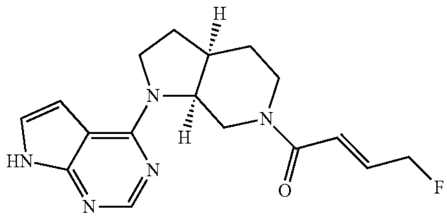 [SMILES: O=C(/C=C/CF)N1CC[C@@H]2CCN(c3ncnc4[nH]ccc34)[C@@H]2C1] | 138.9 | >10000.0 | | | |
| 88 | 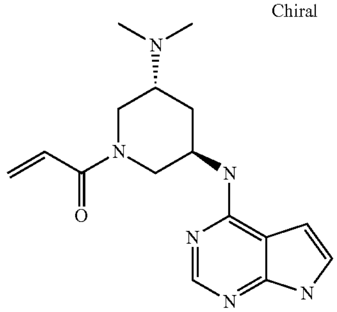 [SMILES: C=CC(=O)N1C[C@H](Nc2ncnc3[nH]ccc23)C[C@@H](N(C)C)C1] | 18.2 | 3388.5 | | | 74 |
| 89 | 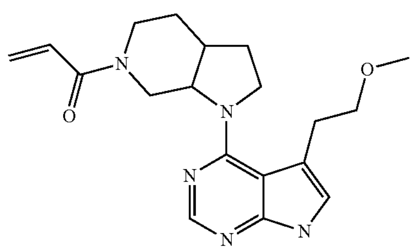 [SMILES: C=CC(=O)N1CCC2CCN(c3ncnc4[nH]cc(CCOC)c34)C2C1] | 35.2 | 3943.9 | >6156.8 | | |
| 90 | 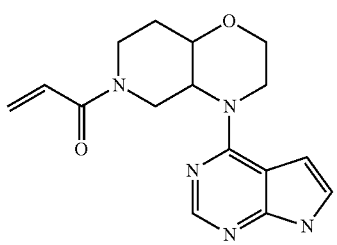 [SMILES: C=CC(=O)N1CCC2OCCN(c3ncnc4[nH]ccc34)C2C1] | 49.3 | 4435.8 | >10000.0 | | 168.2 |
| 91 | 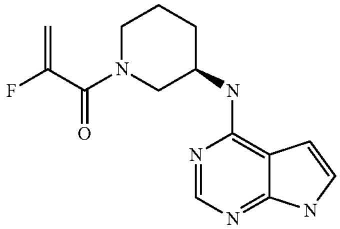 | 56.5 | 4650.7 | | | |
| 92 | 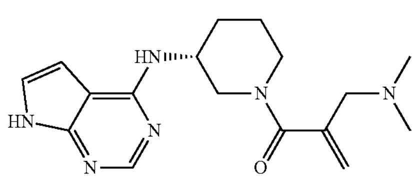 [SMILES: C=C(CN(C)C)C(=O)N1CCC[C@@H](Nc2ncnc3[nH]ccc23)C1] | 4750.2 | >10000.0 | >10000.0 | | |

TABLE 1-continued

Enzyme Assay and Blood Stability Data.

| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 93 | 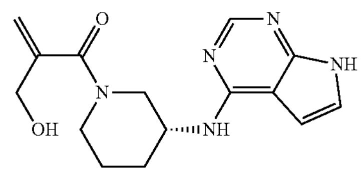 [SMILES: C=C(CO)C(=O)N1CCC[C@@H](Nc2ncnc3[nH]ccc23)C1] | 703 | >10000.0 | >10000.0 | | |
| 94 | 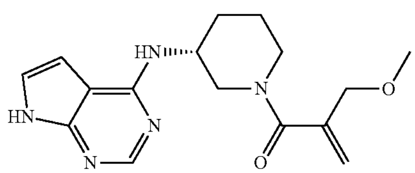 [SMILES: C=C(COC)C(=O)N1CCC[C@@H](Nc2ncnc3[nH]ccc23)C1] | 801.5 | >10000.0 | >10000.0 | | |
| 95 | Chiral | 2477 | >10000.0 | | | >360.0 |
| 96 | 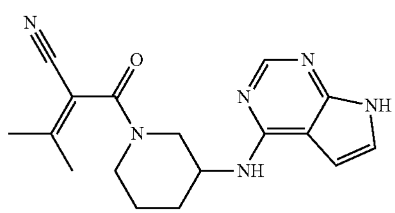 [SMILES: CC(C)=C(C#N)C(=O)N1CCCC(Nc2ncnc3[nH]ccc23)C1] | 2741.7 | >10000.0 | | | |
| 97 | 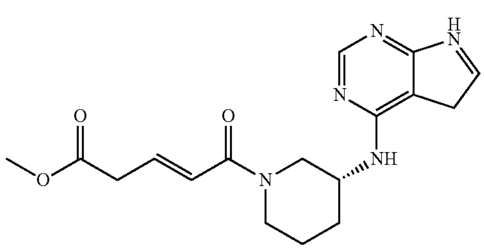 | 904.4 | >10000.0 | | | |
| 98 | 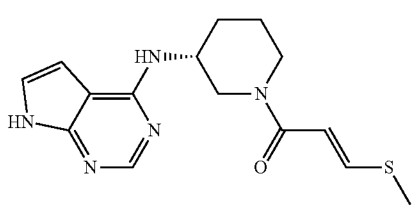 [SMILES: CS/C=C/C(=O)N1CCC[C@@H](Nc2ncnc3[nH]ccc23)C1] | 2632.1 | >10000.0 | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 99 | 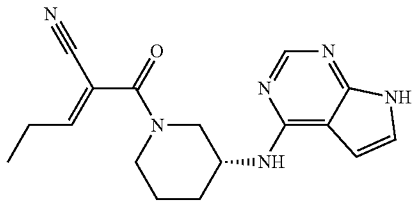 [SMILES: CC/C=C(\C#N)C(=O)N1CCC[C@@H](Nc2ncnc3[nH]ccc23)C1] | 254.7 | >10000.0 | | | |
| 100 | Chiral | 653.9 | >10000.0 | | | |
| 101 | Chiral | 881 | >10000.0 | | | |
| 102 | Chiral | 352.7 | >10000.0 | | | |
| 103 | 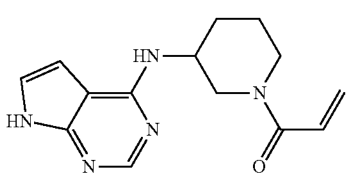 [SMILES: C=CC(=O)N1CCCC(Nc2ncnc3[nH]ccc23)C1] | 4.7 | | | | |
| 104 | 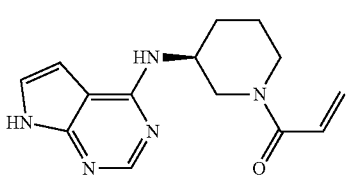 [SMILES: C=CC(=O)N1CCC[C@H](Nc2ncnc3[nH]ccc23)C1] | 64.5 | | | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 105 | Chiral 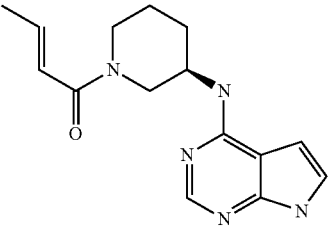 | 2477 | >10000.0 | | | >360.0 |
| 106 | 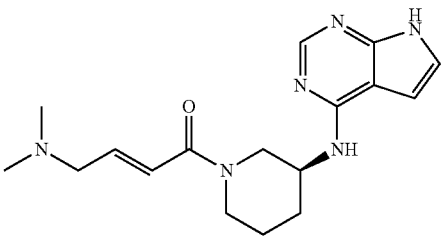 [SMILES: CN(C)C/C=C/C(=O)N1CCC[C@H](Nc2ncnc3[nH]ccc23)C1] | 49.1 | | | | |
| 107 | 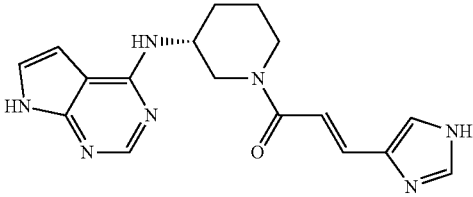 [SMILES: O=C(/C=C/c1c[nH]cn1)N1CCC[C@@H](Nc2ncnc3[nH]ccc23)C1] | 1160.2 | | | | |
| 108 | 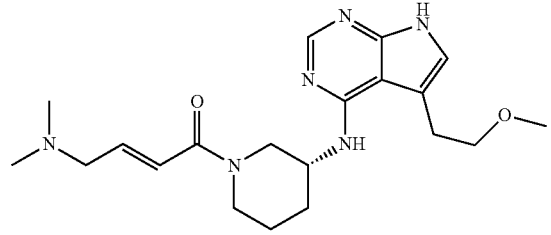 | 527.9 | >10000.0 | | | >360.0 |
| 109 | 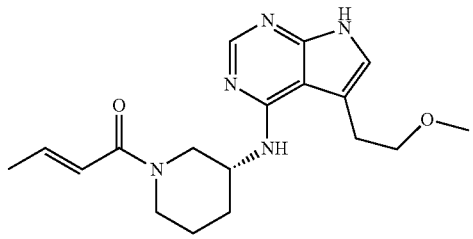 [SMILES: C/C=C/C(=O)N1CCC[C@@H](Nc2ncnc3[nH]cc(CCOC)c23)C1] | 2818.7 | | | | |
| 110 | 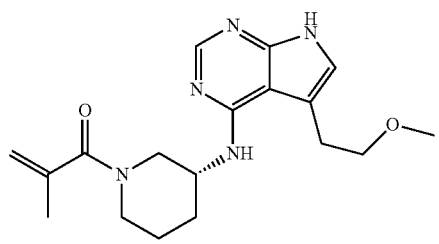 [SMILES: C=C(C)C(=O)N1CCC[C@@H](Nc2ncnc3[nH]cc(CCOC)c23)C1] | 1431.5 | | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15- pSTAT5 IC$_{50}$ (nM) | HWB- IL15- pSTAT5 IC$_{50}$ (nM) | Human blood stability t$_{1/2}$ (min) |
|---|---|---|---|---|---|---|
| 111 | Chiral | 39.2 | 4738.5 | | | |
| 112 | Chiral | 188.7 | 7569.7 | | | 142 |
| 113 | Rac | 42.4 | 8478.1 | >10000.0 | | |
| 114 | Abs | 143.7 | >9514.4 | | | >360.0 |
| 115 | Abs | 462.6 | >10000.0 | | | 185 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 116 | 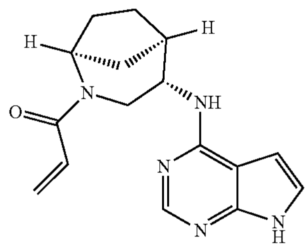 [SMILES: C=CC(=O)N1C[C@@H](Nc2ncnc3[nH]ccc23)[C@@H]2CC[C@H]1C2] | 417.6 | >10000.0 | >10000.0 | >10000.0 | 281 |
| 117 | 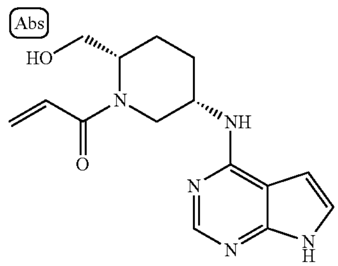 [SMILES: C=CC(=O)N1C[C@@H](Nc2ncnc3[nH]ccc23)CC[C@H]1CO] | 416.5 | >10000.0 | >10000.0 | >10000.0 | >360.0 |
| 118 | 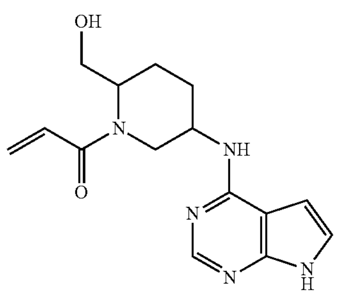 [SMILES: C=CC(=O)N1CC(Nc2ncnc3[nH]ccc23)CCC1CO] | 323.4 | >10000.0 | >10000.0 | | >333.5 |
| 119 | 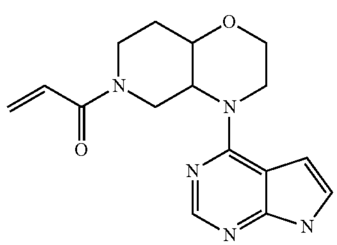 [SMILES: C=CC(=O)N1CCC2OCCN(c3ncnc4[nH]ccc34)C2C1] | 95.9 | >10000.0 | >10000.0 | | |
| 120 | 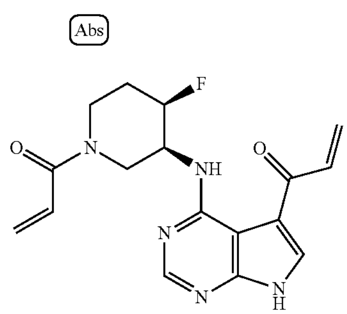 [SMILES: C=CC(=O)c1c[nH]c2ncnc(N[C@H]3CN(C(=O)C=C)CC[C@H]3F)c12] | 692.1 | >10000.0 | >10000.0 | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 121 | 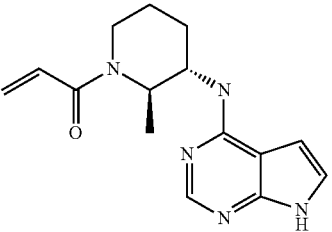 Chiral | 647.9 | >10000.0 | | | >360.0 |
| 122 | 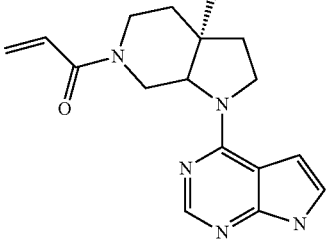 | 75.6 | >10000.0 | | | |
| 123 | 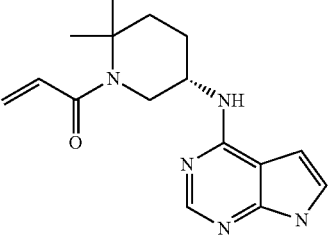 Chiral | 2112.4 | >10000.0 | | | |
| 124 | 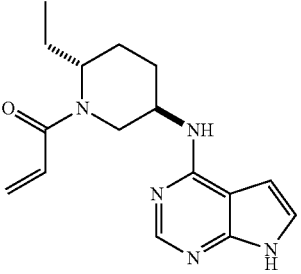 | 264.6 | >10000.0 | | | |
| 125 | 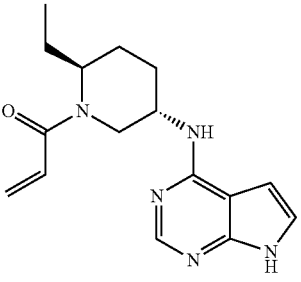 [SMILES: C=CC(=O)N1C[C@@H](Nc2ncnc3[nH]ccc23)CC[C@@H]1CC] | 1424 | >10000.0 | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15- pSTAT5 IC$_{50}$ (nM) | HWB- IL15- pSTAT5 IC$_{50}$ (nM) | Human blood stability t$_{1/2}$ (min) |
|---|---|---|---|---|---|---|
| 126 | 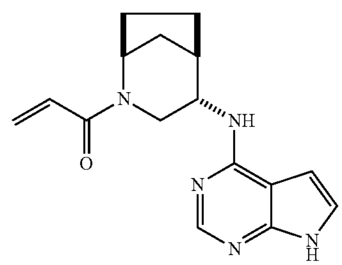 | 602.5 | >10000.0 | | | |
| 127 | 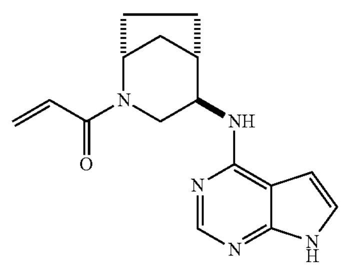 | 190.2 | >10000.0 | | | |
| 128 | 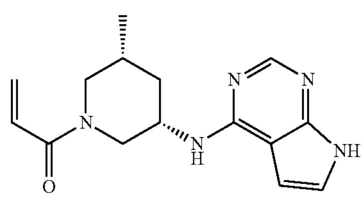 [SMILES: C=CC(=O)N1C[C@H](C)C[C@H](Nc2ncnc3[nH]ccc23)C1] | 443.6 | >10000.0 | | | 304 |
| 129 | 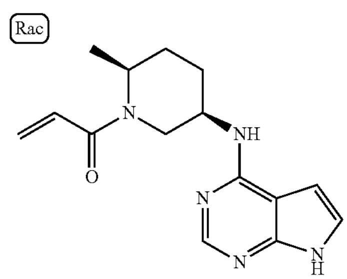 [SMILES: C=CC(=O)N1C[C@H](Nc2ncnc3[nH]ccc23)CC[C@@H]1C] | | | 113.8 | 797.3 | |
| 130 | 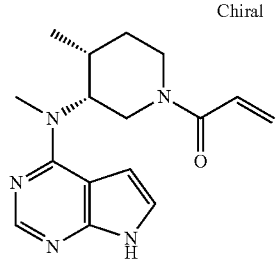 [SMILES: C=CC(=O)N1CC[C@@H](C)[C@@H](N(C)c2ncnc3[nH]ccc23)C1] | 75.2 | | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 131 | Chiral | 988.1 | | | | |
| 132 | Rac | 2076.6 | | | | |
| 133 | Chiral | 18 | | | | |
| 134 | Chiral | 71.2 | | | | |
| 135 | Abs | >10000.0 | | | | |

TABLE 1-continued
Enzyme Assay and Blood Stability Data.
| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 136 | 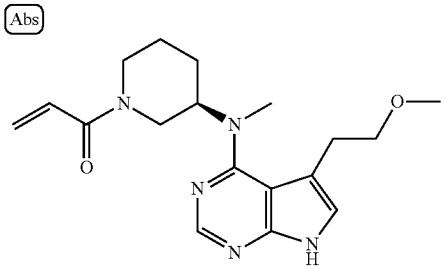 [SMILES: C=CC(=O)N1CCC[C@@H](N(C)c2ncnc3[nH]cc(CCOC)c23)C1] | 238.3 | | | | |
| 137 | 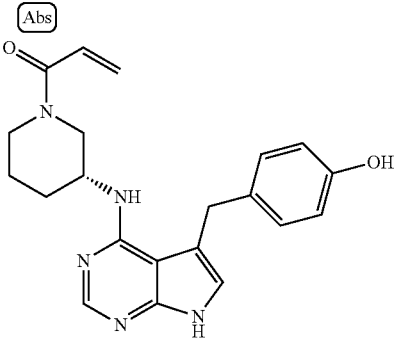 [SMILES: C=CC(=O)N1CCC[C@@H](Nc2ncnc3[nH]cc(Cc4ccc(O)cc4)c23)C1] | 0.3 | | | | |
| 138 | 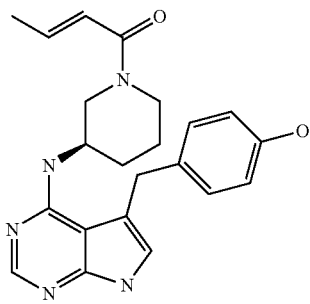 | 110.5 | | | | |
| 139 | 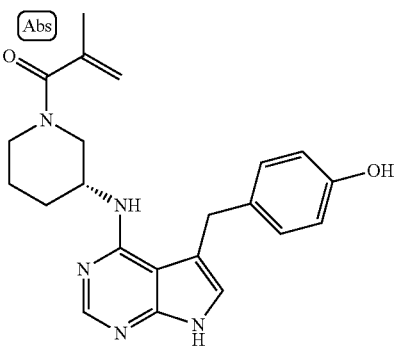 [SMILES: C=C(C)C(=O)N1CCC[C@@H](Nc2ncnc3[nH]cc(Cc4ccc(O)cc4)c23)C1] | 83.1 | | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 142 | 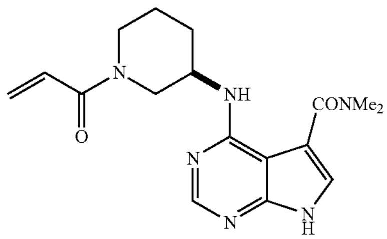 | 225.3 | | | | |
| 143 | 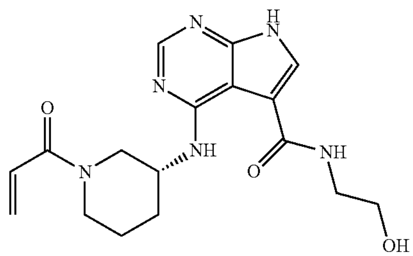 [SMILES: C=CC(=O)N1CCC[C@@H](Nc2ncnc3[nH]cc(C(=O)NCCO)c23)C1] | 144.5 | | | | |
| 144 | 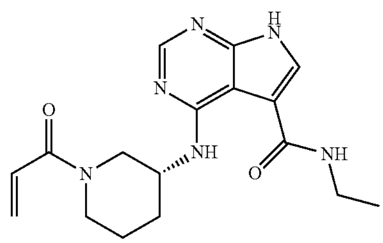 [SMILES: C=CC(=O)N1CCC[C@@H](Nc2ncnc3[nH]cc(C(=O)NCC)c23)C1] | 139.4 | | | | |
| 145 | 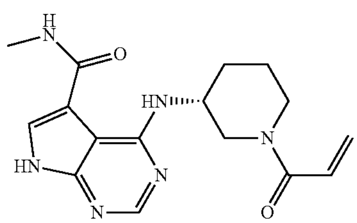 [SMILES: C=CC(=O)N1CCC[C@@H](Nc2ncnc3[nH]cc(C(=O)NC)c23)C1] | 112.1 | | | | |
| 146 | 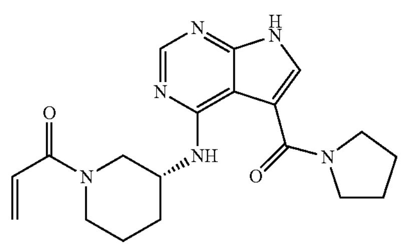 [SMILES: C=CC(=O)N1CCC[C@@H](Nc2ncnc3[nH]cc(C(=O)N4CCCC4)c23)C1] | 957.3 | | | | |
| 147 | 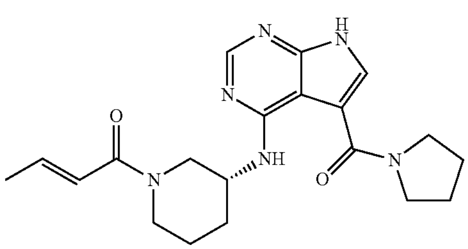 [SMILES: C/C=C/C(=O)N1CCC[C@@H](Nc2ncnc3[nH]cc(C(=O)N4CCCC4)c23)C1] | >10000.0 | | | | |

TABLE 1-continued

Enzyme Assay and Blood Stability Data.

| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 148 | 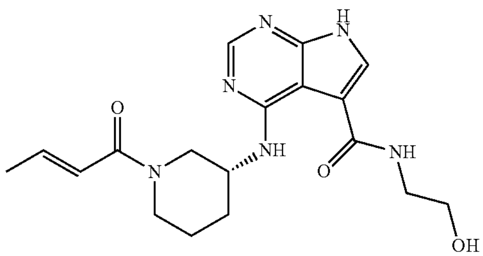 [SMILES: C/C=C/C(=O)N1CCC[C@@H](Nc2ncnc3[nH]cc(C(=O)NCCO)c23)C1] | 6957.2 | | | | |
| 149 | 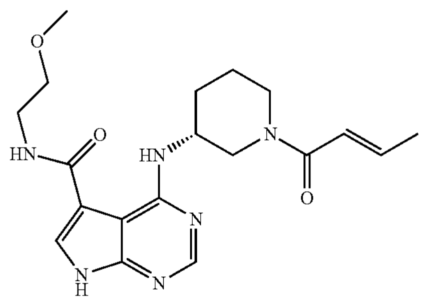 [SMILES: C/C=C/C(=O)N1CCC[C@@H](Nc2ncnc3[nH]cc(C(=O)NCCOC)c23)C1] | >10000.0 | | | | |
| 151 | 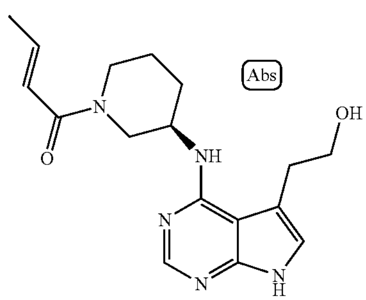 [SMILES: C/C=C/C(=O)N1CCC[C@@H](Nc2ncnc3[nH]cc(CCO)c23)C1] | 3490.6 | | | | |
| 152 | 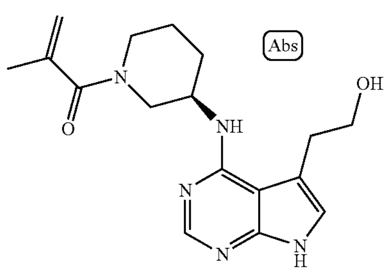 [SMILES: C=C(C)C(=O)N1CCC[C@@H](Nc2ncnc3[nH]cc(CCO)c23)C1] | 4242.8 | | | | |
| 153 | 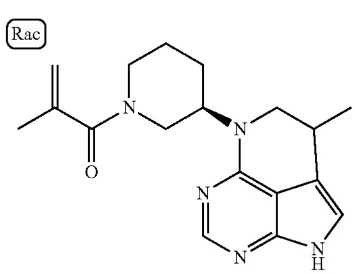 [SMILES: C=C(C)C(=O)N1CCC[C@@H](N2CC(C)c3c[nH]c4ncnc2c34)C1] | 9444.6 | | | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 154 | 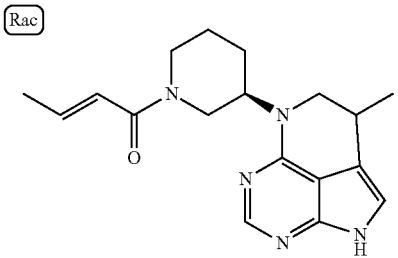 [SMILES: C/C=C/C(=O)N1CCC[C@@H](N2CC(C)c3c[nH]c4ncnc2c34)C1] | 4936.8 | | | | |
| 156 | 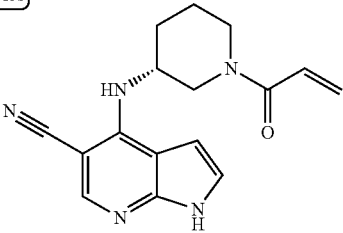 | 7.2 | | | | |
| 157 | 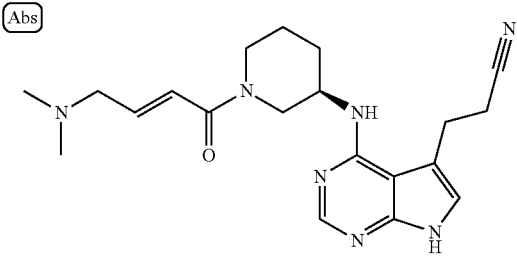 [SMILES: CN(C)C/C=C/C(=O)N1CCC[C@@H](Nc2ncnc3[nH]cc(CCC#N)c23)C1] | 1470.4 | | | | |
| 158 | 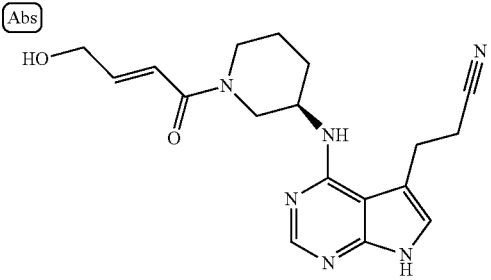 [SMILES: N#CCCc1c[nH]c2ncnc(N[C@@H]3CCCN(C(=O)/C=C/CO)C3)c12] | >10000.0 | | | | |
| 159 | 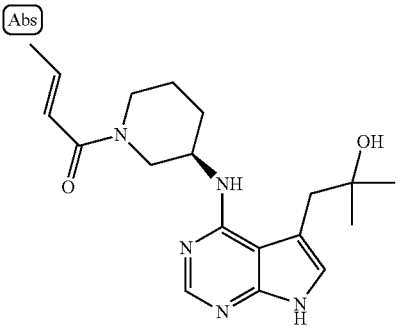 [SMILES: C/C=C/C(=O)N1CCC[C@@H](Nc2ncnc3[nH]cc(CC(C)(C)O)c23)C1] | >10000.0 | | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 160 | [Rac] structure | >10000.0 | | | | |
| 161 | [Abs] structure | 0.3 | 45.3 | 76.9 | 455.3 | >323.5 |
| 162 | structure | 1.2 | 169 | 361.3 | 1003.2 | >360.0 |
| 163 | [Abs] structure | 0.6 | 47.1 | 108.9 | 521.8 | 290.1 |
| 164 | [Abs] structure | 4.1 | 314.4 | 1653.3 | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 165 | 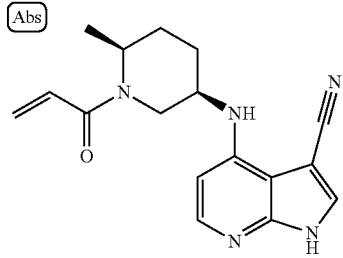 [SMILES: C=CC(=O)N1C[C@H](Nc2ccnc3[nH]cc(C#N)c23)CC[C@@H]1C] | 0.5 | 22.7 | 40.6 | 380.3 | >349.4 |
| 166 | 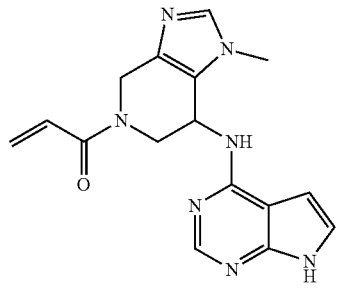 [SMILES: C=CC(=O)N1Cc2ncn(C)c2C(Nc2ncnc3[nH]ccc23)C1] | 369.6 | >10000.0 | | | |
| 167 | 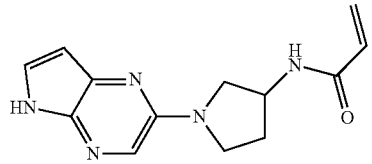 [SMILES: C=CC(=O)NC1CCN(c2cnc3[nH]ccc3n2)C1] | 2410.5 | | | | |
| 168 | 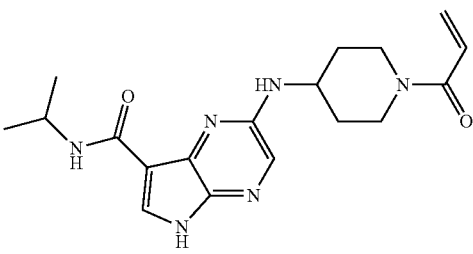 [SMILES: C=CC(=O)N1CCC(Nc2cnc3[nH]cc(C(=O)NC(C)C)c3n2)CC1] | 0.2 | 7.5 | 37.1 | 135.7 | >349.6 |
| 169 | 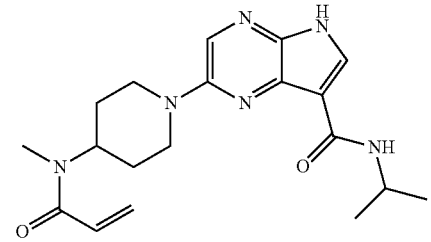 [SMILES: C=CC(=O)N(C)C1CCN(c2cnc3[nH]cc(C(=O)NC(C)C)c3n2)CC1] | 42.8 | 4732.3 | | | |
| 170 | 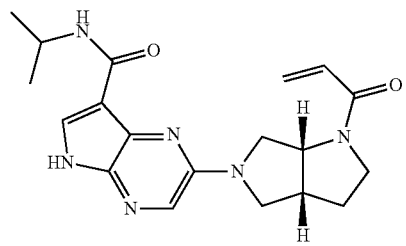 [SMILES: C=CC(=O)N1CC[C@@H]2CN(c3cnc4[nH]cc(C(=O)NC(C)C)c4n3)C[C@@H]21] | 3.3 | 392.5 | 1369 | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 171 | 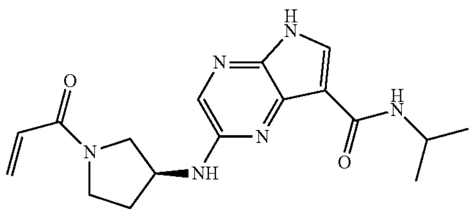 [SMILES: C=CC(=O)N1CC[C@H](Nc2cnc3[nH]cc(C(=O)NC(C)C)c3n2)C1] | 0.4 | 32.7 | 726 | 2951.1 | >360.0 |
| 172 | 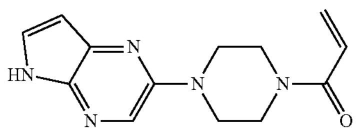 [SMILES: C=CC(=O)N1CCN(c2cnc3[nH]ccc3n2)CC1] | 25.5 | 2230.8 | | | |
| 173 | 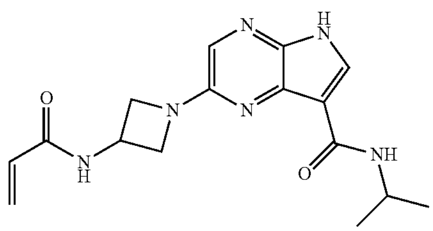 [SMILES: C=CC(=O)NC1CN(c2cnc3[nH]cc(C(=O)NC(C)C)c3n2)C1] | 8.1 | 692.1 | | | |
| 174 | 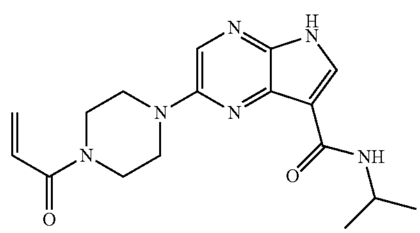 [SMILES: C=CC(=O)N1CCN(c2cnc3[nH]cc(C(=O)NC(C)C)c3n2)CC1] | 0.4 | 34.8 | 58.4 | 622.7 | 249.3 |
| 175 | 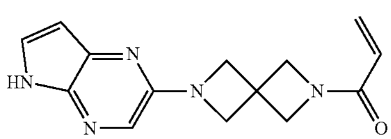 [SMILES: C=CC(=O)N1CC2(C1)CN(c1cnc3[nH]ccc3n1)C2] | 1610.8 | | | | |
| 176 | 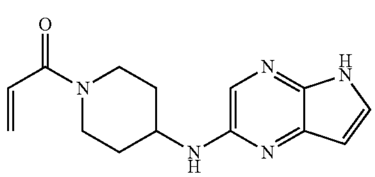 [SMILES: C=CC(=O)N1CCC(Nc2cnc3[nH]ccc3n2)CC1] | 7.2 | 910.3 | | | >360.0 |
| 177 | 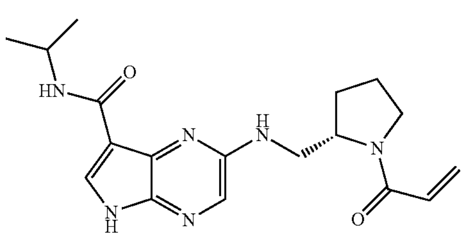 [SMILES: C=CC(=O)N1CCC[C@H]1CNc1cnc2[nH]cc(C(=O)NC(C)C)c2n1] | 0.7 | 44.4 | 107.6 | 804.3 | >321.0 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 178 | 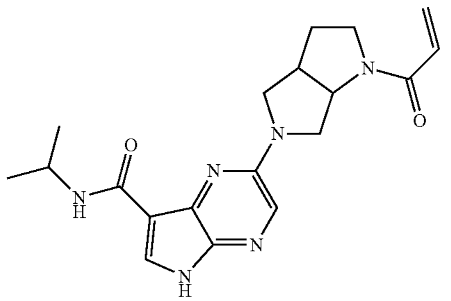 [SMILES: C=CC(=O)N1CCC2CN(c3cnc4[nH]cc(C(=O)NC(C)C)c4n3)CC21] | 1.1 | 102 | 208.2 | 2556.7 | 143 |
| 179 | 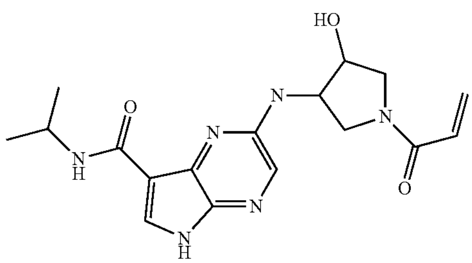 [SMILES: C=CC(=O)N1CC(O)C(Nc2cnc3[nH]cc(C(=O)NC(C)C)c3n2)C1] | 2.3 | 308.6 | >10000.0 | >10000.0 | |
| 180 | 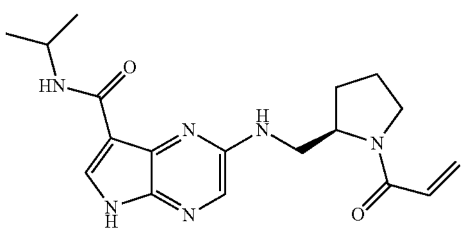 [SMILES: C=CC(=O)N1CCC[C@@H]1CNc1cnc2[nH]cc(C(=O)NC(C)C)c2n1] | 12.4 | 1498.5 | | | |
| 181 | 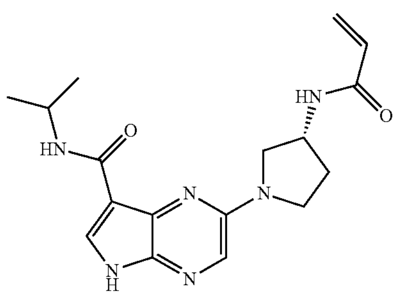 [SMILES: C=CC(=O)N[C@@H]1CCN(c2cnc3[nH]cc(C(=O)NC(C)C)c3n2)C1] | 10.3 | 1016.9 | | | |
| 182 | 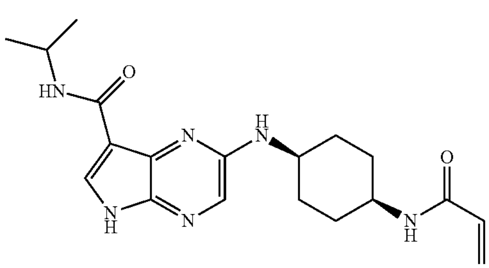 [SMILES: C=CC(=O)N[C@H]1CC[C@@H](Nc2cnc3[nH]cc(C(=O)NC(C)C)c3n2)CC1] | 11.4 | 975.3 | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 183 | 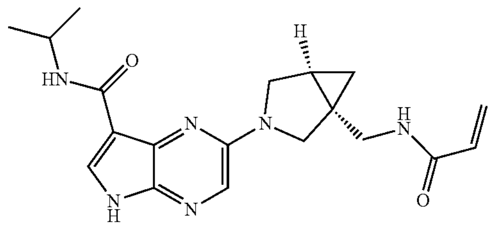 [SMILES: C=CC(=O)NC[C@@]12C[C@@H]1CN(c1cnc3[nH]cc(C(=O)NC(C)C)c3n1)C2] | 9.6 | 793.9 | | | |
| 184 | 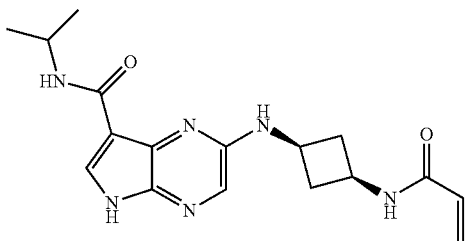 [SMILES: C=CC(=O)N[C@H]1C[C@@H](Nc2cnc3[nH]cc(C(=O)NC(C)C)c3n2)C1] | 1.5 | 210.3 | 3407.1 | >10000.0 | >360.0 |
| 185 | 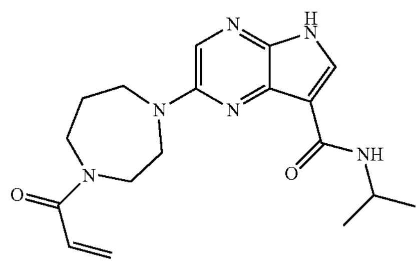 [SMILES: C=CC(=O)N1CCCN(c2cnc3[nH]cc(C(=O)NC(C)C)c3n2)CC1] | 20.4 | 1457 | | | |
| 186 | 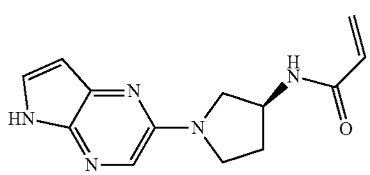 [SMILES: C=CC(=O)N[C@H]1CCN(c2cnc3[nH]ccc3n2)C1] | 2347.6 | | | | |
| 187 | 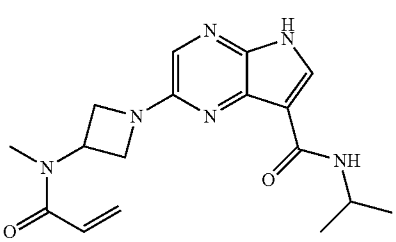 [SMILES: C=CC(=O)N(C)C1CN(c2cnc3[nH]cc(C(=O)NC(C)C)c3n2)C1] | 0.6 | 27.2 | 709.5 | | >360.0 |
| 188 | 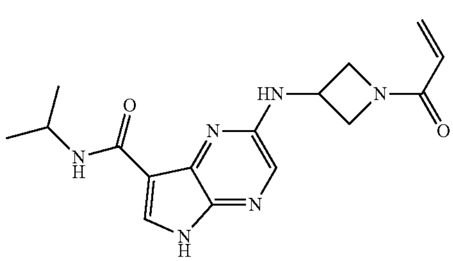 [SMILES: C=CC(=O)N1CC(Nc2cnc3[nH]cc(C(=O)NC(C)C)c3n2)C1] | 0.3 | 8.8 | 154.6 | 245.5 | 96 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 189 | 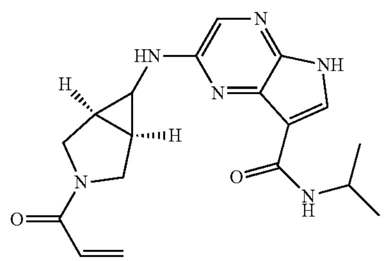 [SMILES: C=CC(=O)N1C[C@@H]2C(Nc3cnc4[nH]cc(C(=O)NC(C)C)c4n3)[C@@H]2C1] | 1.1 | 197.9 | 1735.1 | >10000.0 | >360.0 |
| 190 | 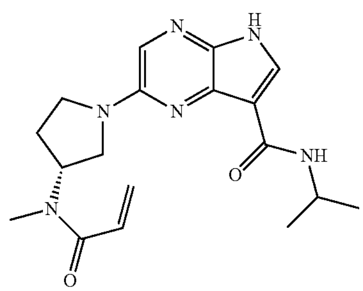 [SMILES: C=CC(=O)N(C)[C@@H]1CCN(c2cnc3[nH]cc(C(=O)NC(C)C)c3n2)C1] | 13.9 | 1014.7 | | | |
| 191 | 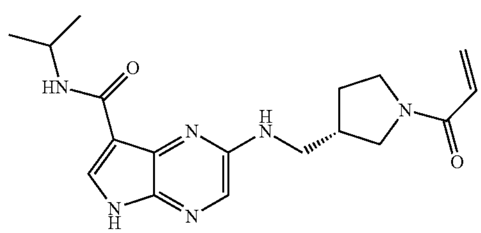 [SMILES: C=CC(=O)N1CC[C@@H](CNc2cnc3[nH]cc(C(=O)NC(C)C)c3n2)C1] | 1.5 | 137.6 | 2647.9 | 9582.3 | >360.0 |
| 192 | 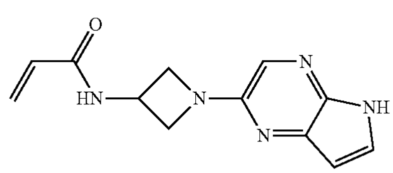 [SMILES: C=CC(=O)NC1CN(c2cnc3[nH]ccc3n2)C1] | 271.6 | | | | |
| 193 | 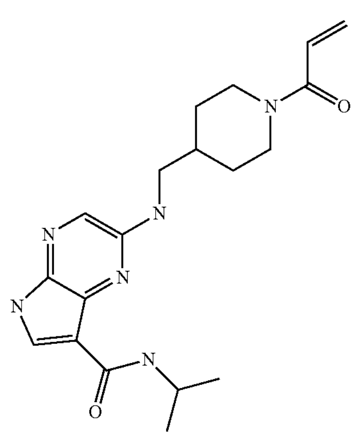 [SMILES: C=CC(=O)N1CCC(CNc2cnc3[nH]cc(C(=O)NC(C)C)c3n2)CC1] | 29 | 2294.2 | | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 194 | 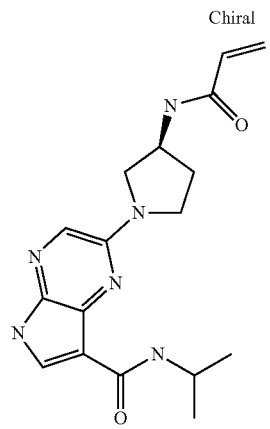 [SMILES: C=CC(=O)N[C@H]1CCN(c2cnc3[nH]cc(C(=O)NC(C)C)c3n2)C1] | 12.7 | 1659.3 | | | |
| 195 | 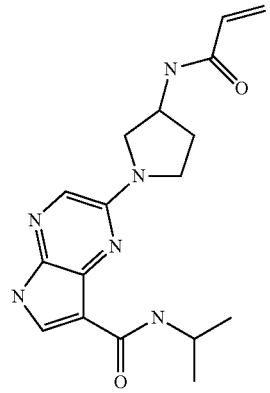 [SMILES: C=CC(=O)NC1CCN(c2cnc3[nH]cc(C(=O)NC(C)C)c3n2)C1] | 12.1 | 970 | | | |
| 196 | 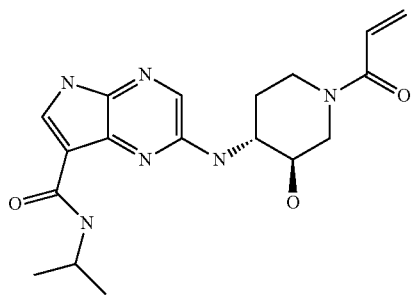 [SMILES: C=CC(=O)N1CC[C@@H](Nc2cnc3[nH]cc(C(=O)NC(C)C)c3n2)[C@H](O)C1] | 0.3 | 30.6 | 1491.8 | 3290.9 | >360.0 |

TABLE 1-continued

Enzyme Assay and Blood Stability Data.

| Ex | Structure | JAK3 (4 µM ATP) IC$_{50}$ (nM) | JAK3 (1 mM ATP) IC$_{50}$ (nM) | PBMC IL15- pSTAT5 IC$_{50}$ (nM) | HWB- IL15- pSTAT5 IC$_{50}$ (nM) | Human blood stability t$_{1/2}$ (min) |
|---|---|---|---|---|---|---|
| 197 | 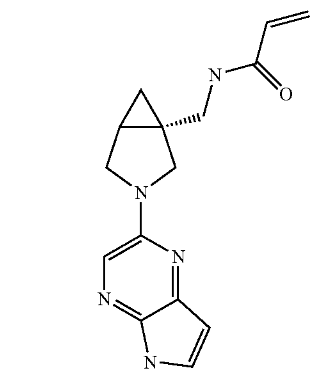 [SMILES: C=CC(=O)NC[C@@]12CC1CN(c1cnc3[nH]ccc3n1)C2] | 3486 | | | | |
| 198 | 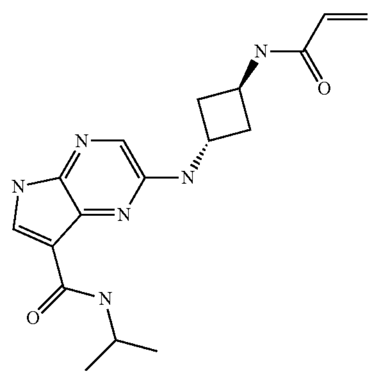 [SMILES: C=CC(=O)N[C@H]1C[C@H](Nc2cnc3[nH]cc(C(=O)NC(C)C)c3n2)C1] | 1 | 77.6 | 1170.4 | | >360.0 |
| 199 | 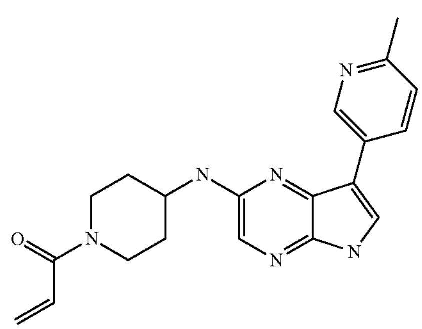 [SMILES: C=CC(=O)N1CCC(Nc2cnc3[nH]cc(-c4ccc(C)nc4)c3n2)CC1] | 1.2 | 101 | 734.9 | >10000.0 | >360.0 |
| 200 | 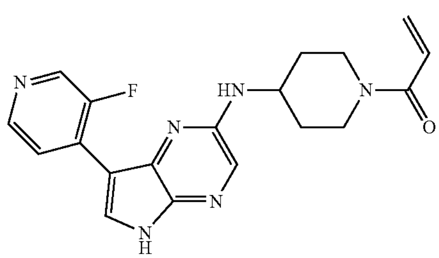 [SMILES: C=CC(=O)N1CCC(Nc2cnc3[nH]cc(-c4ccncc4F)c3n2)CC1] | 0.8 | 88.9 | 818.6 | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 201 | 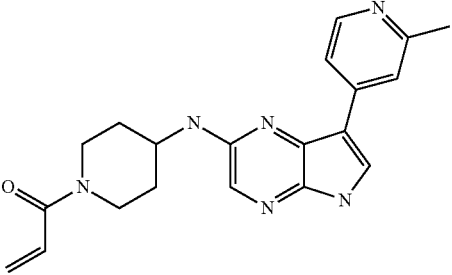 [SMILES: C=CC(=O)N1CCC(Nc2cnc3[nH]cc(-c4ccnc(C)c4)c3n2)CC1] | 0.5 | 28 | 262 | 3478.4 | >360.0 |
| 202 | 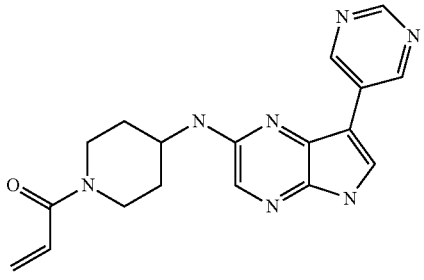 [SMILES: C=CC(=O)N1CCC(Nc2cnc3[nH]cc(-c4cncnc4)c3n2)CC1] | 0.9 | 99.1 | 669.9 | 3739.3 | |
| 203 | 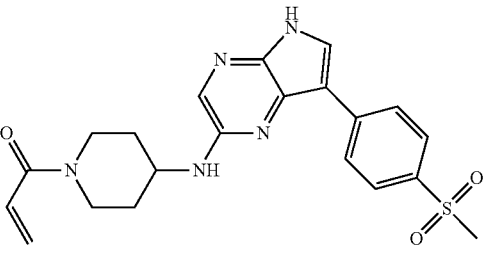 [SMILES: C=CC(=O)N1CCC(Nc2cnc3[nH]cc(-c4ccc(S(C)(=O)=O)cc4)c3n2)CC1] | 2 | 147.8 | 1182.6 | | |
| 204 | 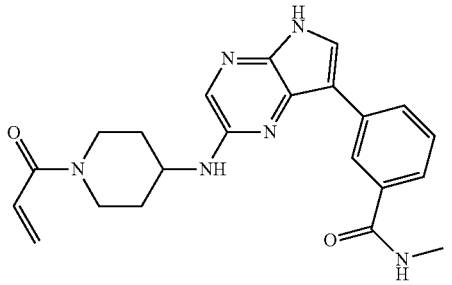 [SMILES: C=CC(=O)N1CCC(Nc2cnc3[nH]cc(-c4cccc(C(=O)NC)c4)c3n2)CC1] | 0.5 | 49.3 | 854.9 | | |
| 205 | 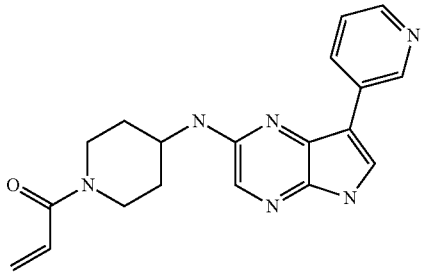 [SMILES: C=CC(=O)N1CCC(Nc2cnc3[nH]cc(-c4cccnc4)c3n2)CC1] | 0.5 | 14.8 | 218.7 | 1884.9 | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 206 | 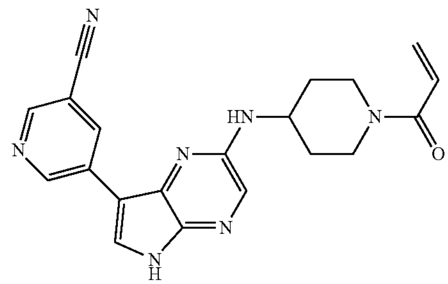 [SMILES: C=CC(=O)N1CCC(Nc2cnc3[nH]cc(-c4cncc(C#N)c4)c3n2)CC1] | 0.1 | 19.6 | 163 | >10000.0 | |
| 207 | 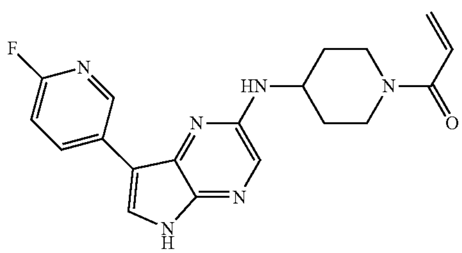 [SMILES: C=CC(=O)N1CCC(Nc2cnc3[nH]cc(-c4ccc(F)nc4)c3n2)CC1] | 0.3 | 28.9 | 185.4 | 2824.3 | >360.0 |
| 208 | 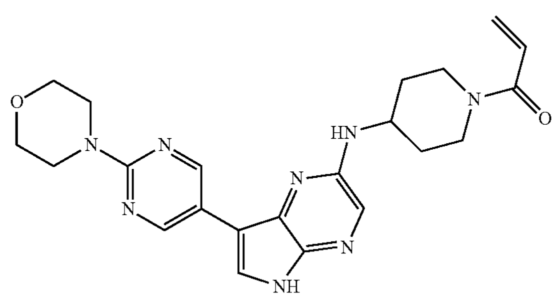 [SMILES: C=CC(=O)N1CCC(Nc2cnc3[nH]cc(-c4cnc(N5CCOCC5)nc4)c3n2)CC1] | 5.9 | 575.8 | | | |
| 209 | 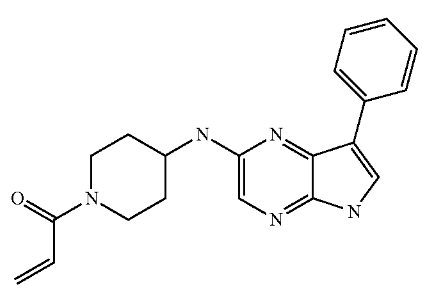 [SMILES: C=CC(=O)N1CCC(Nc2cnc3[nH]cc(-c4ccccc4)c3n2)CC1] | 0.2 | 14.3 | 152.4 | 6685.8 | |
| 210 | 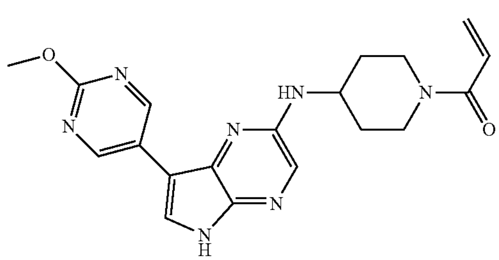 [SMILES: C=CC(=O)N1CCC(Nc2cnc3[nH]cc(-c4cnc(OC)nc4)c3n2)CC1] | 0.4 | 45.4 | 462.5 | 2679.5 | >360.0 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15- pSTAT5 IC$_{50}$ (nM) | HWB- IL15- pSTAT5 IC$_{50}$ (nM) | Human blood stability t$_{1/2}$ (min) |
|---|---|---|---|---|---|---|
| 211 | 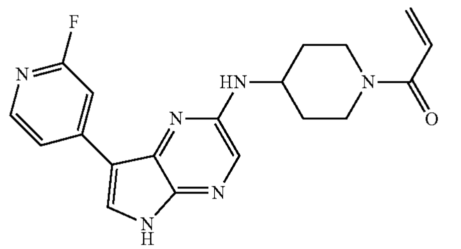 [SMILES: C=CC(=O)N1CCC(Nc2cnc3[nH]cc(-c4ccnc(F)c4)c3n2)CC1] | 0.2 | 34.2 | 205.6 | 4330.1 | |
| 212 | 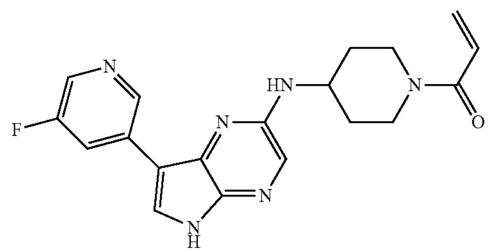 [SMILES: C=CC(=O)N1CCC(Nc2cnc3[nH]cc(-c4cncc(F)c4)c3n2)CC1] | 0.3 | 16 | 154.5 | 2083.3 | |
| 213 | 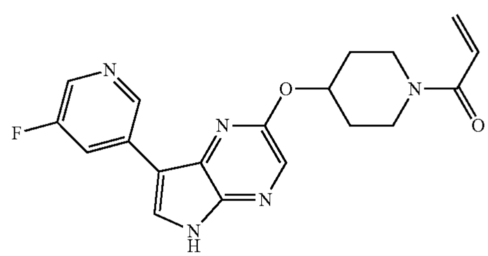 [SMILES: C=CC(=O)N1CCC(Oc2cnc3[nH]cc(-c4cncc(F)c4)c3n2)CC1] | 0.8 | 69.4 | 317.9 | >10000.0 | |
| 214 | 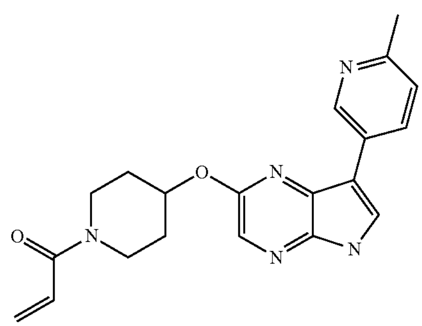 [SMILES: C=CC(=O)N1CCC(Oc2cnc3[nH]cc(-c4ccc(C)nc4)c3n2)CC1] | 2.3 | 308 | 1110.4 | | |
| 215 | 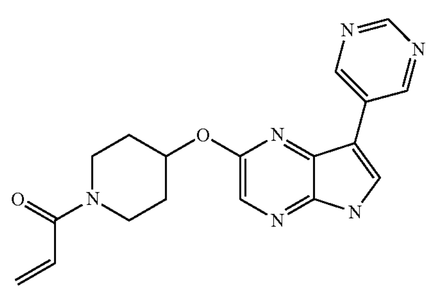 [SMILES: C=CC(=O)N1CCC(Oc2cnc3[nH]cc(-c4cncnc4)c3n2)CC1] | 2.9 | 386 | 1263.3 | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 216 | 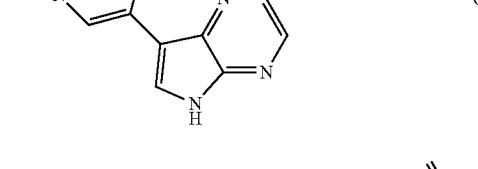 | 12.5 | 1029.4 | | | |
| 217 | 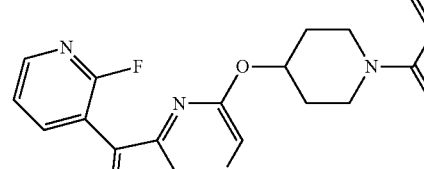 | 0.7 | 42.4 | 129.3 | >10000.0 | |
| 218 | 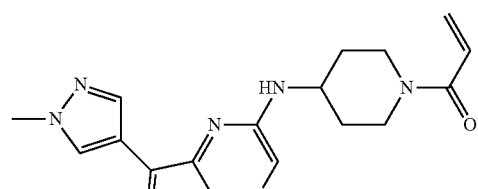 | 0.6 | 81.1 | 345.3 | 6189.6 | >360.0 |
| 219 | 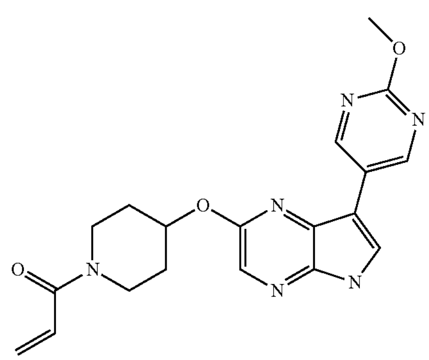 [SMILES: C=CC(=O)N1CCC(Oc2cnc3[nH]cc(-c4cnc(OC)nc4)c3n2)CC1] | 1.7 | 153.3 | 986.7 | | |
| 220 | 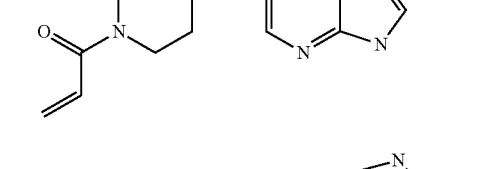 | 0.8 | 70.4 | 464.5 | >10000.0 | >360.0 |

TABLE 1-continued

Enzyme Assay and Blood Stability Data.

| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 221 | 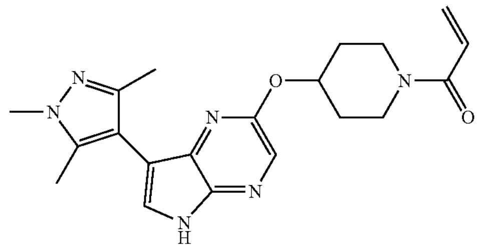 [SMILES: C=CC(=O)N1CCC(Oc2cnc3[nH]cc(-c4c(C)nn(C)c4C)c3n2)CC1] | 15.5 | 1484.7 | | | |
| 222 | 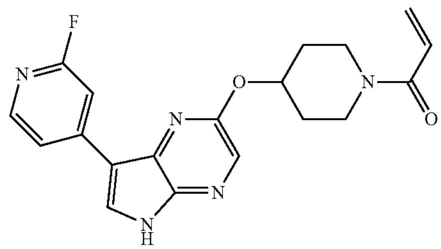 [SMILES: C=CC(=O)N1CCC(Oc2cnc3[nH]cc(-c4ccnc(F)c4)c3n2)CC1] | 1.1 | 125.4 | 756.6 | | |
| 223 | 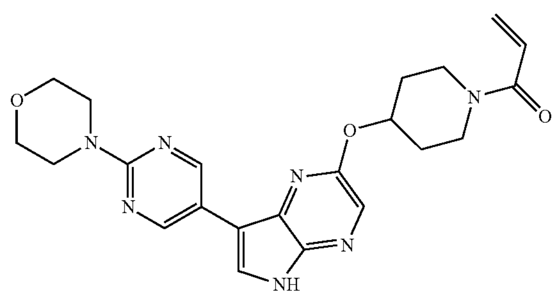 [SMILES: C=CC(=O)N1CCC(Oc2cnc3[nH]cc(-c4cnc(N5CCOCC5)nc4)c3n2)CC1] | 30 | 3358.9 | | | |
| 224 | 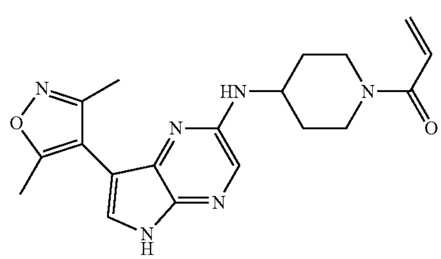 [SMILES: C=CC(=O)N1CCC(Nc2cnc3[nH]cc(-c4c(C)noc4C)c3n2)CC1] | 17.6 | 1544 | | | |
| 225 | 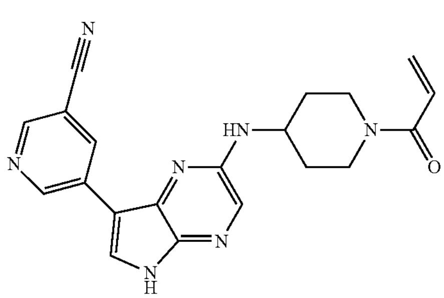 [SMILES: C=CC(=O)N1CCC(Nc2cnc3[nH]cc(-c4cncc(C#N)c4)c3n2)CC1] | 1.4 | 120 | 2906.2 | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 226 | 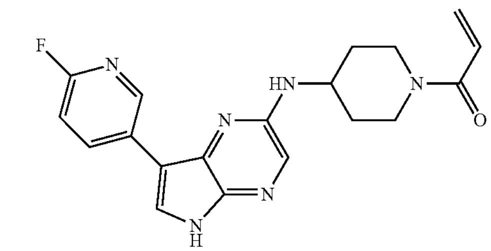 [SMILES: C=CC(=O)N1CCC(Nc2cnc3[nH]cc(-c4ccc(F)nc4)c3n2)CC1] | 1 | 91 | 699 | | |
| 227 | 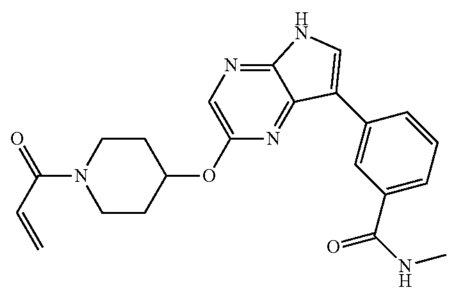 [SMILES: C=CC(=O)N1CCC(Oc2cnc3[nH]cc(-c4cccc(C(=O)NC)c4)c3n2)CC1] | 0.9 | 71.8 | 642.9 | | |
| 229 | 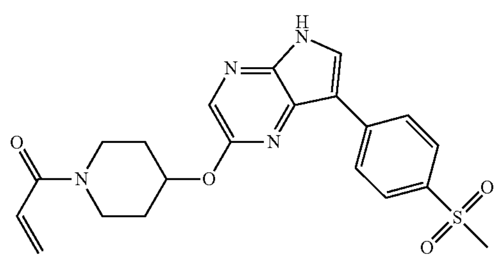 [SMILES: C=CC(=O)N1CCC(Oc2cnc3[nH]cc(-c4ccc(S(C)(=O)=O)cc4)c3n2)CC1] | 7.1 | 744.6 | | | |
| 231 | 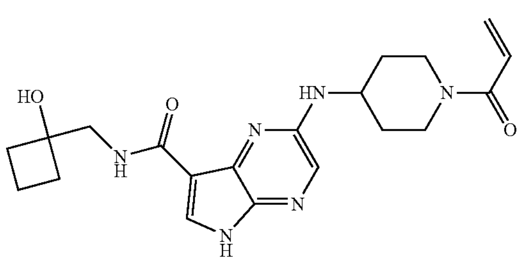 [SMILES: C=CC(=O)N1CCC(Nc2cnc3[nH]cc(C(=O)NCC4(O)CCC4)c3n2)CC1] | 0.6 | 52.6 | 3616.4 | | |
| 232 | 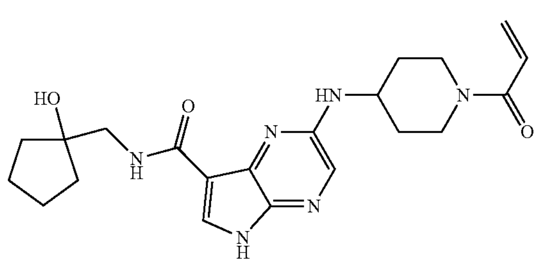 [SMILES: C=CC(=O)N1CCC(Nc2cnc3[nH]cc(C(=O)NCC4(O)CCCC4)c3n2)CC1] | 0.3 | 25 | 1636.3 | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 233 | 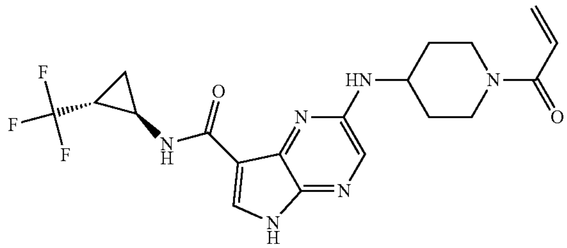 [SMILES: C=CC(=O)N1CCC(Nc2cnc3[nH]cc(C(=O)N[C@@H]4C[C@H]4C(F)(F)F)c3n2)CC1] | 0.2 | 20.6 | 212.8 | 532.3 | |
| 234 | 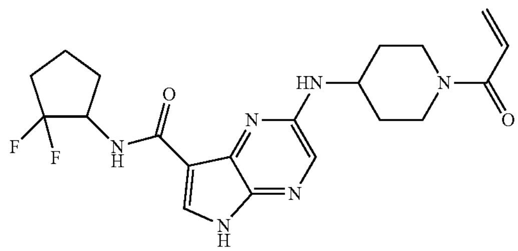 [SMILES: C=CC(=O)N1CCC(Nc2cnc3[nH]cc(C(=O)NC4CCCC4(F)F)c3n2)CC1] | <0.3 | 4.9 | 65.2 | | 296 |
| 235 | 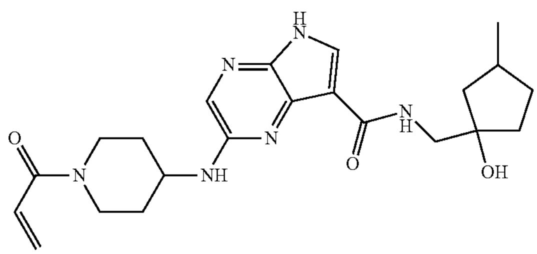 [SMILES: C=CC(=O)N1CCC(Nc2cnc3[nH]cc(C(=O)NCC4(O)CCC(C)C4)c3n2)CC1] | 0.3 | 22.5 | 1703.8 | | |
| 236 | 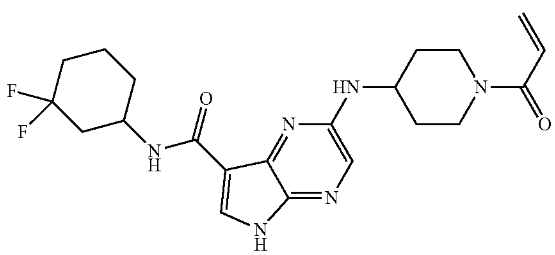 [SMILES: C=CC(=O)N1CCC(Nc2cnc3[nH]cc(C(=O)NC4CCCC(F)(F)C4)c3n2)CC1] | 0.1 | 8.3 | 141.5 | 437.6 | |
| 237 | 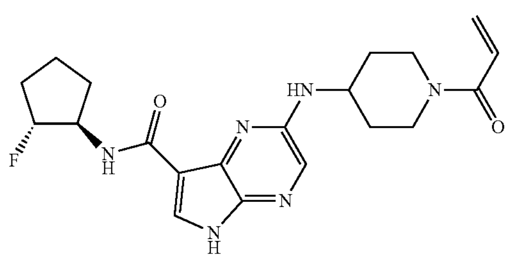 [SMILES: C=CC(=O)N1CCC(Nc2cnc3[nH]cc(C(=O)N[C@@H]4CCC[C@H]4F)c3n2)CC1] | 0.2 | 7.8 | 80.1 | | 243 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 238 | 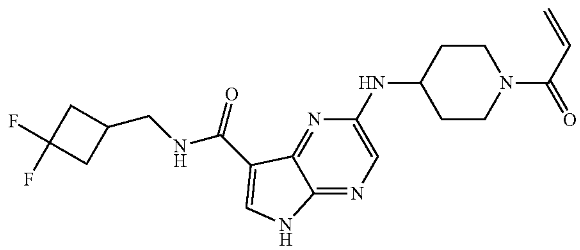 [SMILES: C=CC(=O)N1CCC(Nc2cnc3[nH]cc(C(=O)NCC4CC(F)(F)C4)c3n2)CC1] | 0.2 | 9.3 | 181.3 | 615.1 | 260 |
| 239 | 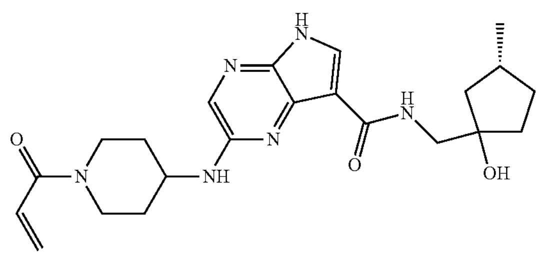 [SMILES: C=CC(=O)N1CCC(Nc2cnc3[nH]cc(C(=O)NCC4(O)CC[C@@H](C)C4)c3n2)CC1] | 0.5 | 38.1 | 1899.3 | | |
| 240 | 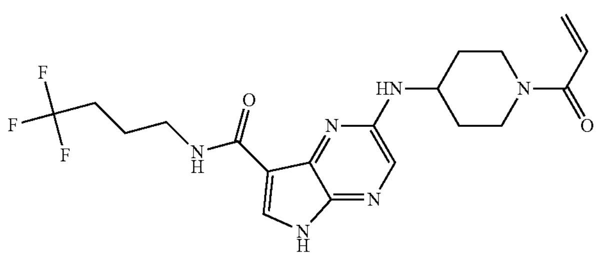 [SMILES: C=CC(=O)N1CCC(Nc2cnc3[nH]cc(C(=O)NCCCC(F)(F)F)c3n2)CC1] | 0.1 | 9.1 | 83.8 | 442.5 | 235 |
| 241 | 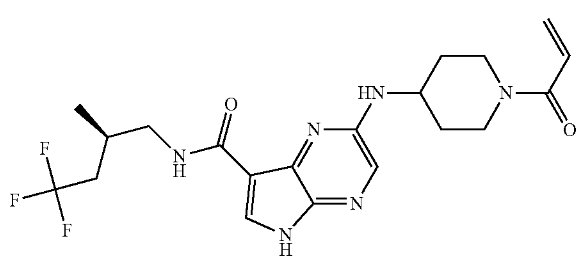 [SMILES: C=CC(=O)N1CCC(Nc2cnc3[nH]cc(C(=O)NC[C@H](C)CC(F)(F)F)c3n2)CC1] | 0.2 | 7.3 | 87.9 | 656.8 | >310.5 |
| 242 | 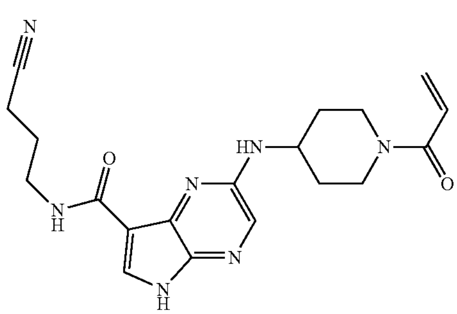 [SMILES: C=CC(=O)N1CCC(Nc2cnc3[nH]cc(C(=O)NCCCC#N)c3n2)CC1] | 0.1 | 10.7 | 1097.2 | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 243 | 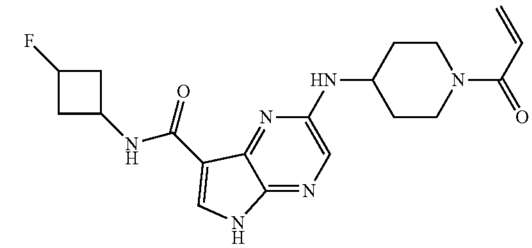 [SMILES: C=CC(=O)N1CCC(Nc2cnc3[nH]cc(C(=O)NC4CC(F)C4)c3n2)CC1] | <0.1 | 9 | 155.4 | 617 | >360.0 |
| 244 | 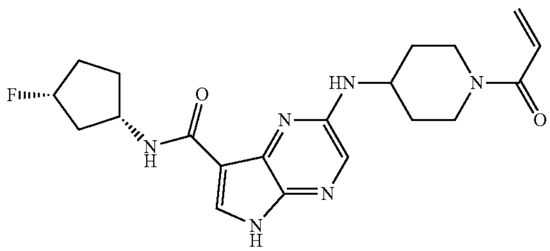 [SMILES: C=CC(=O)N1CCC(Nc2cnc3[nH]cc(C(=O)N[C@H]4CC[C@@H](F)C4)c3n2)CC1] | 0.2 | 7.3 | 126.7 | 403.1 | 284 |
| 245 | 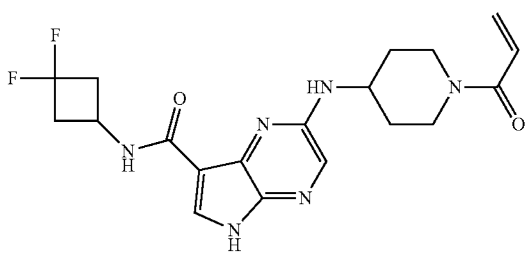 [SMILES: C=CC(=O)N1CCC(Nc2cnc3[nH]cc(C(=O)NC4CC(F)(F)C4)c3n2)CC1] | 0.2 | 17.9 | 228.2 | 901.2 | |
| 246 | 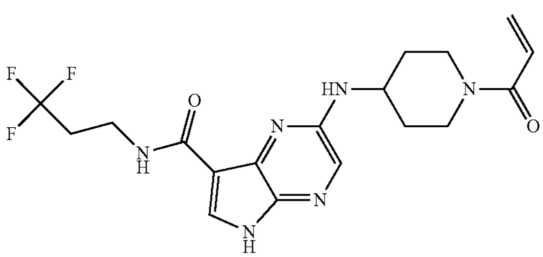 [SMILES: C=CC(=O)N1CCC(Nc2cnc3[nH]cc(C(=O)NCCC(F)(F)F)c3n2)CC1] | 0.3 | 6.4 | 43 | 186.2 | >360.0 |
| 247 | 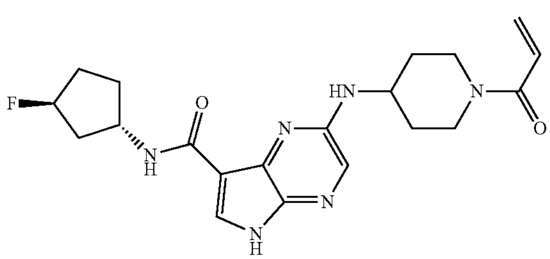 [SMILES: C=CC(=O)N1CCC(Nc2cnc3[nH]cc(C(=O)N[C@H]4CC[C@H](F)C4)c3n2)CC1] | 0.2 | 8.2 | 141.4 | 651 | 272 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 248 | 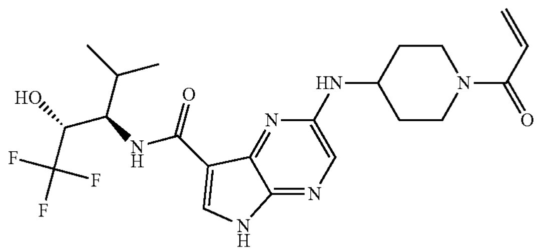 [SMILES: C=CC(=O)N1CCC(Nc2cnc3[nH]cc(C(=O)N[C@H](C(C)C)[C@@H](O)C(F)(F)F)c3n2)CC1] | 0.4 | 40.2 | 892.9 | | |
| 249 | 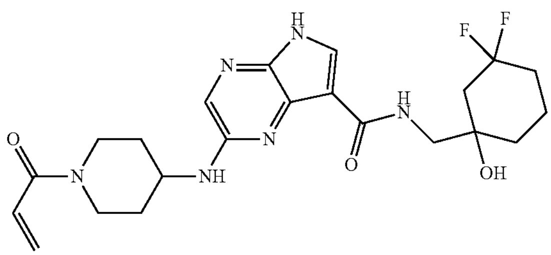 [SMILES: C=CC(=O)N1CCC(Nc2cnc3[nH]cc(C(=O)NCC4(O)CCCC(F)(F)C4)c3n2)CC1] | 0.6 | 47 | 2105.7 | | |
| 250 | 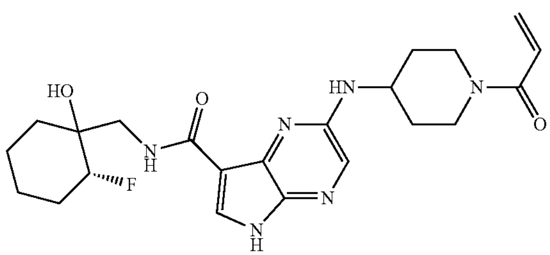 [SMILES: C=CC(=O)N1CCC(Nc2cnc3[nH]cc(C(=O)NCC4(O)CCCC[C@H]4F)c3n2)CC1] | 0.6 | 76.7 | 4118.7 | | |
| 251 | 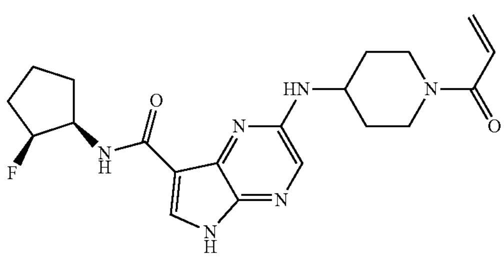 [SMILES: C=CC(=O)N1CCC(Nc2cnc3[nH]cc(C(=O)N[C@@H]4CCC[C@@H]4F)c3n2)CC1] | 0.2 | 8.1 | 73.9 | 809.5 | 201 |
| 252 | 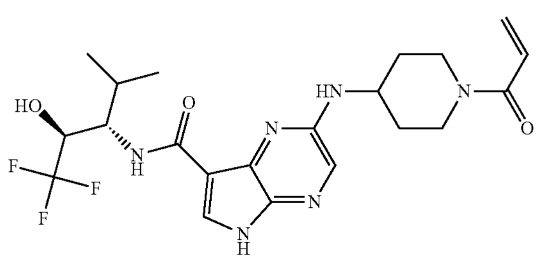 [SMILES: C=CC(=O)N1CCC(Nc2cnc3[nH]cc(C(=O)N[C@@H](C(C)C)[C@H](O)C(F)(F)F)c3n2)CC1] | 0.5 | 37.2 | 673.1 | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 251b | 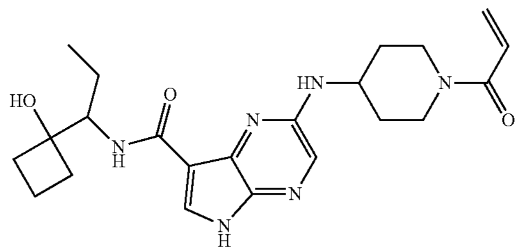 [SMILES: C=CC(=O)N1CCC(Nc2cnc3[nH]cc(C(=O)NC(CC)C4(O)CCC4)c3n2)CC1] | 0.4 | 54.1 | 1512.1 | | |
| 252b | 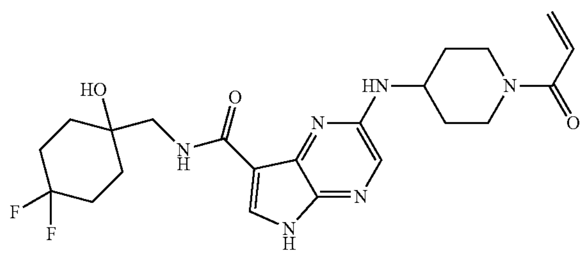 [SMILES: C=CC(=O)N1CCC(Nc2cnc3[nH]cc(C(=O)NCC4(O)CCC(F)(F)CC4)c3n2)CC1] | 0.5 | 40.6 | 2467.9 | | |
| 253 | 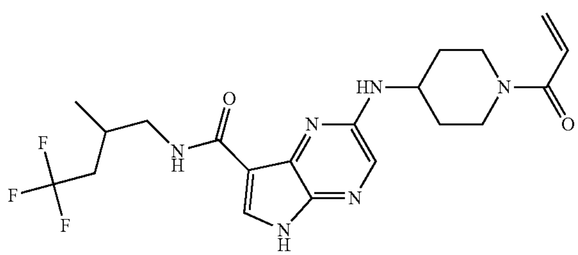 [SMILES: C=CC(=O)N1CCC(Nc2cnc3[nH]cc(C(=O)NCC(C)CC(F)(F)F)c3n2)CC1] | 0.2 | 6.9 | 77.5 | 429.3 | >360.0 |
| 254 | 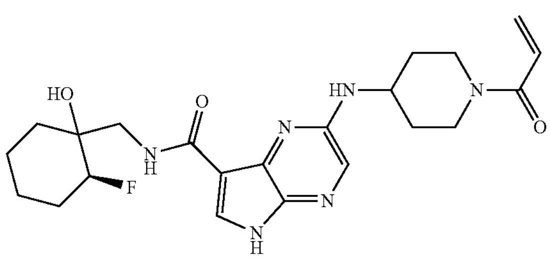 [SMILES: C=CC(=O)N1CCC(Nc2cnc3[nH]cc(C(=O)NCC4(O)CCCC[C@@H]4F)c3n2)CC1] | 0.5 | 41.5 | 836.5 | | |
| 255 | 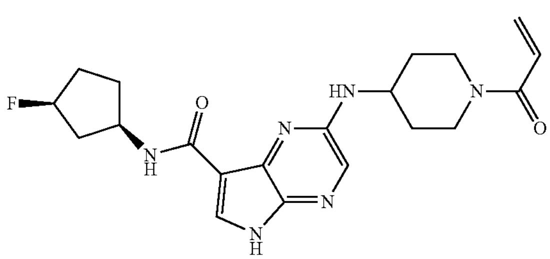 [SMILES: C=CC(=O)N1CCC(Nc2cnc3[nH]cc(C(=O)N[C@@H]4CC[C@H](F)C4)c3n2)CC1] | 0.3 | 9.7 | 130.2 | 817.8 | |

TABLE 1-continued

Enzyme Assay and Blood Stability Data.

| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 256 | 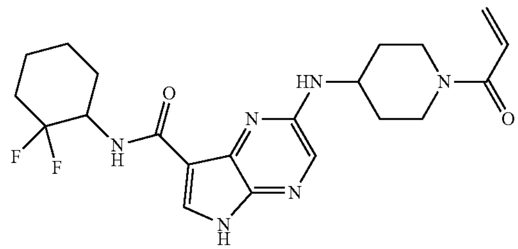 [SMILES: C=CC(=O)N1CCC(Nc2cnc3[nH]cc(C(=O)NC4CCCCC4(F)F)c3n2)CC1] | 0.2 | 7.9 | 48.6 | 550.4 | 239 |
| 257 | 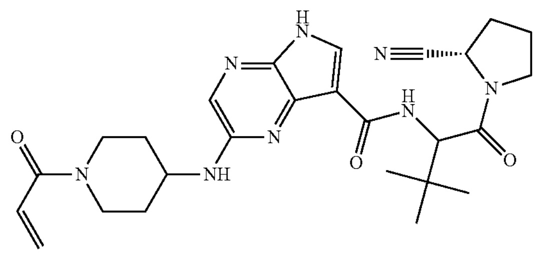 [SMILES: C=CC(=O)N1CCC(Nc2cnc3[nH]cc(C(=O)NC(C(=O)N4CCC[C@H]4C#N)C(C)(C)C)c3n2)CC1] | 108 | | | | |
| 258 | 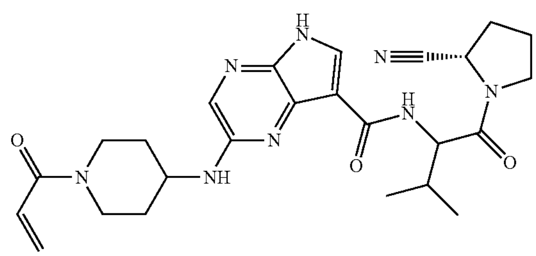 [SMILES: C=CC(=O)N1CCC(Nc2cnc3[nH]cc(C(=O)NC(C(=O)N4CCC[C@H]4C#N)C(C)C)c3n2)CC1] | 4.6 | 547.6 | | | |
| 259 | 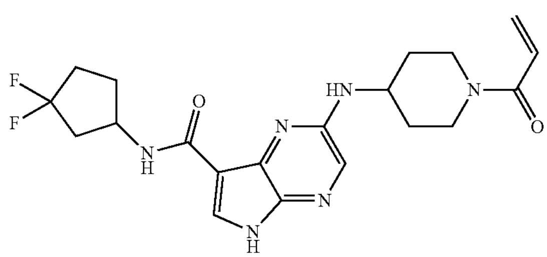 [SMILES: C=CC(=O)N1CCC(Nc2cnc3[nH]cc(C(=O)NC4CCC(F)(F)C4)c3n2)CC1] | 0.2 | 11.1 | 117 | 668.2 | >360.0 |
| 260 | 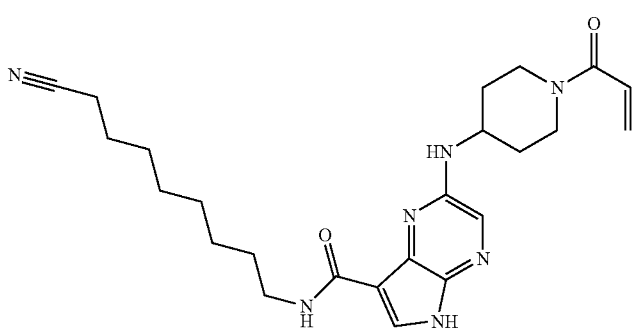 [SMILES: C=CC(=O)N1CCC(Nc2cnc3[nH]cc(C(=O)NCCCCCCCCC#N)c3n2)CC1] | 0.2 | 14.7 | 574.7 | >10000.0 | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 261 | 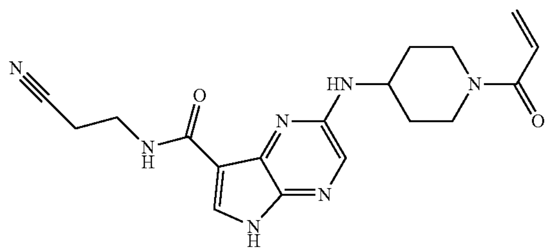 [SMILES: C=CC(=O)N1CCC(Nc2cnc3[nH]cc(C(=O)NCCC#N)c3n2)CC1] | 0.2 | 7.4 | 214.4 | 215.2 | >360.0 |
| 262 | 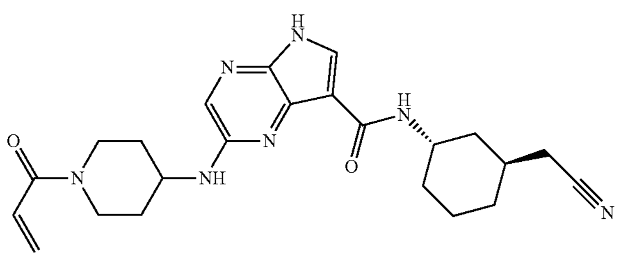 [SMILES: C=CC(=O)N1CCC(Nc2cnc3[nH]cc(C(=O)N[C@H]4CCC[C@H](CC#N)C4)c3n2)CC1] | 0.2 | 30.8 | 1331 | >10000.0 | |
| 263 | 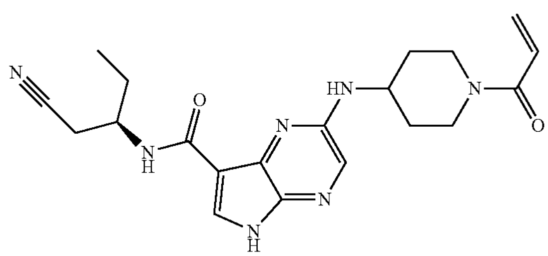 [SMILES: C=CC(=O)N1CCC(Nc2cnc3[nH]cc(C(=O)N[C@H](CC)CC#N)c3n2)CC1] | 0.2 | 8.7 | 74.3 | 431.4 | |
| 264 | 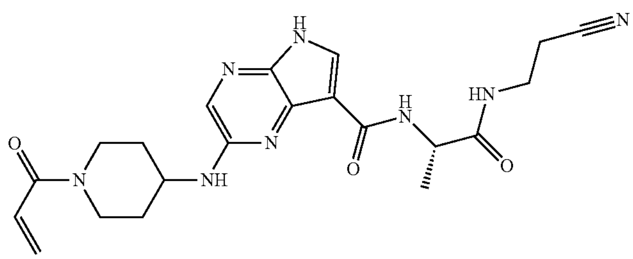 [SMILES: C=CC(=O)N1CCC(Nc2cnc3[nH]cc(C(=O)N[C@@H](C)C(=O)NCCC#N)c3n2)CC1] | 2.6 | 225.8 | 4483 | | |
| 266 | 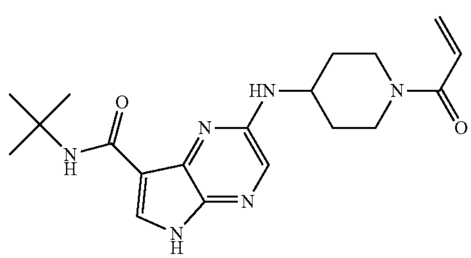 [SMILES: C=CC(=O)N1CCC(Nc2cnc3[nH]cc(C(=O)NC(C)(C)C)c3n2)CC1] | 0.3 | 13.6 | 71 | 386.4 | 336.1 |

TABLE 1-continued
Enzyme Assay and Blood Stability Data.
| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 267 | 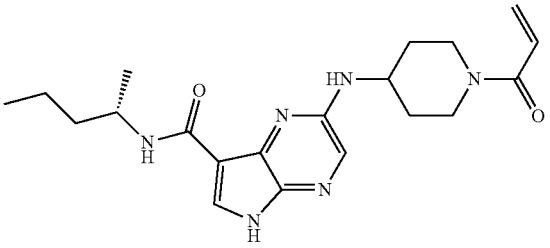 [SMILES: C=CC(=O)N1CCC(Nc2cnc3[nH]cc(C(=O)N[C@@H](C)CCC)c3n2)CC1] | 0.3 | 9 | 36 | 242.4 | 224 |
| 268 | 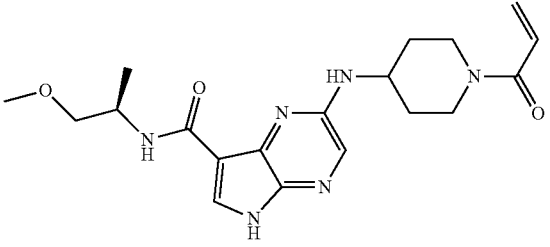 [SMILES: C=CC(=O)N1CCC(Nc2cnc3[nH]cc(C(=O)N[C@H](C)COC)c3n2)CC1] | 0.3 | 7.9 | 43.4 | 263.1 | 288 |
| 269 | 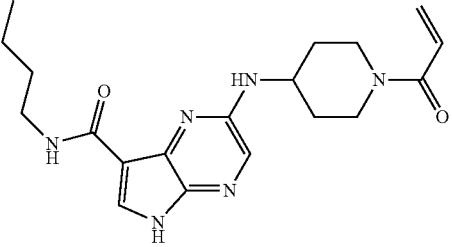 [SMILES: C=CC(=O)N1CCC(Nc2cnc3[nH]cc(C(=O)NCCCC)c3n2)CC1] | 0.2 | 7.3 | 47.9 | 364.1 | 256 |
| 270 | 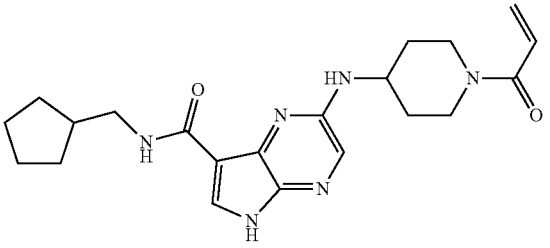 [SMILES: C=CC(=O)N1CCC(Nc2cnc3[nH]cc(C(=O)NCC4CCCC4)c3n2)CC1] | <0.1 | 8.6 | 53.6 | 1223.1 | 232 |
| 271 | 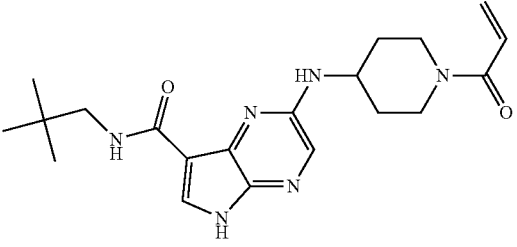 [SMILES: C=CC(=O)N1CCC(Nc2cnc3[nH]cc(C(=O)NCC(C)(C)C)c3n2)CC1] | 0.4 | 14.9 | 134.6 | 790.3 | 137 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 272 | 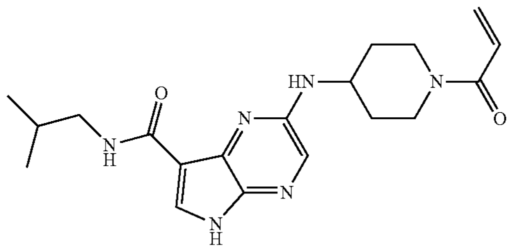 [SMILES: C=CC(=O)N1CCC(Nc2cnc3[nH]cc(C(=O)NCC(C)C)c3n2)CC1] | 0.2 | 8.8 | 72.3 | 258.9 | 217 |
| 273 | 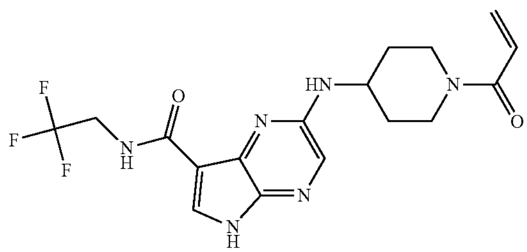 [SMILES: C=CC(=O)N1CCC(Nc2cnc3[nH]cc(C(=O)NCC(F)(F)F)c3n2)CC1] | 0.4 | 11.4 | 56.7 | 214.1 | 218 |
| 274 | 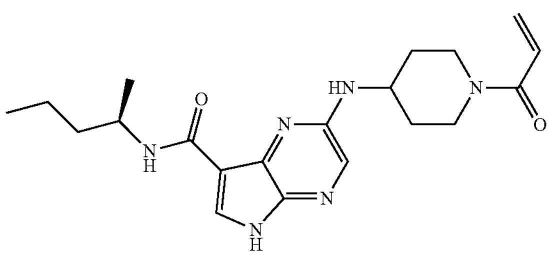 [SMILES: C=CC(=O)N1CCC(Nc2cnc3[nH]cc(C(=O)N[C@H](C)CCC)c3n2)CC1] | 0.2 | 8.2 | 57.9 | 475.7 | >360.0 |
| 275 | 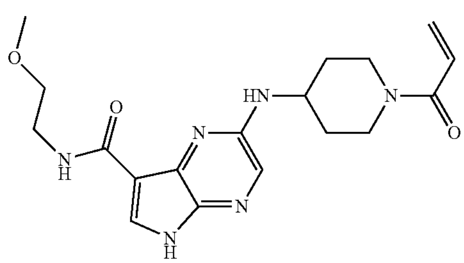 [SMILES: C=CC(=O)N1CCC(Nc2cnc3[nH]cc(C(=O)NCCOC)c3n2)CC1] | 0.4 | 13.1 | 148.8 | 389.2 | >360.0 |
| 276 | 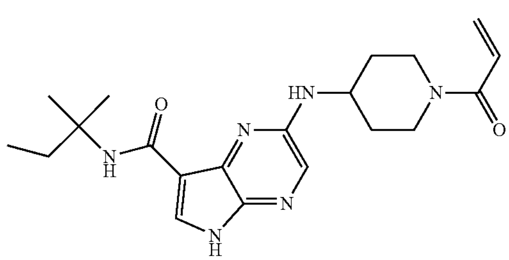 [SMILES: C=CC(=O)N1CCC(Nc2cnc3[nH]cc(C(=O)NC(C)(C)CC)c3n2)CC1] | <0.3 | 11.1 | 57.8 | 486.6 | 225 |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 277 | 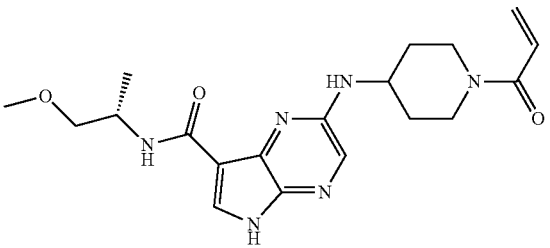 [SMILES: C=CC(=O)N1CCC(Nc2cnc3[nH]cc(C(=O)N[C@@H](C)COC)c3n2)CC1] | 0.3 | 6.6 | 102.8 | 83.2 | >360.0 |
| 278 | 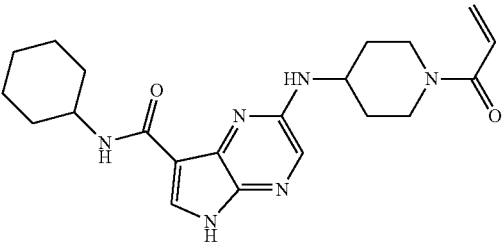 [SMILES: C=CC(=O)N1CCC(Nc2cnc3[nH]cc(C(=O)NC4CCCCC4)c3n2)CC1] | 0.2 | 6.3 | 57.4 | 362.3 | 236 |
| 279 | 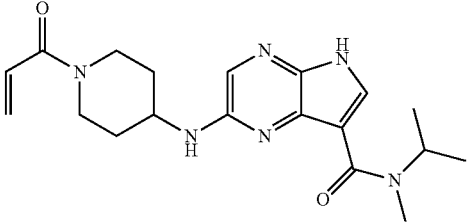 [SMILES: C=CC(=O)N1CCC(Nc2cnc3[nH]cc(C(=O)N(C)C(C)C)c3n2)CC1] | 9.7 | 591.9 | | | |
| 280 | 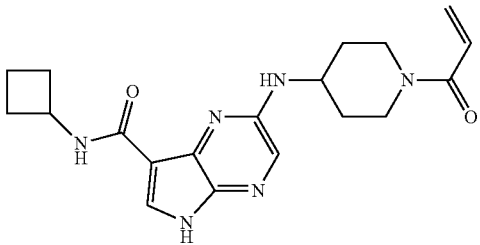 [SMILES: C=CC(=O)N1CCC(Nc2cnc3[nH]cc(C(=O)NC4CCC4)c3n2)CC1] | 0.2 | 4 | 39.4 | 376.3 | >360.0 |
| 281 | 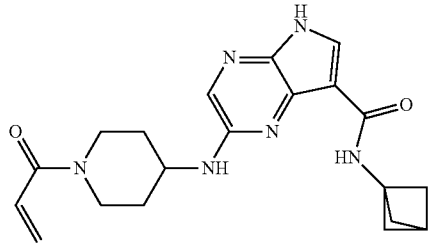 [SMILES: C=CC(=O)N1CCC(Nc2cnc3[nH]cc(C(=O)NC45CC(C4)C5)c3n2)CC1] | 0.4 | 5.2 | 31.5 | 489.4 | 346 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 282 | 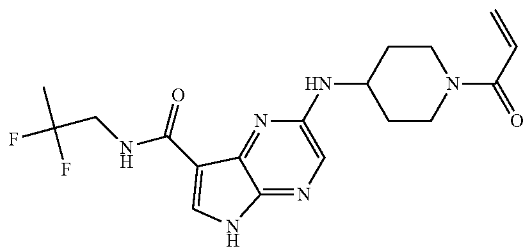 [SMILES: C=CC(=O)N1CCC(Nc2cnc3[nH]cc(C(=O)NCC(C)(F)F)c3n2)CC1] | 0.2 | 12.9 | 71.7 | 432 | 243 |
| 283 | 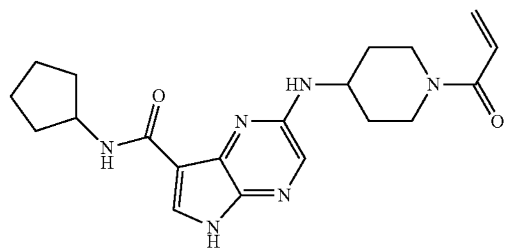 [SMILES: C=CC(=O)N1CCC(Nc2cnc3[nH]cc(C(=O)NC4CCCC4)c3n2)CC1] | 0.3 | 7.6 | 58.4 | 700.3 | >360.0 |
| 284 | 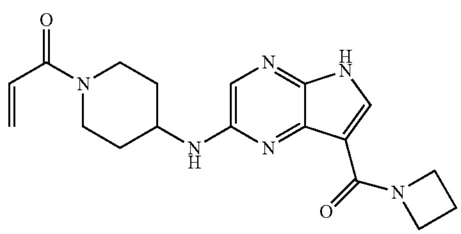 [SMILES: C=CC(=O)N1CCC(Nc2cnc3[nH]cc(C(=O)N4CCC4)c3n2)CC1] | 1.9 | 176.2 | 2789 | | |
| 285 | 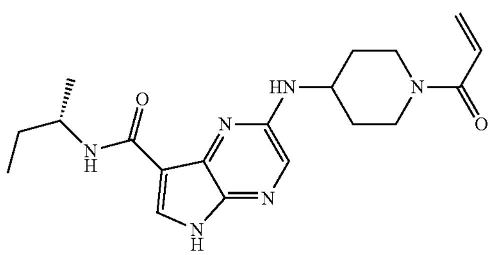 [SMILES: C=CC(=O)N1CCC(Nc2cnc3[nH]cc(C(=O)N[C@@H](C)CC)c3n2)CC1] | 0.3 | 8.5 | 31.4 | 373.2 | 345 |
| 286 | 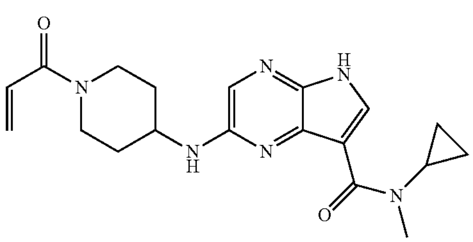 [SMILES: C=CC(=O)N1CCC(Nc2cnc3[nH]cc(C(=O)N(C)C4CC4)c3n2)CC1] | 15.9 | 813.6 | | | |
| 287 | 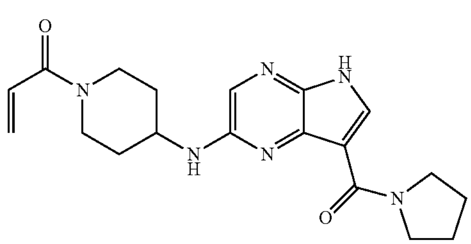 [SMILES: C=CC(=O)N1CCC(Nc2cnc3[nH]cc(C(=O)N4CCCC4)c3n2)CC1] | 4.2 | 345.8 | 7366.3 | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15- pSTAT5 IC$_{50}$ (nM) | HWB- IL15- pSTAT5 IC$_{50}$ (nM) | Human blood stability t$_{1/2}$ (min) |
|---|---|---|---|---|---|---|
| 288 | 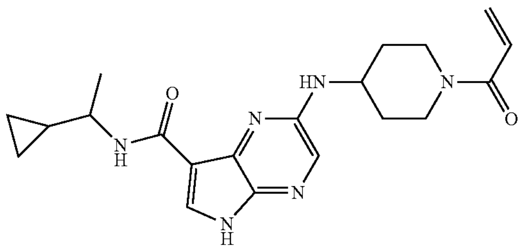 [SMILES: C=CC(=O)N1CCC(Nc2cnc3[nH]cc(C(=O)NC(C)C4CC4)c3n2)CC1] | 0.2 | 7.8 | 44.4 | 357.8 | 220 |
| 289 | 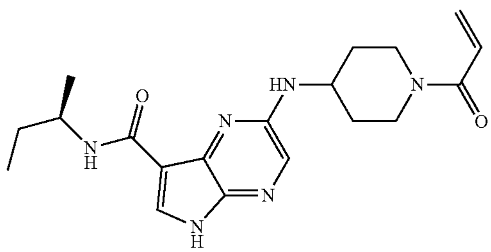 [SMILES: C=CC(=O)N1CCC(Nc2cnc3[nH]cc(C(=O)N[C@H](C)CC)c3n2)CC1] | 0.3 | 7.1 | 37.5 | 106 | >360.0 |
| 291 | 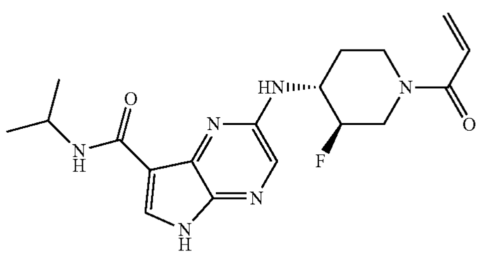 [SMILES: C=CC(=O)N1CC[C@@H](Nc2cnc3[nH]cc(C(=O)NC(C)C)c3n2)[C@H](F)C1] | 0.2 | 9.2 | 168.1 | | 196 |
| 292 | 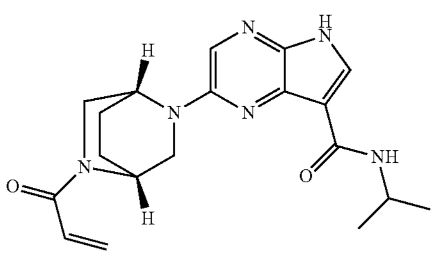 [SMILES: C=CC(=O)N1C[C@H]2CC[C@@H]1CN2c1cnc2[nH]cc(C(=O)NC(C)C)c2n1] | 31 | 3038.4 | | | |
| 293 | 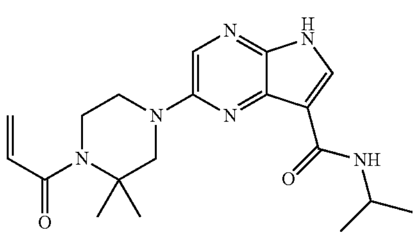 [SMILES: C=CC(=O)N1CCN(c2cnc3[nH]cc(C(=O)NC(C)C)c3n2)CC1(C)C] | 0.6 | 107.1 | 300.3 | 4488.4 | >360.0 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 294 | 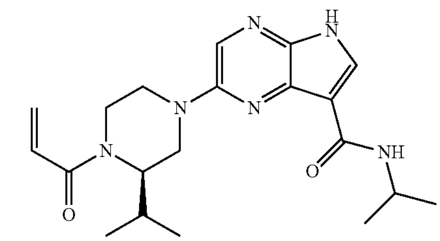 [SMILES: C=CC(=O)N1CCN(c2cnc3[nH]cc(C(=O)NC(C)C)c3n2)C[C@H]1C(C)C] | 1.9 | 234.6 | 1003.2 | | |
| 295 | 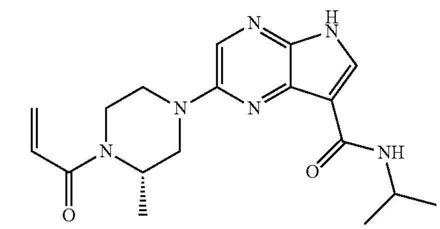 [SMILES: C=CC(=O)N1CCN(c2cnc3[nH]cc(C(=O)NC(C)C)c3n2)C[C@@H]1C] | 1.1 | 89.8 | 334.5 | 2674 | 189 |
| 296 | 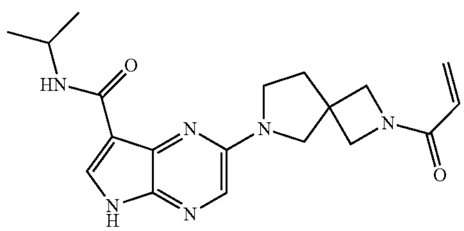 [SMILES: C=CC(=O)N1CC2(CCN(c3cnc4[nH]cc(C(=O)NC(C)C)c4n3)C2)C1] | 56.6 | 4200.8 | | | |
| 297 | 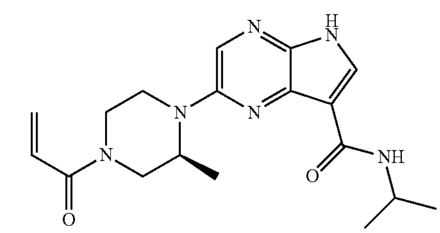 [SMILES: C=CC(=O)N1CCN(c2cnc3[nH]cc(C(=O)NC(C)C)c3n2)[C@@H](C)C1] | 1.5 | 181.4 | 752 | | |
| 298 | 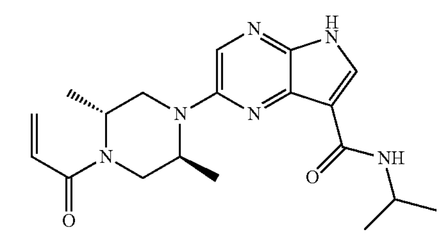 [SMILES: C=CC(=O)N1C[C@H](C)N(c2cnc3[nH]cc(C(=O)NC(C)C)c3n2)C[C@H]1C] | 4.6 | 728.5 | | | |
| 299 | 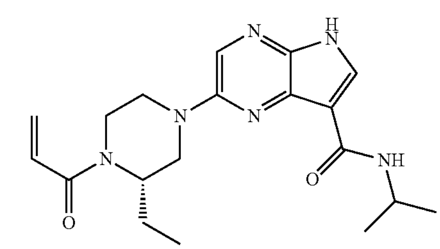 [SMILES: C=CC(=O)N1CCN(c2cnc3[nH]cc(C(=O)NC(C)C)c3n2)C[C@@H]1CC] | 0.7 | 55.6 | 224.8 | 1377.4 | 199 |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 300 | 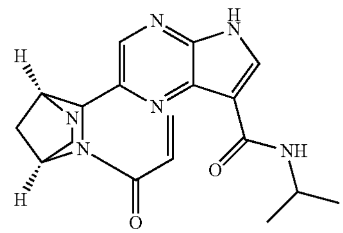 [SMILES: C=CC(=O)N1C(c2cnc3[nH]cc(C(=O)NC(C)C)c3n2)[C@@H]2C[C@H]1CN2] | 0.9 | 84.4 | 714.2 | 3401.1 | 117 |
| 301 | 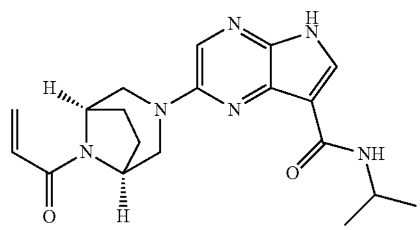 [SMILES: C=CC(=O)N1[C@@H]2CC[C@H]1CN(c1cnc3[nH]cc(C(=O)NC(C)C)c3n1)C2] | 0.6 | 89 | 408.3 | 4896.4 | 84 |
| 302 | 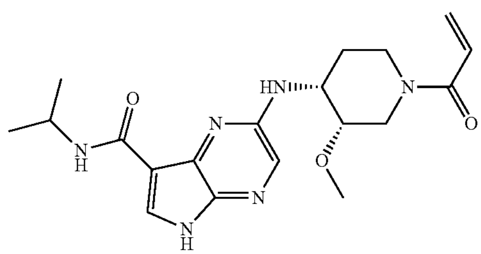 [SMILES: C=CC(=O)N1CC[C@@H](Nc2cnc3[nH]cc(C(=O)NC(C)C)c3n2)[C@@H](OC)C1] | 1.2 | 49.4 | 263.6 | 1306.3 | >360.0 |
| 303 | 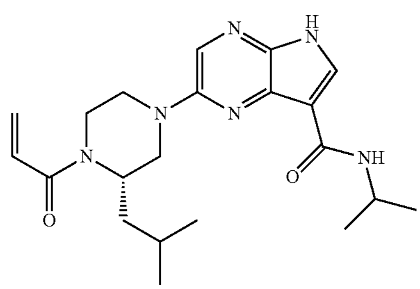 [SMILES: C=CC(=O)N1CCN(c2cnc3[nH]cc(C(=O)NC(C)C)c3n2)C[C@@H]1CC(C)C] | 0.4 | 47.2 | 294 | 2730.9 | 341 |
| 304 | 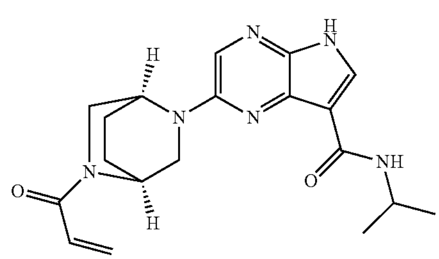 [SMILES: C=CC(=O)N1C[C@@H]2CC[C@H]1CN2c1cnc2[nH]cc(C(=O)NC(C)C)c2n1] | 7.1 | 624.4 | | | |

TABLE 1-continued

Enzyme Assay and Blood Stability Data.

| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 305 | 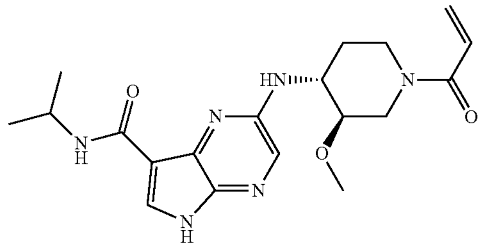 [SMILES: C=CC(=O)N1CC[C@@H](Nc2cnc3[nH]cc(C(=O)NC(C)C)c3n2)[C@H](OC)C1] | 0.8 | 65 | 744.4 | 2644.2 | 357 |
| 306 | 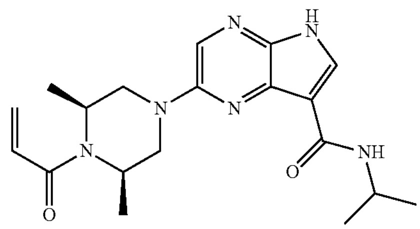 [SMILES: C=CC(=O)N1[C@H](C)CN(c2cnc3[nH]cc(C(=O)NC(C)C)c3n2)C[C@@H]1C] | 3.9 | 325.5 | 1086.8 | | |
| 307 | 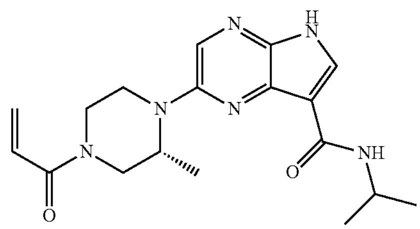 [SMILES: C=CC(=O)N1CCN(c2cnc3[nH]cc(C(=O)NC(C)C)c3n2)[C@H](C)C1] | 1.1 | 128.1 | 456.8 | | 122 |
| 308 | 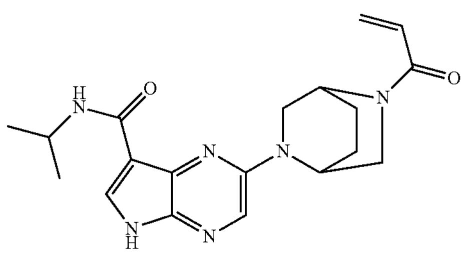 [SMILES: C=CC(=O)N1CC2CCC1CN2c1cnc2[nH]cc(C(=O)NC(C)C)c2n1] | 5.2 | 430.8 | 2236.6 | | |
| 309 | 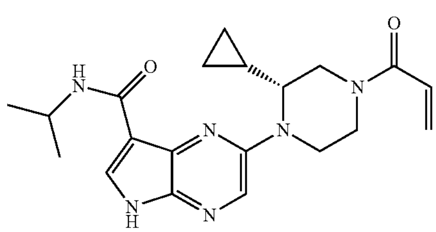 [SMILES: C=CC(=O)N1CCN(c2cnc3[nH]cc(C(=O)NC(C)C)c3n2)[C@H](C2CC2)C1] | 6.6 | 813.9 | | | |
| 310 | 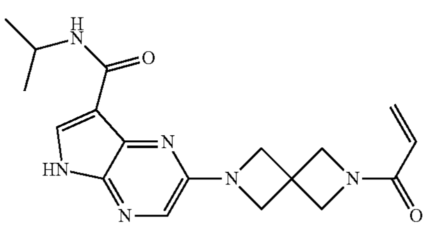 [SMILES: C=CC(=O)N1CC2(C1)CN(c1cnc3[nH]cc(C(=O)NC(C)C)c3n1)C2] | 117 | >10000.0 | | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 311 | 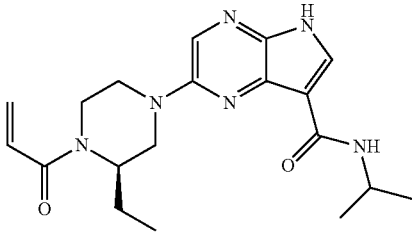 [SMILES: C=CC(=O)N1CCN(c2cnc3[nH]cc(C(=O)NC(C)C)c3n2)C[C@H]1CC] | 1.2 | 220 | 695.9 | | |
| 312 | 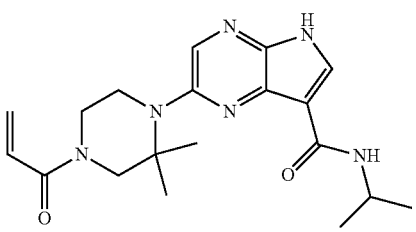 [SMILES: C=CC(=O)N1CCN(c2cnc3[nH]cc(C(=O)NC(C)C)c3n2)C(C)(C)C1] | 4.5 | 592.1 | | | |
| 313 | 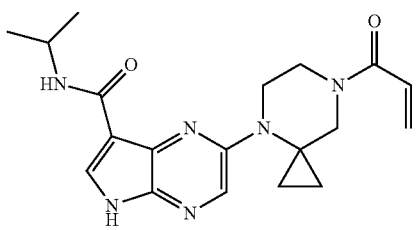 [SMILES: C=CC(=O)N1CCN(c2cnc3[nH]cc(C(=O)NC(C)C)c3n2)C2(CC2)C1] | 1.4 | 182.8 | 706.4 | | |
| 314 | 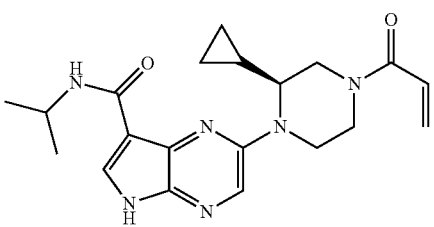 [SMILES: C=CC(=O)N1CCN(c2cnc3[nH]cc(C(=O)NC(C)C)c3n2)[C@@H](C2CC2)C1] | 5 | 661.6 | | | |
| 315 | 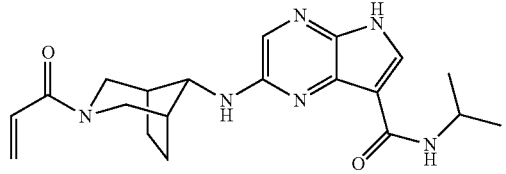 [SMILES: C=CC(=O)N1CC2CCC(C1)C2Nc1cnc2[nH]cc(C(=O)NC(C)C)c2n1] | 60.5 | 5192.6 | | | |
| 316 | 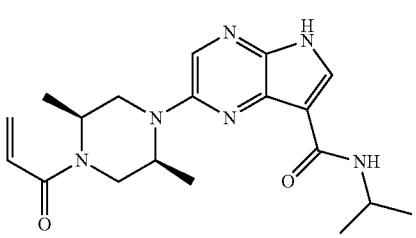 [SMILES: C=CC(=O)N1C[C@H](C)N(c2cnc3[nH]cc(C(=O)NC(C)C)c3n2)C[C@@H]1C] | 18.7 | 1530.7 | | | |

TABLE 1-continued

Enzyme Assay and Blood Stability Data.

| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 317 | 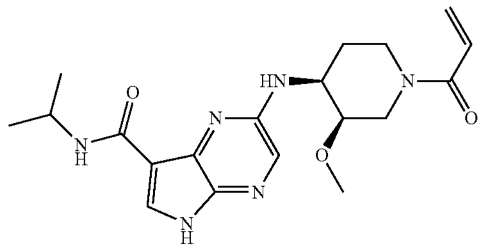 [SMILES: C=CC(=O)N1CC[C@H](Nc2cnc3[nH]cc(C(=O)NC(C)C)c3n2)[C@H](OC)C1] | 0.5 | 44.6 | 242.6 | 420 | >360.0 |
| 318 | 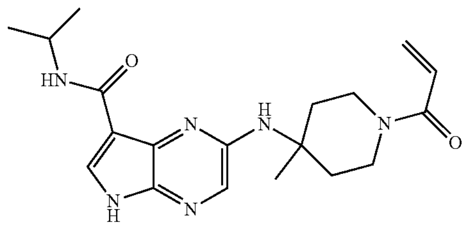 [SMILES: C=CC(=O)N1CCC(C)(Nc2cnc3[nH]cc(C(=O)NC(C)C)c3n2)CC1] | 0.3 | 21.3 | 260.5 | 2081.7 | 352 |
| 319 | 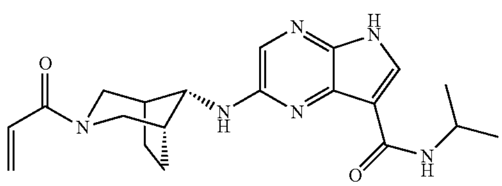 [SMILES: C=CC(=O)N1CC2CC[C@H](C1)[C@H]2Nc1cnc2[nH]cc(C(=O)NC(C)C)c2n1] | 0.5 | 26.7 | 325.3 | | 278 |
| 320 | 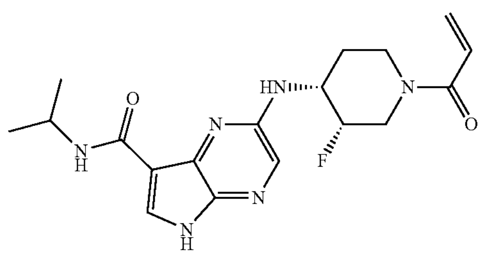 [SMILES: C=CC(=O)N1CC[C@@H](Nc2cnc3[nH]cc(C(=O)NC(C)C)c3n2)[C@@H](F)C1] | 0.4 | 10.7 | 61.1 | 343.3 | 190 |
| 321 | 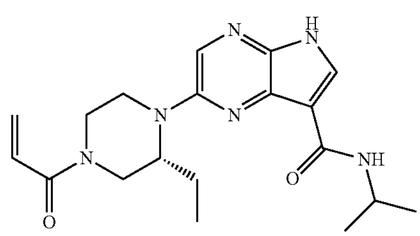 [SMILES: C=CC(=O)N1CCN(c2cnc3[nH]cc(C(=O)NC(C)C)c3n2)[C@H](CC)C1] | 0.9 | 144.3 | 414.7 | | |
| 322 | 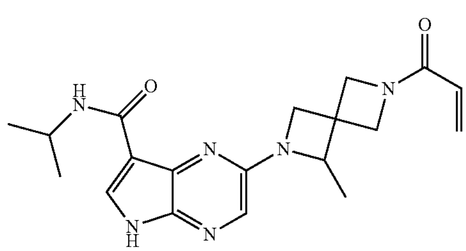 [SMILES: C=CC(=O)N1CC2(C1)CN(c1cnc3[nH]cc(C(=O)NC(C)C)c3n1)C2C] | 29.4 | 3440.9 | | | |

TABLE 1-continued

Enzyme Assay and Blood Stability Data.

| Ex | Structure | JAK3 (4 µM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 323 | 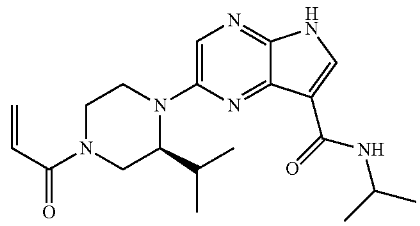 [SMILES: C=CC(=O)N1CCN(c2cnc3[nH]cc(C(=O)NC(C)C)c3n2)[C@@H](C(C)C)C1] | 11.9 | 885.8 | | | |
| 324 | 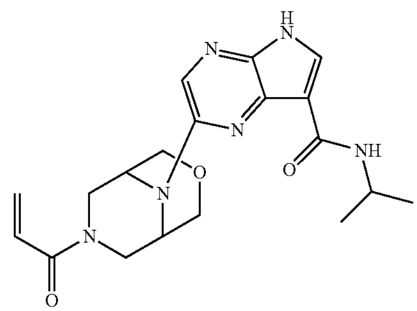 [SMILES: C=CC(=O)N1CC2COCC(C1)N2c1cnc2[nH]cc(C(=O)NC(C)C)c2n1] | 37.5 | 3097.1 | | | |
| 325 | 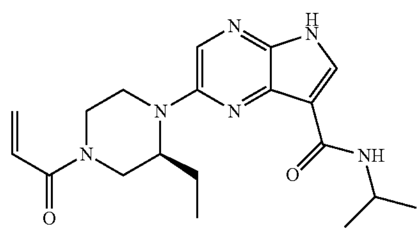 [SMILES: C=CC(=O)N1CCN(c2cnc3[nH]cc(C(=O)NC(C)C)c3n2)[C@@H](CC)C1] | 5 | 479.8 | 1555.1 | | |
| 326 | 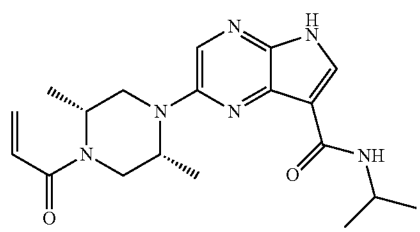 [SMILES: C=CC(=O)N1C[C@@H](C)N(c2cnc3[nH]cc(C(=O)NC(C)C)c3n2)C[C@H]1C] | 4.9 | 506.1 | | | |
| 327 | 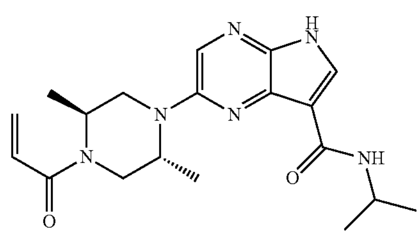 [SMILES: C=CC(=O)N1C[C@@H](C)N(c2cnc3[nH]cc(C(=O)NC(C)C)c3n2)C[C@@H]1C] | 6 | 569.4 | | | |
| 328 | 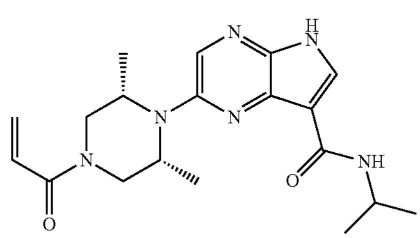 [SMILES: C=CC(=O)N1C[C@@H](C)N(c2cnc3[nH]cc(C(=O)NC(C)C)c3n2)[C@@H](C)C1] | 1.6 | 221.9 | 891.4 | | |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 335 | 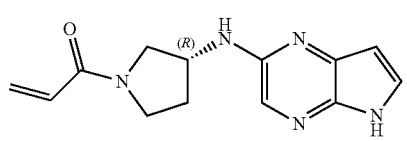 | 621.5 | >10000.0 | >10000.0 | | |
| 336 | 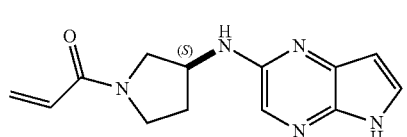 | 30.6 | 3398.9 | >10000.0 | | |
| 337 | 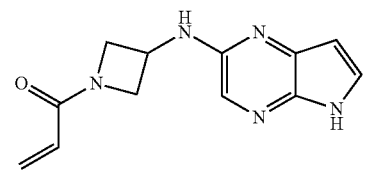 [SMILES: C=CC(=O)N1CC(Nc2cnc3[nH]ccc3n2)C1] | 1.1 | 95.6 | 237 | 631 | 81 |
| 338 | 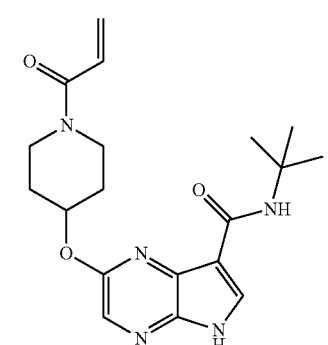 | 0.4 | 114.6 | 479.9 | >10000.0 | 328 |
| 339 | 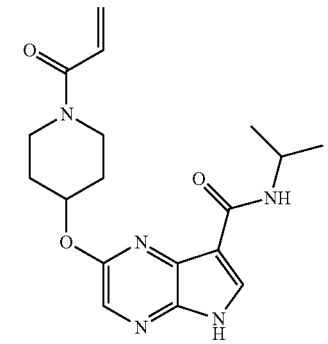 [SMILES: C=CC(=O)N1CCC(Oc2cnc3[nH]cc(C(=O)NC(C)C)c3n2)CC1] | 0.2 | 17.5 | 80.6 | 502.1 | 227 |

TABLE 1-continued
Enzyme Assay and Blood Stability Data.
| Ex | Structure | JAK3 (4 μM ATP) IC$_{50}$ (nM) | JAK3 (1 mM ATP) IC$_{50}$ (nM) | PBMC IL15-pSTAT5 IC$_{50}$ (nM) | HWB-IL15-pSTAT5 IC$_{50}$ (nM) | Human blood stability t$_{1/2}$ (min) |
|---|---|---|---|---|---|---|
| 340 | 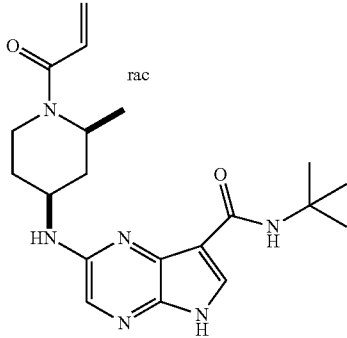 [SMILES: C=CC(=O)N1CC[C@H](Nc2cnc3[nH]cc(C(=O)NC(C)(C)C)c3n2)C[C@@H]1C] rac | 21.1 | 1394.1 | | | >360.0 |
| 341 | 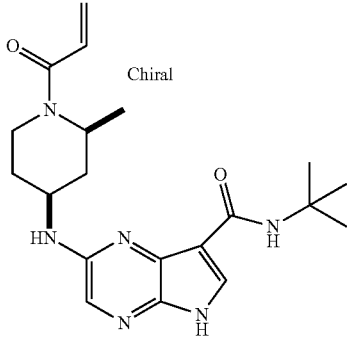 [SMILES: C=CC(=O)N1CC[C@H](Nc2cnc3[nH]cc(C(=O)NC(C)(C)C)c3n2)C[C@@H]1C] Chiral | 15.6 | 1093.3 | | | >360.0 |
| 342 | 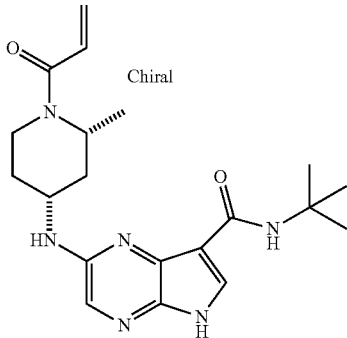 [SMILES: C=CC(=O)N1CC[C@@H](Nc2cnc3[nH]cc(C(=O)NC(C)(C)C)c3n2)C[C@H]1C] Chiral | 81.1 | 5970.9 | | | >360.0 |
| 343 | 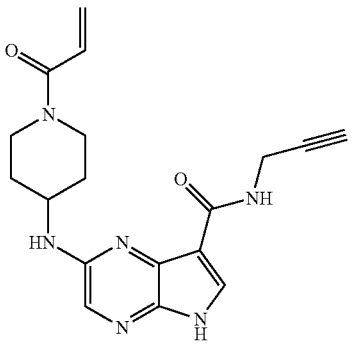 [SMILES: C#CCNC(=O)c1c[nH]c2ncc(NC3CCN(C(=O)C=C)CC3)nc12] | 0.1 | 3.4 | 36.8 | 105.3 | >351.0 |

The invention claimed is:
1. A method for treating a disorder or condition selected from the group consisting of rheumatoid arthritis, inflammatory bowel disease, Crohn's disease, and ulcerative colitis, comprising the step of administering to a subject an effective amount of a compound having the structure:

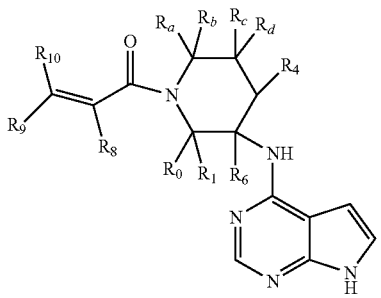

or a pharmaceutically acceptable salt or solvate thereof, or an enantiomer or diastereomer thereof, and wherein $R_a$, $R_b$, $R_c$ and $R_d$ are independently selected from hydrogen, $C_1$-$C_6$ linear or branched chain alkyl, $C_{1-6}$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_1$-$C_6$ cycloalkyl;

$R_0$, $R_1$, $R_4$, and $R_6$ are independently selected from hydrogen, $C_{1-6}$ linear or branched chain alkyl, $C_1$-$C_6$ linear or branched chain perfluoroalkyl, $C_1$-$C_6$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_1$-$C_6$ cycloalkyl; where, alternatively, $R_0$ or $R_1$, and/or $R_6$, respectively together with either of $R_4$, $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and, $R_8$, $R_9$ and $R_{10}$ are all hydrogen.

2. A method for treating a disorder or condition selected from rheumatoid arthritis, inflammatory bowel disease, Crohn's disease, and ulcerative colitis, comprising the step of administering to a subject an effective amount of a compound selected from the group consisting of:

(R)-1-(3-(5-chloro-7H-pyrrolo[2,3-d]pyrimidin-4-ylamino)piperidin-1-yl)prop-2-en-1-one;
1-((2S,5R)-5-(7H-pyrrolo[2,3-d]pyrimidin-4-ylamino)-2-methylpiperidin-1-yl)prop-2-en-1-one;
1-((3R,5S)-3-(7H-pyrrolo[2,3-d]pyrimidin-4-ylamino)-5-hydroxypiperidin-1-yl)prop-2-en-1-one;
(R)-1-(3-(5-(2-methoxyethyl)-7H-pyrrolo[2,3-d]pyrimidin-4-ylamino)piperidin-1-yl)prop-2-en-1-one;
1-(5-(7H-pyrrolo[2,3-d]pyrimidin-4-ylamino)-2-(hydroxymethyl)piperidin-1-yl)prop-2-en-1-one;
1-((3R,5S)-3-(7H-pyrrolo[2,3-d]pyrimidin-4-ylamino)-5-fluoropiperidin-1-yl)prop-2-en-1-one;
1-((3R,4S)-3-(7H-pyrrolo[2,3-d]pyrimidin-4-ylamino)-4-methylpiperidin-1-yl)prop-2-en-1-one;
1-((3S,4R)-3-(7H-pyrrolo[2,3-d]pyrimidin-4-ylamino)-4-fluoropiperidin-1-yl)prop-2-en-1-one;
1-((2S,5R)-5-(7H-pyrrolo[2,3-d]pyrimidin-4-ylamino)-2-ethylpiperidin-1-yl)prop-2-en-1-one;
(R)-1-(3-(7H-pyrrolo[2,3-d]pyrimidin-4-ylamino)piperidin-1-yl)prop-2-en-1-one;
(R)-1-(3-(3-chloro-1H-pyrrolo[2,3-b]pyridin-4-ylamino)piperidin-1-yl)prop-2-en-1-one;
1-((2R,5R)-5-(7H-pyrrolo[2,3-d]pyrimidin-4-ylamino)-2-(hydroxymethyl)piperidin-1-yl)prop-2-en-1-one;
1-((3R,5R)-3-(7H-pyrrolo[2,3-d]pyrimidin-4-ylamino)-5-fluoropiperidin-1-yl)prop-2-en-1-one;
(R)-1-(3-(5-methyl-7H-pyrrolo[2,3-d]pyrimidin-4-ylamino)piperidin-1-yl)prop-2-en-1-one;
1-((3R,5S)-3-(7H-pyrrolo[2,3-d]pyrimidin-4-ylamino)-5-methylpiperidin-1-yl)prop-2-en-1-one;
1-((2S,5R)-5-(5-(2-methoxyethyl)-7H-pyrrolo[2,3-d]pyrimidin-4-ylamino)-2-methylpiperidin-1-yl)prop-2-en-1-one;
1-((3R,5S)-3-(7H-pyrrolo[2,3-d]pyrimidin-4-ylamino)-5-methylpiperidin-1-yl)prop-2-en-1-one;
1-((3R,4S)-3-(7H-pyrrolo[2,3-d]pyrimidin-4-ylamino)-4-methylpiperidin-1-yl)prop-2-en-1-one;
(R)-1-(3-(5-ethyl-7H-pyrrolo[2,3-d]pyrimidin-4-ylamino)piperidin-1-yl)prop-2-en-1-one;
1-((2S,5R)-5-(7H-pyrrolo[2,3-d]pyrimidin-4-ylamino)-2-methylpiperidin-1-yl)prop-2-en-1-one;
(R)-1-(3-(5-fluoro-7H-pyrrolo[2,3-d]pyrimidin-4-ylamino)piperidin-1-yl)prop-2-en-1-one;
(R)-4-(1-acryloylpiperidin-3-ylamino)-7H-pyrrolo[2,3-d]pyrimidine-5-carbonitrile; and,
(3R,5R)-5-(7H-pyrrolo[2,3-d]pyrimidin-4-ylamino)-1-acryloylpiperidine-3-carbonitrile; or, a pharmaceutically acceptable salt thereof.

3. A method for treating inflammatory bowel disease by administering to a mammal in need a therapeutically effective amount of a compound having the structure:

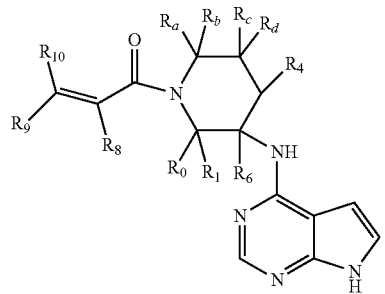

or a pharmaceutically acceptable salt or solvate thereof, or an enantiomer or diastereomer thereof, and wherein $R_a$, $R_b$, $R_c$ and $R_d$ are independently selected from hydrogen, $C_1$-$C_6$ linear or branched chain alkyl, $C_1$-$C_6$ linear or branched chain perfluoroalkyl, aryl, alkylaryl, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl;

$R_0$, $R_1$, $R_4$, and $R_6$ are independently selected from hydrogen, $C_1$-$C_6$ linear or branched chain alkyl, $C_1$-$C_6$ linear or branched chain perfluoroalkyl, $C_6$-$C_{10}$ aryl, monocyclic or bicyclic heteroaryl, comprising 5- and/or 6-membered rings, (aryl)$C_1$-$C_6$ linear or branched chain alkyl, (heteroaryl)$C_1$-$C_6$ linear or branched chain alkyl, heteroaryl, halogen, cyano, hydroxyl, $C_1$-$C_6$ linear or branched chain alkoxy, amino, carboxy, aminocarbonyl, (heterocyclic)$C_1$-$C_6$ linear or branched chain alkyl, ($C_1$-$C_6$ linear or branched chain alkyl)aryl, ($C_1$-$C_6$ linear or branched chain alkyl)heteroaryl, and ($C_1$-$C_6$ linear or branched chain alkyl)heterocyclic, where said alkyl is further optionally substituted with one or more substituents selected from the group consisting of halo, hydroxy, methoxy, amino, alkylamino, dialkylamino, $CF_3$, and $C_3$-$C_6$ cycloalkyl; where, alternatively, $R_0$ or $R_1$, and/or $R_6$, respectively together with either of $R_4$, $R_a$, $R_b$, $R_c$ or $R_d$, may independently form a bond or a $C_1$-$C_6$ linear alkyl chain; and/or, alternatively, $R_4$, respectively together with either of $R_a$, $R_b$, $R_c$ or $R_d$, may independently form a bond or a $C_1$-$C_6$ linear alkyl chain; and, $R_8$, $R_9$ and $R_{10}$ are all hydrogen.

4. The method of claim 1, wherein the compound is 1-(2R,5R)-5-(7H-pyrrolo[2,3-d]pyrimidin-4-ylamino)-2-(hydroxymethyl)piperidin-1-yl)prop-2-en-1-one, or, a pharmaceutically acceptable salt thereof.

5. The method of claim 1, wherein the compound is 1-((3R,5R)-3-(7H-pyrrolo[2,3-d]pyrimidin-4-ylamino)-5-fluoropiperidin-1-yl)prop-2-en-1-one; or, a pharmaceutically acceptable salt thereof.

6. The method of claim 1, wherein the compound is 1-(3R,5S)-3-(7H-pyrrolo[2,3-d]pyrimidin-4-ylamino)-5-methylpiperidin-1-yl)prop-2-en-1-one; or, a pharmaceutically acceptable salt thereof.

7. The method of claim 1, wherein the compound is 1-(3R,4S)-3-(7H-pyrrolo[2,3-d]pyrimidin-4-ylamino)-4-methylpiperidin-1-yl)prop-2-en-1-one; or, a pharmaceutically acceptable salt thereof.

8. A method for treating a disorder or condition selected from the group consisting of rheumatoid arthritis, inflammatory bowel disease, Crohn's disease, and ulcerative colitis, comprising the step of administering to a subject an effective amount of the compound 1-((2S,5R)-5-(7H-pyrrolo[2,3-d]pyrimidin-4-ylamino)-2-methyl piperidin-1-yl)prop-2-en-1-one; or, a pharmaceutically acceptable salt thereof.

9. The method of claim 1, wherein the compound is 1-((3R,5S)-3-(7H-pyrrolo[2,3-d]pyrimidin-4-ylamino)-5-fluoropiperidin-1-yl)prop-2-en-1-one; or, a pharmaceutically acceptable salt thereof.

10. The method of claim 1, wherein the compound is 1-(3S,4R)-3-(7H-pyrrolo[2,3-d]pyrimidin-4-ylamino)-4-fluoropiperidin-1-yl)prop-2-en-1-one; or, a pharmaceutically acceptable salt thereof.

11. The method of claim 1, wherein the compound is 1-(2S,5R)-5-(7H-pyrrolo[2,3-d]pyrimidin-4-ylamino)-2-ethylpiperidin-1-yl)prop-2-en-1-one; or, a pharmaceutically acceptable salt thereof.

12. The method of claim 1, wherein the compound is (R)-1-(3-(7H-pyrrolo[2,3-d]pyrimidin-4-ylamino)piperidin-1-yl)prop-2-en-1-one; or, a pharmaceutically acceptable salt thereof.

* * * * *